(12) United States Patent
Gray et al.

(10) Patent No.: US 12,161,914 B2
(45) Date of Patent: Dec. 10, 2024

(54) VARIABLE CAPACITIVE FORCE SENSING STRUCTURE

(71) Applicant: SigmaSense, LLC., Wilmington, DE (US)

(72) Inventors: Michael Shawn Gray, Elgin, TX (US); Richard Stuart Seger, Jr., Belton, TX (US); Timothy W. Markison, Mesa, AZ (US); Kevin Joseph Derichs, Buda, TX (US)

(73) Assignee: SigmaSense, LLC., Austin, TX (US)

( * ) Notice: Subject to any disclaimer, the term of this patent is extended or adjusted under 35 U.S.C. 154(b) by 71 days.

(21) Appl. No.: 18/059,866

(22) Filed: Nov. 29, 2022

(65) Prior Publication Data

US 2023/0087019 A1 Mar. 23, 2023

Related U.S. Application Data

(63) Continuation of application No. 17/649,523, filed on Jan. 31, 2022, which is a continuation-in-part of
(Continued)

(51) Int. Cl.
*G01L 5/00* (2006.01)
*A43B 3/44* (2022.01)
(Continued)

(52) U.S. Cl.
CPC ............ *A63B 24/0062* (2013.01); *A43B 3/44* (2022.01); *G01L 5/0052* (2013.01); *G01L 5/161* (2013.01);
(Continued)

(58) Field of Classification Search
CPC . G01L 1/146; G01L 1/26; G01L 1/205; G01L 5/166; G01L 1/122; A43B 3/44;
(Continued)

(56) References Cited

U.S. PATENT DOCUMENTS

| 3,184,739 A | 5/1965 | Frederick |
| 3,795,911 A | 3/1974 | Hammack |

(Continued)

FOREIGN PATENT DOCUMENTS

| CN | 104182105 A | 12/2014 |
| CN | 104536627 A | 4/2015 |

(Continued)

OTHER PUBLICATIONS

European Patent Office; Extended European Search Report; Application No. 19853507.2; Jun. 13, 2023; 7 pgs.
"F-Scan System." Tekscan, Inc. https://www.tekscan.com/products-solutions/systems/f-scan-system. Accessed Aug. 18, 2017.
Baker; How delta-sigma ADCs work, Part 1; Analog Applications Journal; Oct. 1, 2011; 6 pgs.
Brian Pisani, Digital Filter Types in Delta-Sigma ADCs, Application Report SBAA230, May 2017, pp. 1-8, Texas Instruments Incorporated, Dallas, Texas.
(Continued)

*Primary Examiner* — Brandi N Hopkins
(74) *Attorney, Agent, or Firm* — GARLICK & MARKISON; Timothy W. Markison

(57) ABSTRACT

A force detection system includes first and second sets of pressure sensors, memory, and a processing module. The first set of pressure sensors are in an insole of a shoe and the second set of pressure sensors are in an outsole of a shoe. The processing module receives first data regarding the first set of pressure sensors and generates a first digital representation of the first data. The processing module also receives second data regarding the second set of pressure sensors and generates a second digital representation of the second data. The processing module also writes the first and second digital representations to the memory.

16 Claims, 103 Drawing Sheets

Related U.S. Application Data application No. 15/679,831, filed on Aug. 17, 2017, now Pat. No. 11,246,507, said application No. 17/649,523 is a continuation-in-part of application No. 17/575,594, filed on Jan. 13, 2022.

(60) Provisional application No. 62/376,555, filed on Aug. 18, 2016, provisional application No. 63/202,251, filed on Jun. 3, 2021.

(51) Int. Cl.

| | | |
|---|---|---|
| *A63B 24/00* | (2006.01) | |
| *G01L 5/161* | (2020.01) | |
| *G01L 5/164* | (2020.01) | |
| *G01L 5/165* | (2020.01) | |
| *G01L 5/167* | (2020.01) | |
| *G16H 40/67* | (2018.01) | |

(52) U.S. Cl.
 CPC .............. *G01L 5/164* (2013.01); *G01L 5/165* (2013.01); *G01L 5/167* (2013.01); *G16H 40/67* (2018.01); *A63B 2220/13* (2013.01); *A63B 2220/56* (2013.01); *A63B 2220/58* (2013.01); *A63B 2220/836* (2013.01); *A63B 2220/89* (2013.01); *A63B 2225/20* (2013.01)

(58) Field of Classification Search
 CPC ... A61B 5/1038; A61B 5/6807; A61B 5/7225; A61B 2562/0247; A61B 2562/046; G06F 3/04162; G06F 3/017; G06F 3/011; G09B 19/0038; A43C 11/165; G16H 20/30
 See application file for complete search history.

(56) References Cited

U.S. PATENT DOCUMENTS

| | | | |
|---|---|---|---|
| 3,953,856 A | 4/1976 | Hammack | |
| 4,992,797 A | 2/1991 | Gjessing | |
| 5,247,307 A | 9/1993 | Gandar | |
| 5,410,314 A | 4/1995 | Frush | |
| 5,437,178 A | 8/1995 | Esin et al. | |
| 5,925,001 A | 7/1999 | Hoyt | |
| 6,218,972 B1 | 4/2001 | Groshong | |
| 6,222,481 B1 | 4/2001 | Abrahamson | |
| 6,665,013 B1 | 12/2003 | Fossum et al. | |
| 7,394,046 B2 | 7/2008 | Olsson | |
| 7,476,233 B1 | 1/2009 | Wiener et al. | |
| 7,528,755 B2 | 5/2009 | Hammerschmidt | |
| 7,648,441 B2 | 1/2010 | Silk | |
| 7,717,962 B2 | 5/2010 | Wilson | |
| 7,911,339 B2 | 3/2011 | Vock | |
| 8,011,229 B2 | 9/2011 | Lieberman | |
| 8,031,094 B2 | 10/2011 | Hotelling | |
| 8,089,289 B1 | 1/2012 | Kremin et al. | |
| 8,113,843 B2 | 2/2012 | Naya | |
| 8,279,180 B2 | 10/2012 | Hotelling et al. | |
| 8,280,681 B2 | 10/2012 | Vock | |
| 8,375,784 B2 | 2/2013 | Bamberg | |
| 8,384,551 B2 | 2/2013 | Ross | |
| 8,467,979 B2 | 6/2013 | Sobolewski | |
| 8,537,110 B2 | 9/2013 | Kruglick | |
| 8,547,114 B2 | 10/2013 | Kremin | |
| 8,587,535 B2 | 11/2013 | Oda et al. | |
| 8,625,726 B2 | 1/2014 | Kuan | |
| 8,657,681 B2 | 2/2014 | Kim | |
| 8,686,862 B2 | 4/2014 | Dunham | |
| 8,692,675 B2 | 4/2014 | Agrawal | |
| 8,784,115 B1 | 7/2014 | Chuang | |
| 8,821,417 B2 | 9/2014 | McGregor | |
| 8,870,795 B2 | 10/2014 | Kim | |
| 8,966,400 B2 | 2/2015 | Yeap | |
| 8,968,218 B2 | 3/2015 | Wukasch | |
| 8,982,097 B1 | 3/2015 | Kuzo et al. | |
| 9,081,437 B2 | 7/2015 | Oda | |
| 9,201,547 B2 | 12/2015 | Elias | |
| 9,256,281 B2 | 2/2016 | Ur | |
| 9,349,301 B2 | 5/2016 | Ur | |
| 9,352,207 B2 | 5/2016 | Balakrishnan | |
| 9,393,697 B1 | 7/2016 | Beardsley | |
| 9,756,895 B2 | 9/2017 | Rice | |
| 9,763,489 B2 | 9/2017 | Amos | |
| 9,810,591 B2 | 11/2017 | Walker | |
| 9,810,709 B2 | 11/2017 | Balakrishnan | |
| 9,962,111 B2 | 5/2018 | Balakrishnan | |
| 10,007,335 B2 | 6/2018 | Lee | |
| 10,070,682 B2 | 9/2018 | Rubin | |
| 10,307,081 B2 | 6/2019 | Nino | |
| 2003/0052657 A1 | 3/2003 | Koernle et al. | |
| 2004/0138575 A1 | 7/2004 | Jeyama | |
| 2005/0049816 A1 | 3/2005 | Oda | |
| 2005/0162065 A1* | 7/2005 | Kojima | H01J 29/864 |
| | | | 313/292 |
| 2005/0235758 A1 | 10/2005 | Kowal et al. | |
| 2007/0068244 A1 | 3/2007 | Billing | |
| 2007/0112285 A1 | 5/2007 | Dar | |
| 2007/0142955 A1 | 6/2007 | Lin | |
| 2007/0173903 A1 | 7/2007 | Goren | |
| 2007/0246334 A1 | 10/2007 | Elkins | |
| 2007/0247306 A1 | 10/2007 | Case | |
| 2008/0082025 A1 | 4/2008 | Hughes | |
| 2008/0108913 A1 | 5/2008 | Lengsfeld | |
| 2008/0243265 A1 | 10/2008 | Lanier | |
| 2008/0285805 A1 | 11/2008 | Luinge | |
| 2008/0287832 A1 | 11/2008 | Collins | |
| 2009/0069898 A1 | 3/2009 | Wilson | |
| 2009/0235739 A1 | 9/2009 | Morris Bamberg | |
| 2009/0240171 A1 | 9/2009 | Morris Bamberg | |
| 2010/0041959 A1 | 2/2010 | Iwata | |
| 2011/0054359 A1 | 3/2011 | Sazonov | |
| 2011/0063154 A1 | 3/2011 | Hotelling et al. | |
| 2011/0087445 A1 | 4/2011 | Sobolewski | |
| 2011/0119027 A1 | 5/2011 | Zhu | |
| 2011/0131838 A1 | 6/2011 | Pas | |
| 2011/0152695 A1 | 6/2011 | Granqvist | |
| 2011/0251520 A1 | 10/2011 | Shieh | |
| 2011/0267219 A1 | 11/2011 | Kislianksy | |
| 2011/0298745 A1 | 12/2011 | Souchkov | |
| 2011/0304497 A1 | 12/2011 | Molyneux | |
| 2012/0059235 A1 | 3/2012 | Davies | |
| 2012/0092169 A1 | 4/2012 | Kaiser | |
| 2012/0095356 A1 | 4/2012 | Oleson | |
| 2012/0234111 A1 | 9/2012 | Molyneux | |
| 2012/0253234 A1 | 10/2012 | Yang | |
| 2012/0278031 A1 | 11/2012 | Oda | |
| 2012/0291563 A1 | 11/2012 | Schrock | |
| 2013/0041617 A1 | 2/2013 | Pease | |
| 2013/0110011 A1 | 5/2013 | McGregor | |
| 2013/0190903 A1 | 7/2013 | Balakrishnan | |
| 2013/0278447 A1 | 10/2013 | Kremin | |
| 2014/0024972 A1 | 1/2014 | Greene | |
| 2014/0174205 A1 | 6/2014 | Clarke | |
| 2014/0222173 A1 | 8/2014 | Giedowyn | |
| 2014/0327644 A1 | 11/2014 | Mohindra | |
| 2015/0091847 A1 | 4/2015 | Chang | |
| 2015/0133754 A1 | 5/2015 | Freeman | |
| 2015/0157272 A1 | 6/2015 | Balakrishnan | |
| 2015/0289820 A1 | 10/2015 | Miller | |
| 2015/0313308 A1 | 11/2015 | Rice | |
| 2015/0346889 A1 | 12/2015 | Chen | |
| 2016/0058326 A1 | 3/2016 | Winfree | |
| 2016/0143562 A1 | 5/2016 | Ashby | |
| 2016/0174899 A1 | 6/2016 | Besnard | |
| 2016/0188049 A1 | 6/2016 | Yang et al. | |
| 2016/0287937 A1 | 10/2016 | Fitzgerald | |
| 2016/0324445 A1 | 11/2016 | Kim | |
| 2016/0338411 A1 | 11/2016 | Liu | |
| 2016/0037534 A1 | 12/2016 | Czaja | |
| 2016/0345664 A1 | 12/2016 | Kohatsu | |
| 2016/0351771 A1 | 12/2016 | Schneider | |
| 2016/0370854 A1 | 12/2016 | Steele | |
| 2016/0375346 A1 | 12/2016 | Czaja | |
| 2017/0164684 A1 | 6/2017 | Vock | |

(56) References Cited

U.S. PATENT DOCUMENTS

| | | |
|---|---|---|
| 2017/0225033 A1 | 8/2017 | Czaja |
| 2017/0265560 A1 | 9/2017 | Beers |
| 2017/0265594 A1* | 9/2017 | Walker ................. A61B 5/1036 |
| 2018/0049670 A1 | 2/2018 | Markison |
| 2018/0049671 A1 | 2/2018 | Markison |
| 2018/0049703 A1 | 2/2018 | Markison |
| 2018/0157354 A1 | 6/2018 | Blondin et al. |
| 2018/0256071 A1 | 9/2018 | Mathieu |
| 2018/0275824 A1 | 9/2018 | Li |
| 2020/0158770 A1* | 5/2020 | Huynh ................... G01R 29/26 |

FOREIGN PATENT DOCUMENTS

| | | |
|---|---|---|
| CN | 107771273 A | 3/2018 |
| EP | 2284637 A1 | 2/2011 |
| IN | 103995626 A | 8/2014 |

OTHER PUBLICATIONS

Munk-Stander, Jacob. "Evaluation of Piezoelectric Film Sensors for In-Shoe Pressure Measurement." Technical Report No. 06/04. Dept. of Computer Science, University of Copenhagen, Denmark. Feburary 16, 2006. 21 pages.

Rampp, A., Barth, J., Schulein, S., Gar..mann, K. G., Klucken, J., & Eskofier, B. M. (2014). Inertial sensor-based stride parameter calculation from gait sequences in geriatric patients. IEEE transactions on biomedical engineering, 62(4), 1089-1097. (Year: 2014).

Willson, J. D., & Kemnozek, T. W. (1999). Plantar loading and cadence alterations with fatigue. Medicine and science in sports and exercise, 31(12), 1828-1833. (Year: 1999).

* cited by examiner medial side view cross-section
medial side view

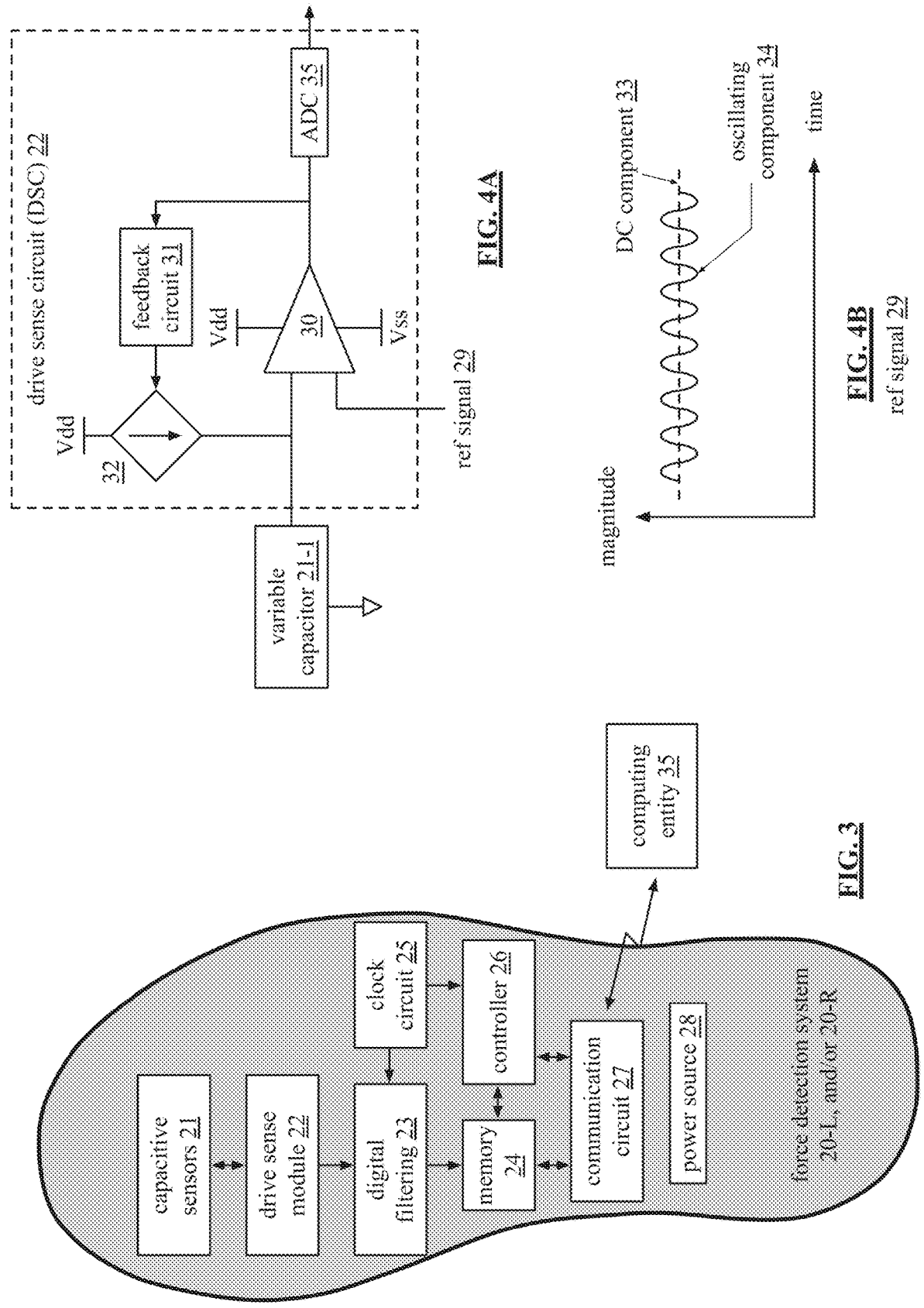

computing device 40 computing device 40 computing device 40 computing device 40

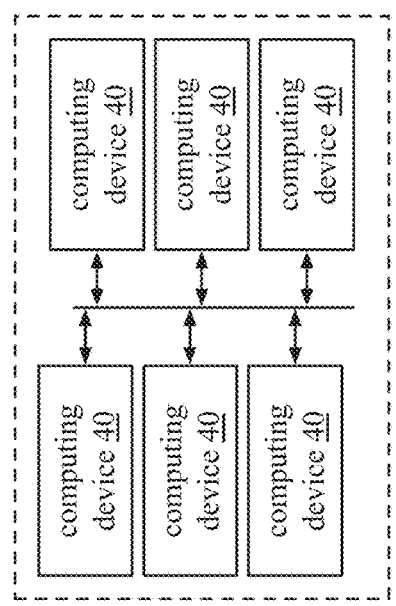
FIG. 5E
computing entity 35
FIG. 5F
computing entity 35
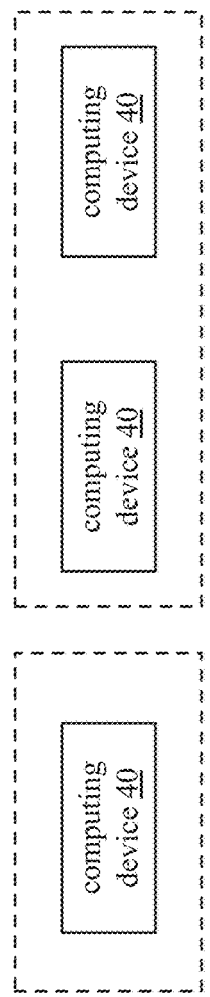
FIG. 5G
computing entity 35
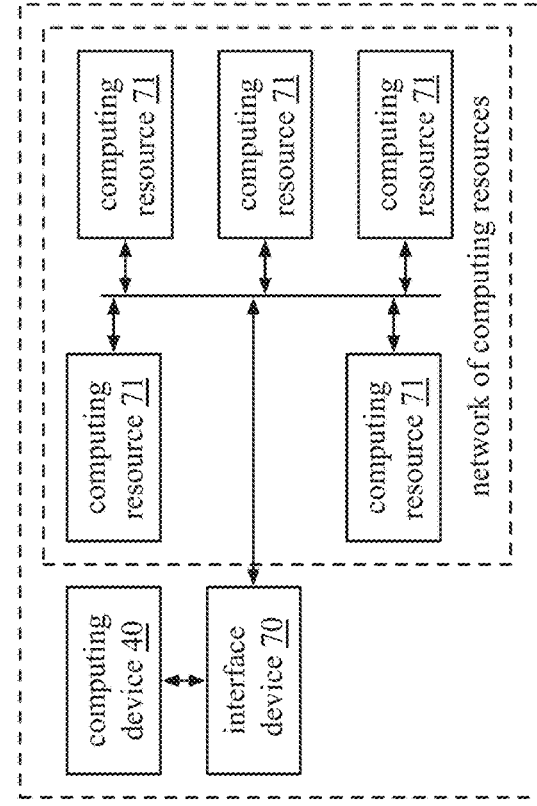
FIG. 5I
computing entity 35
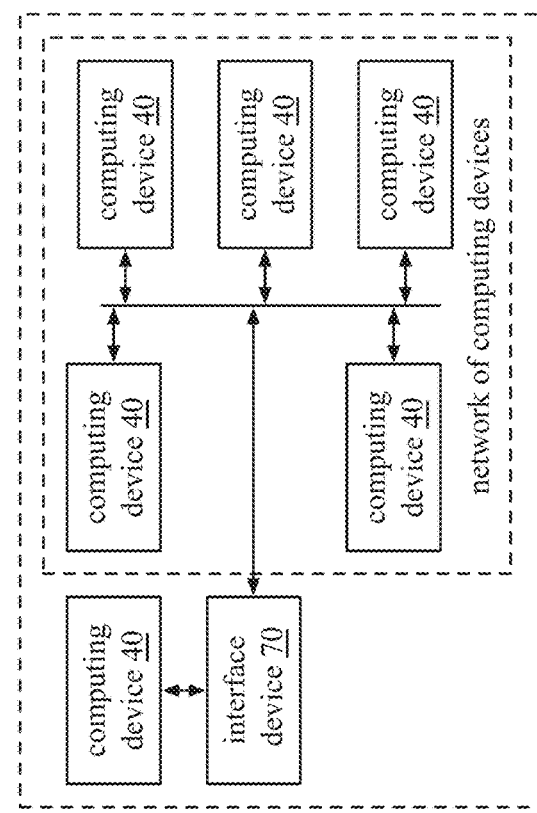
FIG. 5H
computing entity 35

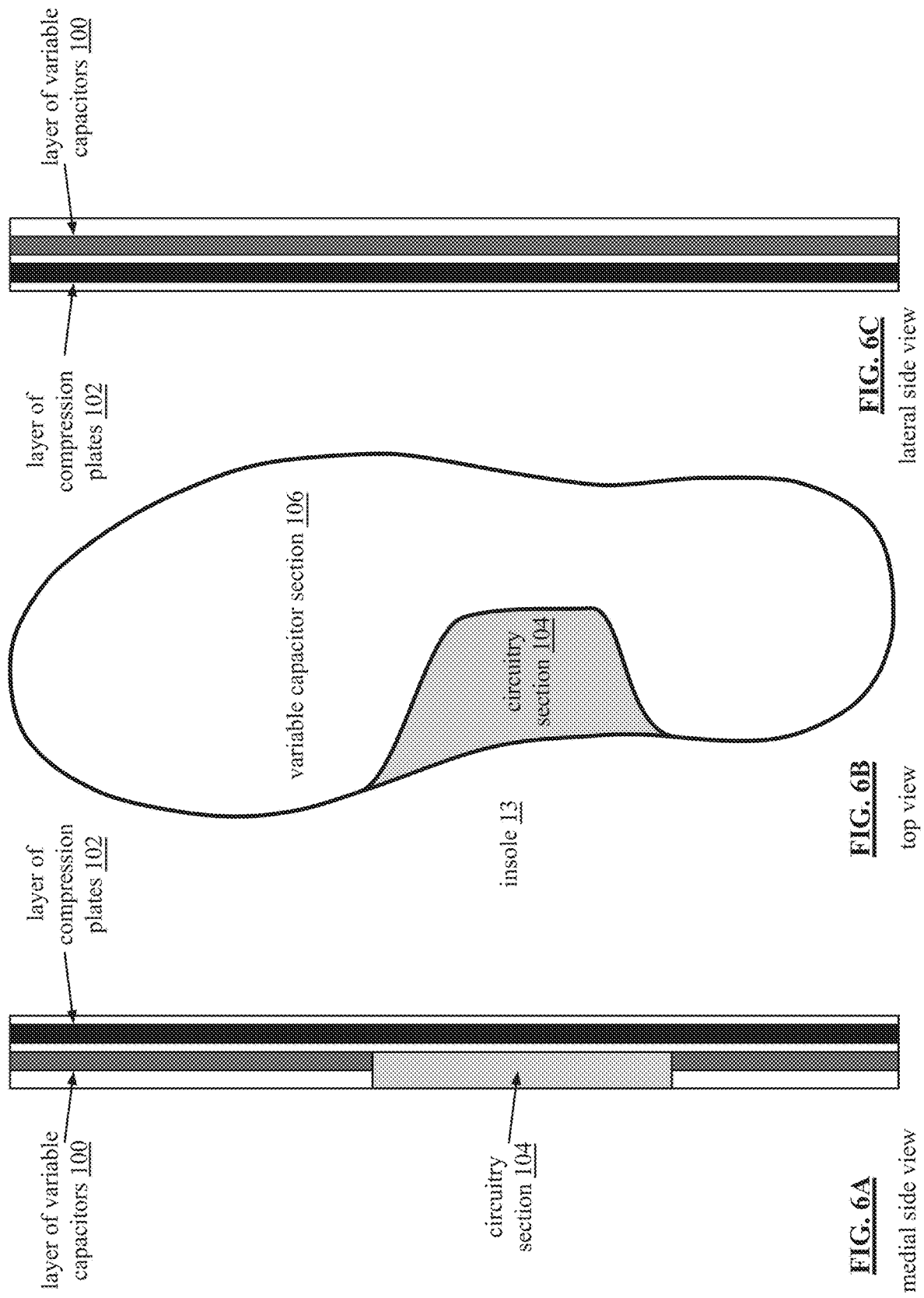

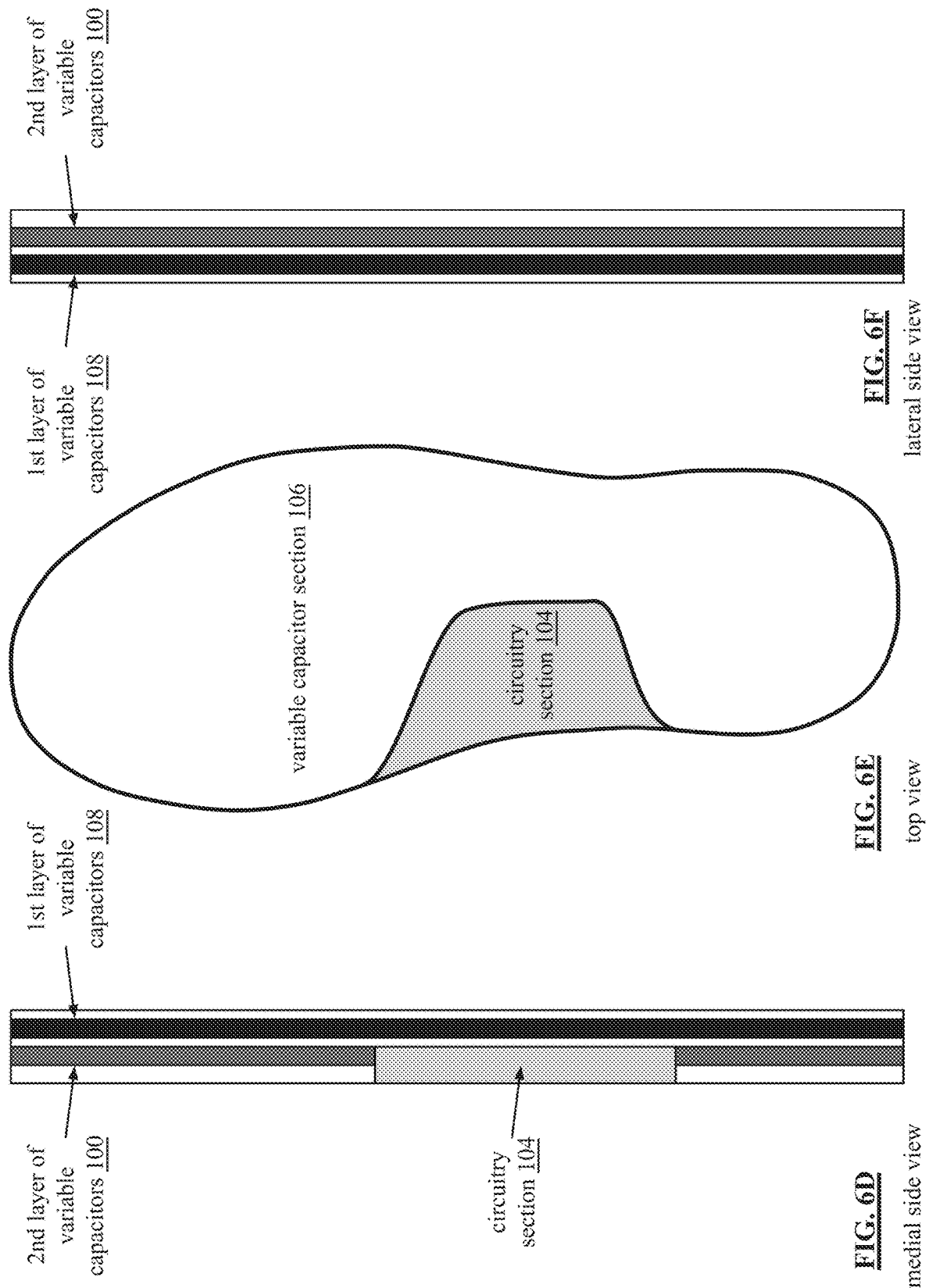

lateral side view top view medial side view

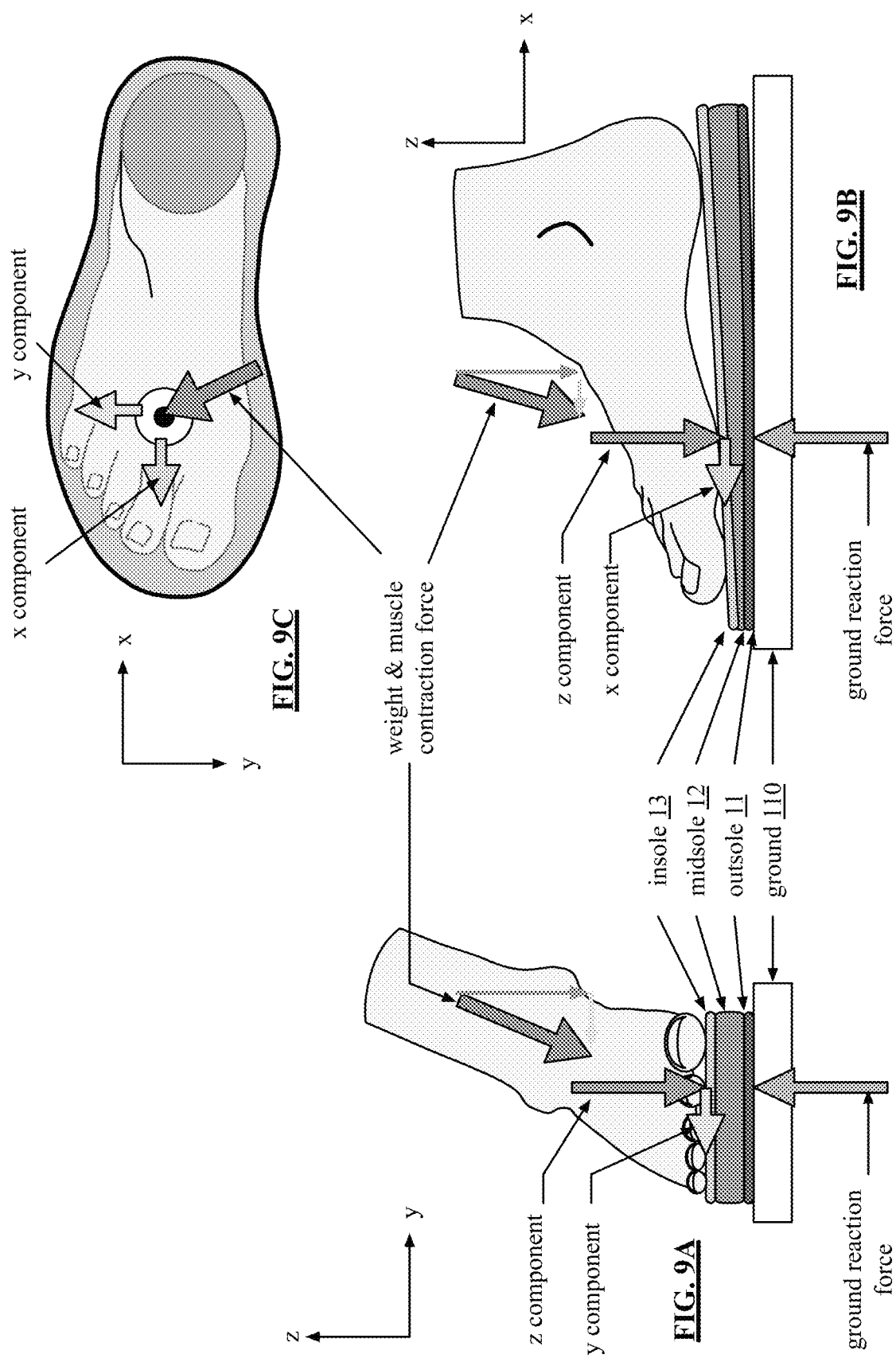

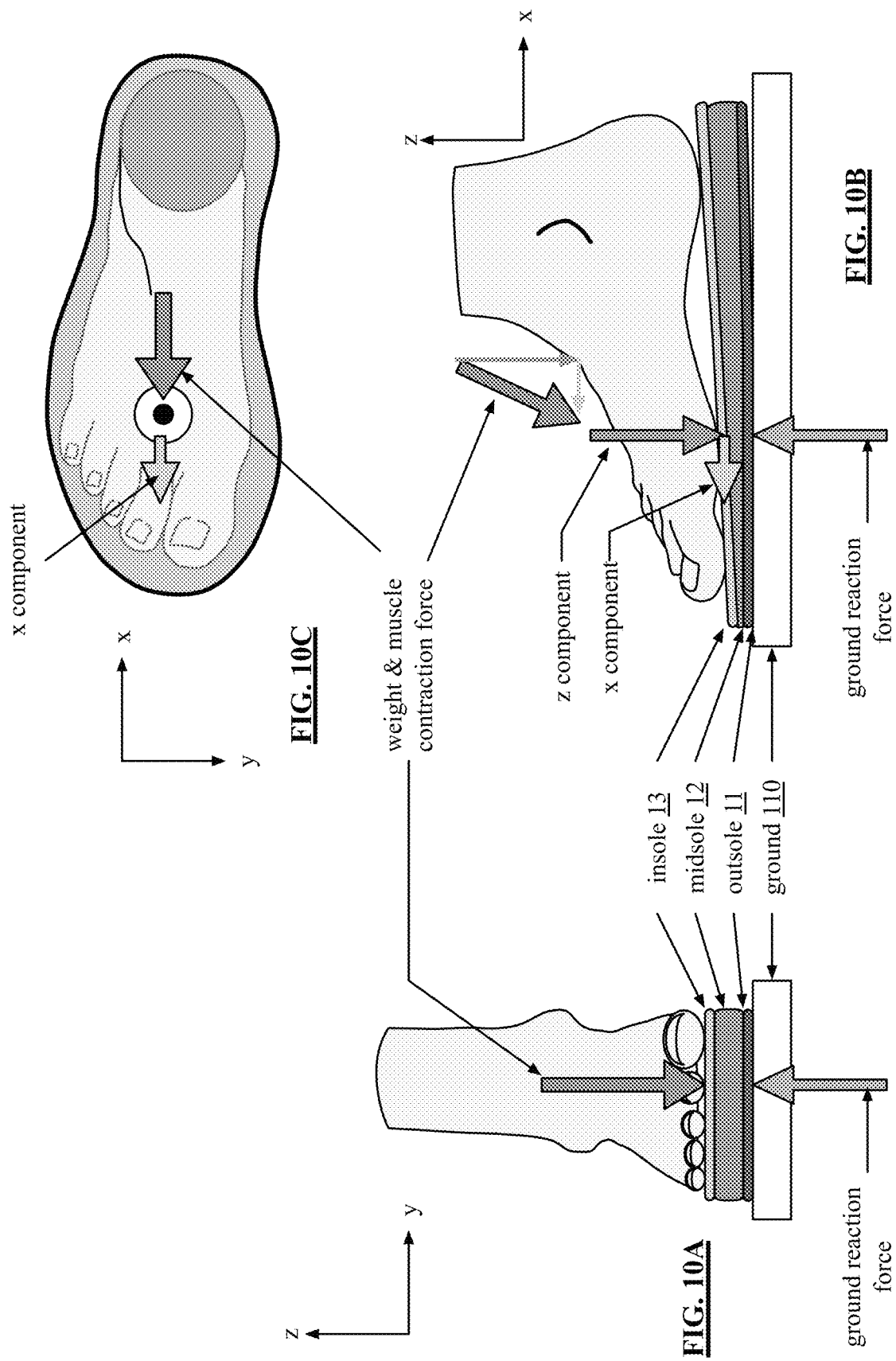

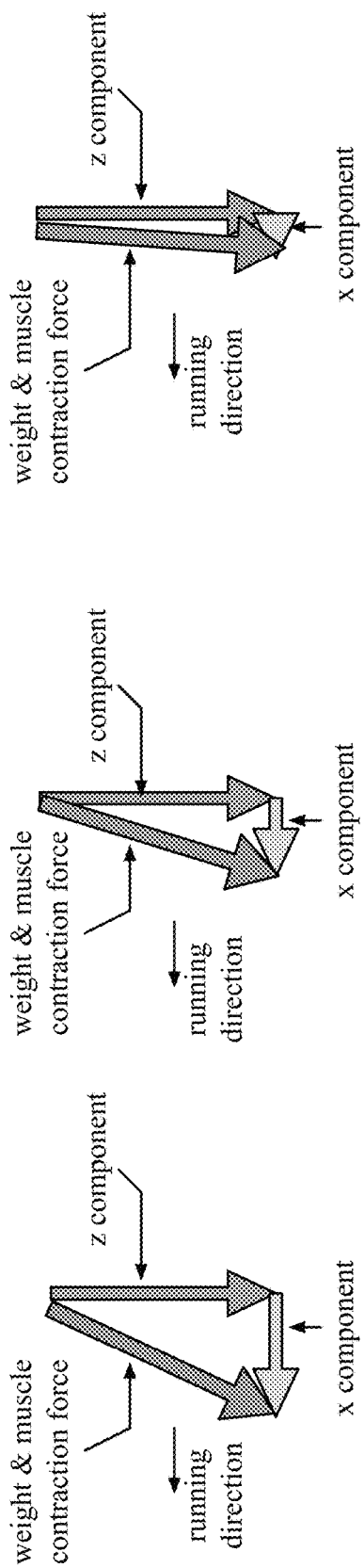
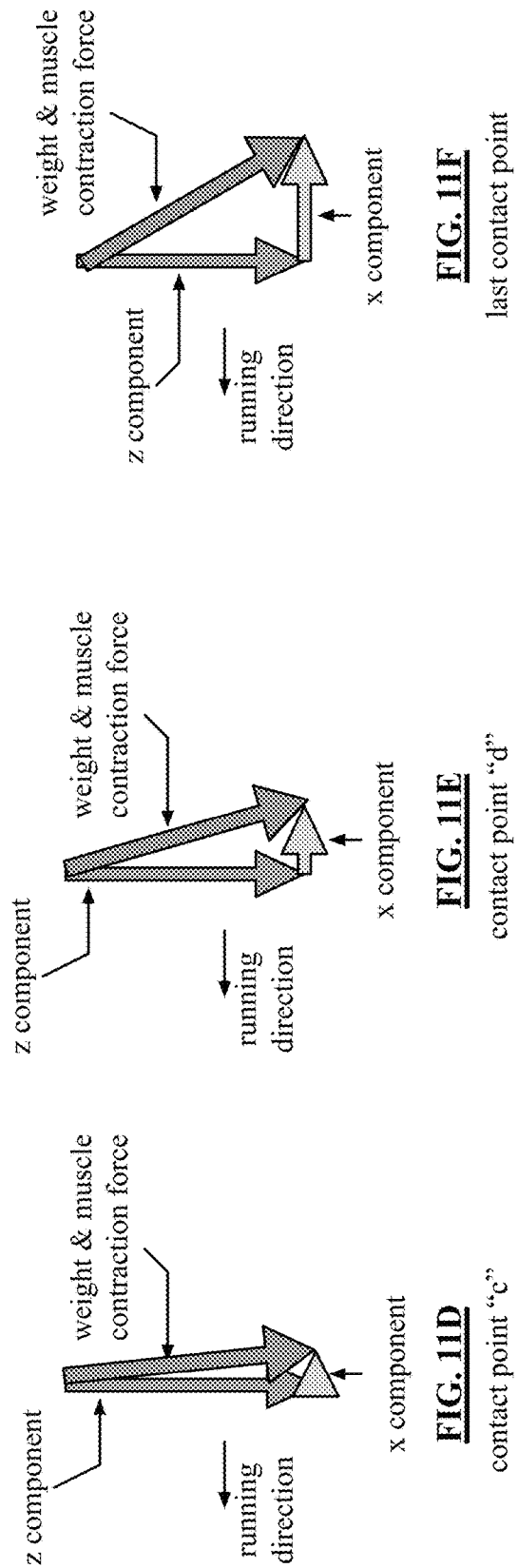

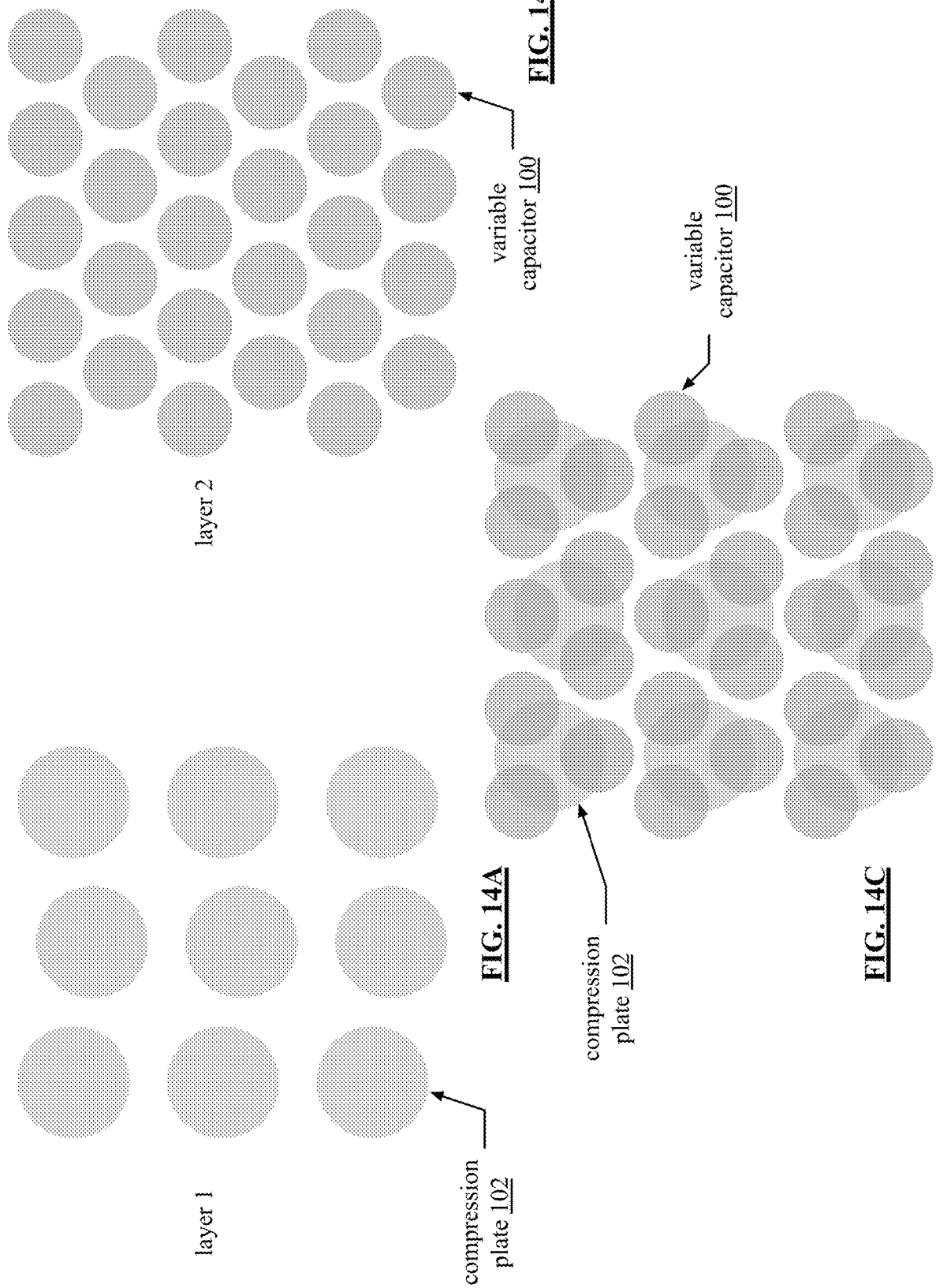

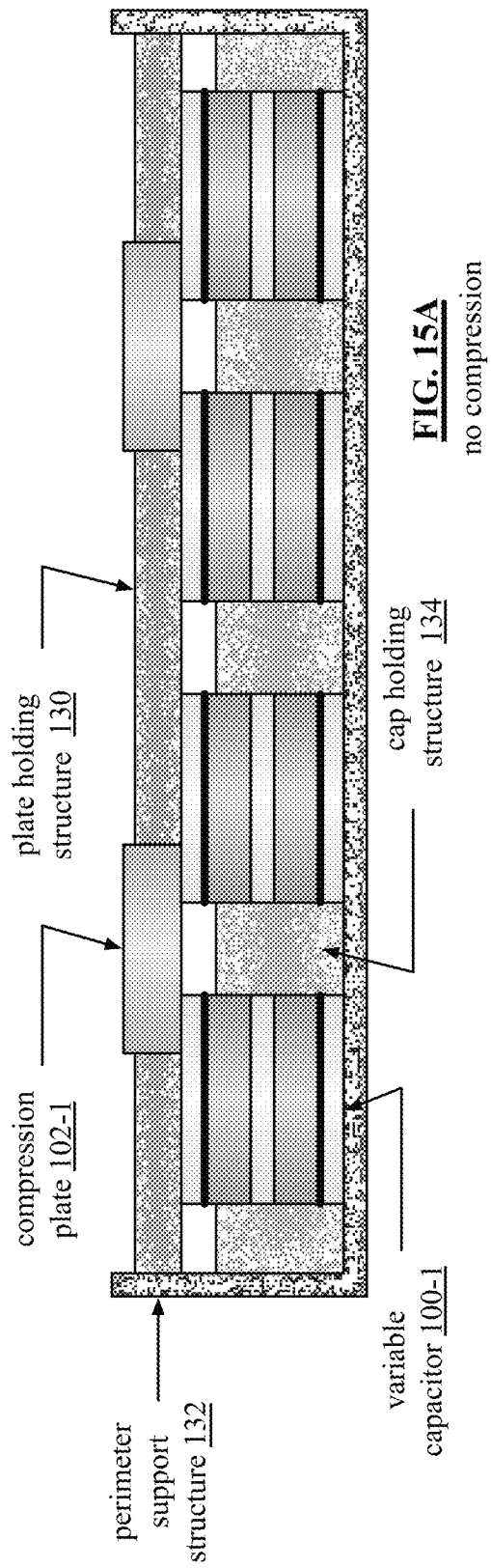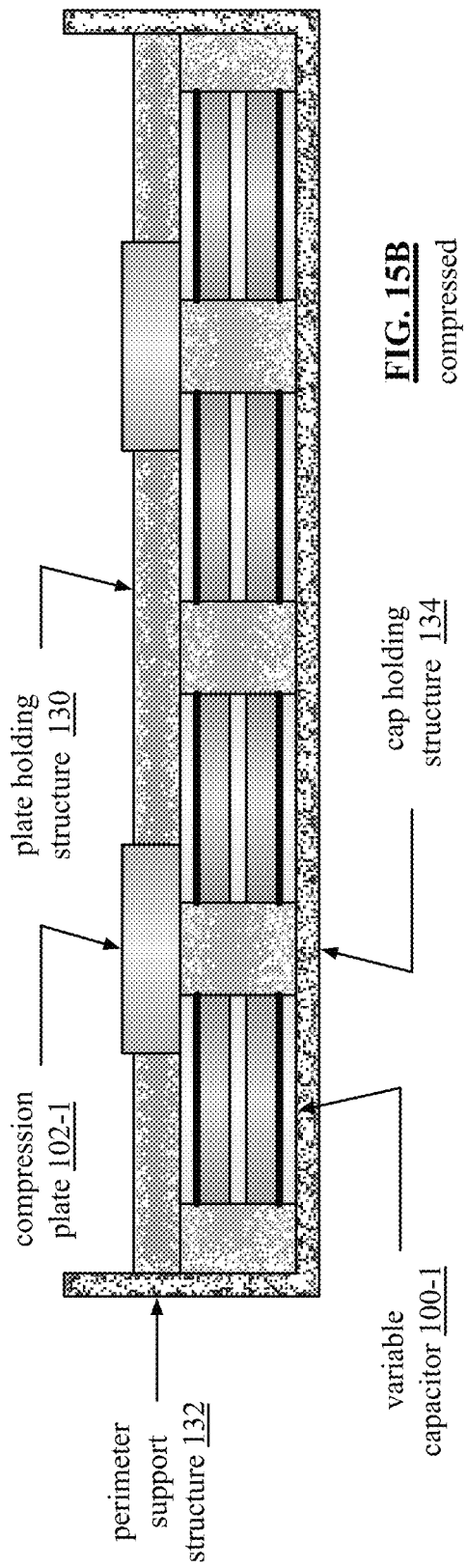

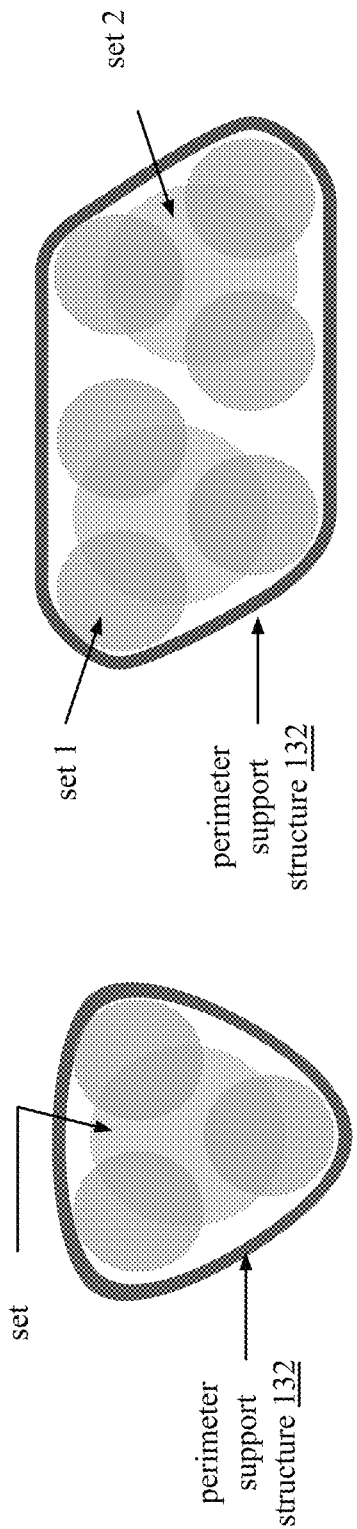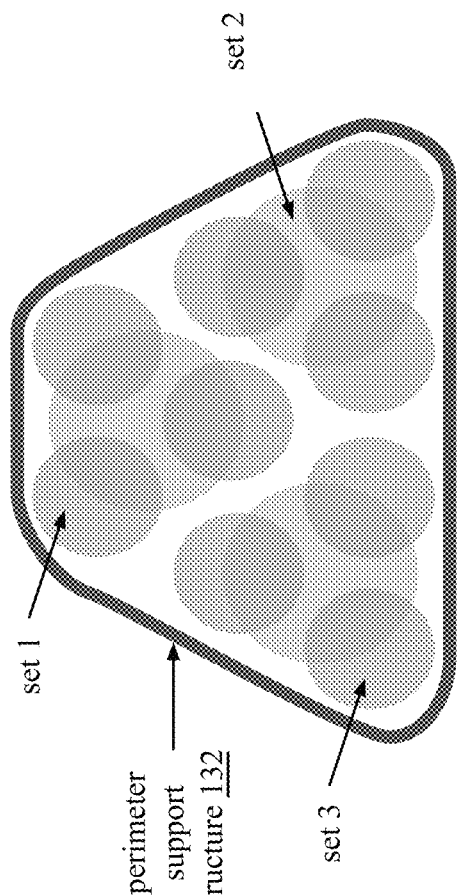
FIG. 15C
FIG. 15D
FIG. 15E

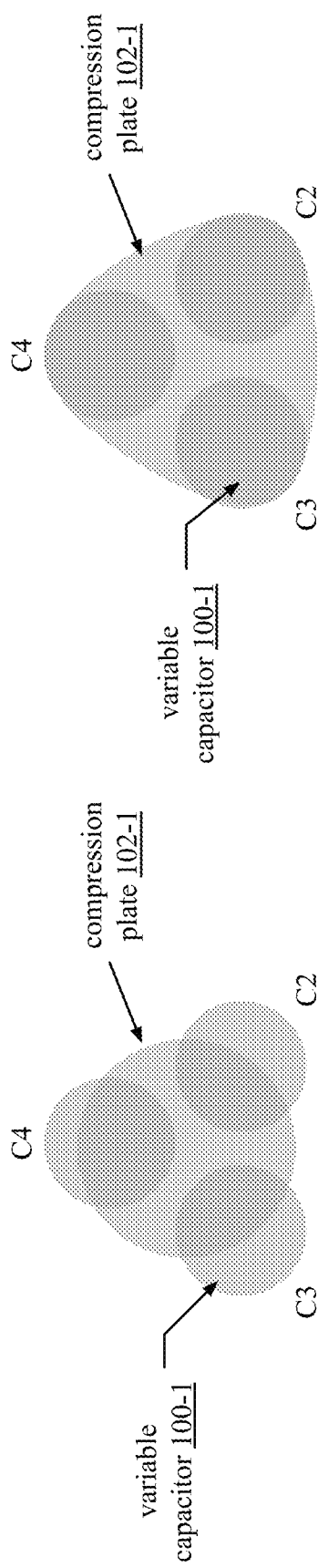
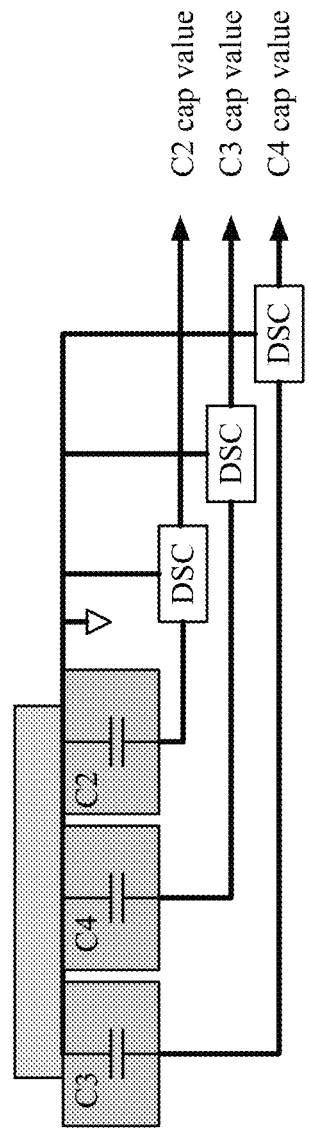
FIG. 16A
FIG. 16B
FIG. 16C top view side view side view top view side view side view

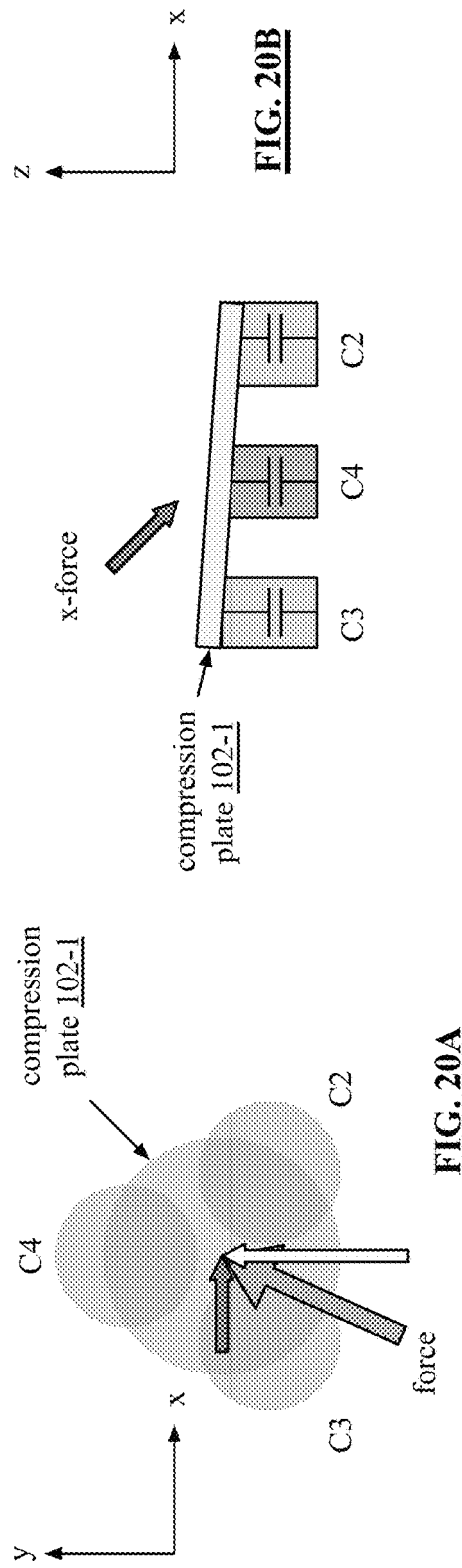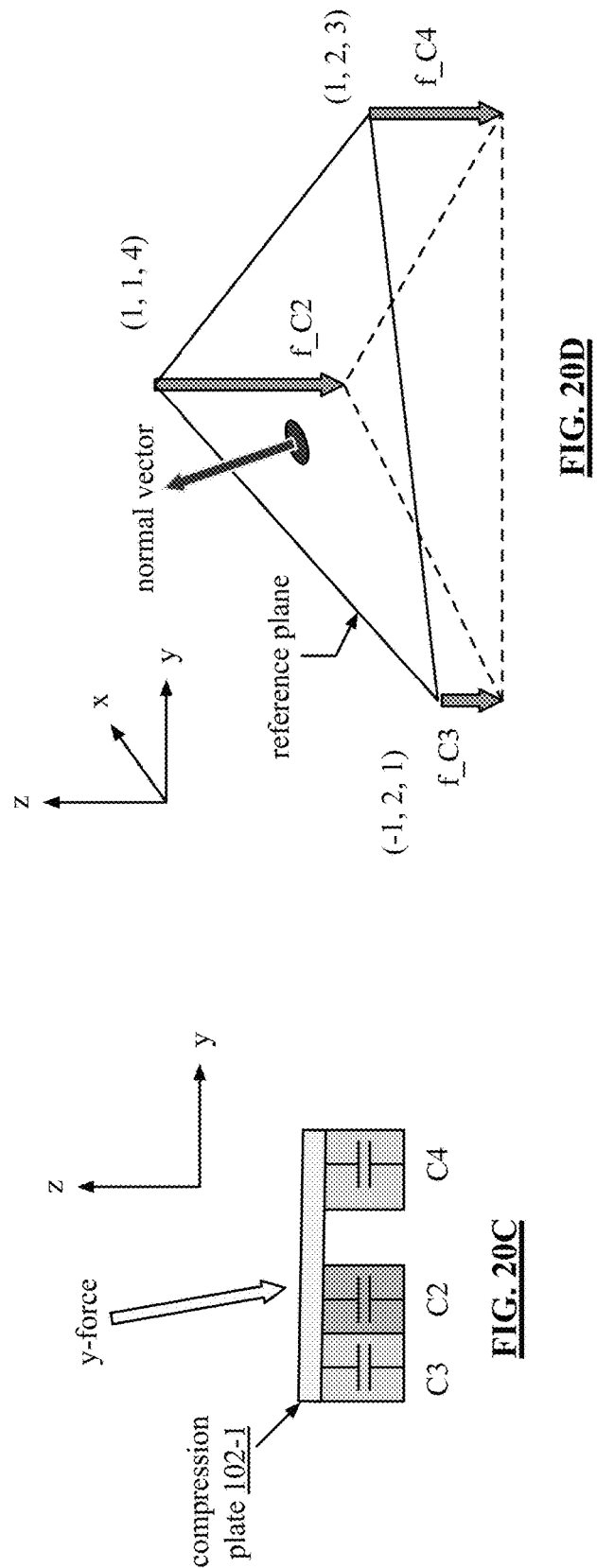
FIG. 20A
FIG. 20B
FIG. 20C
FIG. 20D

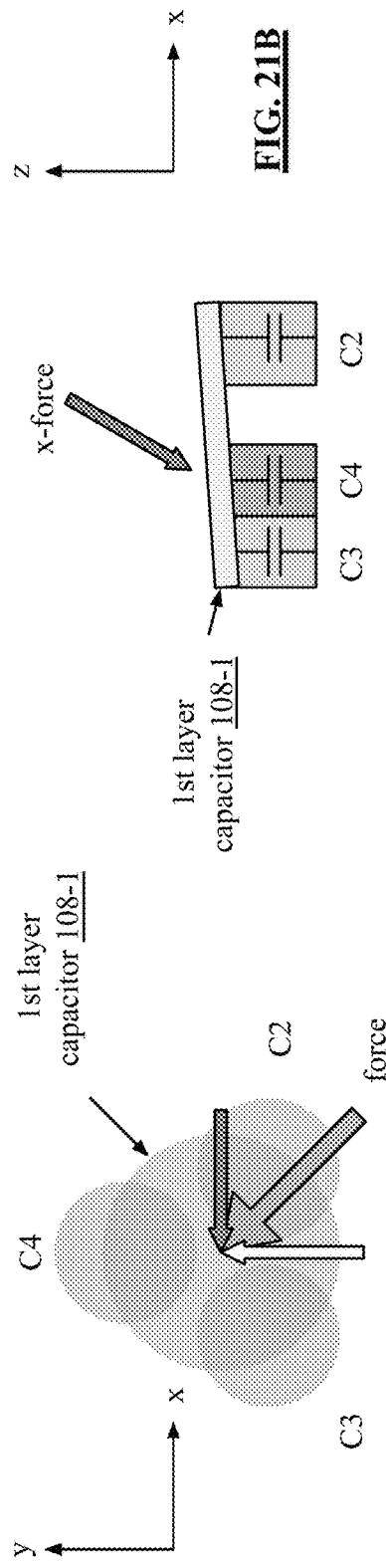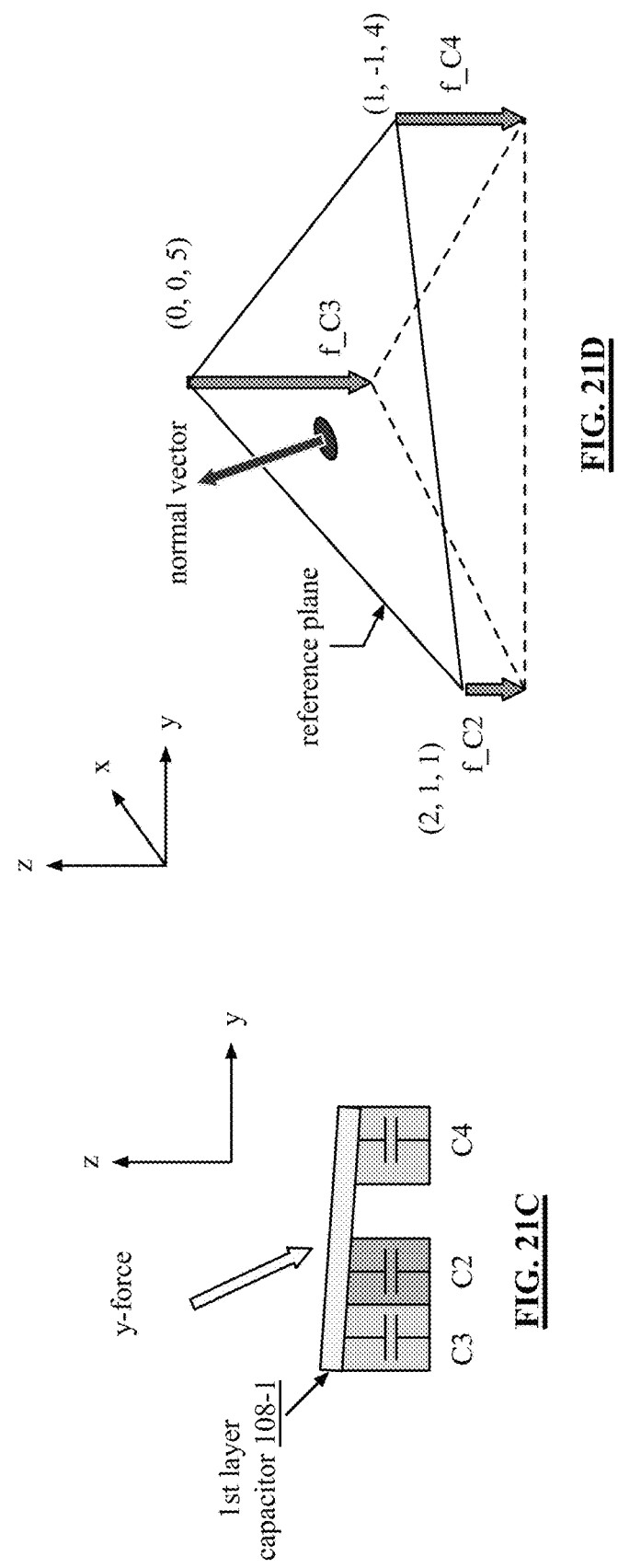

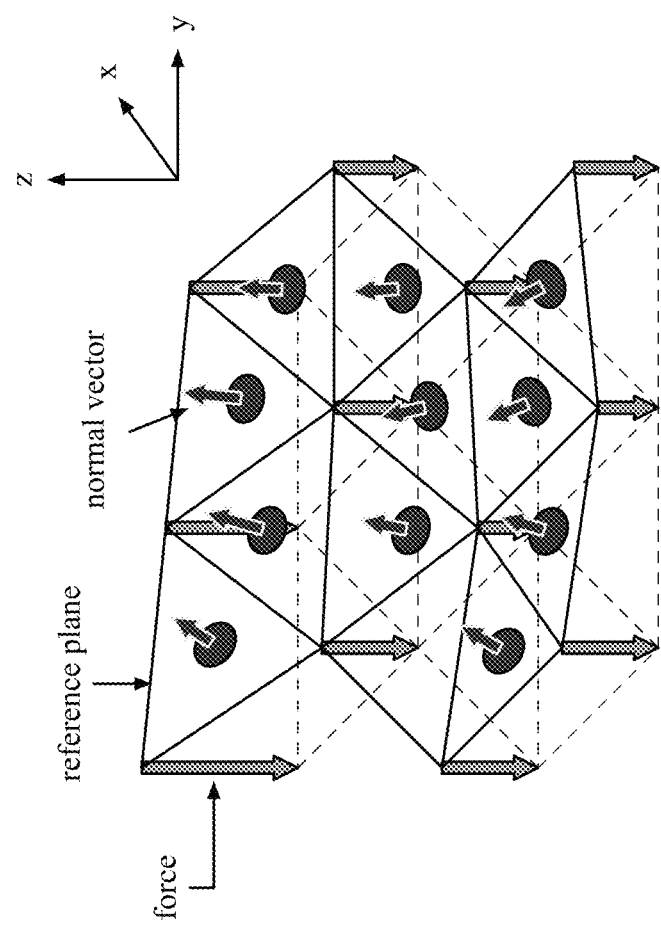
| f_C1 | f_C2 | f_C3 | f_C6 |
|------|------|------|------|
|      | f_C4 | f_C5 |      |
| f_C7 | f_C8 | f_C9 | f_C12 |
|      | f_C10 | f_C11 |     |
FIG. 22B
force pattern
FIG. 22C
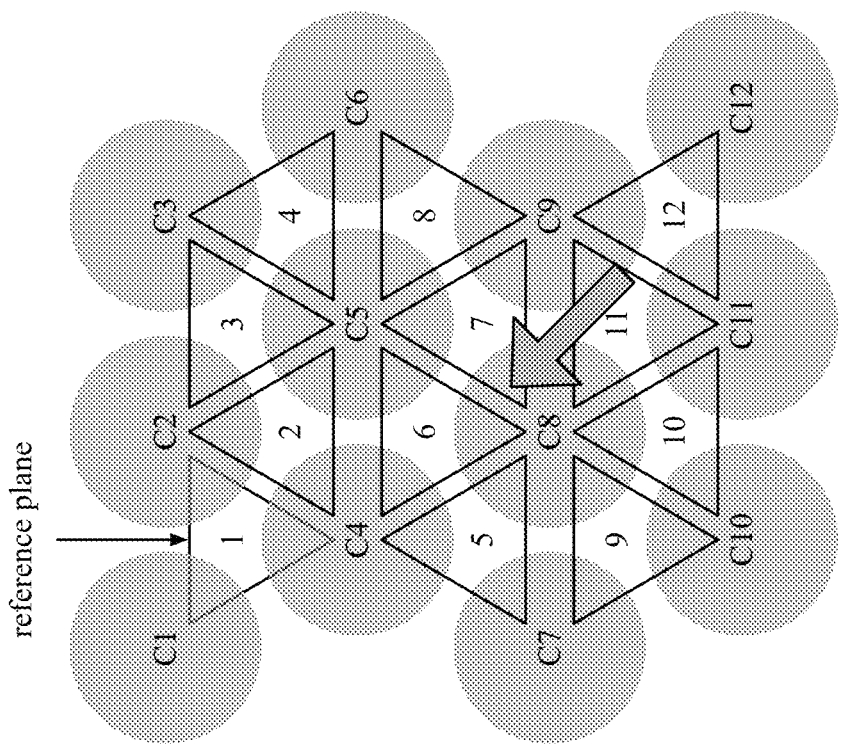
FIG. 22A red = TC2 cell    green = TC6 cell
blue = TC3 cell    black = TC7 cell

| row-column | capacitors | r-c score |
|---|---|---|
| 1-3 | C5, C7 | 16 |
| 1-4 | C5, C6 | 8 |
| 1-5 | C9, C11 | 4 |
| 1-6 | C9, C10 | 12 |
| 2-3 | C8, C7 | 8 |
| 2-4 | C8, C6 | 4 |
| 2-5 | C12, C11 | 2 |
| 2-6 | C12, C10 | 6 |
| 3-3 | C21, C23 | 4 |
| 3-4 | C21, C22 | 2 |
| 3-5 | C25, C27 | 1 |
| 3-6 | C25, C26 | 3 |
| 4-3 | C24, C23 | 12 |
| 4-4 | C24, C22 | 6 |
| 4-5 | C28, C27 | 3 |
| 3-6 | C28, C26 | 9 |

TC2 score = 16 + 8 + 8 + 4 = 36
TC3 score = 4 + 12 + 2 + 6 = 24
TC6 score = 4 + 2 + 12 + 6 = 24
TC7 score = 1 + 3 + 3 + 9 = 16

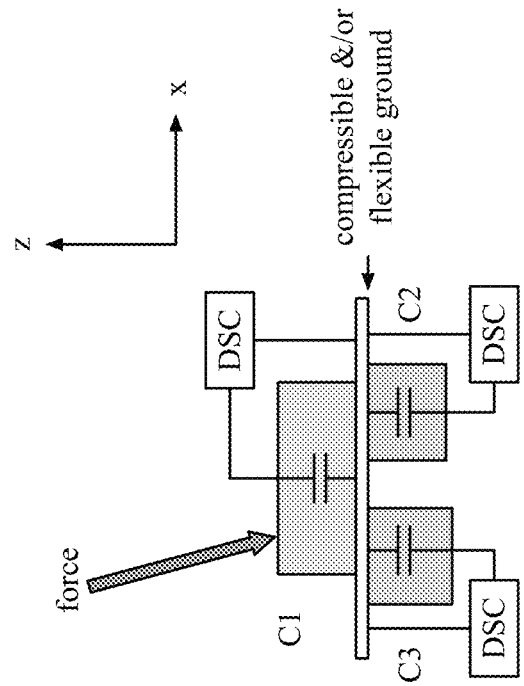
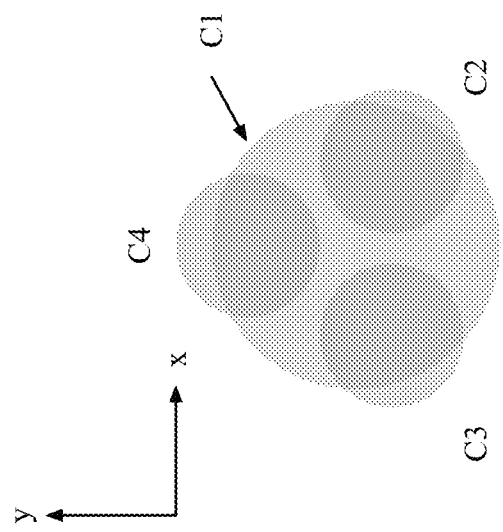
FIG. 27A
top view
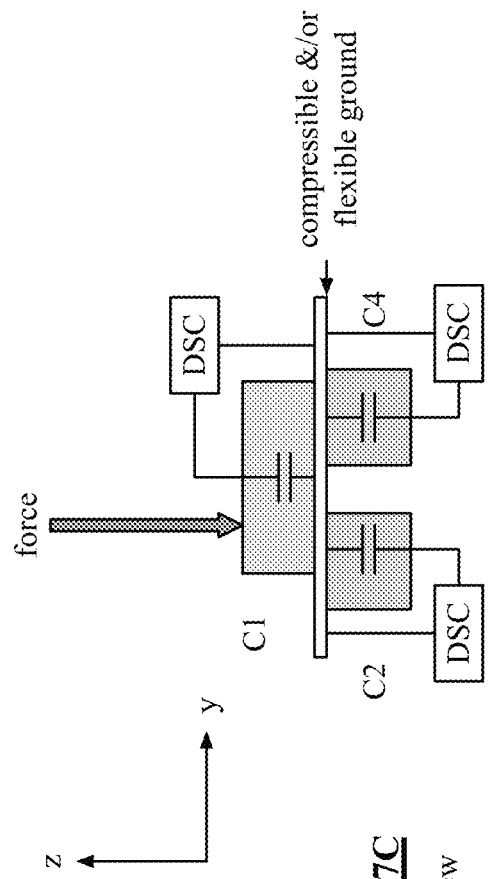
FIG. 27B
side view
FIG. 27C
side view select coverage of foot area full coverage of foot area key pressure points of foot area

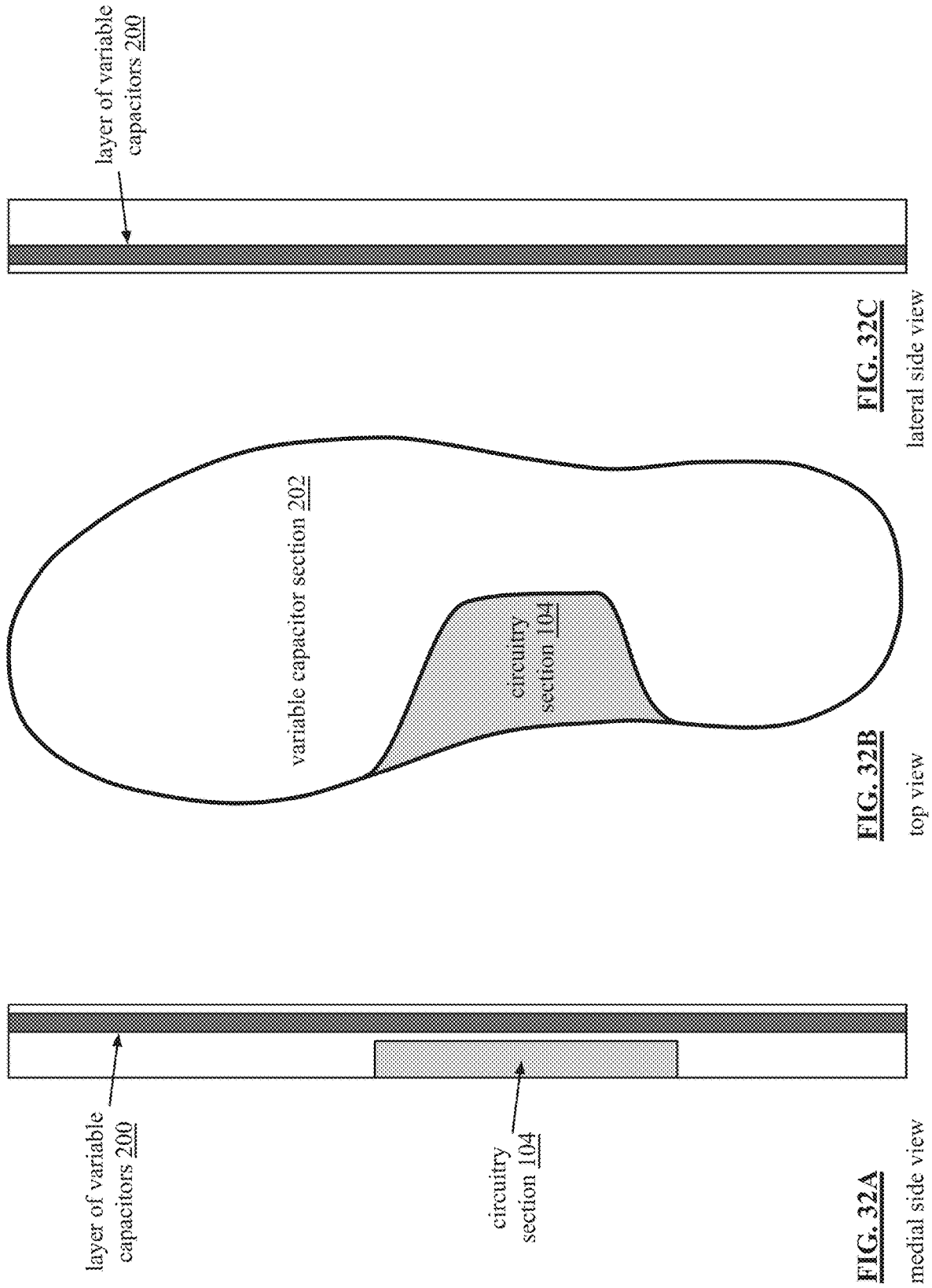

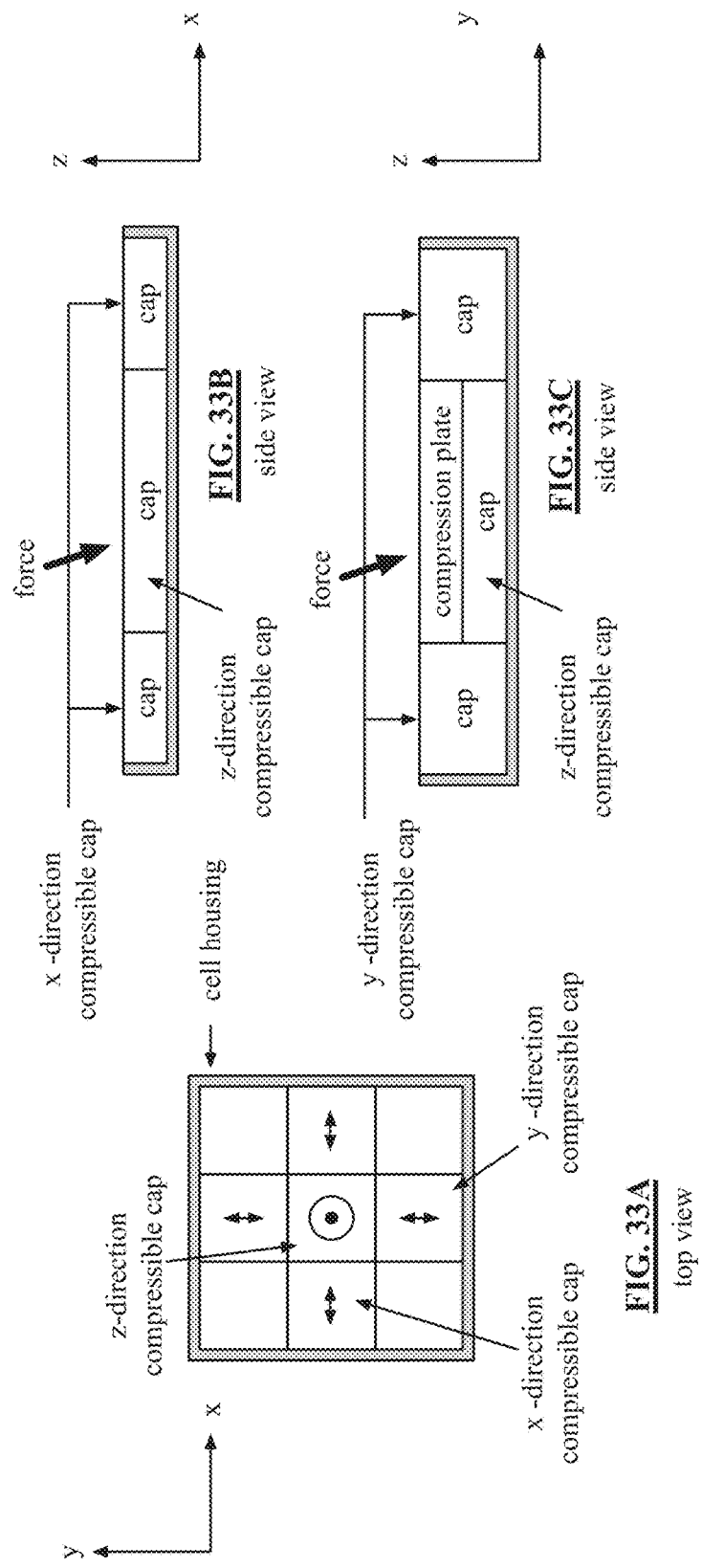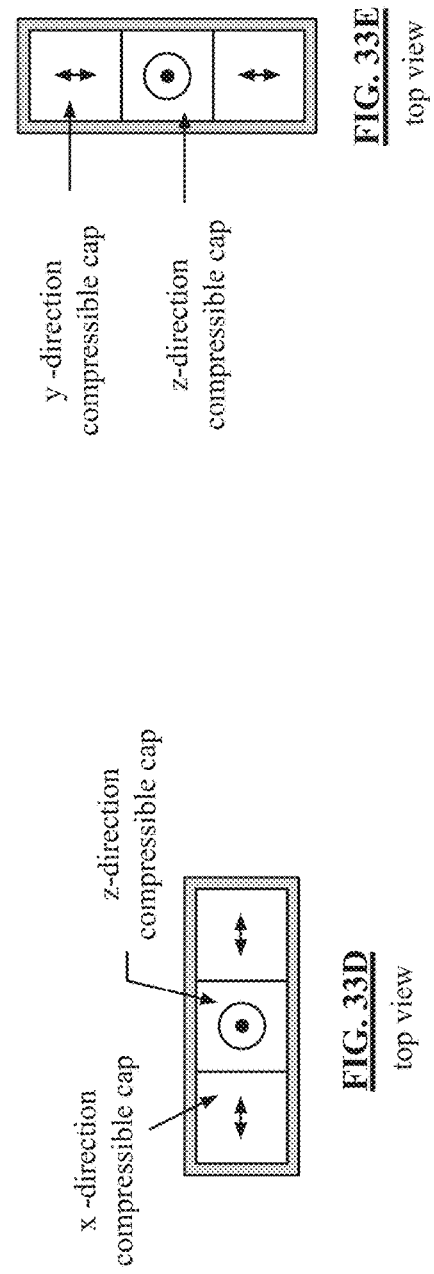

walking running

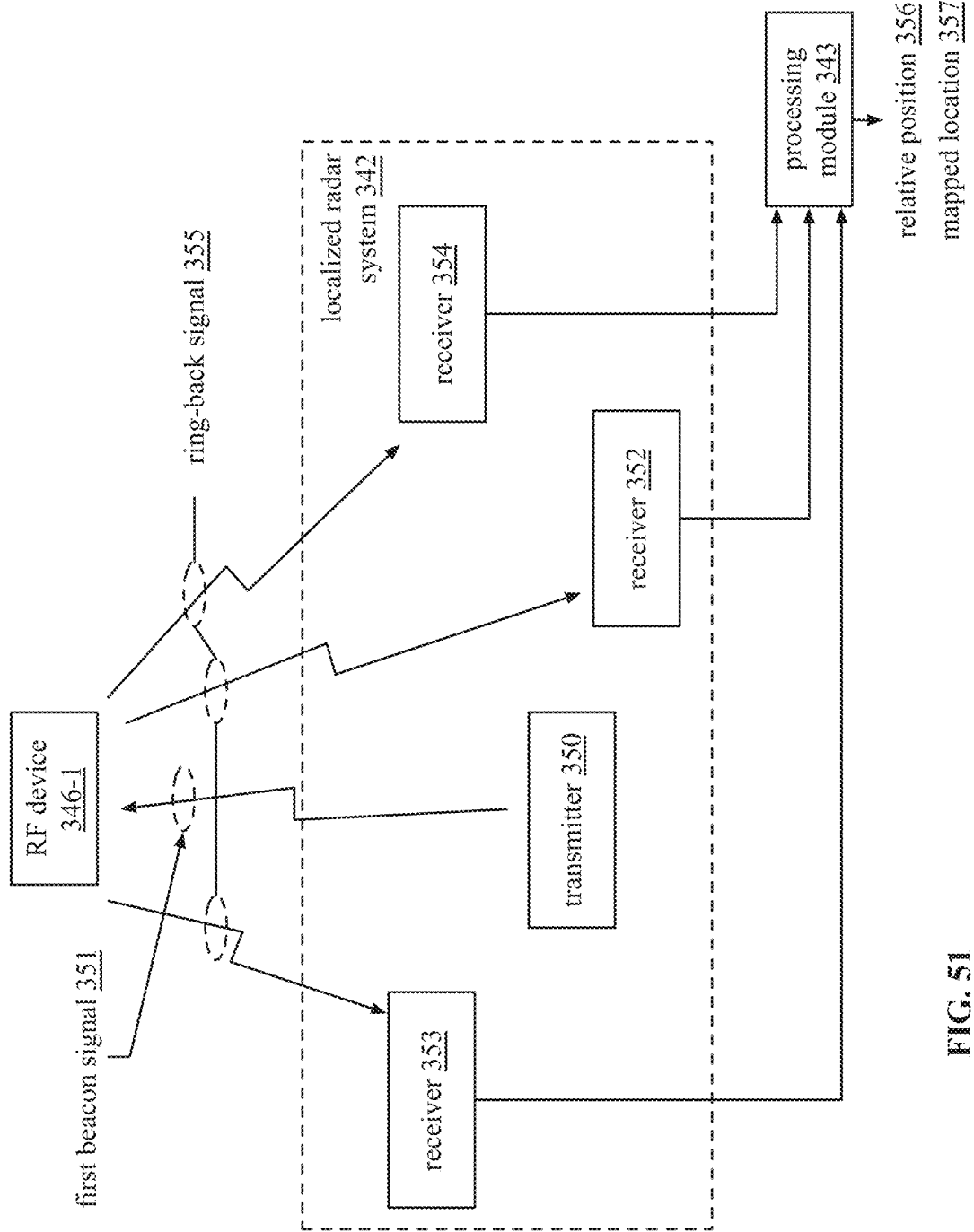

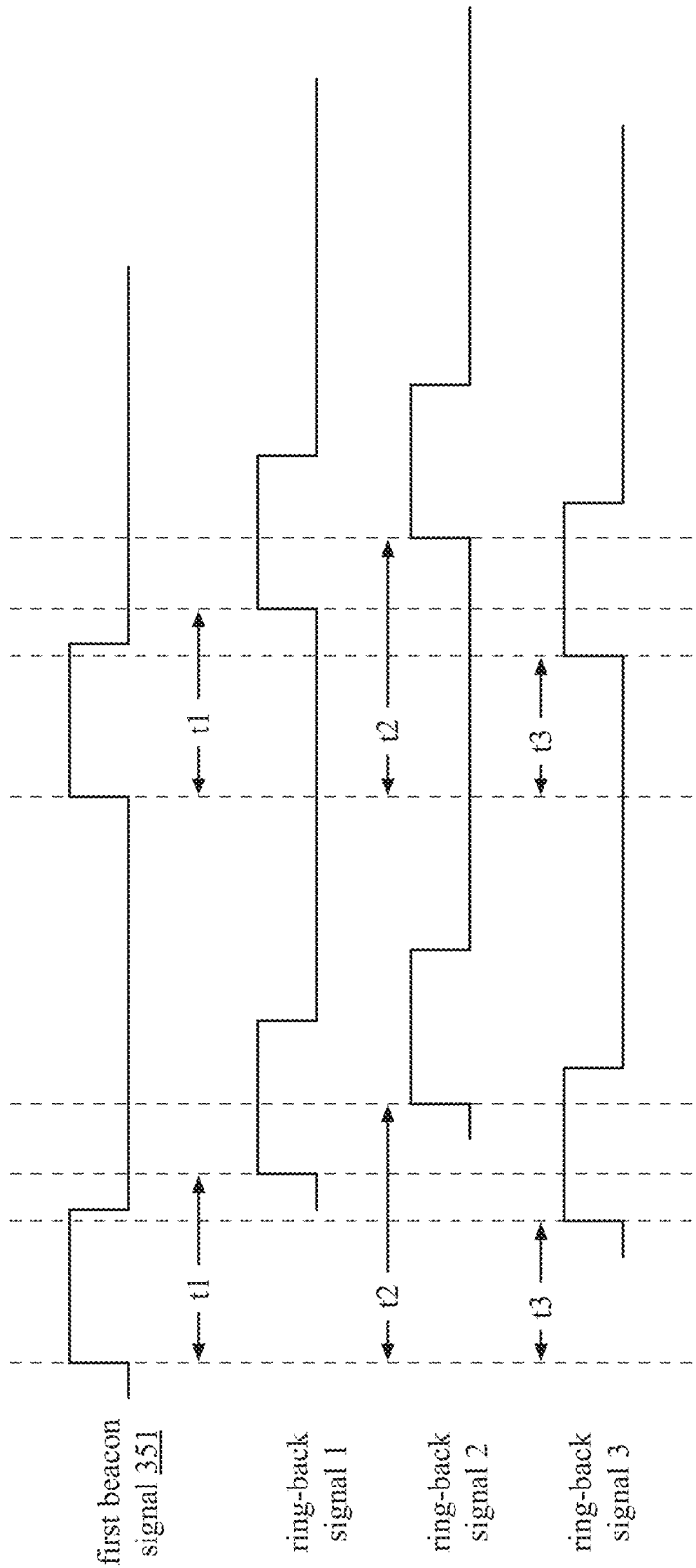

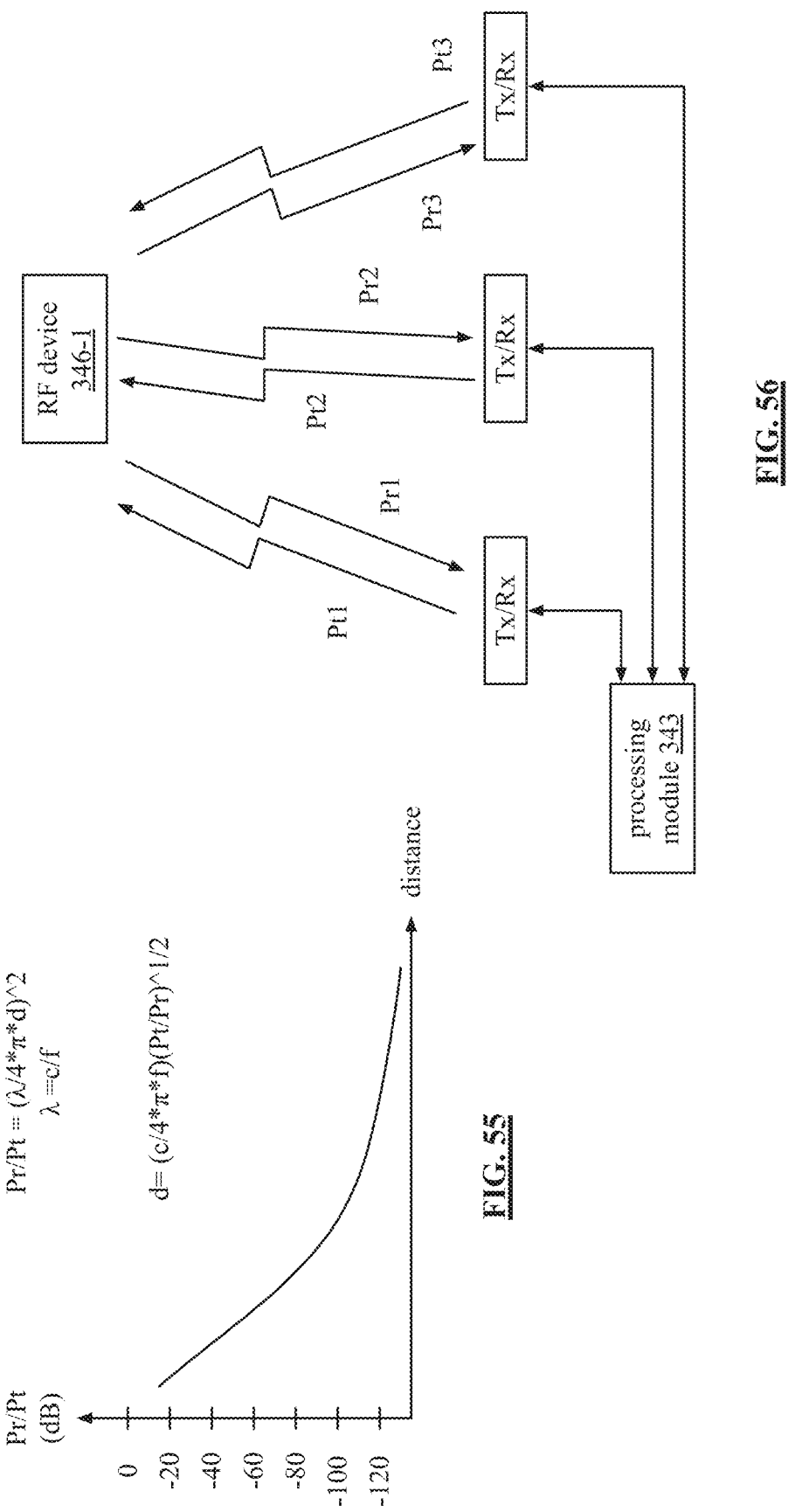

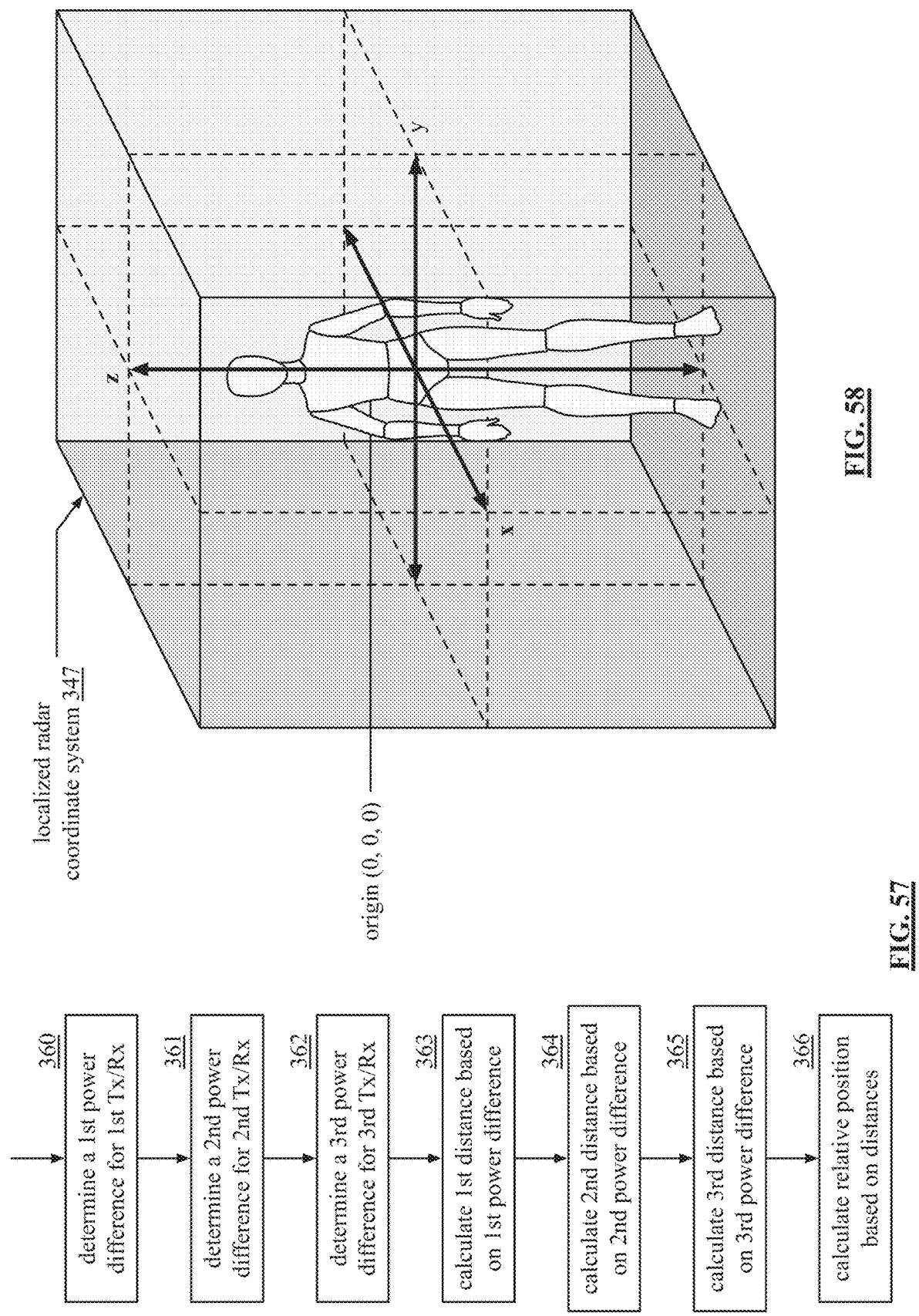

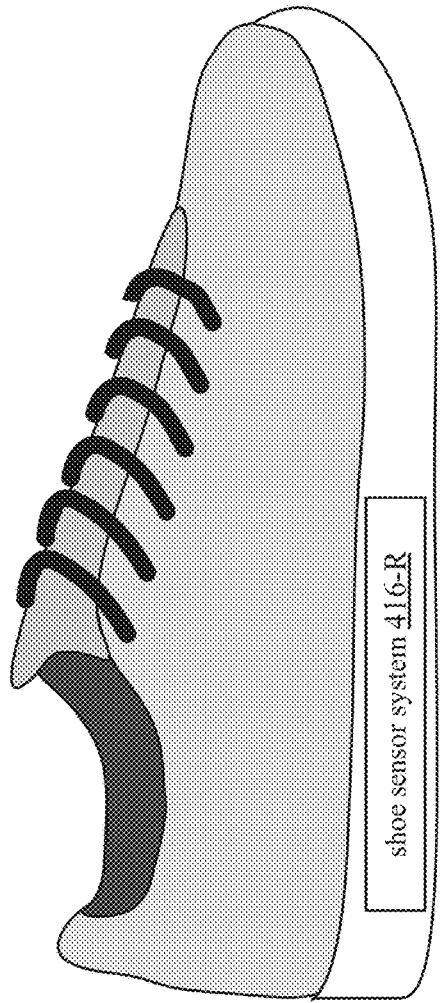
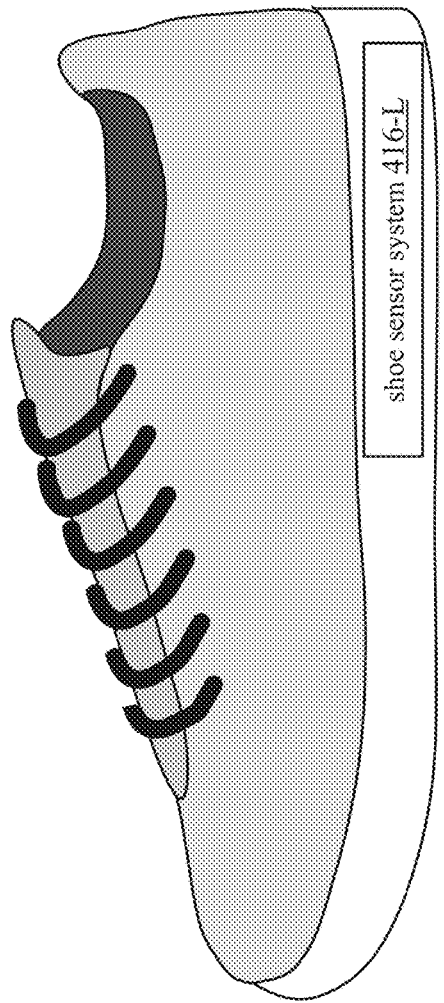
FIG. 66A side view
FIG. 66B side view

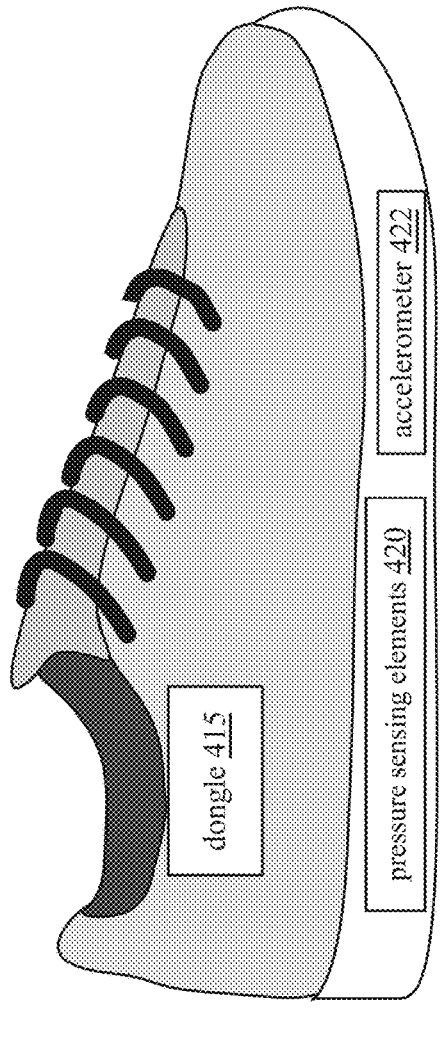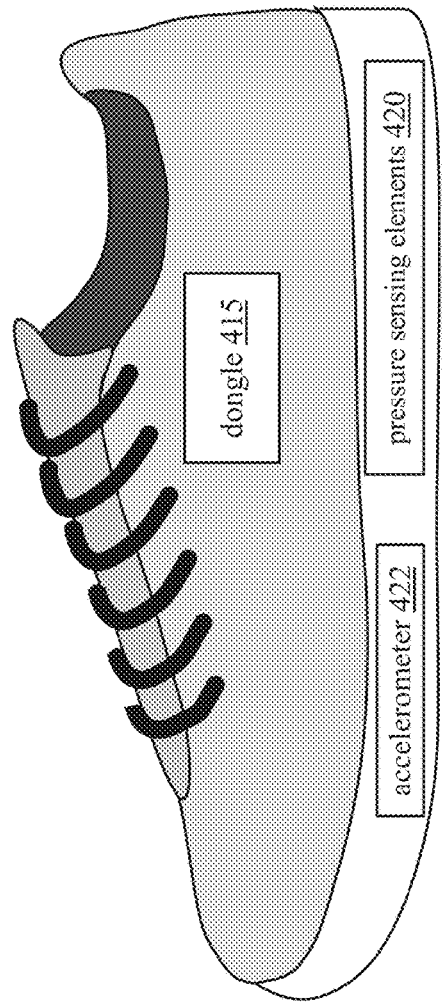

shoe sensor system 416-R & L

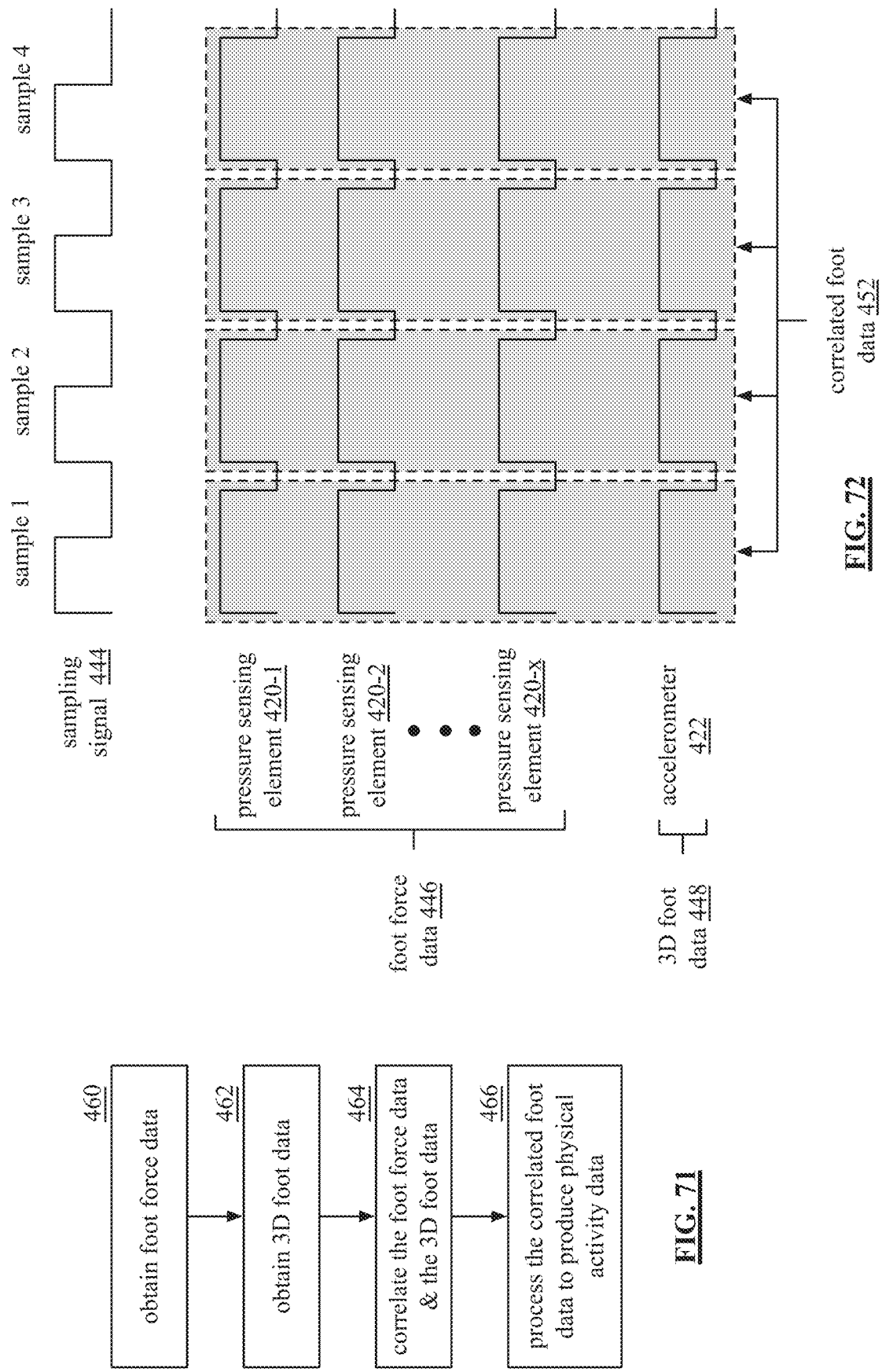

side view of shoe side view of shoe

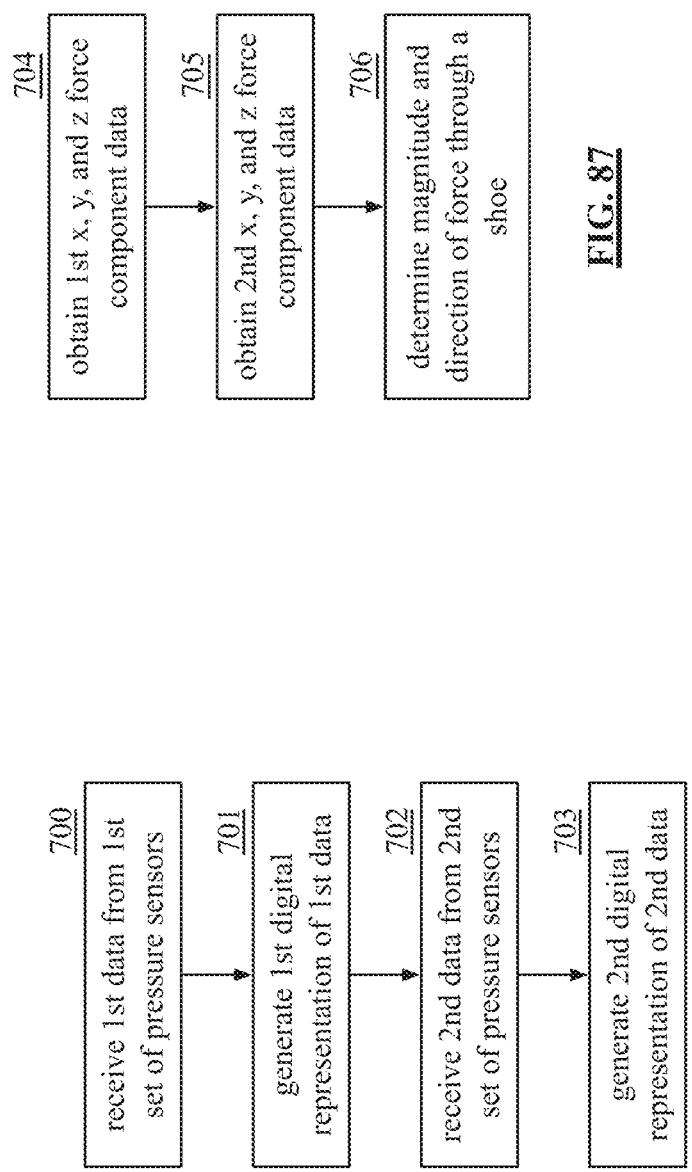

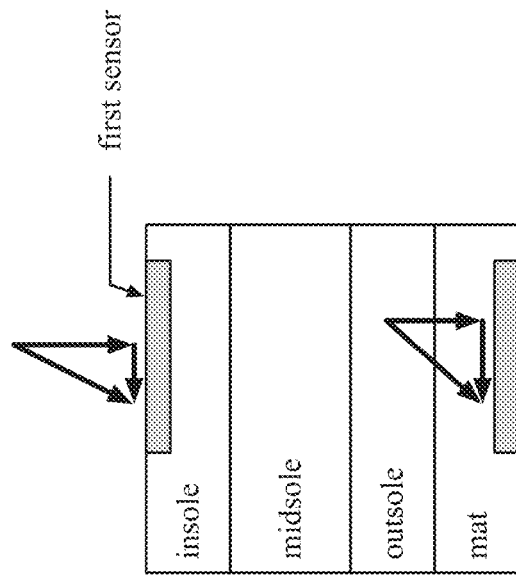
FIG. 89
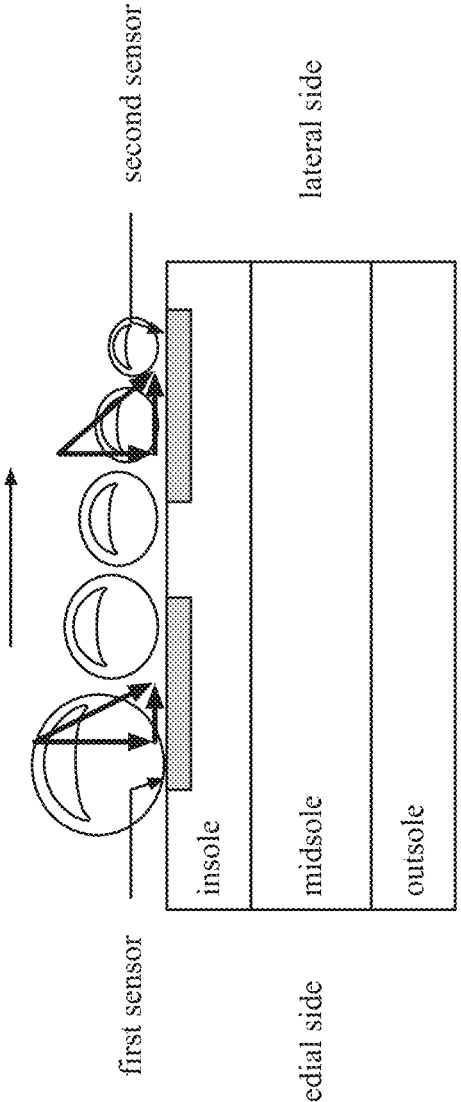
FIG. 88
FIG. 90 shoe sensor system 416-R & L shoe sensor system 416-R & L

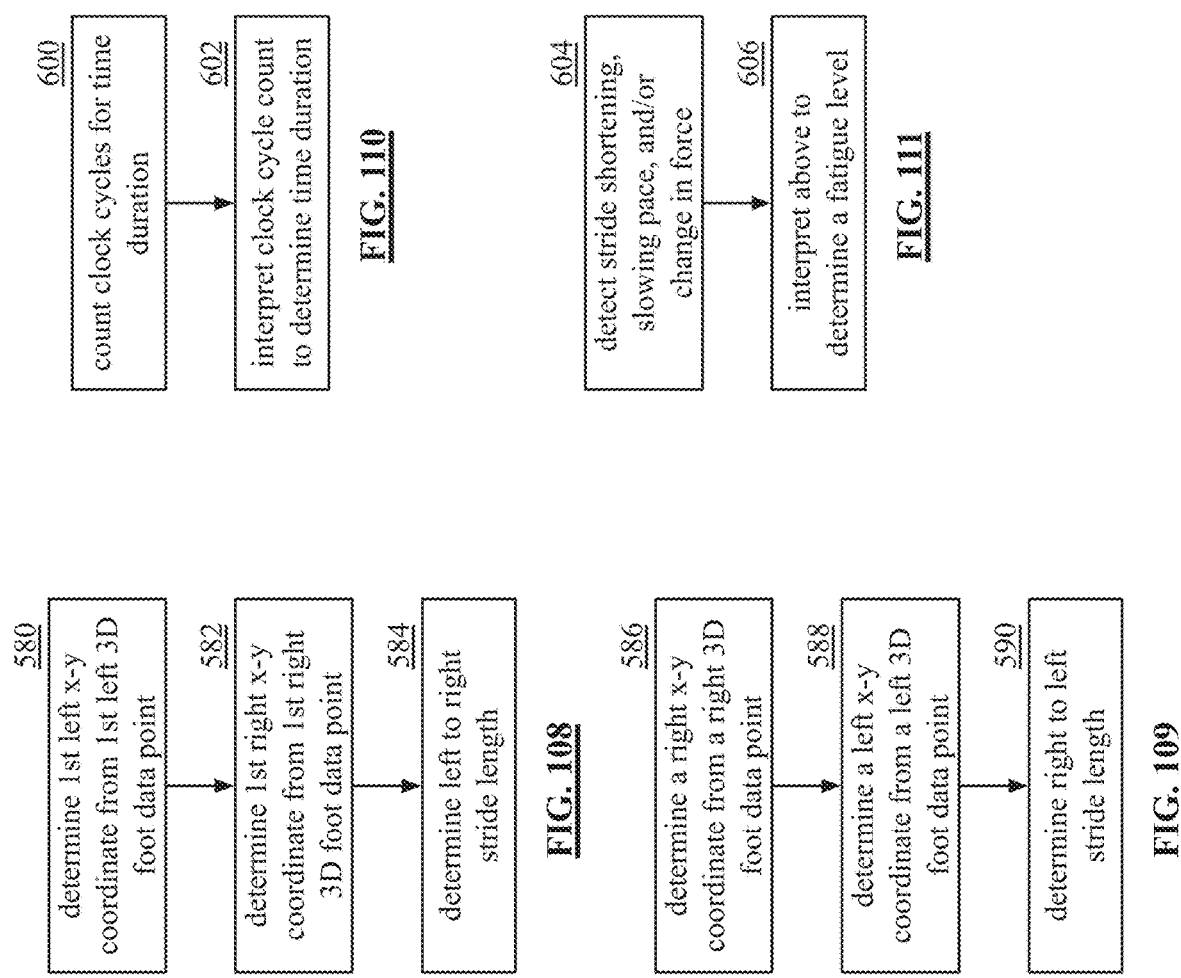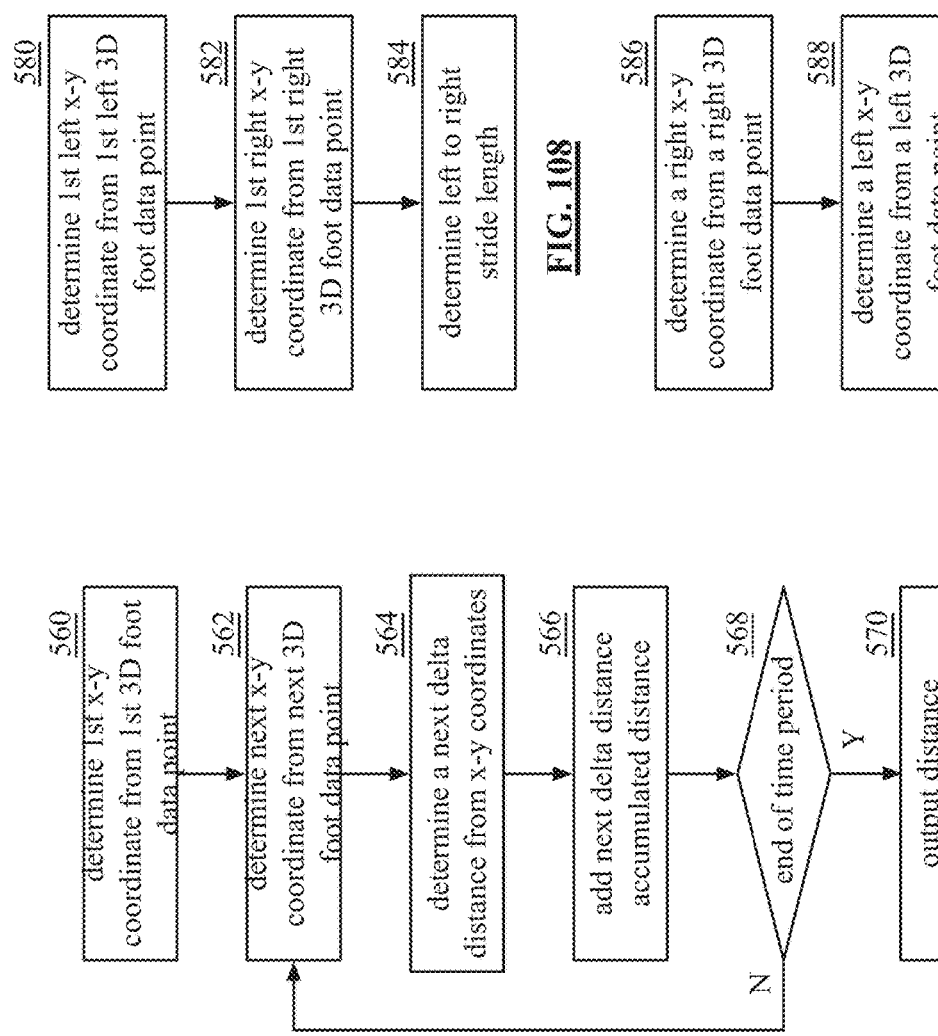

VARIABLE CAPACITIVE FORCE SENSING STRUCTURE

CROSS-REFERENCE TO RELATED APPLICATIONS

The present U.S. Utility patent application claims priority under 35 USC § 120 as a continuation of U.S. Utility patent application Ser. No. 17/649,523, entitled "PLURALITY OF LAYERS OF PRESSURE SENSORS WITHIN A FOOT FORCE DETECTION SYSTEM", filed Jan. 31, 2022, which is a continuation-in-part of U.S. Utility patent application Ser. No. 15/679,831, entitled "WIRELESS IN-SHOE PHYSICAL ACTIVITY MONITORING APPARATUS," filed Aug. 17, 2017, issued as U.S. Pat. No. 11,246,507 on Feb. 15, 2022, which claims priority pursuant to 35 U.S.C. § 119(e) to U.S. Provisional Application No. 62/376,555, entitled "IN-SHOE GROUND REACTIVE FORCE MEASURING SYSTEM," filed Aug. 18, 2016, all of which are hereby incorporated herein by reference in their entirety and made part of the present U.S. Utility patent application for all purposes.

U.S. Utility patent application Ser. No. 17/649,523 also claims priority pursuant to 35 U.S.C. § 120 as a continuation-in-part of U.S. Utility patent application Ser. No. 17/575,594, entitled "INSOLE XYZ FORCE DETECTION SYSTEM," filed Jan. 13, 2022, which claims priority pursuant to 35 U.S.C. § 119(e) to U.S. Provisional Application No. 63/202,251, entitled "INSOLE XYZ FORCE DETECTION SYSTEM," filed Jun. 3, 2021, all of which are hereby incorporated herein by reference in their entirety and made part of the present U.S. Utility patent application for all purposes.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

Technical Field of the Invention

This disclosure relates generally to athletic data gathering and analysis and more particularly to force data.

Description of Related Art

Technology is being used more and more to monitor a person's physical activities, rest patterns, diet, and vital signs. Some of this technology is wearable. For example, there are wrist wearable devices to monitor the number of steps a person takes in a day, the approximate distance traveled, heart rate, and/or sleep patterns. As another example, there are chest straps that communicate wirelessly with a module for monitoring heart rate.

As yet another example, there are shoe insert systems to monitor forces of the foot during walking. One such system includes a flexible circuit board insert that includes a resistive sensor grid that is hard wired to a module that straps to the ankle. The two ankle modules are then hard wired to another module that straps to the waist. The waist module collects the data and communicates it to a computer via a wired or wireless connection.

Another technology for monitoring foot force is to use a pressure sensitive mat on which a person stands to perform a physical activity (e.g., golf). The mat detects variations in foot forces during the execution of the physical activity, which is then analyzed to evaluate the performance of the physical activity.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

FIG. 3 is a schematic block diagram of an embodiment of force detection system that is capable of communicating with a computing device;

FIG. 4A is a schematic block diagram of an embodiment of a drive sense circuit coupled to a variable capacitor and to an ADC;

FIG. 4B is a schematic block diagram of an example of a reference signal;

FIGS. 5E-5I are schematic block diagrams of embodiments of computing entities;

FIGS. 6A-6C are schematic block diagrams of an embodiment of force detection system that includes a layer of variable capacitors, a layer of compression plates, and a circuitry section;

FIGS. 6D-6F are schematic block diagrams of another embodiment of force detection system that includes a layer of variable capacitors, a layer of compression plates, and a circuitry section;

FIGS. 9A-9C are schematic block diagrams of another example of force applied by a foot to the force detection system;

FIGS. 10A-10C are schematic block diagrams of another example of force applied by a foot to the force detection system;

FIGS. 11A-11F are schematic block diagrams of another example of forces applied by a foot to the force detection system when a person is running;

FIGS. 14A-14C are schematic block diagrams of an example of a layer of variable capacitors and a layer of compression plates of a force detection system;

FIGS. 15A-15E are schematic block diagrams of an example of a layer of variable capacitors and a layer of compression plates of a force detection system with and without compression of the capacitors;

FIGS. 16A-16C are schematic block diagrams of examples of a geometric and electrical relationship between variable capacitors of a second layer and a compression plate of a first layer within a force detection system;

FIGS. 20A-20D are schematic block diagrams of another example of determining a normal vector of a reference plane of a cell of a force detection system in response to an impact force;

FIGS. 21A-21D are schematic block diagrams of another example of determining a normal vector of a reference plane of a cell of a force detection system in response to an impact force;

FIGS. 22A-22C are schematic block diagrams of an example of determining a plurality of normal vectors of a plurality of reference planes of a plurality of cells of a force detection system in response to an impact force;

FIGS. 27A-27C are schematic block diagrams of an example of determining a normal vector of a cell of a force detection system in response to an impact force;

FIGS. 32A-32C are schematic block diagrams of another embodiment of force detection system that includes a layer of variable capacitors, a layer of compression plates, and a circuitry section;

FIGS. 33A-33E are schematic block diagrams of an example of a capacitor cell of the force detection system of FIGS. 32A-32C;

FIG. 51 is a schematic block diagram of an example of athlete monitoring;

FIG. 54 is a schematic block diagram of an example of determining athlete relative positioning;

FIG. 55 is a schematic block diagram of another example of determining athlete relative positioning;

FIG. 56 is a schematic block diagram of another example of determining athlete relative positioning;

FIG. 57 is a logic diagram of an example of method for determining athlete positioning;

FIG. 58 is a schematic block diagram of another example of athlete positioning;

FIGS. 66A-66D are side view diagrams of other embodiments of a pair of shoes that each include a shoe sensor system;

FIG. 71 is a logic diagram of an example of a method executed by a processing module;

FIGS. 72-75 are examples of timing and data diagrams of a shoe sensor system;

FIG. 86 is a logic diagram of an example of generating foot force data;

FIG. 87 is a logic diagram of another example of generating foot force data;

FIG. 88 is a schematic block diagram of another example of generating foot force data;

FIG. 89 is a schematic block diagram of another example of generating foot force data;

FIG. 90 is a schematic block diagram of another example of generating foot force data;

FIG. 107 is a logic diagram of another example of a method executed by a shoe sensor system;

FIG. 108 is a logic diagram of another example of a method executed by a shoe sensor system;

FIG. 109 is a logic diagram of another example of a method executed by a shoe sensor system;

FIG. 110 is a logic diagram of another example of a method executed by a shoe sensor system;

FIG. 111 is a logic diagram of another example of a method executed by a shoe sensor system;

FIG. 11B is a logic diagram of another example of a method executed by a shoe sensor system in accordance with the present invention.

DETAILED DESCRIPTION OF THE INVENTION

Figure 1A:
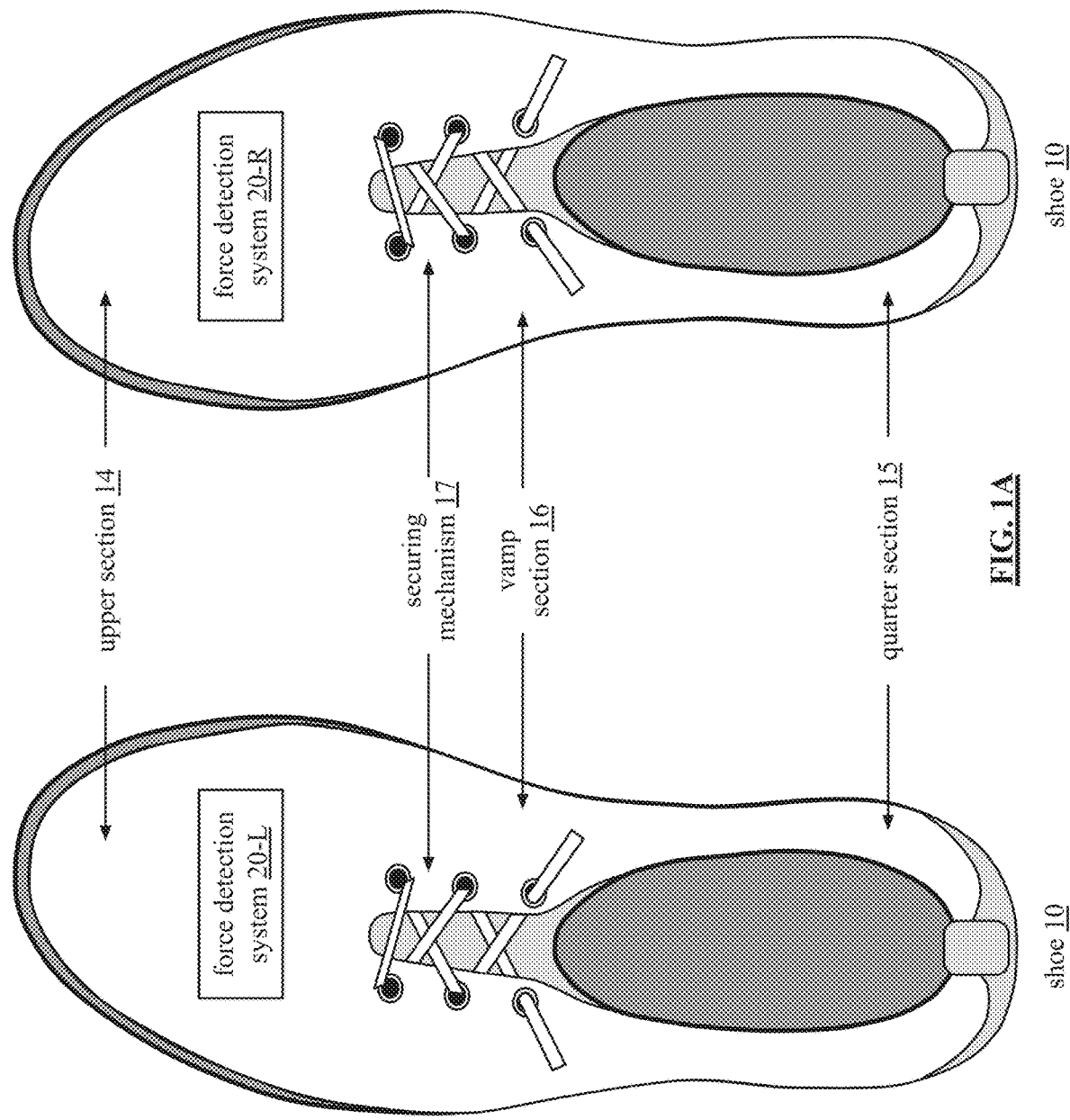
FIG. 1A is a top side view diagram of an embodiment of shoes that include a force detection system.

FIG. 1A is a top side view diagram of an embodiment of shoes 10 that include a force detection system 20. Each shoe includes an upper section 14, a vamp section 16, a quarter section 15, a securing mechanism 17, and at least a portion of the force detection system 20. For example, the left shoe includes a left shoe portion of the force detection system 20-L and the right shoe includes a right shoe portion of the force detection system 20-R.

The upper section 14 includes the vamp section 16, which covers at least a portion of a midfoot area of the shoe, and the quarter section 15, which is the rear portion of the shoe. The vamp section and the quarter section may be constructed from one or more the same materials or one or more of different materials. The materials include, but is not limited to, a leather, a molded plastic, a molded carbon fiber, a polyurethane (PU), a thermoplastic polyurethane (TPU), a faux leather, a PU leather, cloth, etc. In a specific example, the vamp section and the quarter section are constructed of leather. In another specific example, the vamp section is constructed for leather and the quarter section is constructed of a PU leather.

The securing mechanism 17 functions to tighten the shoe 10 around a foot when placed in the shoe 10. The securing mechanism 17 may be implemented in a variety of ways and positioned within the vamp section 16 is a variety of locations. For example, the securing mechanism 17 includes eyelets and a shoelace that is positioned approximately along a center line of the vamp section 16. With respect to FIG. 1A, the center line is approximately along a midline between a medial edge of the shoe and a lateral edge of the shoe running the length of the vamp section 16. In another example, the securing mechanism 17 includes Velcro™ straps. In another embodiment, the securing mechanism 17 includes a Boa™ structure.

The force detection system 20 is included in one or both shoes. In general, the force detection system 20 provides X, Y, and/or Z force data of a foot within the shoe with respect to the ground. The force data can be used to evaluate human movement, which includes athletic movement. For a body to move, it applies a force on the ground and the ground pushes back with an equal and opposite force. The ground pushing back is called ground reaction force, which traverses through the shoes.

The direction and magnitude of ground reaction force effect human movement, especially athletic movements. Performance of almost every athletic movement is improved by increasing power and/or increasing consistency. Power is a function of energy divided by time. Energy is a function of force excreted over a distance. Thus, power is a function of force exerted over a distance in a given time frame. As such, power is increased by increasing the force, increasing the distance, and/or reducing the time frame.

For an athletic movement, the force is ground reaction force. As such, an athlete's power is a function of the ground reaction force being used to move the body, and may further includes moving an object (e.g., a club, a bat, a ball, a racket, etc.), over a distance in a given time frame. Thus, improving ground reaction force for the same distance and time of movement, improves an athlete's power. Accordingly, determining the magnitude of ground reaction force during an athletic movement is an important data point for improving athletic performance.

In athletics, consistency involves being able to move the body in a nearly identical matter time after time. The direction of the ground reaction force effects an athlete's consistency. Ideally, an athlete wants the direction of the ground reaction force to be parallel to the line of the legs. In the ideal case, there is no wasted force, all of it is going into the body. It also keeps the body in the properly alignment for the athletic movement (e.g., a golf swing).

The more the direction of the ground reaction force deviates from parallel to the leg, the more of it is wasted and the more the athlete has to compensate for the deviation. Having to compensate for ground reaction force's angle deviation adds an extra element to the athletic movement, which too must be executed nearly identical time after time to achieve the desired athletic consistency. Thus, determining the direction of ground reaction force during an athletic movement is an important data point for improving athletic performance.

Commercially available foot force systems suffer from one or more of the following. (a) Due to the bulk of the system, it cannot be used in game or in practice. It has to be used in a lab setting. (b) The force sensors break down too quickly for elite athletes. When an athlete jumps, they can have a landing impact of six times their body weight. For a professional football player that weighs over three hundred pounds, that is a landing force per jump of almost one ton. Most sensors are design for a walking impact of about two times the body weight, hence they fail quickly when used by elite athletes. (c) The batteries of a system need to be recharged too frequently. Most athletes, especially at the elite level, will not recharge the batteries on a regular basis (e.g., daily, every other day, multiple times per day, etc.). (d) The system only provides Z force information; there is no angular information, only magnitude information in the Z direction. (e) The system has a low sampling rate (e.g., a few hundred Hertz), thus high-speed data is often missed or incomplete. For example, the foot strike of a sprinter happens in 10's of milliseconds; with a 200 Hertz sampling rate, that is one sample per 5 milliseconds, thus, very few samples will be captured for each foot strike, which will miss the granularity and force transition of a foot strike.

The force detection system 20 is a force system that can be used in game and/or in practice. A capacitor-based sensor array allows for hundreds to thousands of hours of reliable use. The force detection system is ultra-low power such that the batteries can be charged infrequently. The force detection system provides X, Y, and Z force data such that direction and magnitude of ground reaction force can be determined and evaluating with respect to athletic performance. The force detection system is capable of sampling data in the thousands to tens of thousands of Hertz so a significant number of data points is obtained for each foot strike.

Figure 1B:
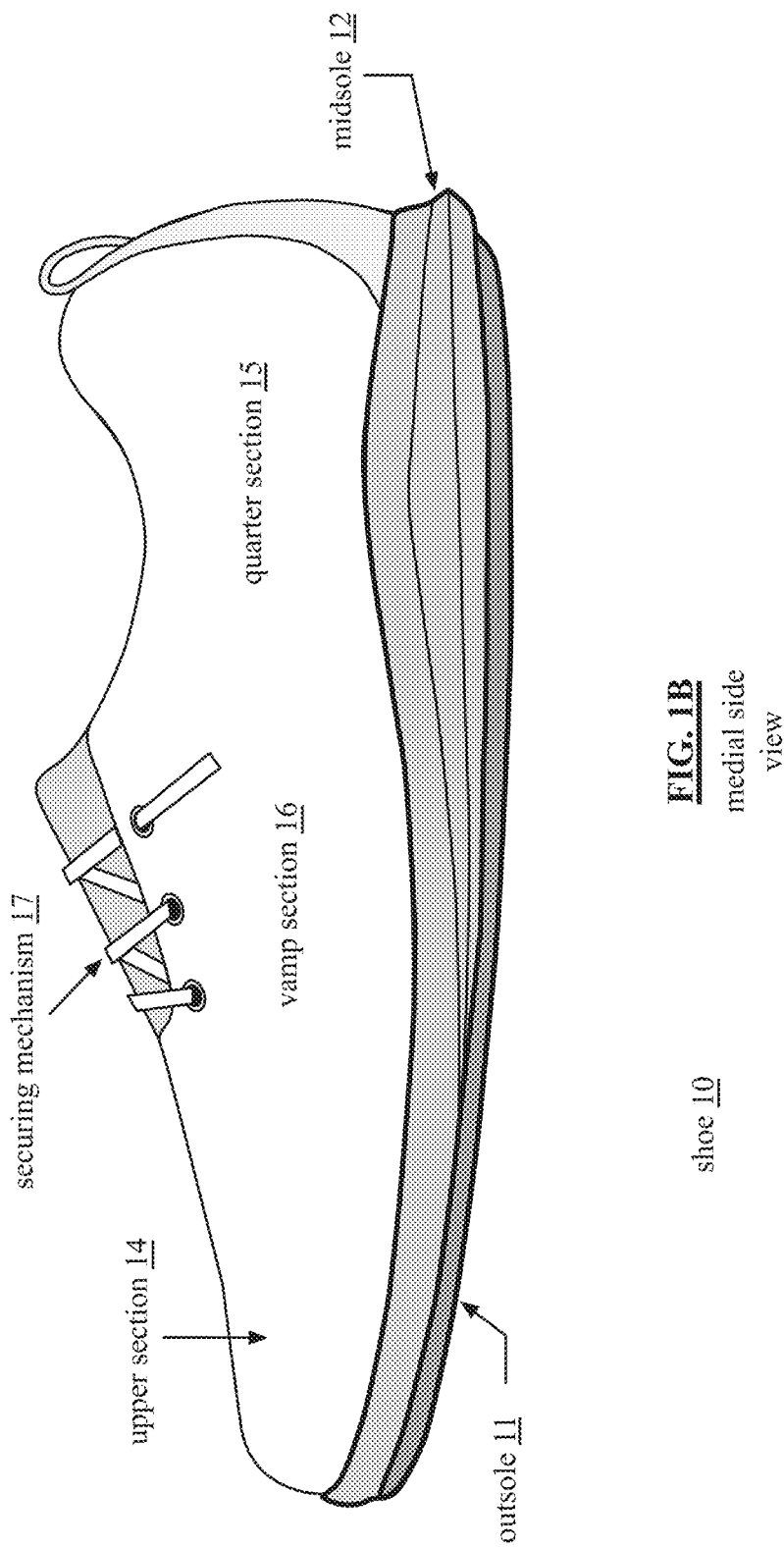
FIG. 1B is a medial side view diagram of an embodiment of a shoe of FIG. 1A.

FIG. 1B is a medial side view diagram of an embodiment of a shoe 10 of FIG. 1A. In this view, the shoe 10 is further shown to include a midsole 12 and an outsole 11. The midsole 12 is constructed of one or more materials that include, but is not limited to, Ethylene-vinyl acetate (EVA), poly (ethylene-vinyl acetate) (PEVA), rubber, carbon fiber, cork, etc.

The outsole 11 is constructed of one or more materials that include, but is not limited to, rubber, EVA, PEVA, TPU, carbon fiber, plastic, etc. For an athletic shoe, the outsole 11 includes a tread pattern for a particular sport. For example, the tread pattern for a baseball shoe includes plastic and/or metal cleats arranged to provide traction for running, throwing, hitting, and/or fielding in grass, in dirt, and/or on artificial surface. As another example, a training shoe will have a tread pattern for weightlifting, cardio activities, etc. that occur on a gym floor (e.g., wood, concrete, carpet, etc.).

Figure 2:
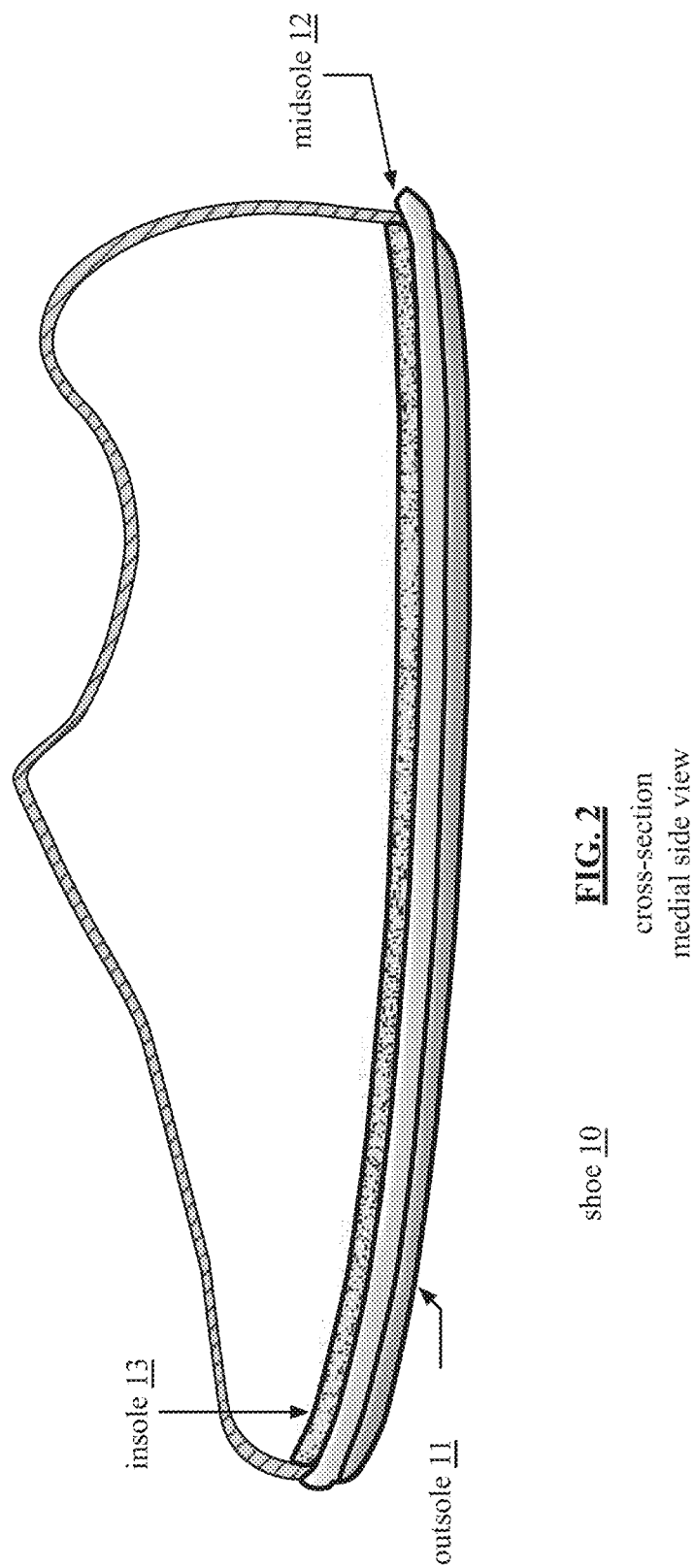
FIG. 2 is a schematic block diagram of a cross-section an embodiment of a shoe including a force detection system.

FIG. 2 is a schematic block diagram of a cross-section an embodiment of a shoe 10. As shown, the sole of the shoe 10 includes the outsole 11, the midsole 12, and/or an insole 13. The force detection system 20, or portion thereof, may be housed in the insole, the midsole, and/or the outsole. For example, pressure sensors are housed in the insole and the circuitry is housed in the midsole.

FIG. 3 is a schematic block diagram of an embodiment of force detection system 20, 20-L, and/or 20-R that is capable of communicating with a computing entity 35. A computing entity 35 includes one or more computing devices 40 as shown in one or more of FIGS. 5E through SI. The computing device 40 is implemented as shown in one or more of FIGS. 5A through 5F.

The force detection system 20 includes capacitor sensors 21, a drive sense module 22, digital filtering circuit 23, memory 24, a clock circuit 25, a controller 26, a communication circuit 27, and a power source 28. The capacitor sensors 21 are positioned within the shoe to sense pressure between a foot and the ground through the shoe. A force detection system 20 may include a few capacitor sensors per shoe to scores of capacitor sensors per shoe. Various embodiments of the capacitor sensors and their positioning are discussed with reference to one or more of FIGS. 12-31, 33, and 34.

The drive sense module 22 includes a plurality of drive sense circuits, where a drive sense circuit is coupled to one or more capacitor sensors 21 (e.g., variable capacitors). The drive sense circuit 22 provides power to a capacitor sensor and senses capacitance changes of the sensor 21 due to pressure applied on the capacitor. An embodiment of the drive sense circuit 22 is described in greater detail with reference to FIG. 4A.

The digital filtering circuit 23, which may be implemented by a processing module, converts digital signals it receives from a drive sense circuit 22 into a digital value that is representative of a characteristic of the variable capacitor (e.g., impedance, capacitance, impedance change, capacitance change, etc.). The digital filtering circuit 23 provides a digital value per sampling of the capacitor sensor 21 to the memory 24 for storage therein.

The memory 24 includes volatile and/or non-volatile memory. The memory also stores operational instructions to enable the system 20 to sense and store data. The operational instructions may further include an instruction set regarding the processing of stored capacitance data to produce force data. Examples of converting capacitance data into force data will described with reference to one or more of the subsequent figures.

The controller 26, which, in an embodiment, is implemented via a processing module as defined herein, coordinates the operation of the force detection system 20. For example, the controller executes the operational instructions that enable operation of the system. In addition, the controller 26 enables the clock circuit 25 to generate a sampling clock, a real-time clock, and digital clock.

The sampling clock includes a crystal oscillator, or the like, to provide a reference clock and further includes one or more phased locked loops (PLL) to generate the desired clock signals. For example, the clock circuit generates the sampling clock to establish a rate for sampling the capacitor sensors. The sampling rate may equal the sampling clock, it may be a multiple of the sampling clock, or a fraction of the sampling clock.

The digital clock is used by the controller 26 and memory 24. Depending on the amount of data to be stored and/or processed, the digital clock can be set at a few MHz or hundreds of MHz or higher. It can also be adjustable to balance power consumption with data storage and/or data processing efficiency.

The controller uses the real-time clock to timestamp the data being stored in memory. The real time clock is synced with a reference real time clock so that the foot force data and can time aligned with a recording of body movements.

The controller 26 instructs the communication circuit 27 to output stored data from the memory 24 to the computing entity. The communication circuit 27 is a wired and/or wireless transceiver. For example, a wired communication circuit 27 is an $I^2C$ (inter integrated circuit) communication unit, an SPI (serial peripheral interface) communication unit, a CAN (controller area network) communication unit, a USB (universal serial bus) communication unit, a UART (universal asynchronous receiver/transmitter) communication unit, an IEEE 1394 communication unit, etc. As another example, a wireless communication circuit 27 is a Bluetooth communication unit, a wireless local area network communication unit, a Zigbee communication unit, a Z-wave communication unit, a low power wireless personal area network, a radio frequency identification (RFID) communication unit, a near field communication unit, etc.

The power source 28 includes one or more batteries and provides power to the other components of the system 20. The power source 28 may further include a power supply, a battery charger, a power harvesting circuit, and/or a power management module. The power supply functions to convert the battery voltage into one or more DC voltages ranging from 0.5 volts to 5 volts or more. The power supply may be implemented in a variety of ways. As an example, the power supply is a linear regulator. As another example, the power supply is a buck power supply. As another example, the power supply is a boost power supply.

The power harvesting circuit may be implemented in a variety of ways and may include a variety of implementations. In an example, the power harvesting circuit functions to generate a DC voltage from one or more radio frequency (RF) signals, such as a cell phone signal, a Bluetooth signal, an RFID signal, etc. In another example, the power harvesting circuit functions to generate a DC voltage from compression of a piezoelectric material in the shoe and the wearer applies force on the shoe. In another example, the power harvesting circuit functions to generate a DC voltage from heat of the wearer.

FIG. 4A is a schematic block diagram of an embodiment of a drive sense circuit 22 coupled to a variable capacitor 21-1 of the capacitive sensors 21. The drive sense circuit (DSC) 22 includes an operational amplifier (op amp) 30, a feedback circuit 31, a dependent current source, and an analog-to-digital converter (ADC) 35. The op amp 30 receives a reference signal 29, which as shown in FIG. 4B, includes a DC component 33 and an oscillating component 34.

The magnitude and frequency of the oscillating component 34 vary depending on the desired resolution of sensing capacitance differences and on achieving minimal power consumption. For example, since power equals voltage times current, minimal voltage and minimal current are needed for minimal power consumption. Voltage is tied to the granularity of sensing capacitance change and current is tied to the impedance of the capacitor and the voltage. With high signal-to-noise (SRN) of the drive sense circuit and subsequent filtering, micro-voltages of change can be detected. To have a current in the micro-amps, the frequency of the oscillating component is determined to provide an impedance of the capacitor that produces a micro-volt scale change from a micro-amp scale current source.

Returning to FIG. 4A, the op amp 30 ideally functions to force the voltages on its inputs to be the same. Thus, the voltage on the input coupled to the variable capacitor 21-1 is the same as the voltage of the reference signal 29. Since no current flows into an op amp 30, the current produced by dependent current source 32 flows into the variable capacitor 21-1. As the impedance of the variable capacitor changes, the dependent current source 32, based on a signal from the feedback circuit 31, produces a varying current to keep the voltage of the variable capacitor matching that of the reference signal 29.

The feedback circuit 31, which includes one or more components to provide a loop gain of unit to open loop, scales the output of the op amp 30 to provide the control signal to the dependent current source 32. The output of the op amp 30 is a voltage that represents the impedance of the variable capacitor 21-1 and changes of the impedance. With the force detection system 20, the variable capacitor changes it capacitance based on pressure. In an embodiment, as pressure on the capacitor increases, its capacitance increases (e.g., plates get closer together and/or dielectric changes), which decreases the capacitor's impedance. In another embodiment, as pressure on the capacitor decreases, its capacitance decreases (e.g., plates get further apart and/or dielectric changes), which increases the capacitor's impedance.

The analog to digital converter (ADC) 23 converts the output of the op amp 30 into unfiltered digital values. For a sigma delta ADC, the digital values are a stream of one-bit digital values. The digital filtering circuit 23, which, in an embodiment, includes a bandpass filter and a decimation filter, converts the stream of one-bit digital values into digital words at a desired sampling rate. The digital words are stored in the memory 24.

Figure 5A:
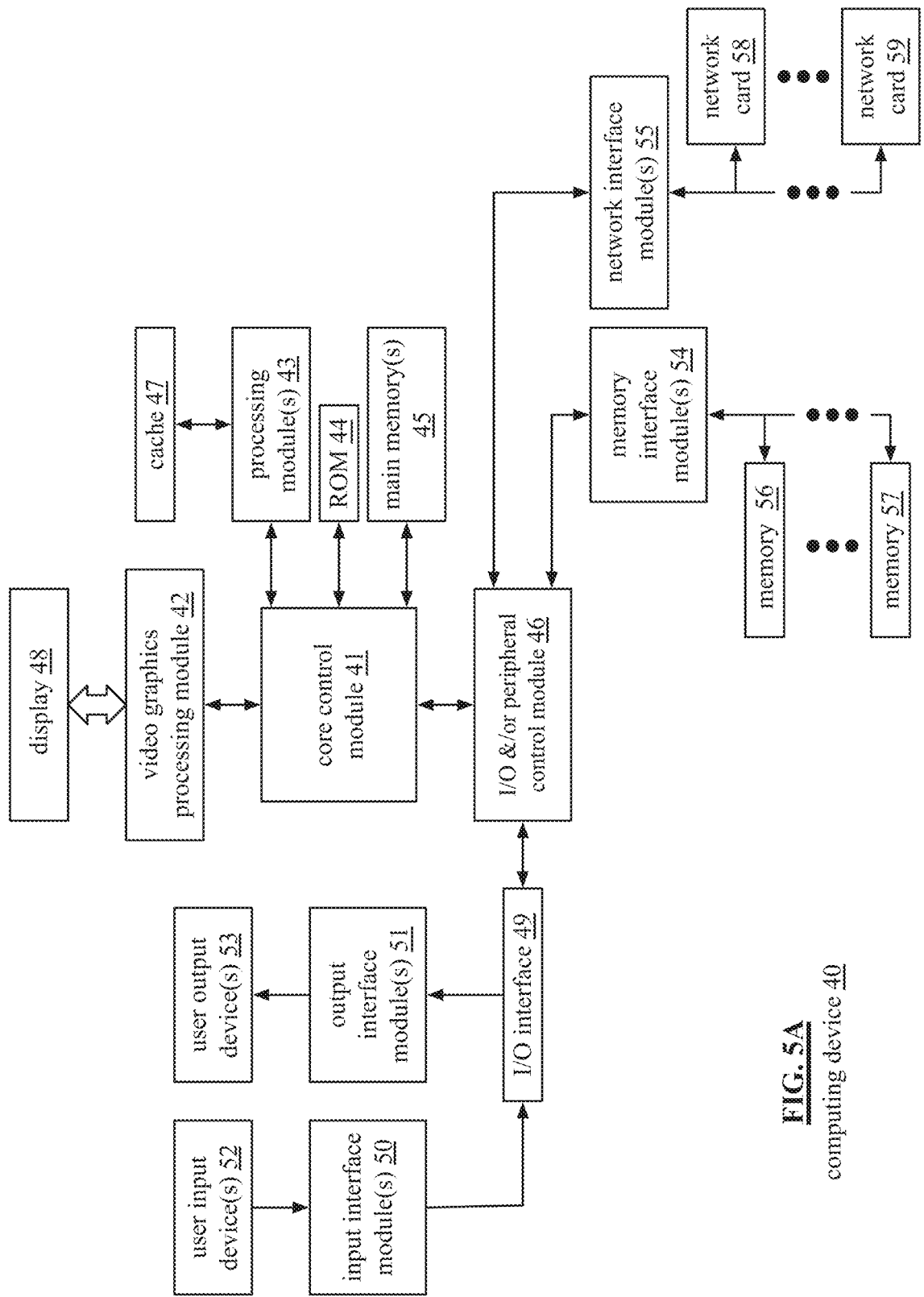
FIGS. 5A-5D are schematic block diagrams of embodiments of computing devices.

FIG. 5A is a schematic block diagram of an embodiment of a computing device 40 that includes a plurality of computing resources. The computing resource include a core control module 41, one or more processing modules 43, one or more main memories 45, a read only memory (ROM) 44 for a boot up sequence, cache memory 47, a video graphics processing module 42, a display 48 (optional), an Input-Output (I/O) peripheral control module 46, an I/O interface module 49 (which could be omitted), one or more input interface modules 50, one or more output interface modules 51, one or more network interface modules 55, and one or more memory interface modules 54. A processing module 43 is described in greater detail at the end of the detailed description section and, in an alternative embodiment, has a direction connection to the main memory 45. In an alternate embodiment, the core control module 41 and the I/O and/or peripheral control module 46 are one module, such as a chipset, a quick path interconnect (QPI), and/or an ultra-path interconnect (UPI).

Each of the main memories 45 includes one or more Random Access Memory (RAM) integrated circuits, or chips. For example, a main memory 45 includes four DDR4 ($4^{th}$ generation of double data rate) RAM chips, each running at a rate of 2,400 MHz. In general, the main memory 45 stores data and operational instructions most relevant for the processing module 43. For example, the core control module 41 coordinates the transfer of data and/or operational instructions between the main memory 45 and the memory 56-57. The data and/or operational instructions retrieve from memory 56-57 are the data and/or operational instructions requested by the processing module or will most likely be needed by the processing module. When the processing module is done with the data and/or operational instructions in main memory, the core control module 41 coordinates sending updated data to the memory 56-57 for storage.

The memory 56-57 includes one or more hard drives, one or more solid state memory chips, and/or one or more other large capacity storage devices that, in comparison to cache memory and main memory devices, is/are relatively inexpensive with respect to cost per amount of data stored. The memory 56-57 is coupled to the core control module 41 via the I/O and/or peripheral control module 46 and via one or more memory interface modules 54. In an embodiment, the I/O and/or peripheral control module 46 includes one or more Peripheral Component Interface (PCI) buses to which peripheral components connect to the core control module 41. A memory interface module 54 includes a software driver and a hardware connector for coupling a memory device to the I/O and/or peripheral control module 46. For example, a memory interface 54 is in accordance with a Serial Advanced Technology Attachment (SATA) port.

The core control module 41 coordinates data communications between the processing module(s) 43 and the network(s) 14 via the I/O and/or peripheral control module 46, the network interface module(s) 55, and a network card 58 or 59. A network card 58 or 59 includes a wireless communication unit or a wired communication unit. A wireless communication unit includes a wireless local area network (WLAN) communication device, a cellular communication device, a Bluetooth device, and/or a ZigBee communication device. A wired communication unit includes a Gigabit LAN connection, a Firewire connection, and/or a proprietary computer wired connection. A network interface module 55 includes a software driver and a hardware connector for coupling the network card to the I/O and/or peripheral control module 46. For example, the network interface module 55 is in accordance with one or more versions of IEEE 802.11, cellular telephone protocols, 10/100/1000 Gigabit LAN protocols, etc.

The core control module 41 coordinates data communications between the processing module(s) 43 and input device(s) 52 via the input interface module(s) 50, the I/O interface 49, and the I/O and/or peripheral control module 46. An input device 52 includes a keypad, a keyboard, control switches, a touchpad, a microphone, a camera, etc. An input interface module 50 includes a software driver and a hardware connector for coupling an input device to the I/O and/or peripheral control module 46. In an embodiment, an input interface module 50 is in accordance with one or more Universal Serial Bus (USB) protocols.

The core control module 41 coordinates data communications between the processing module(s) 43 and output device(s) 53 via the output interface module(s) 51 and the I/O and/or peripheral control module 46. An output device 53 includes a speaker, auxiliary memory, headphones, etc. An output interface module 51 includes a software driver and a hardware connector for coupling an output device to the I/O and/or peripheral control module 46. In an embodiment, an output interface module 46 is in accordance with one or more audio codec protocols.

The processing module 43 communicates directly with a video graphics processing module 42 to display data on the display 48. The display 48 includes an LED (light emitting diode) display, an LCD (liquid crystal display), and/or other type of display technology. The display has a resolution, an aspect ratio, and other features that affect the quality of the display. The video graphics processing module 42 receives data from the processing module 43, processes the data to produce rendered data in accordance with the characteristics of the display, and provides the rendered data to the display 48.

Figure 5B:
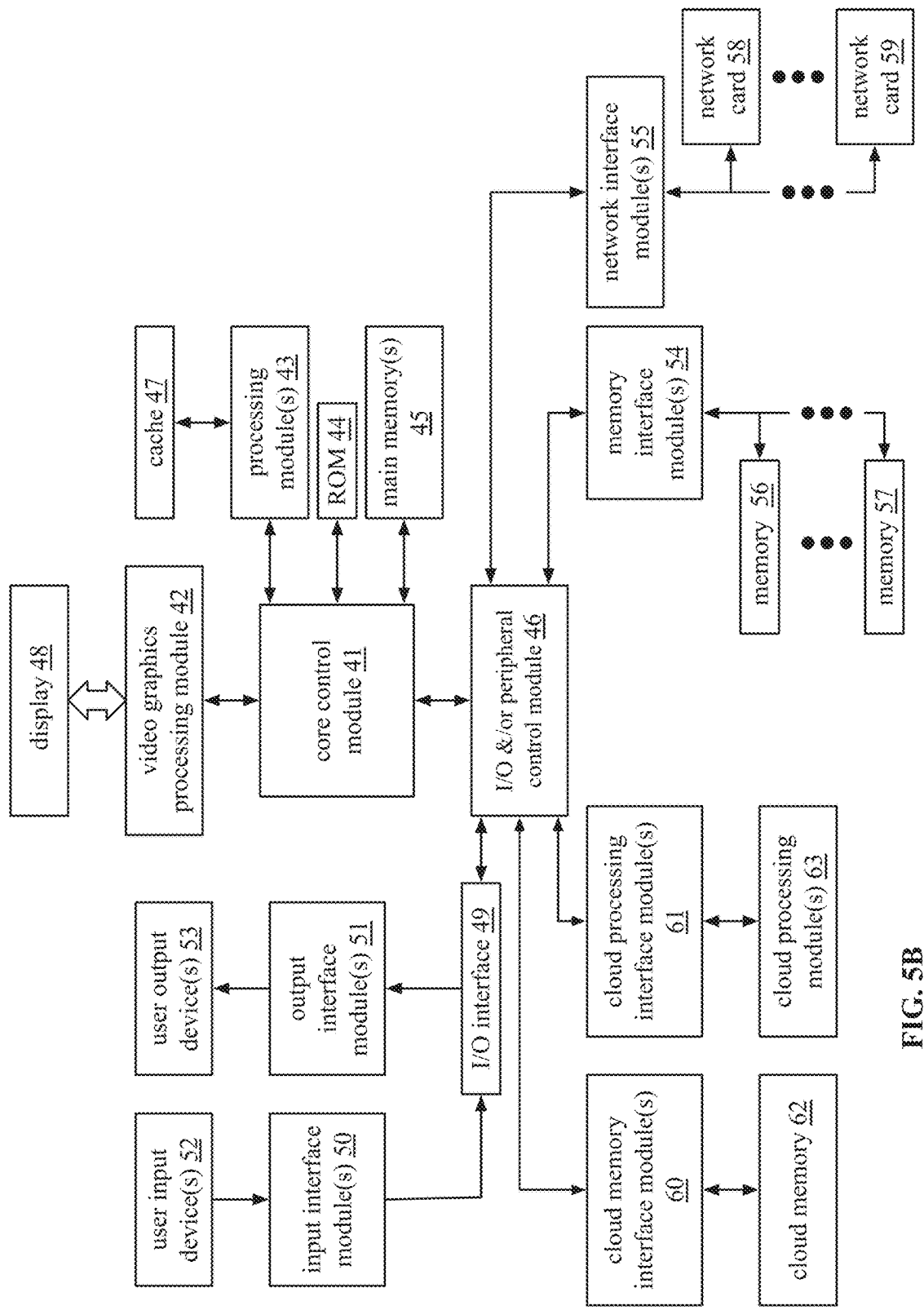

FIG. 5B is a schematic block diagram of an embodiment of a computing device 40 that includes a plurality of computing resources similar to the computing resources of FIG. 2A with the addition of one or more cloud memory interface modules 60, one or more cloud processing interface modules 61, cloud memory 62, and one or more cloud processing modules 63. The cloud memory 62 includes one or more tiers of memory (e.g., ROM, volatile (RAM, main, etc.), non-volatile (hard drive, solid-state, etc.) and/or backup (hard drive, tape, etc.)) that is remoted from the core control module and is accessed via a network (WAN and/or LAN). The cloud processing module 63 is similar to processing module 43 but is remoted from the core control module and is accessed via a network.

Figure 5C:
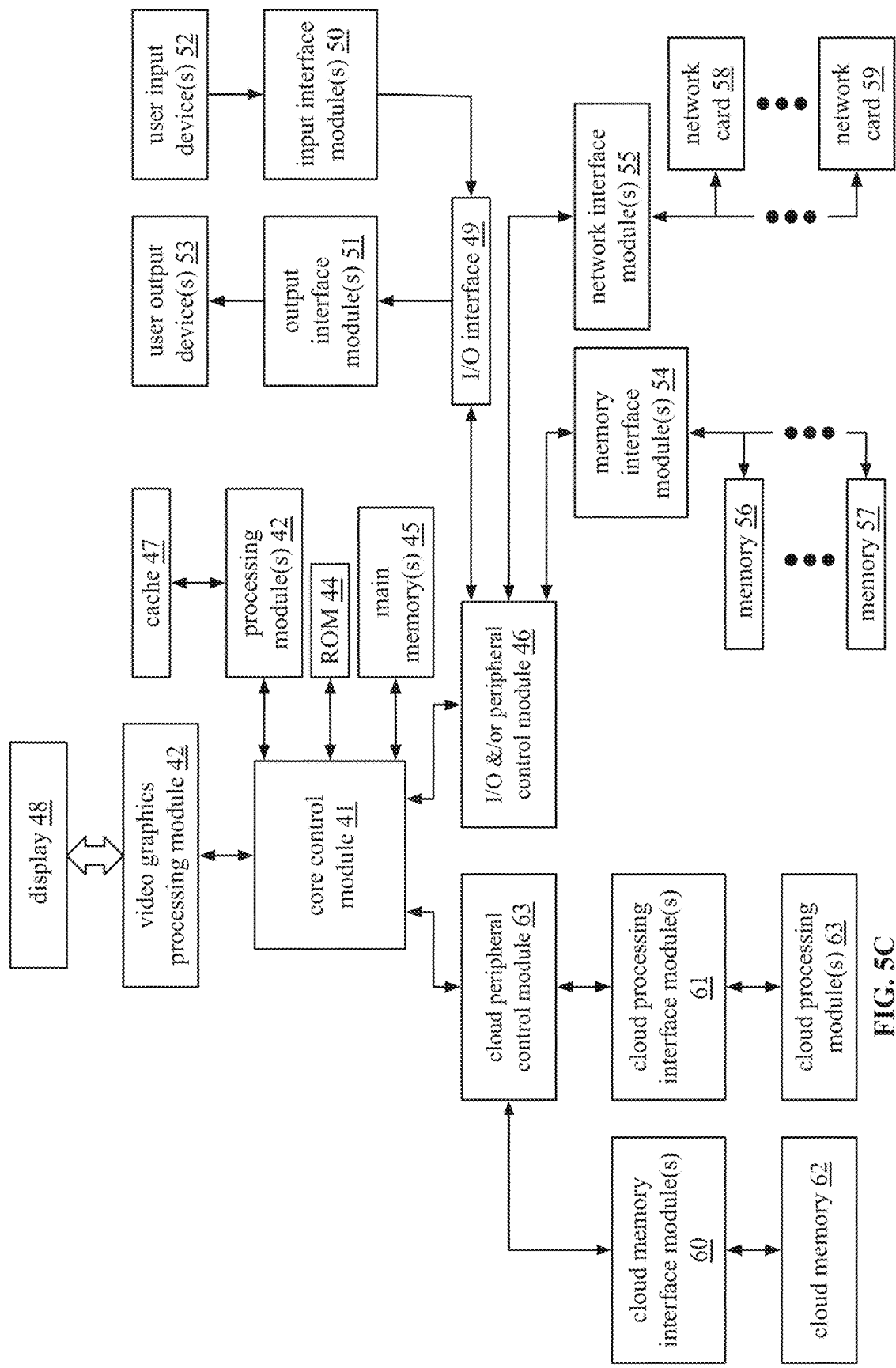

FIG. 5C is a schematic block diagram of an embodiment of a computing device 40 that includes a plurality of computing resources similar to the computing resources of FIG. 2B with a change in how the cloud memory interface module(s) 60 and the cloud processing interface module(s) 61 are coupled to the core control module 41. In this embodiment, the interface modules 60 and 61 are coupled to a cloud peripheral control module 63 that directly couples to the core control module 41.

Figure 5D:
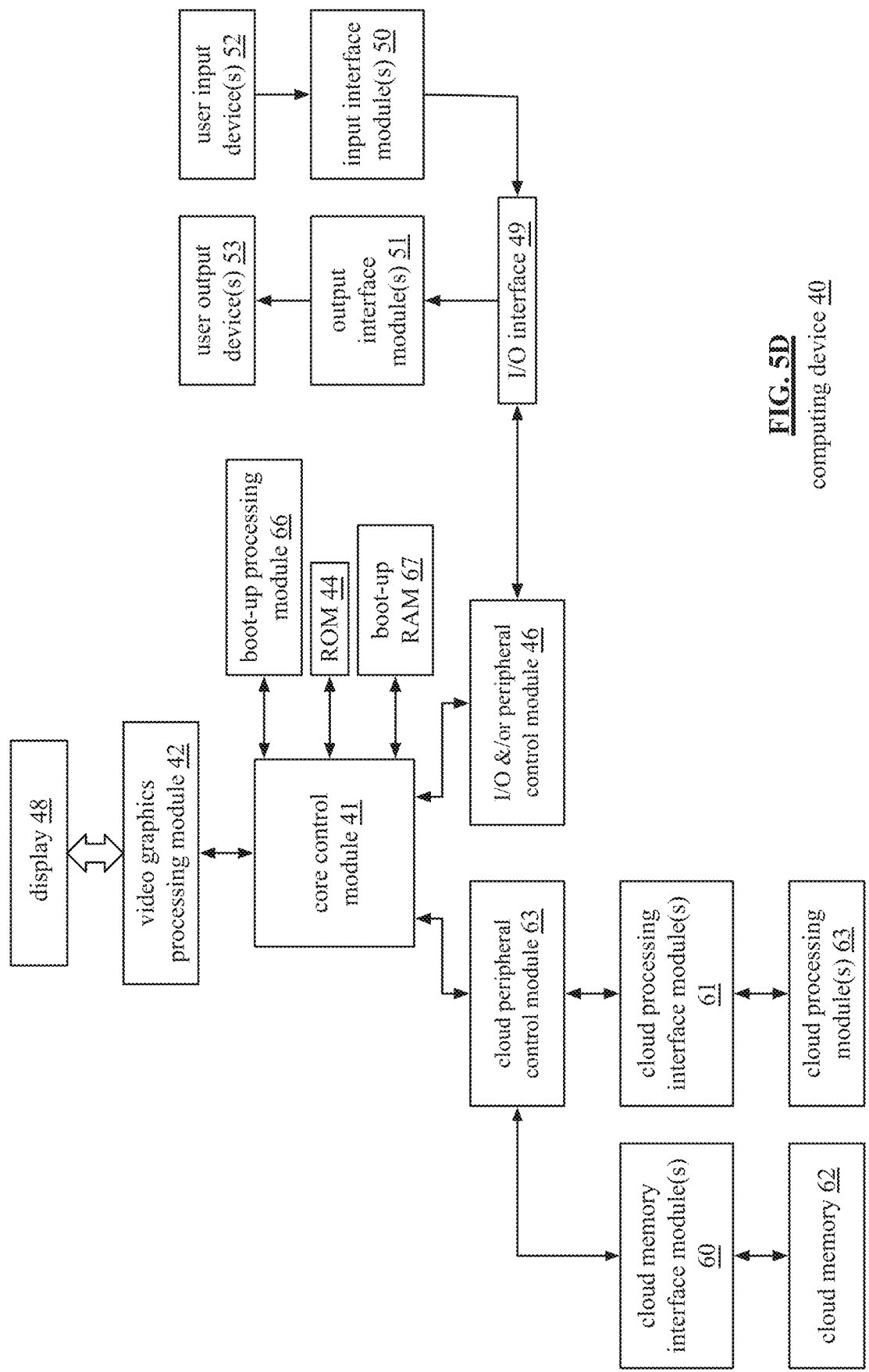

FIG. 5D is a schematic block diagram of an embodiment of a computing device 40 that includes a plurality of computing resources, which includes include a core control module 41, a boot up processing module 66, boot up RAM 67, a read only memory (ROM) 45, a video graphics processing module 42, a display 48 (optional), an Input-Output (I/O) peripheral control module 46, one or more input interface modules 50, one or more output interface modules 51, one or more cloud memory interface modules 60, one or more cloud processing interface modules 61, cloud memory 62, and cloud processing module(s) 63.

In this embodiment, the computing device 40 includes enough processing resources (e.g., module 66, ROM 44, and RAM 67) to boot up. Once booted up, the cloud memory 62 and the cloud processing module(s) 63 function as the computing device's memory (e.g., main and hard drive) and processing module.

FIG. 5E is schematic block diagram of an embodiment of a computing entity 16 that includes a computing device 40 (e.g., one of the embodiments of FIGS. 2A-2D). A computing device may function as a user computing device, a server, a system computing device, a data storage device, a data security device, a networking device, a user access device, a cell phone, a tablet, a laptop, a printer, a game console, a satellite control box, a cable box, etc.

FIG. 5F is schematic block diagram of an embodiment of a computing entity 16 that includes two or more computing devices 40 (e.g., two or more from any combination of the embodiments of FIGS. 2A-2D). The computing devices 40 perform the functions of a computing entity in a peer processing manner (e.g., coordinate together to perform the functions), in a master-slave manner (e.g., one computing device coordinates and the other support it), and/or in another manner.

FIG. 5G is schematic block diagram of an embodiment of a computing entity 16 that includes a network of computing devices 40 (e.g., two or more from any combination of the embodiments of FIGS. 2A-2D). The computing devices are coupled together via one or more network connections (e.g., WAN, LAN, cellular data, WLAN, etc.) and preform the functions of the computing entity.

FIG. 5H is schematic block diagram of an embodiment of a computing entity 16 that includes a primary computing device (e.g., any one of the computing devices of FIGS. 2A-2D), an interface device (e.g., a network connection), and a network of computing devices 40 (e.g., one or more from any combination of the embodiments of FIGS. 2A-2D). The primary computing device utilizes the other computing devices as co-processors to execute one or more the functions of the computing entity, as storage for data, for other data processing functions, and/or storage purposes.

FIG. 5I is schematic block diagram of an embodiment of a computing entity 16 that includes a primary computing device (e.g., any one of the computing devices of FIGS. 2A-2D), an interface device (e.g., a network connection) 70, and a network of computing resources 71 (e.g., two or more resources from any combination of the embodiments of FIGS. 2A-2D). The primary computing device utilizes the computing resources as co-processors to execute one or more the functions of the computing entity, as storage for data, for other data processing functions, and/or storage purposes.

FIGS. 6A-6C are a medial side, top view, and lateral side view diagrams of an embodiment of force detection system 20 implemented in the sole of a shoe. The force detection system 20 includes a layer of variable capacitors 100, a layer of compression plates 102, and a circuitry section 104. The layer of variable capacitors 100 and the layer of compression plates 102 are positioned within the variable capacitor section 106.

The circuitry section 104 includes the circuit components of the force detection system 20 as shown in FIG. 3, excluding the capacitor sensors 21. The circuit components may be discrete components and/or included in an integrated circuit (IC). For example, the drive sense circuits and digital filtering circuitry are implemented as an integrated circuit. The circuitry components, as ICs and/or discrete components, are mounted on one or more circuit boards (e.g., rigid and/or flexible) that fit within the circuitry section 104.

The capacitor sensors 21 include the layer of variable capacitors 100 and the layer of compression plates 102. The compression plates are positioned closer to the foot than the variable capacitors. When a force is applied to a compression plate as a result of a person wearing a shoe, the compression plate pushes on a set of variable capacitors. The magnitude and angle of the force applied to the compression plate is calculable based on the changes to the capacitances of the set of variable capacitors. One or more examples will be described with reference to at least one subsequent figure.

FIGS. 6D-6F are a medial side, top view, and lateral side view diagrams of an embodiment of force detection system 20 implemented in the sole of a shoe. The force detection system 20 includes a first layer of variable capacitors 100, a second layer of variable capacitors 108, and a circuitry section 104. The first and second layers of variable capacitors 100 and 108 are positioned within the variable capacitor section 106. The circuitry section 104 includes the circuit components of the force detection system 20 as shown in FIG. 3, excluding the capacitor sensors 21, as previously discussed.

The capacitor sensors 21 include the first and second layers of variable capacitors 100 and 108. The first layer of variable capacitors is positioned closer to the foot than the first layer of variable capacitors. When a force is applied to a variable capacitor of the first layer as a result of a person wearing a shoe, the first layer variable capacitor pushes on a set of second layer variable capacitors. The magnitude and angle of the force applied to the first layer variable capacitor is calculable based on the changes to the capacitances of the first layer variable capacitor and set of second layer variable capacitors. One or more examples will be described with reference to at least one subsequent figure.

Figure 7C:
FIGS. 7A-7C are schematic block diagrams of an embodiment of force detection system that includes a layer of variable capacitors and a circuitry section.
Figure 7B:
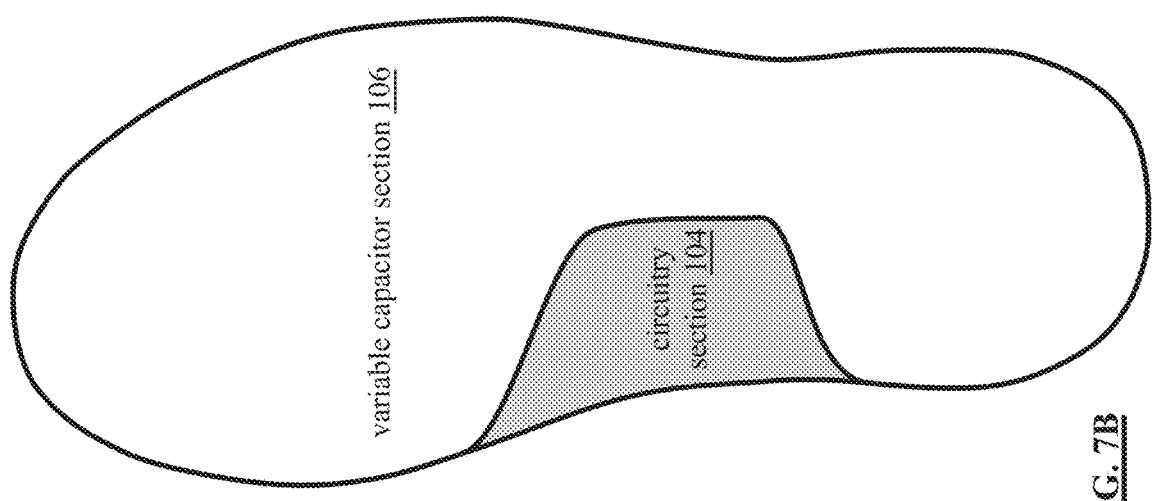
Figure 7A:
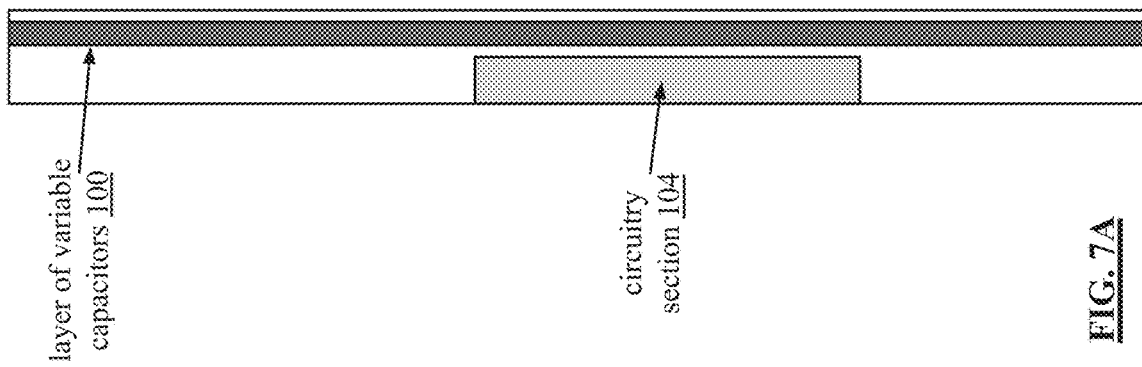

FIGS. 7A-7C are a medial side, top view, and lateral side view diagrams of an embodiment of force detection system 20 implemented in the sole of a shoe. The force detection system 20 includes a layer of variable capacitors 100 and a circuitry section 104. The layer of variable capacitors 100 is positioned within the variable capacitor section 106. The circuitry section 104 includes the circuit components of the force detection system 20 as shown in FIG. 3, excluding the capacitor sensors 21, as previously discussed.

The capacitor sensors 21 include the layer of variable capacitors 100. When a force is applied to a set of variable capacitors as a result of a person wearing a shoe, the set of variable capacitors are compressed. The magnitude and angle of the force applied to the set of variable capacitors is calculable based on the changes to the capacitances of the set of variable capacitors. One or more examples will be described with reference to at least one subsequent figure.

Figure 8C:
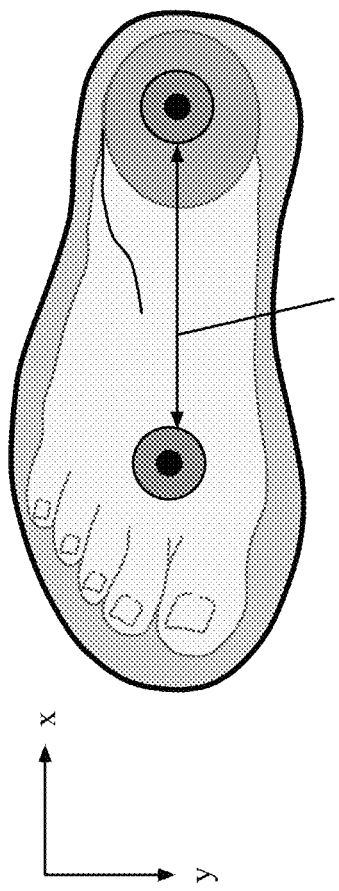
FIGS. 8A-8C are schematic block diagrams of an example of force applied by a foot to the force detection system.
Figure 8B:
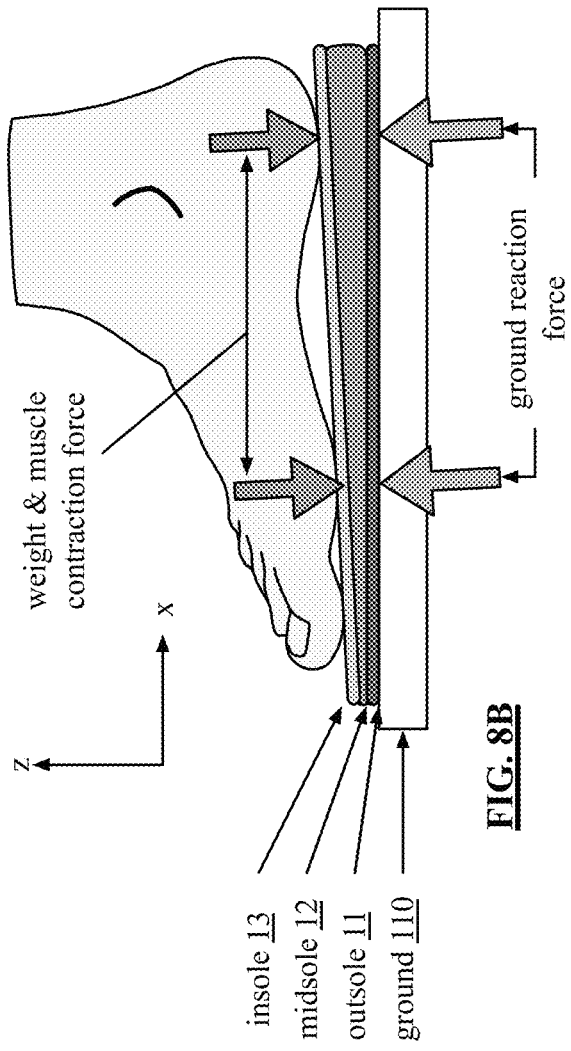
Figure 8A:
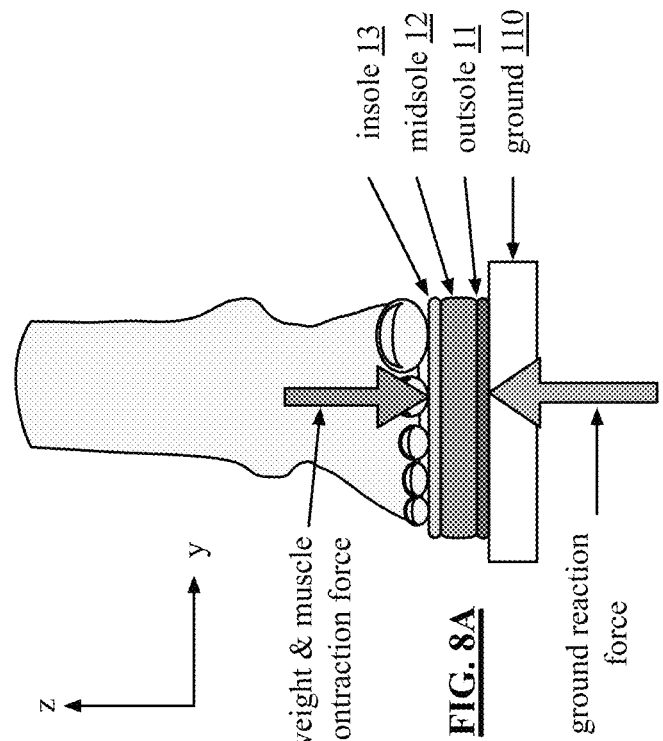

FIGS. 8A-8C are front, side, and top views of an example of force applied by a foot to the force detection system 20 when a wearer is standing. With a wearer standing, the force applied to the shoe is normal to the ground in the front view and in the top view, and it is distributed between the forefoot and the heel. The force applied to the shoe is weight & muscle contraction of the wearer and is represented by a red arrow. With the wearer standing, there is little to no muscle contraction force, thus the force is primarily a weight force.

The weight force traverses through the insole 13, the midsole 12, and the outsole 11 of a shoe to the ground 110. The ground pushes back with an equal and opposite force with ground reaction force, which is represented by a green arrow. To help illustrate the mirroring nature of the weight and muscle contraction force and the ground reaction force, the complementary colors of green and red are used.

In the side view of FIG. 8, the midsole 12 includes an angular section that slopes upward from the toes to the heel. The angular section shifts, from the side view perspective, how the weight and muscle contraction force traverses through the shoe to the ground 110. As shown, the red weight and muscle contraction force is at an angle to ground. The angle of the force is orthogonal to the angle of the midsole 12. The green ground reaction force is equal and opposite to the weight and muscle contraction force and includes a commentary angle.

With the force detection system 20 implemented in the sole of the shoe (e.g., in the insole, midsole, and/or outsole), the magnitude and direction of the weight and muscle contraction force and the ground reaction force can be determined. This is a vast improvement over conventional foot force analysis systems that only measure the normalized magnitude of the force (i.e., the resulting Z component of the force), not the true magnitude of the force. Examples of computing the magnitude and direction of the forces will be discussed with reference to one or more subsequent figures.

FIGS. 9A-9C are front, side, and top views of an example of force applied by a foot to the force detection system 20 when a wearer is executed a lateral push-off. A wide variety of athletes execute a lateral push-off in playing their respective sport. For example, a golfer executes a lateral push-off on the back leg during the backswing and down swing and then on the front leg during the follow through. A baseball player goes through a similar lateral push-off for hitting and for pitching. A tennis player uses a lateral push-off to hit a tennis ball, but also to stop or change directions while running. A football player, a soccer player, an ice hockey player, and a skier all use a lateral push-off to stop and/or to change direction of movement.

In this example, the majority of the weight and muscle contraction force is in the ball of the foot with none shown in the heel section. Note that some athletes may executed a lateral push-off with up to half of their weight in the heel section.

For a lateral push-off the weight and muscle contraction force, as represented by the red arrow, traverses down the leg towards the foot. For an athletic movement, the athlete is contracting his or her muscles, which adds up to six times the athlete's body weight to the overall weight and muscle contraction force. Assuming the shoe is firmly planted on the ground (i.e., no roll over or slipping), the weight and muscle contraction force is divided into perpendicular force components as represented by the blue arrows and parallel force components as represented by the yellow arrows in the y direction and orange arrows in the x direction at the foot and into the shoe.

Within the shoe, the perpendicular Z force component traverses through the shoe to the ground. The ground produces the ground reaction force, which is represented by the green arrow, that is equal to and opposite of the perpendicular Z force. In this example, the ground reaction force is not equal to and opposite of the weight and muscle contraction force, but of the perpendicular Z component, which is less than the weight and muscle contraction force. The magnitude of the perpendicular Z component is calculated the cosine of $\varphi$ times the magnitude of the weight and muscle contraction force. "$\varphi$" represents the angle of the weight and muscle contraction force with respect the slopes of the sole in the y direction and in the x direction. In this example, the sole has no medial to lateral slope and has a slight toe to heel slope.

The horizontal y component, as expressed by the yellow arrow in the front view and top view, is parallel to the surface of the sole and to the ground. If the shoe does not include a mechanism to apply a force that is equal and opposite of the horizontal y component, the foot will move laterally within the shoe, which increases the angle and reduces the ground reaction force.

The horizontal x component, as expressed by the orange arrow in the side view and top view, is parallel to the surface of the sole and at a slight angle to the ground. If the shoe does not include a mechanism to apply a force that is equal and opposite of the horizontal x component, the foot will move linearly within the shoe, which increases the angle and further reduces the ground reaction force.

The force detection system 20 is operable to detect the magnitude and angles of the ground reaction force, the perpendicular Z force component, the horizontal Y force component, and the horizontal X force component. From these data points, the weight and muscle contraction force can be calculated.

FIGS. 10A-10C are front, side, and top views of an example of force applied by a foot to the force detection system 20 when a wearer is running and the foot is impacting the ground. In an efficient sprint, the first contact of the landing foot should almost be directly underneath the athlete. The athlete pulls his or her leg back after initial contact of the foot until the foot is released from the ground. How the foot engages the ground and the duration of ground impact effect the efficiency of running.

In this example, the weight and muscle contraction force is shown for an inefficient runner since the contact point with the ground is in front of the body as evidenced by the angle of the force. Further, the example illustrates the weight and muscle contraction force only has an angle in the linear direction and not one in the lateral to medial direction.

The weight and muscle contraction force, as represented by the red arrow, traverses down the leg towards the foot. For a stride impact when running, the athlete is contracting his or her muscles and landing on the ground, which adds up to six times the athlete's body weight to the overall weight and muscle contraction force. Assuming the shoe is firmly planted on the ground (i.e., no roll over or slipping), the weight and muscle contraction force is divided into perpendicular force components as represented by the blue arrows and parallel X force components as represented by the orange arrow in the x direction at the foot and into the shoe.

Within the shoe, the perpendicular Z force component traverses through the shoe to the ground. The ground produces the ground reaction force, which is represented by the green arrow, that is equal to and opposite of the perpendicular Z force. In this example, the ground reaction force is not equal to and opposite of the weight and muscle contraction force, but of the perpendicular Z component, which is less than the weight and muscle contraction force. The magnitude of the perpendicular Z component is calculated the cosine of φ times the magnitude of the weight and muscle contraction force. "φ" represents the angle of the weight and muscle contraction force with respect the slopes of the sole in the x direction. In this example, the sole has no medial to lateral slope and has a slight toe to heel slope.

The horizontal x component, as expressed by the orange arrow in the side view and top view, is parallel to the surface of the sole and at a slight angle to the ground. If the shoe does not include a mechanism to apply a force that is equal and opposite of the horizontal x component, the foot will move linearly within the shoe, which increases the angle and further reduces the ground reaction force.

The force detection system 20 is operable to detect the magnitude and angles of the ground reaction force, the perpendicular Z force component, the horizontal Y force component (if any), and the horizontal X force component. From these data points, the weight and muscle contraction force can be calculated.

FIGS. 11A-11F are schematic block diagrams of another example of forces applied by a foot to the force detection system when a person is running. In the examples of FIGS. 11A through 11F, the relationship between the weight and muscle contraction force, the z force component, and the x force component vary based on where the foot to ground contact is for a stride.

In FIG. 11A, the foot is making initial contact with the ground for a given stride. This is similar to the foot-ground connection discussed with reference to FIGS. 10A-10C. In the remaining figures, the foot-ground contact varies as the runner executes the stride. Within each figure, the relationship between weight and muscle contraction force, the Z force component, and the X force component varies.

With the high sampling rate of the force detection system 20 (e.g., 5 KHz or more), dozens to hundreds of samples are obtained for a single foot strike. This provides a level of granularity to better understand how the foot engages with the ground during a running. It further enables identifying efficiencies and inefficiencies in running. With inefficiencies identified, corrective measures can be determined to improve a runner's form and/or running efficiency.

Figure 12:
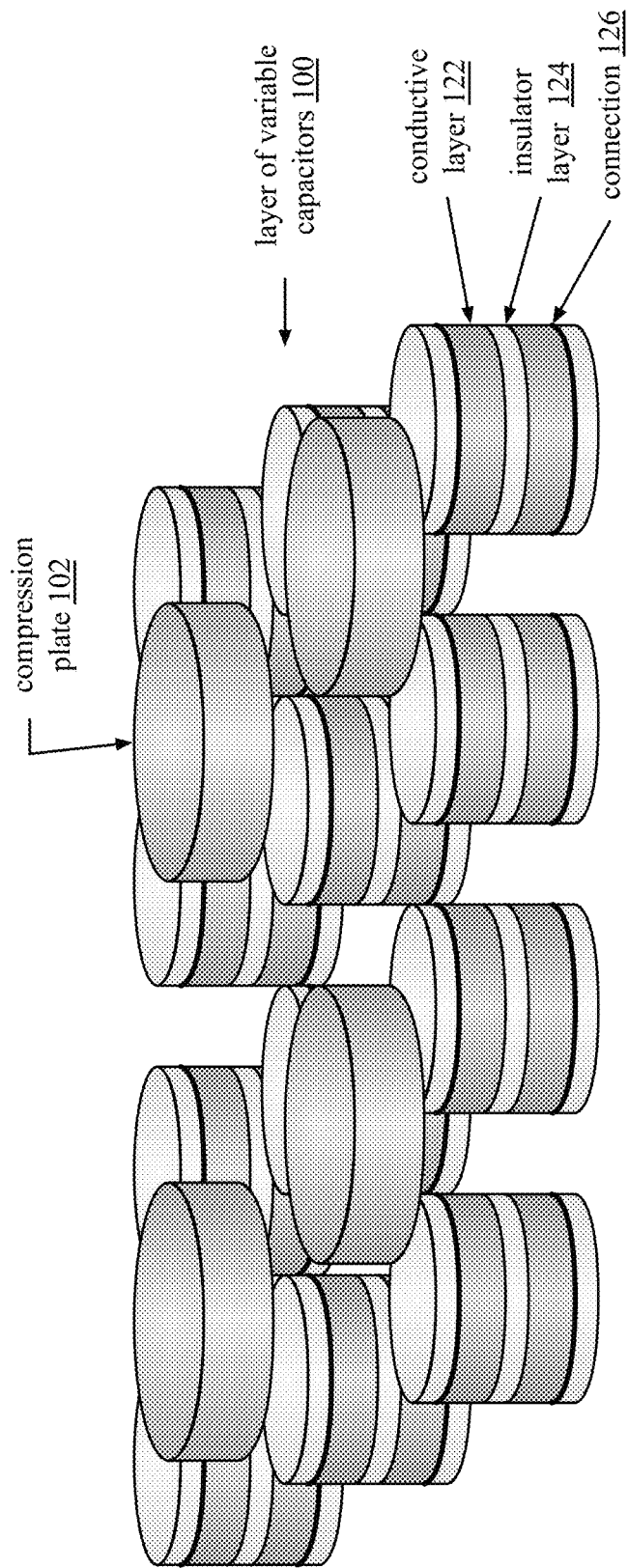
FIG. 12 is a schematic block diagram of another embodiment of a layer of variable capacitors and a layer of compression plates of a force detection system.

FIG. 12 is a schematic block diagram of another embodiment of a layer of variable capacitors and a layer of compression plates of a force detection system 20. In this example, the compression plates 102 are represented by green discs. A variable capacitor includes one or more conductive layers, two or more insulating layers, and two connections (i.e., capacitor plates). In this example, the insulating layers are represented as yellow disc shapes, the conductive layers are represented as blue disc shapes, and the connectors are represented as black ring-like, or plate-like, shapes.

The compression plates 102 may be comprised of one or more materials to form a rigid structure. For example, the compression plates are comprised of plastic. As another example, the compression plates are comprised on fiberglass. As another example, the compression plates are comprised on carbon fiber. As yet another example, the compression plates are comprised on a metal.

The dimensions of a compression plate will vary depending on the material, or materials, it is comprised of, the size of the variable capacitors, the distance between the variable capacitors, the number of variable capacitors it overlaps, and a maximum force load. For example, the thickness of a compression plate, which should be in the range of a few microns to a few millimeters, is based on the rigidity of the material, the maximum force load, and a flexion range of the compression plate under a force load. Ideally, the flexion of the compression plate should be negligible with respect to the compression range of the variable capacitors. In the ideal case, the flexion of the compression plate can be ignored when calculating the applied force; the calculations will be based on the compression of the variable capacitors. If the flexion of the compression plate is not negligible, the flexion should be factored into the calculations of the applied force, which makes the calculations more complex than in the ideal case.

The perimeter dimension of a compression plate should be comparable to the perimeter of the variable capacitors the compression plate overlaps. For example, a compression plate, which overlaps three variable capacitors having a circular shape from a top perspective, has a circular shape with a diameter in the range of 1.25 times to 2.25 times the diameter of a variable capacitor. As another example, a compression plate, which overlaps three variable capacitors having a circular shape from a top perspective, has a rounded equilateral triangular shape with each of a base dimension and of a height dimension of 1.25 times to 2.25 times the diameter of a variable capacitor.

For a variable capacitor, the number of conductive layers and the number of insulator layers depend on the desired capacitance range, desired thickness of the layer of capacitors, and the materials of composition. A variable capacitor may be fabricated in a variety of ways. For example, a variable capacitor is fabricated from a Z electrometric conductor (ZEC). In another example, a variable capacitor is fabricated from one or more dielectric elastomers. The capacitance value and the range of capacitance values varies based on the materials used and their compression ratio. The materials include acrylates, silicones, polyurethanes (PU), rubbers, latex rubbers, acrylonitrile butadiene rubbers, olefinic, polymer foams, fluorinated and styrenic copolymers, etc.

The equation for a parallel capacitor is:

$$C = \epsilon_0 \epsilon_r A/d$$

Where C is the capacitance, $\epsilon_0$ is the permittivity of a vacuum, $\epsilon_r$ is the relative permittivity, A is the area of the plates, and d is the distance between the plates. The relative permittivity can range from 1 to 10 or more.

In an example, a variable capacitor is formed with a compressible dielectric material layer between two conductive plates that are separated by a distance from each other. The variable capacitor may further include two non-compressive insulting layers. The dielectric material has a relative permittivity of 2.8 and is compresses by 50% from no compression to fully compressed, which occurs at 825 kg (kilograms) of force.

For this example, the two conductive plates have an area of 71.26 millimeters squared (mm²) (i.e., ⅜ inch diameter) and the uncompressed distance between the plates of 0.79 mm (i.e., 1/32 of an inch). In the uncompressed state, the variable capacitor has a capacitance value of 2.25 pico Farads (pF). When the distance between the plates compresses by 50%, the variable capacitor has a capacitance of 4.45 pF. To increase the capacitance, the variable capacitor includes 4 conductive, or dielectric, layers, separated by insulating layer and are coupled in parallel to provide a compressed capacitance of 8.9 pF and a compressed capacitance of 17.8 pF. With a four conductive layer variable capacitance, its total thickness would be about 3.5 to 4.3 mm thick; less than the thickness of a conventional insole.

For a weight sensing range of 0 kg to 825 kg, the variable capacitor will correspondingly range from no compression to fully compressed. The variable capacitor's capacitance value to compress level curve is factored into the determination of a weight force causing a current compression of the capacitor. If the capacitance value to compress level is fairly linear, then the capacitance value for a particular sample can be multiplied by a constant to obtain a weight force value. If the capacitance value to compress level is not linear, then a non-linear equation will be applied to the capacitance value to obtain a corresponding weight force value.

For this example, assume that the desired granulating for weight force changes is 0.5 kg, then, for a range of 0 to 825 kg, there are 1650 different values of capacitances that need to be measured. As such, a capacitance difference of 0.005 pF represents a 0.5 kg difference.

Continuing with the example and with respect to the drive sense circuit, a 50 mV (milli volt) sinusoidal signal having a frequency of 100 kHz is used as the reference signal, offset by the DC component. The impedance of a capacitor is expressed as:

$$z = \frac{1}{2\pi f C}$$

Where z is the impedance, f is the frequency of the reference signal, and C is the capacitance value. For the uncompressed capacitance value of 8.9 pF, the impedance is 179 K Ohms. Since I=V/Z, the current supplied by the drive sense circuit is 276 nA (nano Amps), yielding a power of 13.9 nW (nano Watts).

To sense a 0.5 kg change in the weight force, the drive sense circuit needs to detect a 0.0054 pF capacitance change, which, for the 50 mV reference signals, corresponds to a current change of 169 nA (e.g., $1.69*10^{-10}$ amps). The assignee's drive sense circuit has a signal-to-noise ration of at least 120 dB, which means in can detect a change at a ratio of 1 to $1*10^{12}$. As such, the assignee's drive sense circuit is more than sensitive enough to detect a 169 nA change.

With a 120 dB or more of signal to noise ratio, there is ample room to adjust capacitor size and shape, the magnitude of the reference signal, the number of capacitors in the force detection system, and so on. For example, the shape of the capacitor from a top perspective is a four, five, six, seven, eight, or more, sided polygon. The compression plate would have a corresponding shape from the top perspective. Examples of how the compression plate effects the capacitance values of the capacitors it compresses will be discussed with reference to one or more subsequent figures.

Figure 13:
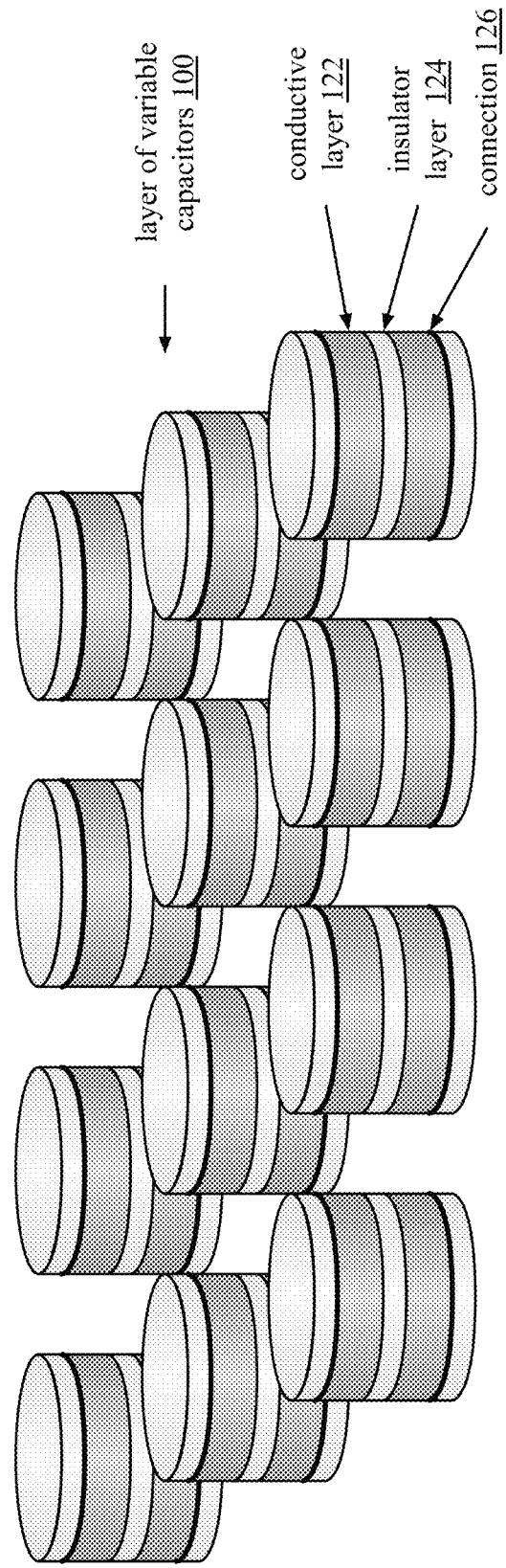
FIG. 13 is a schematic block diagram of another embodiment of a layer of variable capacitors FIG. 12 without a layer of compression plates of a force detection system.

FIG. 13 is a schematic block diagram of another embodiment of a layer of variable capacitors of FIG. 12 without a layer of compression plates. Within an area of the force detection system, a group of variable capacitors are arranged as rows and columns. The positioning of a variable capacitor in a group and variable capacitors and within the force detection system allows the forces it senses to be equated to a portion of a foot of a wearer.

FIGS. 14A-14C are schematic block diagrams of an example of a layer of variable capacitors 100 and a layer of compression plates 102 of a force detection system. FIG. 14A illustrates a top view of the layer of compression plates 102 only, which are represented by green circles. FIG. 14B illustrates a top view of the layer of variable capacitors 100 only, which are represented by blue circles. FIG. 14C illustrates a top view of the layer of compression plates 102 (i.e., partially translucent green circles) position over the layer of variable capacitors 100 (i.e., the blue circles). In this example, one compression plate overlaps three variable capacitors. When a force is applied to the compression plate, it transfers the force to the three variable capacitors. The force applied to each of the variable capacitors is measured and used to determine the magnitude and direction of the force on the compression plate.

FIGS. 15A-15E are schematic block diagrams of an example of a layer of variable capacitors 100 and a layer of compression plates 102 of a force detection system with and without compression of the capacitors. FIG. 15A illustrates the variable capacitors 100-1 in a non-compress state (i.e., no force is being applied to the compression plate 102-1) and FIG. 15B illustrates the variable capacitors 100-1 in a fully compressed state (i.e., maximum force is being applied to the compression plate 102-1).

The variable capacitors 100-1, with the blue conductive layers and the yellow insulating layers, are held in place by a capacitor (cap) holding structure 134. The cap holding structure 134 is comprised of a flexible material that allows the capacitors to expanding horizontally and they are compressed vertically while staying in place. For example, the cap holding structure 134 is comprised of one or more of rubber, silicon, EVA, PEVA, foam, a gel, etc.

The compression plates 102-1 (e.g., the green discs) are held in place by a plate holding structure 130. The plate holding structure 130 is comprised of a flexible material that allows for each compression plate to move freely and independently. The plate holding structure 130 is comprised of one or more of rubber, silicon, EVA, PEVA, foam, a gel, etc.

The variable capacitors 100-1, the cap holding structure 134, the compression plates 102-1, and the plate holding structure 130 are housed within a perimeter support structure 132. The perimeter support structure 132 is comprised of a rigid material and may house one or more sets of a compression plate and associated variable capacitors. As for the rigid material, it is one or more of a hard rubber, plastic, carbon fiber, etc.

In an example as shown in FIG. 15C, the perimeter support structure 132 houses one set of a compression plate and associated variable capacitors. In this example, the force detection system 20 would include a plurality of perimeter support structures 132. In another example as shown in FIG. 15D, the perimeter support structure 132 houses two sets of a compression plate and associated variable capacitors. In yet another example as shown in FIG. 15E, the perimeter support structure 132 houses three sets of a compression plate and associated variable capacitors.

FIGS. 16A-16C are schematic block diagrams of examples of a geometric and electrical relationship between variable capacitors of a second layer and a compression plate of a first layer within a force detection system. FIG. 16A illustrates from a top view, a circular compression plate 102-1 that partially overlaps three variable capacitors 100-1 (e.g., C2, C3, and C4). FIG. 16B illustrates from a top view, a triangular compression plate 102-1 that substantially overlaps three variable capacitors 100-1 (e.g., C2, C3, and C4).

FIG. 16C illustrates a schematic block diagram of the three variable capacitors of FIGS. 16A and 16B coupled to respective drive sense circuits (DSC). One plate of each of the capacitors C2-C4 is coupled to a reference ground and the other plate is coupled to a respective DSC. The output of each drive sense circuit is a digital value, at a desired sampling rate, of the capacitance of the respective capacitor. For example, one of the DSCs outputs a digital value of the capacitance value for C2; another of the DSCs outputs a digital value of the capacitance value for C3; and third one of the DSCs outputs a digital value of the capacitance value for C4.

Figure 17:
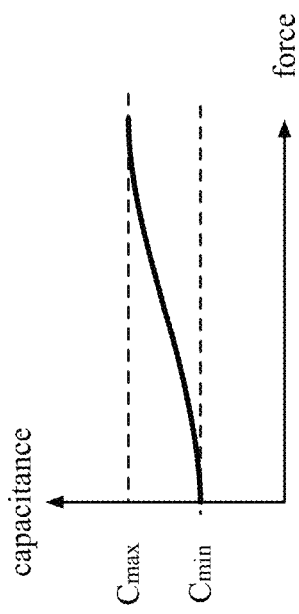
FIG. 17 is a schematic block diagram of an example of a graph that depicts capacitance variance with respect to compression of a of variable capacitor.

FIG. 17 is a schematic block diagram of an example of a graph that depicts capacitance variance with respect to compression of a of variable capacitor. In this example, as force is applied to a variable capacitor, the capacitance increases. When no force is applied, the capacitance is at a minimum capacitance value. The capacitance value increases with force until it reaches a maximum value. At this point, the variable capacitor is fully compressed and a further increase in force will not increase the capacitance.

For an ideal variable capacitor, its capacitance changes linearly with the force applied. For many variable capacitors, there is at least a range of capacitance values where the change in force is substantially linear. As such, the applied force can be accurately determined based on the measured capacitance for the range of capacitances.

In equation form, $C_0 = C_{min} + \Delta x \cdot \Delta C$, where $C_0$ is the capacitance of the variable capacitor; $C_{min}$ is the capacitance of the variable capacitor with no compression, $\Delta x$ is the percentage of displacement with respect to a maximum displacement (i.e., compression), where $\Delta x = x_0 / x_{max}$, and $\Delta C$ is the difference between $C_{max}$ and $C_{min}$. Also, the force to compress the variable capacitor is expressed as $F = k \cdot x_0$, where F is the force, k is the compression factor of the variable capacitor, and x is the displacement. The compression factor "k" is a constant that reflects the stiffness of the variable capacitor (i.e., its resistance to compression).

Through substitution:

$$F = \frac{k \cdot x_{max}}{\Delta C} \cdot (C_0 - C_{min})$$

In this form, the applied force is readily calculated from a measured capacitance ($C_0$) of the variable capacitor on a per sampling rate basis. The forces measured by multiple variable capacitors can be used to determine the magnitude and direction of the force applied to a corresponding compression plate. Note that non-linearities between force and capacitance value can be factored into the above equation. In such non-linear applications, k is not a constant but a variable that represents the shape of the curve.

Figure 18A:
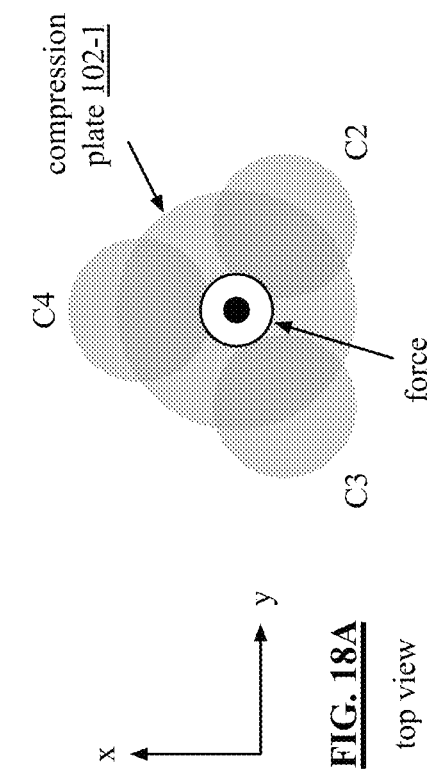
FIGS. 18A-18C are schematic block diagrams of examples of an impact force applied to a cell of a force detection system, wherein the cell includes a compression plate and three or more variable capacitors.
Figure 18C:
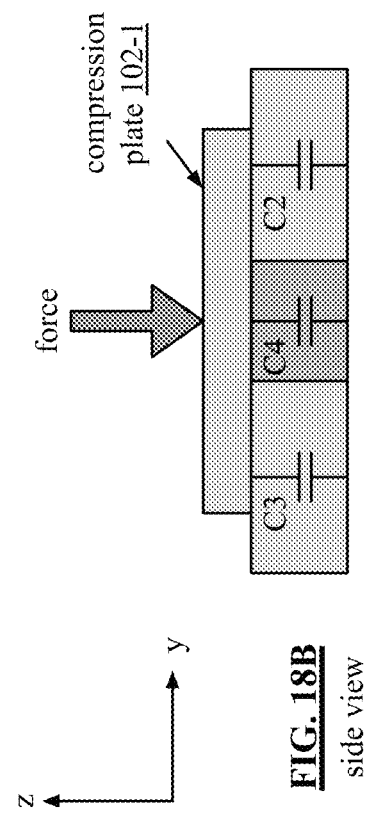
Figure 18B:
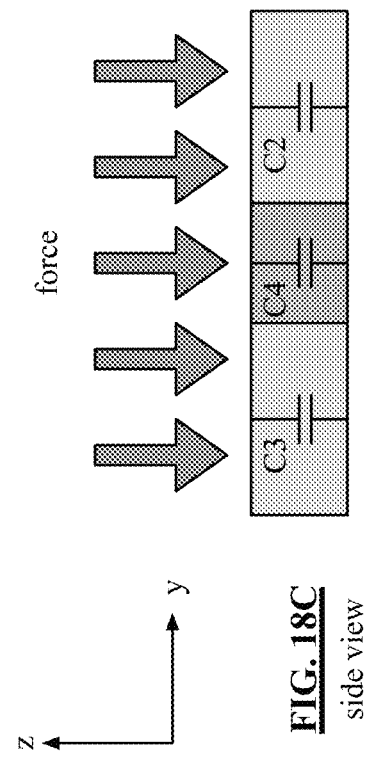

FIGS. 18A-18C are schematic block diagrams of examples of an impact force applied to a cell of a force detection system (e.g., a compression plate and three variable capacitors). In this example, the variable capacitors C2-C4 are substantially identical in terms of size, shape, compression factor (k), minimum capacitance, maximum displacement, and maximum capacitance. As such, when an equal force is applied to the variable capacitors, they each produce a capacitance value that are substantially identical (i.e., negligible differences).

FIGS. 18A and 18B illustrate a top view and a side view of a force being applied to the cell. The force is normal to the compression plate 102-1, which transfers the force equally among the variable capacitors C2-C4, as shown in FIG. 18C. FIG. 18C is also applicable for a cell embodiment that does not include a compression plate; it includes, for example the three variable capacitors provided that the wearer's foot makes contact with the variable capacitors.

With the force equally applied to the capacitors, they each have the same capacitance change. The force applied to each capacitor is then readily calculatable. The magnitude and direction of the applied force is then calculated from the forces detected by the capacitors. An example of the calculation will be discussed with reference to one or more of FIGS. 19A-24B.

Figure 18D:
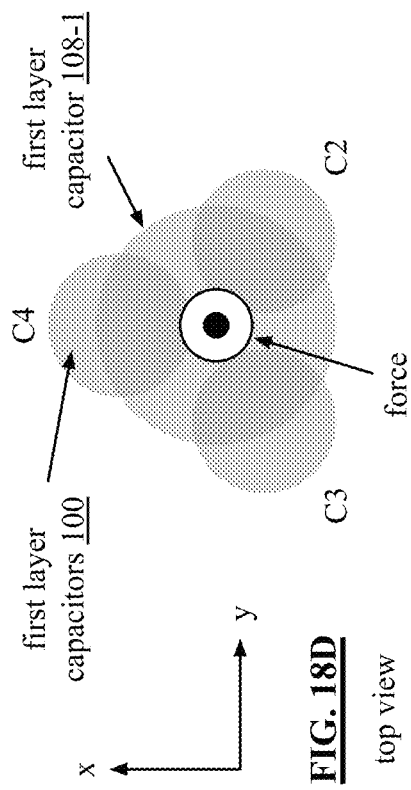
FIGS. 18D-18F are schematic block diagrams of examples of an impact force applied to a cell of a force detection system (e.g., a first layer capacitor and three second layer capacitors)
Figure 18F:
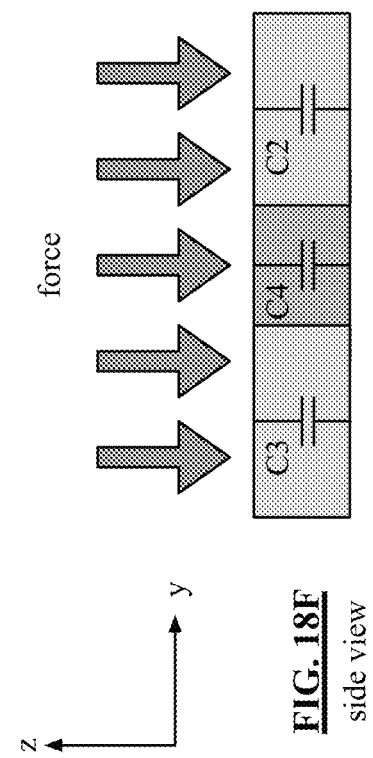
Figure 18E:
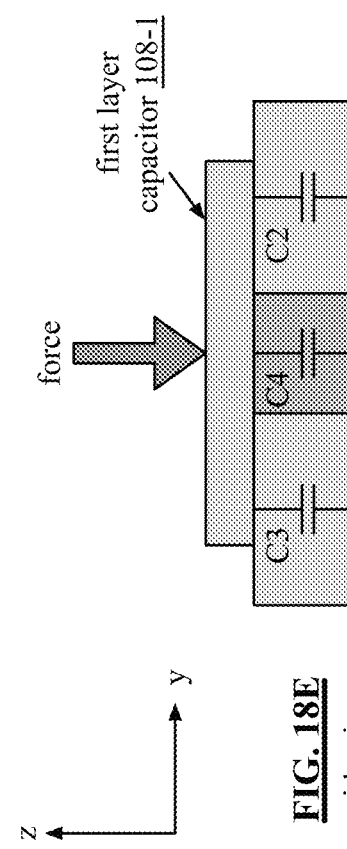

FIGS. 18D-18F are schematic block diagrams of examples of an impact force applied to a cell of a force detection system (e.g., a first layer capacitor and three second layer capacitors). In this example, the top layer is another variable capacitor. In this instance, the magnitude of the applied force is calculable from the capacitance change of the first layer capacitor 108-1 and the direction is calculable from the capacitance change of the second layer capacitors 100.

Figure 19B:
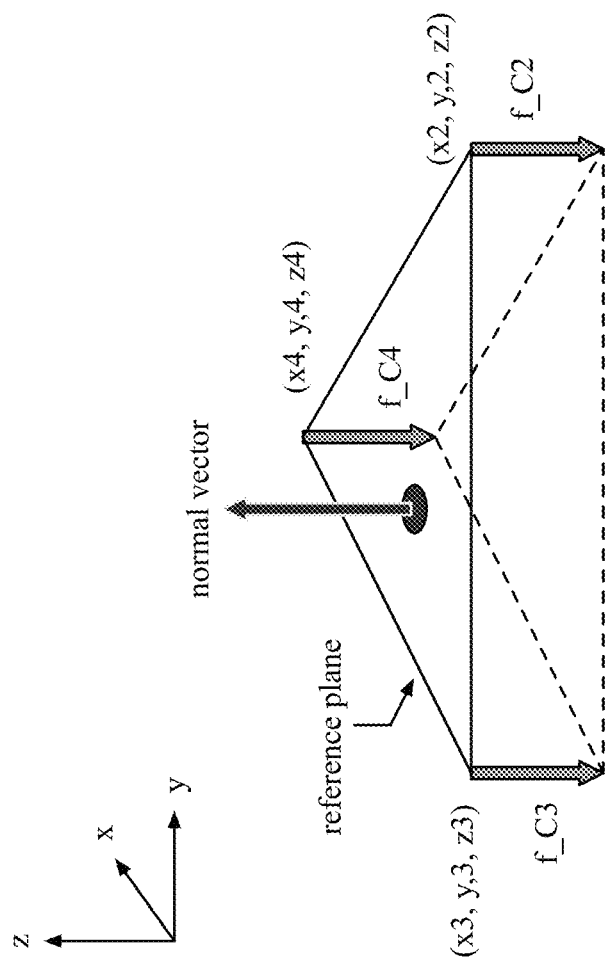
FIGS. 19A-19B are schematic block diagrams of an example of determining a normal vector of a reference plane of a cell of a force detection system in response to an impact force.
Figure 19A:
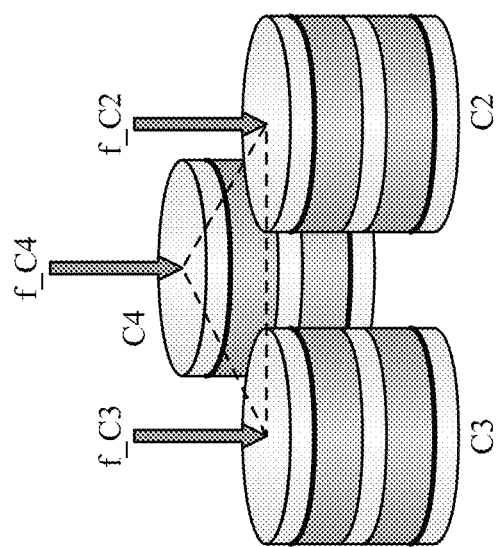

FIGS. 19A-19B are schematic block diagrams of an example of determining a normal vector of a reference plane of a cell of a force detection system in response to an impact force, wherein the normal vector corresponds to the impact force yielding x, y, and z direction force data. From the examples of FIGS. 18A-18F, the second layer of variable capacitors (C2-C4) yield a corresponding force vector f_C2 through f_C4 that are equal as shown in FIG. 19A.

The force vectors are used to create a reference plane as shown in FIG. 19B, which is then used to determine a normal vector that represents the magnitude and direction of the applied force. To calculate the reference plane, the force vectors f_C2 through f_C4 are mapped to a coordinate system (e.g., a Cartesian system or a polar system, this example is based on a Cartesian coordinate system). In this example, the x-y plane of the Cartesian coordinate system is parallel to the bottom of a shoe and the z direction is perpendicular to the bottom of the shoe.

As shown, f_C2 is mapped to a coordinate point of x2, y2, z2; f_C3 is mapped to a coordinate point of x3, y3, z3; and f_C4 is mapped to a coordinate point of x4, y4, z4. The three coordinate points are used to determine the reference plane. For example, the equation of a plane of D=Ax+By+Cz. Coefficients A, B, and C are determined such that each coordinate point (e.g., coordinate points of C2, C3, and C4) on the plane satisfies this equation.

As a specific example, assume that coordinate point C2 is 1, 1, 1; coordinate point C3 is 2, 3, 1; and coordinate point C4 is 4, 2, 1. From these coordinate points, three equations emerge.

$1A+1B+1C=D$ for coordinate point $C2$;

$2A+3B+1C=D$ for coordinate point $C3$; and $4A+2B+1C=D$ for coordinate point $C4$.

Solving the three equations yields A=0; B=0; and C=1. From the plane equation of D=(1)z, the normal vector of the plane is calculable. For example, equation for the normal vector (n)=Ai+Bj+Ck, where i is the unity vector in the x direction, j is the unity vector in the y direction, and k is the unity vector in the z direction. Thus, for this example the normal vector (n) (i.e., the applied force)=(1)k, which means that the applied force has a magnitude of 1 and a direction that is perpendicular to the x-y plane.

FIGS. 20A-20D are schematic block diagrams of another example of determining a normal vector of a reference plane of a cell of a force detection system. In this example, the applied force on a cell (e.g., a set of variable capacitors and a compression plate) is at angle from the z axis with respect to both the x and y. An example is shown the top view perspective of FIG. 20A. The impact force, as represented by the orange arrow includes an x force component that is represented by the red arrow and a y-force component that is represented by the yellow arrow.

FIG. 20B is a side view from an x-z plane of the cell that depicts it being impacted by the x-force (i.e., the red arrow). The x-force pushes on the compression plate causing it to slant in the direction of the x-force. This causes more compression of capacitor C2 than of capacitor C4, which compresses more that capacitor C3.

FIG. 20C is a side view from a y-z plane of the cell that depicts it being impacted by the y-force (i.e., the yellow arrow). The y-force is more vertical than the x-force, thus it pushes on the compression plate more perpendicularly, which causes a more even distribution of the force among the capacitors. Even so, there is a bit more force applied to capacitor C4 than capacitors C2 and C3. With respect to both FIGS. 20B and 20C, capacitor C2 has the more force applied to it than capacitor C4, which has more forced applied to it than capacitor C3. As such, the capacitance value for C2, will be higher than the value for C4, which will be higher than the value for C3.

FIG. 20D illustrates an example of a reference plane resulting from the impact force (e.g., the orange arrow). For this example, assume that coordinate point C2 is 1, 1, 4; coordinate point C3 is −1, 2, 1; and coordinate point C4 is 1, 2, 3. From these coordinate points, three equations emerge.

$1A+1B+4C=D$ for coordinate point $C2$;

$-1A+2B+1C=D$ for coordinate point $C3$; and $1A+2B+3C=D$ for coordinate point $C4$.

Solving the three equations yields A=−¼; B=¼; and C=¼. From the plane equation of 1=−(¼)x+(¼)y+(¼)z, the normal vector of the plane is calculable. For example, equation for the normal vector (n)=Ai+Bj+Ck, where i is the unity vector in the x direction, j is the unity vector in the y direction, and k is the unity vector in the z direction. Thus, for this example the normal vector (n) (i.e., the applied force)=−(¼)i+(¼)j+(¼)k. The impact force is equal to and opposite of the normal vector.

FIGS. 21A-21D are schematic block diagrams of another example of determining a normal vector of a reference plane of a cell of a force detection system. In this example, the applied force on a cell (e.g., a set of variable capacitors and a first layer capacitor) is at angle from the z axis with respect to both the x and y. An example is shown the top view perspective of FIG. 21A. The impact force, as represented by the orange arrow includes an x force component that is represented by the red arrow and a y-force component that is represented by the yellow arrow.

FIG. 21B is a side view from an x-z plane of the cell that depicts it being impacted by the x-force (i.e., the red arrow). The x-force pushes on the first layer capacitor 108-1 causing it to slant in the direction of the x-force. This causes more compression of capacitor C3 than of capacitor C4, which compresses more than capacitor C2. With the angle of the x-force, the compression of capacitor C3 is slightly greater than that of capacitor C4.

FIG. 21C is a side view from a y-z plane of the cell that depicts it being impacted by the y-force (i.e., the yellow arrow). The y-force has approximately the same angle as the x-force, thus it pushes on the first layer capacitor in a similar manner. This causes more compression of capacitor C4 than of capacitors C3 and C2. With the angle of the x-force, the compression of capacitors C3 and C2 are comparable.

With respect to both FIGS. 21B and 21C, capacitor C3 has the more force applied to it than capacitor C4, which has more forced applied to it than capacitor C3. As such, the capacitance value for C2, will be higher than the value for C4, which will be higher than the value for C3.

FIG. 21D illustrates an example of a reference plane resulting from the impact force (e.g., the orange arrow) through the first layer capacitor to the second layer of capacitors. The capacitance change of the first layer capacitor in combination with the second layer capacitors determines the magnitude and direction of the impact force. For this example, assume that coordinate point C2 is 2, 1, 1; coordinate point C3 is 0, 0, 5; and coordinate point C4 is 1, −1, 4. From these coordinate points, three equations emerge.

$2A+1B+1C=D$ for coordinate point $C2$;

$5C=D$ for coordinate point $C3$; and $1A+(-1)B+4C=D$ for coordinate point $C4$.

Solving the three equations yields A=⅓; B=2/15; and C=⅕. From the plane equation of 1=(⅓)x+(2/15)y+(⅕)z, the normal vector of the plane is calculable. For example, equation for the normal vector (n)=Ai+Bj+Ck, where i is the unity vector in the x direction, j is the unity vector in the y direction, and k is the unity vector in the z direction. Thus, for this example the normal vector (n) (i.e., the applied force)=(⅓)i+(2/15)1+(⅕)k. The direction of the impact force is opposite of the normal vector and its magnitude is the sum of the magnitude of the normal vector and the force determined from the compression of the top layer capacitor.

FIGS. 22A-22C are schematic block diagrams of an example of determining a plurality of normal vectors of a plurality of reference planes of a plurality of cells of a force detection system in response to an impact force. FIG. 22A illustrates twelve second layer variable capacitors (C1-C12) arranged in a pattern to form 12 triangles, which represent independent reference planes. In this example, the impact force is shown as an orange arrow that applies a force to the variable capacitors at different levels creating a force pattern as shown in FIG. 22B.

For each reference plane a normal force is determined as previously discussed. In an example, the magnitude and direction of the impact force is determined from resulting normal vectors. As a specific example, the normal vectors are added together to produce a final normal vector. The impact force is equal to and opposite of the final normal vector. In another example, the twelve normal vectors are used to determine twelve impact force components to produce an impact force gradient.

Figure 23:
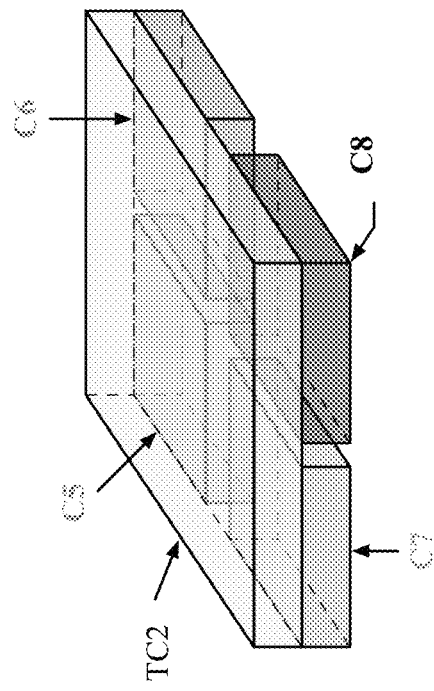
FIG. 23 is a schematic block diagram of an example of two cells, each having a top layer capacitor (TC) (light green) and a four lower layer capacitors (green, blue, red, black)

FIG. 23 is a schematic block diagram of an example of two cells for a force detection system. Each includes a top layer capacitor (TC) (light green) and four lower layer capacitors (green, blue, red, black). In the first cell, the top layer capacitor TC1 substantially overlaps the four lower layer capacitors (C1-C4), where C1 is the blue shaded capacitor, C2 is the red shaded capacitor, C3 is the green shaded capacitor, and C4 is the black shaded capacitor. In the second cell, the top layer capacitor TC2 substantially overlaps the four lower layer capacitors (C5-C8), where C5 is the blue shaded capacitor, C6 is the red shaded capacitor, C7 is the green shaded capacitor, and C8 is the black shaded capacitor. There is a gap of a few microns to a millimeter or more between the lower layer capacitors to allow for horizontal expansion from a vertical compression.

Figure 24A:
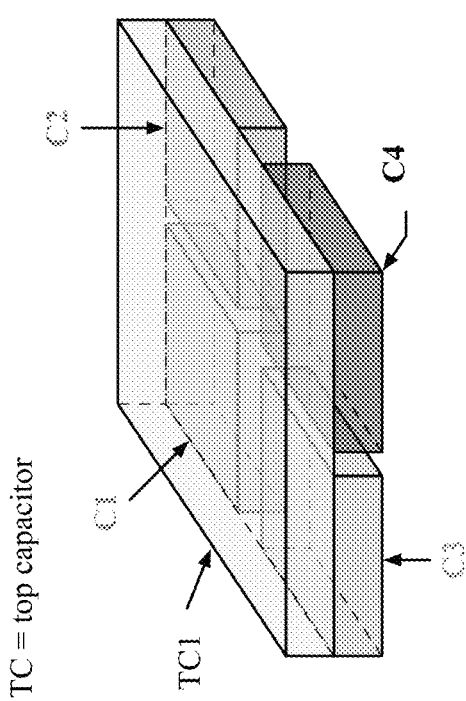
FIGS. 24A-24B are schematic block diagrams of examples of impact forces impacting a cell of FIG. 23.
Figure 24B:
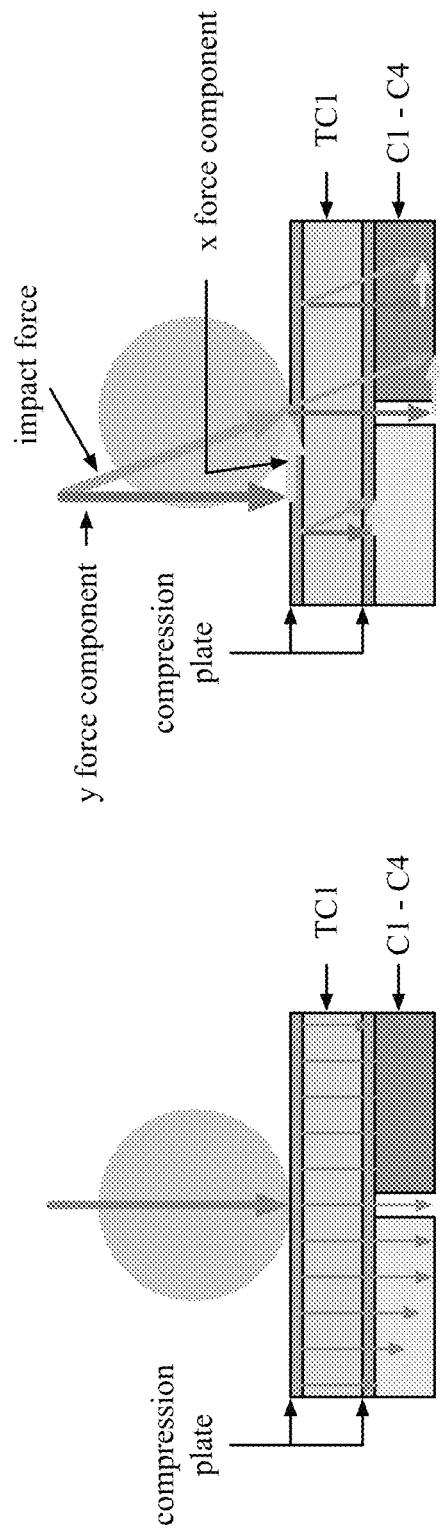

FIGS. 24A-24B are schematic block diagrams of examples of impact forces impacting a cell of FIG. 23. FIG. 24A is a front view of the first cell of FIG. 23. The cell is receiving a perpendicular force via an object. In this example, the object has a rounded outer shape resembling a cross section of a toe.

The top layer capacitor TCI is sandwiched between two compression plates. The first compression plate receives the impact force applied by the object. The impact area is small due to the shape of the object. The first compression plate transfers the impact force to the top layer capacitor TC1 in a three-dimension parabolic pattern. The force applied to the top layer capacitor TC1 is the largest and decreases in a parabolic manner the further away from the impact force area it gets. While this produces a nonlinear force gradient applied to the top layer capacitor TC1, the change is change in capacitance is measured as a single value to represent an average, or median, force.

The top layer capacitor TC1, as it is compressed, applies the parabolic force gradient to the second compression plate. The second compression plate transfers the parabolic force gradient to the lower layer capacitors (C1-C4). Each of the lower layer capacitors are compressed based on the force it receives. The capacitance change is used to determine the individual forces received by the lower layer capacitors. The combination of the capacitance changes to TC1 and to C1-C4 are used to determine the magnitude and direction of the impact force.

FIG. 24B is another front view of the first cell of FIG. 23. In this example, the top compression plate is receiving an impact force (e.g., the orange arrow) at an angle. As such, in this plane of view, the impact force includes an x force component (e.g., the yellow arrow) and a y force component (e.g., the red arrow). The impact force, and its x and y components, traverse through the cell. Due to the angle of the impact force, more force is transferred to C4 (e.g., the black shaded capacitor) than to C3 (the green shaded capacitor). As such, C4 will have a greater capacitance change than C3. The combination of capacitance changes of TC1 and C1 through C4 are used to calculate the magnitude and direction of the impact force as previously discussed.

As an alternative embodiment, a cell includes one compression plate and the four lower capacitors, omitting the top compression plate and the top layer capacitor. In another alterative embodiment, a cell includes the top layer capacitor and the four lower layer capacitors, omitting the compression plates.

Figure 25:
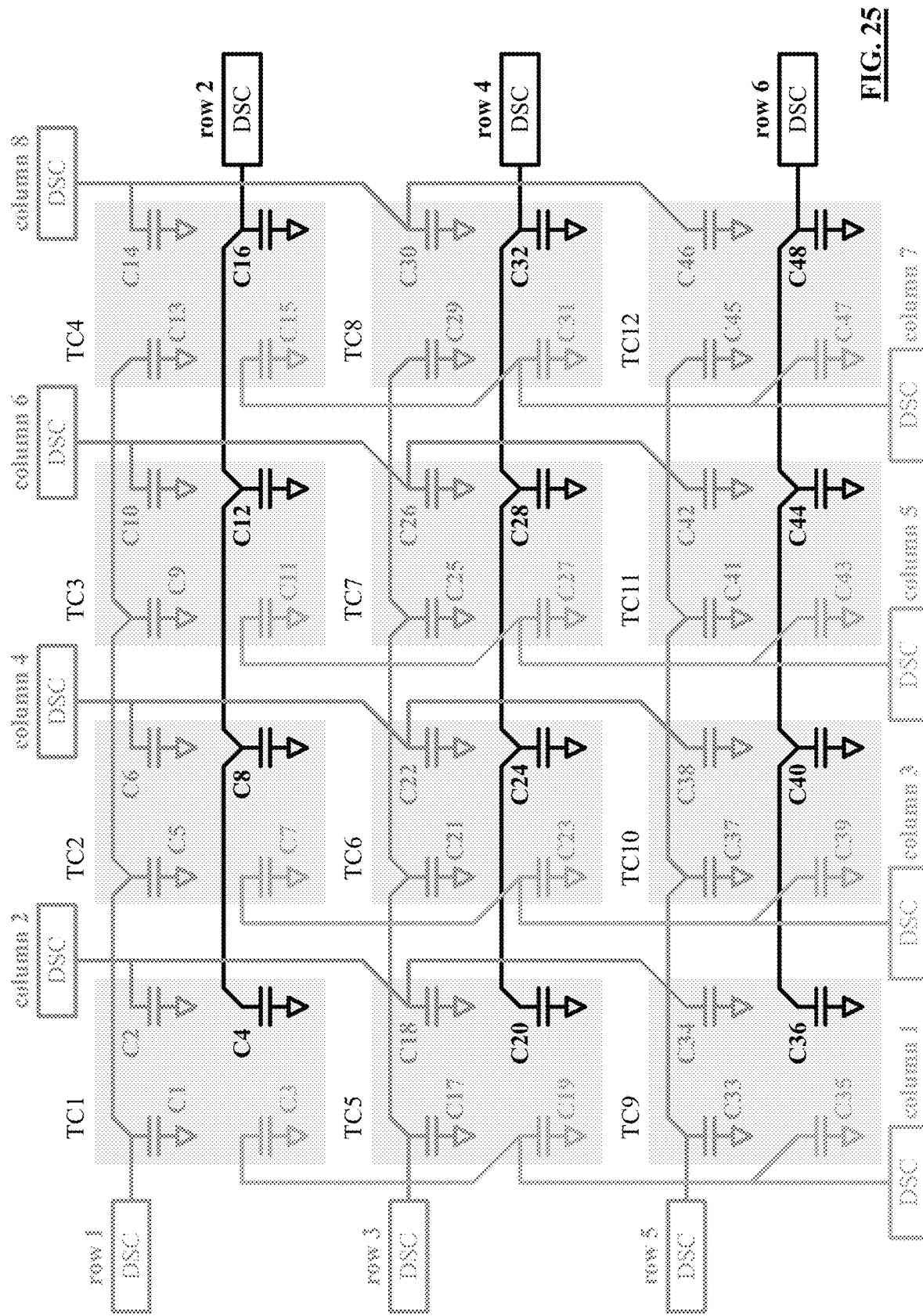
FIG. 25 is a schematic block diagram of an example of a plurality of cells.

FIG. 25 is a schematic block diagram of an example of a plurality of cells. Each cell includes three or more lower-level capacitors. Four shown in this example: C1=blue, C2=red, C3=green, and C4=black). The cell may further includes a top layer capacitor and/or one or more compression plates. In this example, the cell includes a top layer capacitor and two compression plates as shown in FIGS. 24A and 24B.

The cells are arranged in rows and columns. In this example, there are three rows and four columns of cells. From a capacitor perspective, there are six rows of capacitors and eight columns of capacitors. Each row and each column of capacitors is coupled to a drive sense circuit (DSC). For example, each blue capacitor of a cell in a row of cells (e.g., C1, C5, C9, C13) is coupled to a blue outlined drive sense circuit (DCS). The blue capacitors of the cells comprise rows 1, 3, and 5.

As another example, each black capacitor of a cell in a row of cells (e.g., C4, C8, C12, C16) is coupled to a block outlined drive sense circuit (DCS). The black capacitors of the cells comprise rows 2, 4, and 6.

As yet another example, each red capacitor of a cell in a column of cells (e.g., C2, C18, C34) is coupled to a red outlined drive sense circuit (DCS). The red capacitors of the cells comprise columns 2, 4, 6, and 8.

As a further example, each green capacitor of a cell in a column of cells (e.g., C3, C19, C35) is coupled to a green outlined drive sense circuit (DCS). The green capacitors of the cells comprise columns 1, 3, 5, and 7. In this example, there are forty-eight capacitors (c1-C48) and only fourteen drive sense circuits.

In an example, the row 1 DSC circuit drives and senses the blue capacitors in the first row of cells (C1, C5, C9, and C13). The blue capacitors are coupled in parallel, thus their collective capacitance with no compression is four times the minimum capacitance (assuming the capacitors are similar). If one or more of the capacitors is compressed, the collective capacitance of row 1 changes and is detected by the row 1 DSC. The row 1 DSC, however, cannot detect which of the four capacitors is experience the compression.

The same applies for each of the other row DSCs. For instance, the row 2 DSC drives and senses the collective capacitance of the black capacitors C4, C8, C12, and C16; the row 3 DSC drives and senses the collective capacitance of the blue capacitors C17, C21, C25, and C29; the row 4 DSC drives and senses the collective capacitance of the black capacitors C20, C24, C28, and C32; the row 5 DSC drives and senses the collective capacitance of the blue capacitors C33, C37, C41, and C45; and the row 6 DSC drives and senses the collective capacitance of the black capacitors C36, C40, C44, and C48.

Continuing with the example, the column 1 DSC circuit drives and senses the green capacitors in the first column of cells (C3, C19, and C35). The green capacitors are coupled in parallel, thus their collective capacitance with no compression is three times the minimum capacitance (assuming the capacitors are similar). If one or more of the capacitors is compressed, the collective capacitance of column 1 changes and is detected by the column 1 DSC. The column 1 DSC, however, cannot detect which of the three capacitors is experience the compression.

The same applies for each of the other column DSCs. For instance, the column 2 DSC drives and senses the collective capacitance of the red capacitors C2, C18, and C34; the column 3 DSC drives and senses the collective capacitance of the green capacitors C7, C23, and C39; the column 4 DSC drives and senses the collective capacitance of the red capacitors C6, C22, and C38; the column 5 DSC drives and senses the collective capacitance of the green capacitors C11, C27, and C43; the column 6 DSC drives and senses the collective capacitance of the red capacitors C10, C26, and C42; the column 7 DSC drives and senses the collective capacitance of the green capacitors C15, C31, and C47; and the column 8 DSC drives and senses the collective capacitance of the red capacitors C14, C30, and C46.

To identify a particular cell experiencing compression, capacitance changes for at least one of its rows and at least one of its columns are detected. For example, when row 1 DSC detects a capacitance change and column 4 DSC circuit detects a capacitance change, then it is determined that the cell labeled TC2 is experience compression. In particular, blue capacitor C5 and red capacitor C6 are being compressed. If row 1 and column 4 are the only capacitor row and capacitor column to experience a capacitance change, then the row capacitance change is attributable to capacitor C5 and the column capacitance change is attributable to capacitor C6.

If, however, row 1 and column 4 are not the only capacitor row and capacitor column to experience a capacitance change, then further processing is required to determine the capacitance change of each capacitor experiencing compression. FIGS. 26A-26D are schematic block diagrams of an example of such further processing.

Figure 26A:
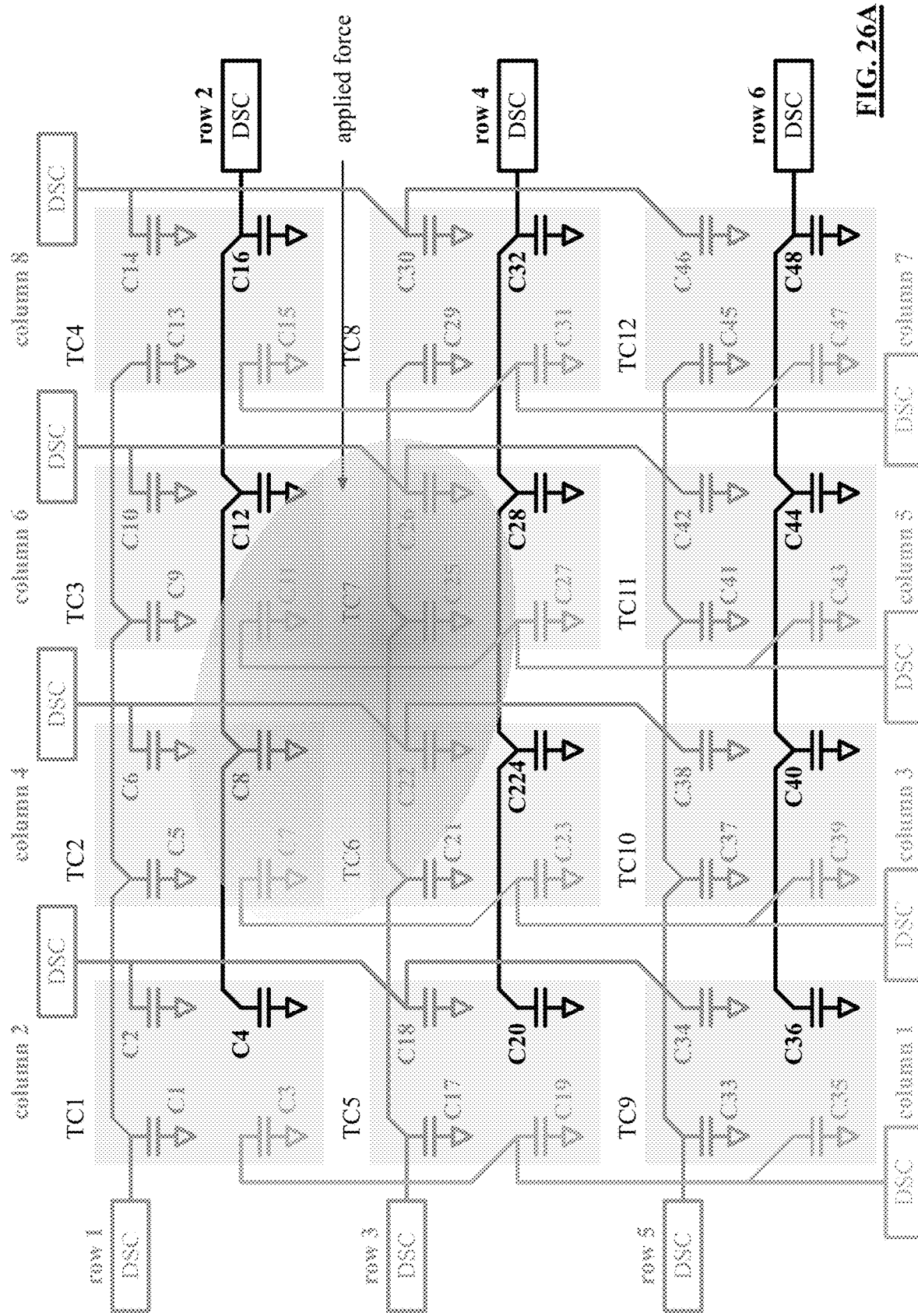
FIGS. 26A-26D are schematic block diagrams of an example of determining one or more normal vectors in response to an impact force.

FIG. 26A illustrates an applied force overlapping cells TC2, TC3, TC6, and TC7. The applied force has a magnitude gradient, where more force is represented by the color red and less force by the color yellow. In an example, the shape of the applied force corresponds to the ball of foot or a big toe.

Figure 26B:
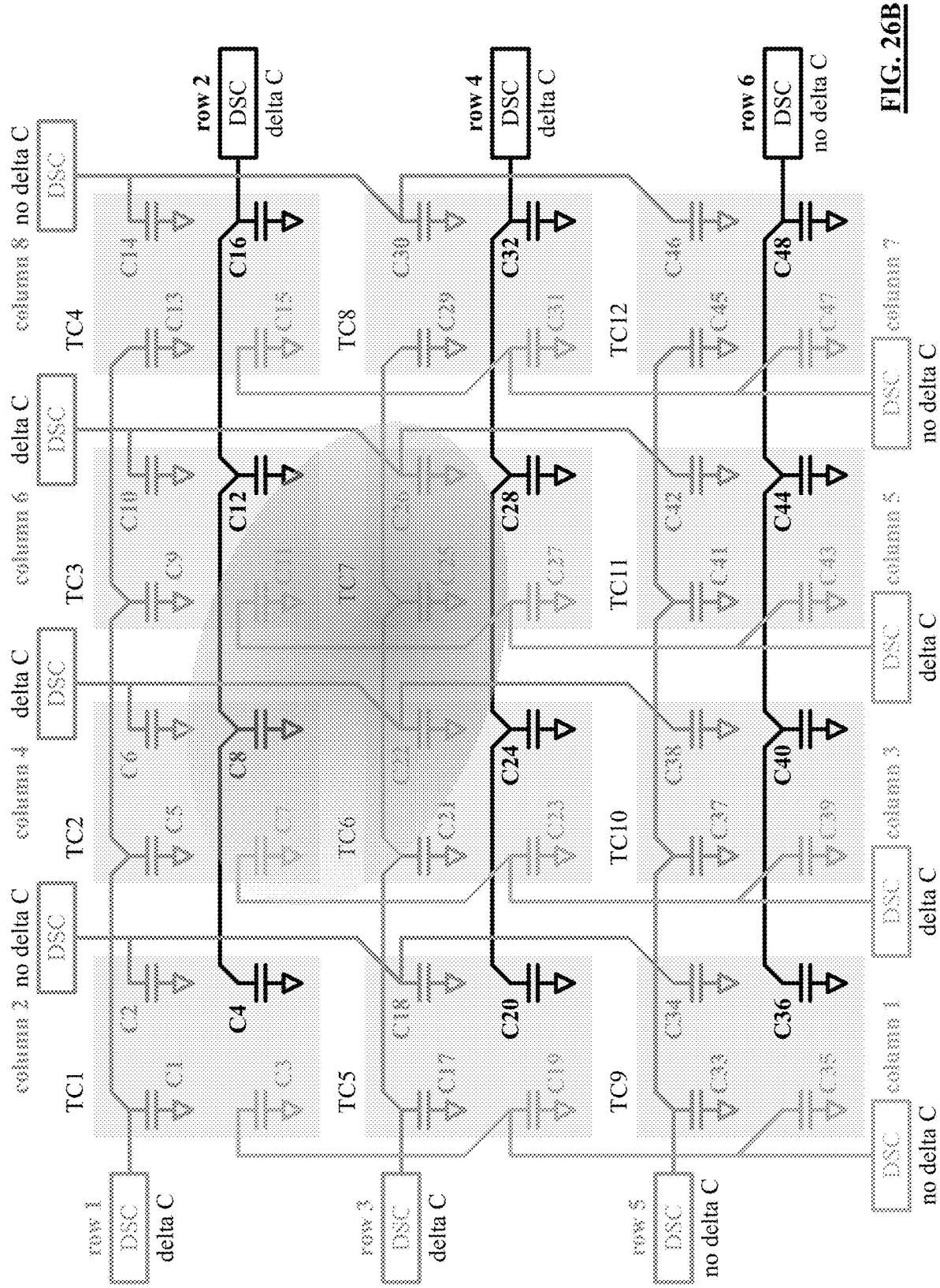

FIG. 26B illustrates which of the drive sense circuits (DSC) detects a capacitance as a result of the applied force. In this example, a capacitance change is represented as "delta C" and no capacitance change is represented as "no delta C". As shown, rows 1-4 and column 3-6 are experience a capacitance change and rows 5-8, columns 1, 2, 7, and 8 do not experience a capacitance change.

Figure 26C:
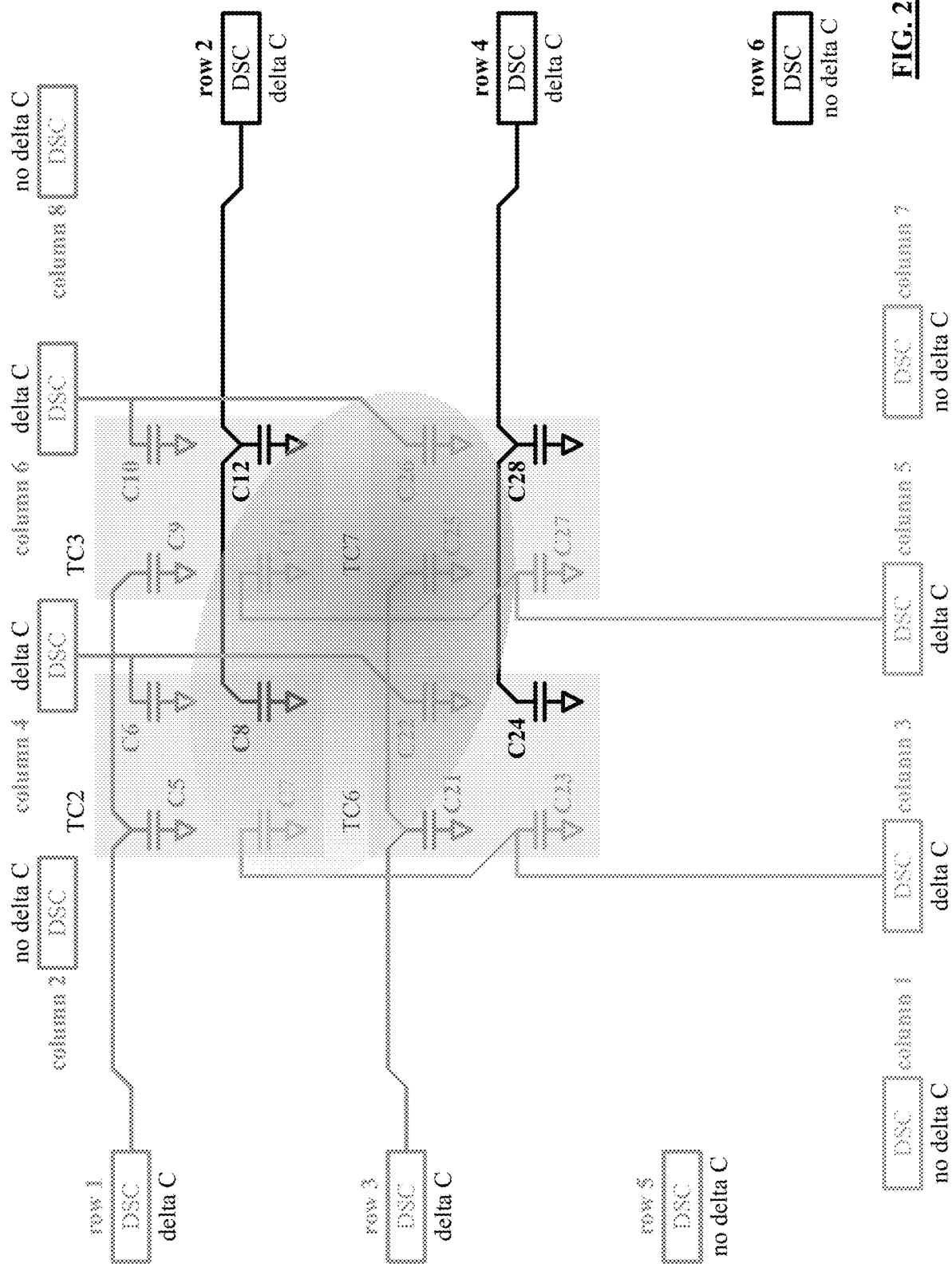

FIG. 26C illustrates the effected DSCs and capacitors of FIG. 26B. In this example, only capacitors C5 and C9 contribute to the capacitor change of row 1; only capacitors C8 and C12 contribute to the capacitor change of row 2; only capacitors C21 and C25 contribute to the capacitor change of row 3; and only capacitors C24 and C28 contribute to the capacitor change of row 4.

Also in this example, only capacitors C7 and C23 contribute to the capacitor change of column 3; only capacitors C6 and C22 contribute to the capacitor change of column 4; only capacitors C11 and C27 contribute to the capacitor change of column 5; and only capacitors C10 and C26 contribute to the capacitor change of column 7. The next processing task for each effected row and column is to determine the amount of change for each of the two effected capacitors. As an example, the next processing task is to determine the capacitance change of each of capacitors C5 and C9 for row 1.

As part of the next processing step, the capacitance changes on the row are ranked from lowest to highest and the capacitance changes on the columns are ranked from lowest to highest. For this example, row 3 has the highest capacitance change, then row 2, then row 4, and row 1 had the lowest capacitance change. For the columns, column 5 had the highest capacitance change, then column 4, then column 6, and column 3 had the lowest capacitance change.

Figure 26D:
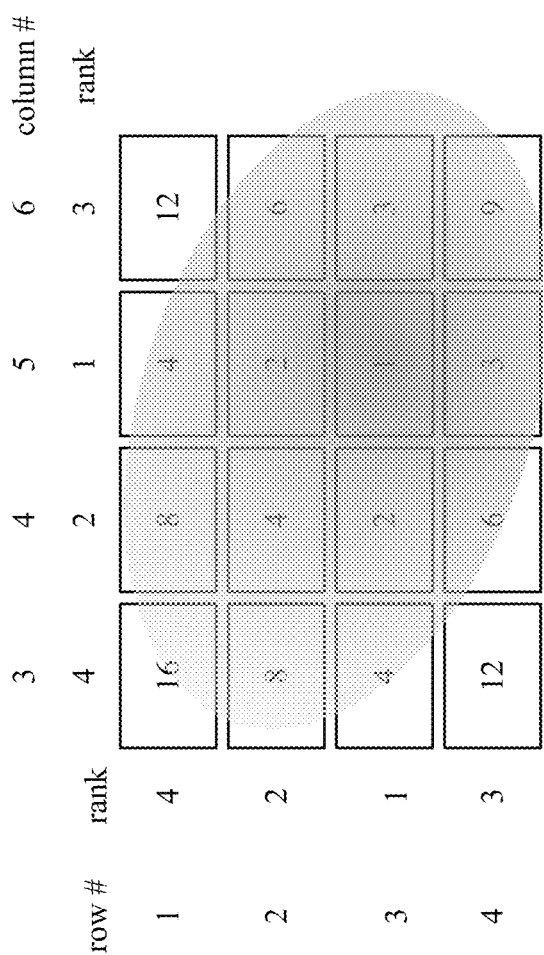

FIG. 26D illustrates the row and column rankings for capacitive changes. The row and column rankings are used to establish a row-column intersect ranking. In this example, the row ranking is multiplied by the column ranking to establish a row-column intersect score. The lower the row-column intersect score, the higher the capacitance change, which equates to more applied force. In this example, the approximate center of the applied force is at the intersection row 3 and column 5 since it has the lowest row-column intersect score.

The row-column intersect scores are then processed to determine a cell score. For example, the score for cell TC2 is the sum of the relevant row-column scores, which are in red text in the table. The resulting score is 36. The score for TC3 is 24, which is blue text; the score for TC6 is 24, which is green text, and the score for TC7 is 16, which is in black text. The cell scores are used to determine a capacitance change ratio between the capacitances in an effected for and in an effected column.

For example, the capacitance change detected by a row DCS is $\Delta C\_total = A*\Delta Ci + B*\Delta Cj + C*\Delta Ck + D*\Delta Cl$, with four capacitors in the row. The coefficients A, B, C, and D are determined based on the corresponding cell scores. As a specific example, row 4 includes capacitor C20 in cell TC5, capacitor C24 in cell TC6, capacitor C28 in cell TC7, and capacitor C32 in cell TC8. The cell scores for TC5 and TC8 are zero. Thus, for row 4, the capacitance change equation is $\Delta C\_total = 0*\Delta Ci + B*\Delta Cj + C*\Delta Ck + 0*\Delta Cl$, which equals $B*\Delta Cj + C*\Delta Ck$.

The coefficients B and C are determined from the cell scores of TC6 and TC7. For instance, $B = 1 - [TC6\ score/(TC6\ score + TC7\ score)]$ and coefficient $C = 1 - [TC7\ score/(TC6\ score + TC7\ score)]$. Using the data of the table in FIG. 26D, $B = 1 - (24/(24+16))$, which equals 0.4 and $C = 1 - (16/(24+16))$, which equals 0.6. Thus, 40% of the total capacitance change detected by the row 4 DSC is attributable to C24 and 60% of the total capacitance change is attributable to C28. Similar functions are used to determine the individual capacitance changes of the capacitors in cells TC2, TC3, TC6, and TC7. With the individual capacitances determined, the corresponding force is calculable, then the reference plane, then the normal vector, and then the magnitude and direction of the applied impact force.

Note that the various calculations as discussed with reference to FIGS. 17 through 26D are performed by the processing module of the force detection system 20 and/or by the computing entity. In an embodiment, the force detection system stores impedance values of the variable capacitors per sampling interval. The computing entity functions to convert the impedance into a capacitance value and the capacitance value into a pressure value (e.g., force over the area of a capacitor). The computing entity then determines the reference plane and the normal vector.

FIGS. 27A-27C are schematic block diagrams of an example of determining a normal vector of a cell of a force detection system in response to an impact force. In this example, the cell includes a top layer capacitor C1, a compressible and/or flexible ground plane, and three lower layer capacitors C2 and C3. FIG. 27A illustrates a top view of the cell where the top layer capacitor C1 substantially overlaps the three lower-level capacitors. FIGS. 27B and 27C illustrate side views of the cell. In this example, the cell is coupled to four drive sense circuits (DSC), one to each of the capacitors. The cell functions similarly to previously discussed cells.

Figure 28B:
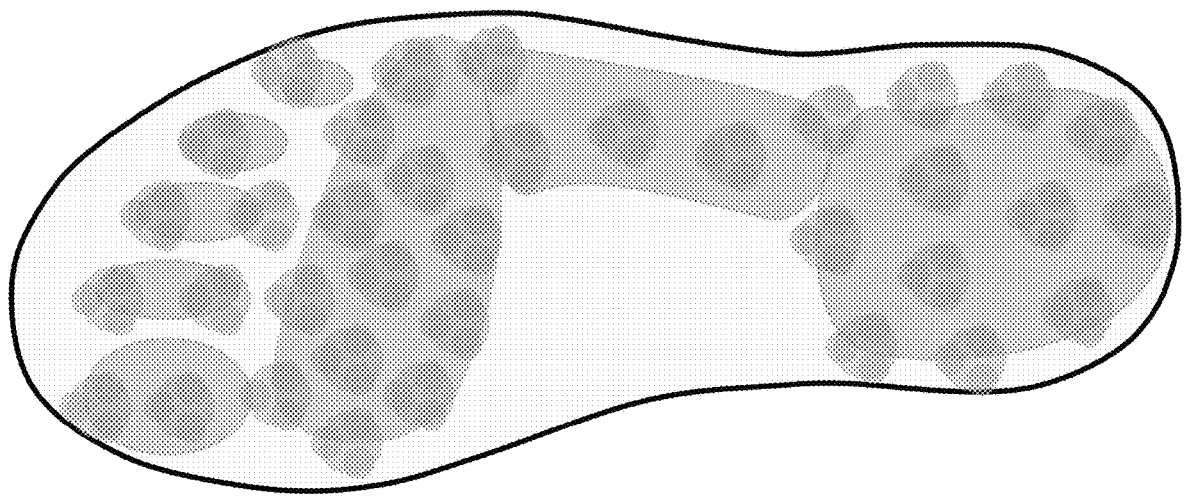
FIGS. 28A and 28B are schematic block diagrams of examples of placement of force cells within a sole of a shoe with respect to expected forces applied by a foot.
Figure 28A:
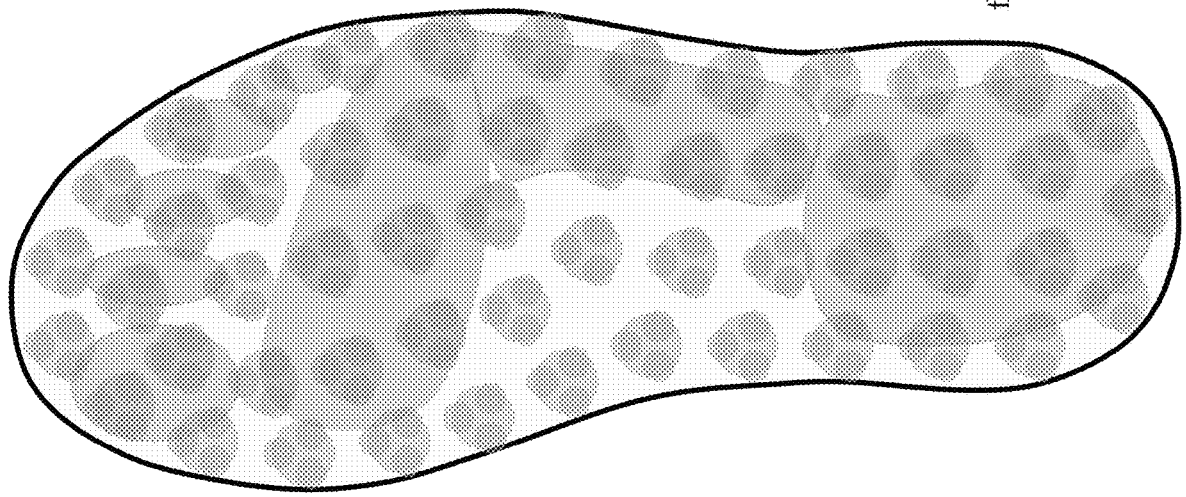

FIGS. 28A and 28B are schematic block diagrams of examples of placement of force cells within a sole of a shoe with respect to expected forces applied by a foot. FIG. 28A shows a full coverage cell placement pattern where the cells are substantially evenly distributed throughout the sole from a top view perspective. FIG. 28B shows the pressure sensor cells arranged in a toe zone, a ball of foot zone, a later midfoot zone, and a heal zone, wherein, within one of the zones, the pressure sensor cells are of approximately equal size. In another embodiment, the cells may be of different sizes. For example, a cell under the ball of foot is larger than a cell under a toe. In another embodiment, less cells are used in the selected coverage pattern.

Figure 29:
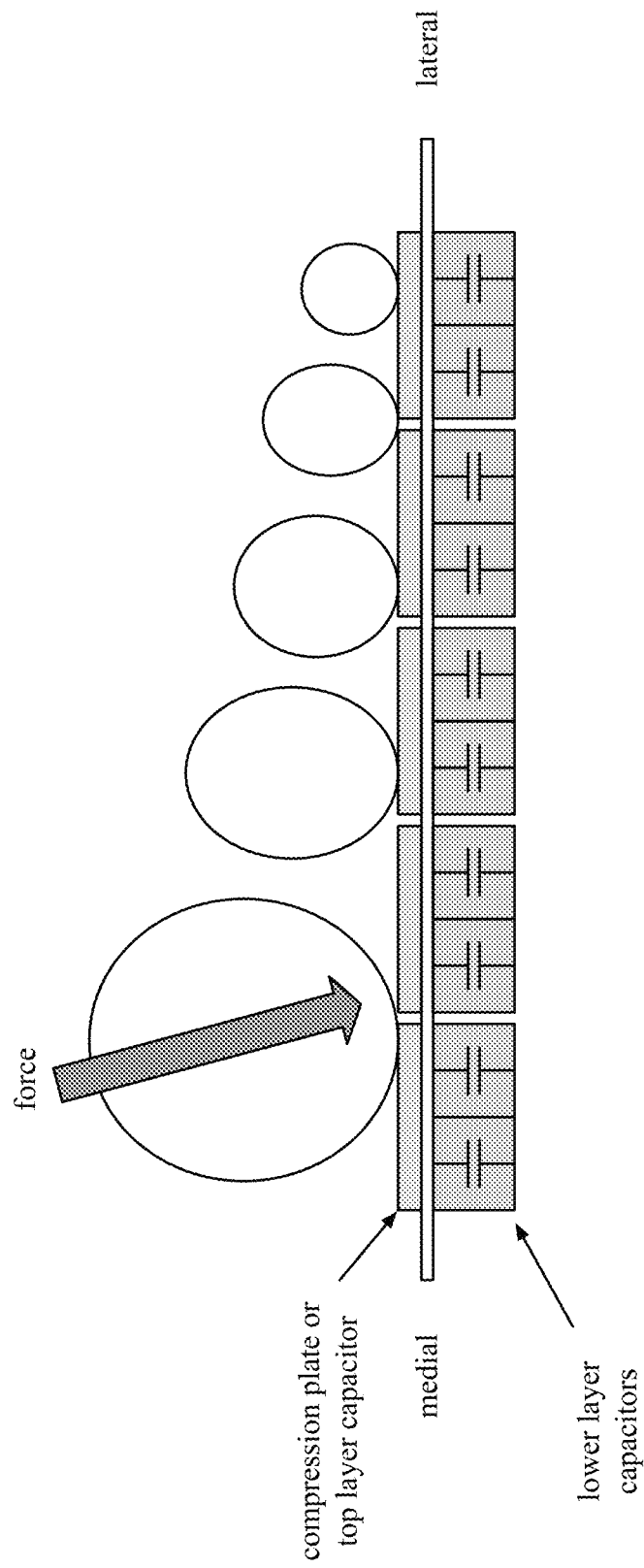
FIG. 29 is a schematic block diagram of an example of an angular impact force applied by a foot on the force detection system.

FIG. 29 is a schematic block diagram of an example of an angular impact force applied by a foot on the force detection system. In this example, a plurality of force cells is positioned from the medial side of a sole to the lateral side of the sole. As positioned, the cells are underneath the toes (from a front of the shoe perspective) and able to detect forces as previously described.

Figure 30:
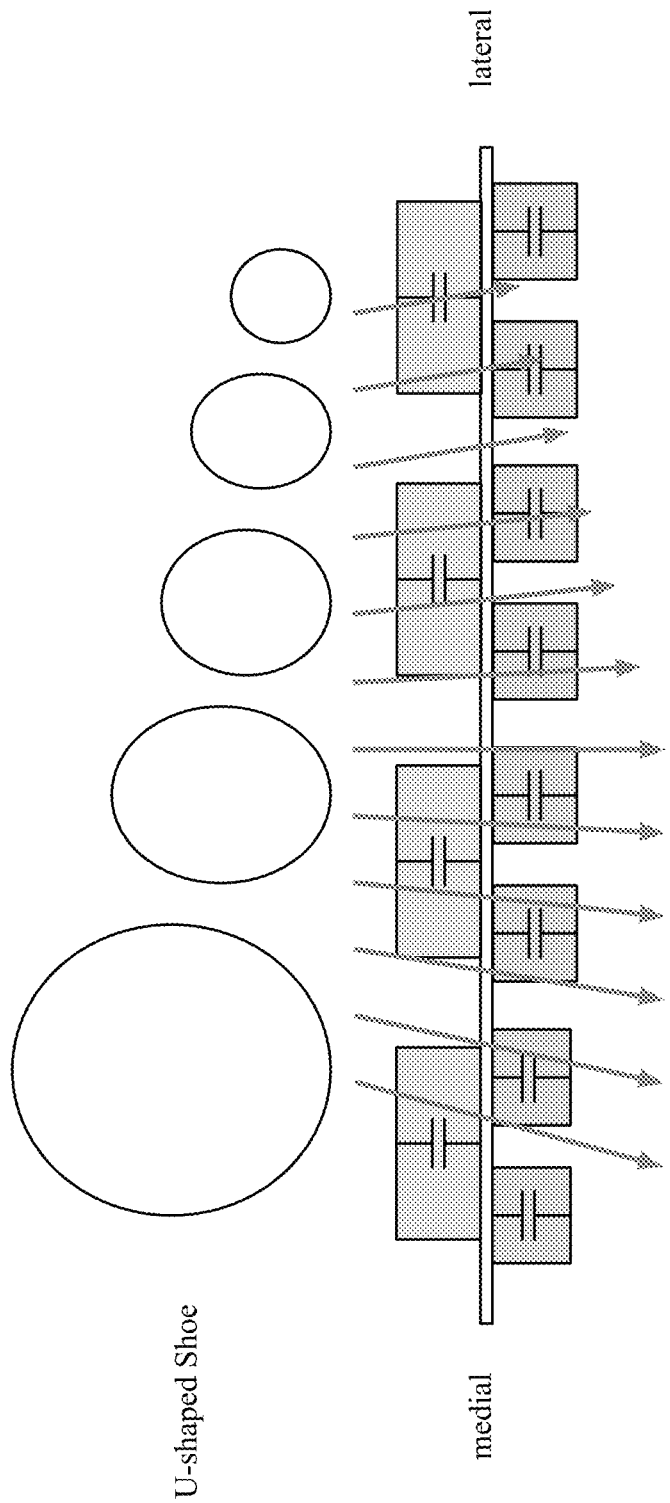
FIG. 30 is a schematic block diagram of another example of an angular impact force applied by a foot on the force detection system.

FIG. 30 is a schematic block diagram of another example of an angular impact force applied by a foot on the force detection system. In this example, the midsole has a U-shape, which causes the force to be radiated in a pattern has shown. This causes the ground reaction force to be angled away from the body, which adversely affects athletic performance. With the force detection system, such ground reaction force inefficiencies can be detected.

Figure 31:
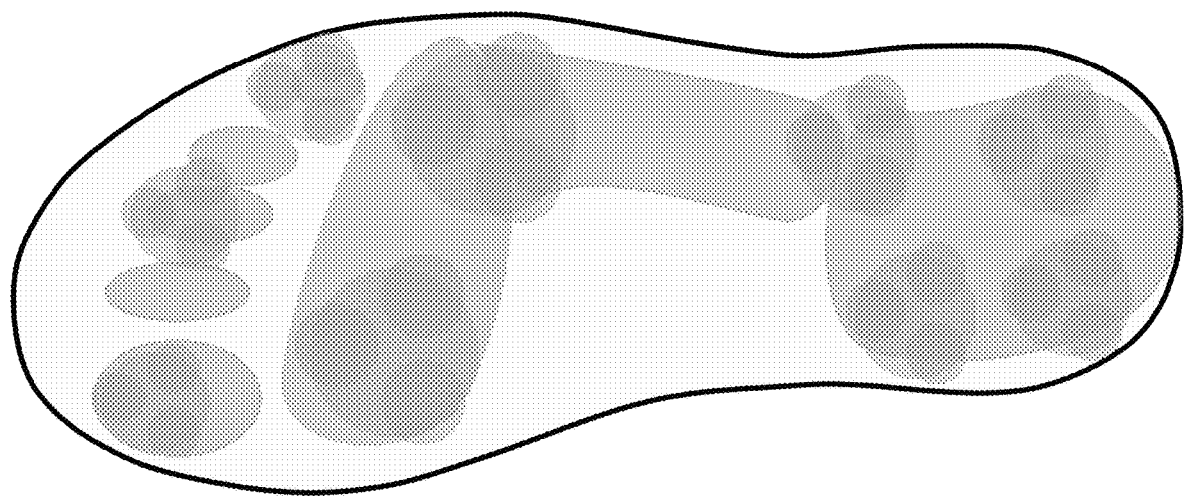
FIG. 31 is a schematic block diagram of another example of cell placement in a sole with respect to expected forces applied by a foot.

FIG. 31 is a schematic block diagram of another example of cell placement in a sole with respect to expected forces applied by a foot. In this example, nine cells are used and are of different sizes. Larger cells are positioned in the ball of foot area and smaller cells are positioned by the toes. The heal cells are smaller than the ball of foot cells but larger than the toe cells.

FIGS. 32A-32C are schematic block diagrams of another embodiment of force detection system 20. The force detection system 20 includes a layer of variable capacitors 200 and a circuitry section 104 in a sole of a shoe. The circuitry section 104 houses the circuitry of FIG. 3.

The layer of variable capacitors 200 includes variable capacitors that compress in the z-direction, variable capacitors that compress in the y-direction, and/or variable capacitors that compress in the x-direction. The different compression orientated variable capacitors may be on the same layer or in different layers. In an embodiment, the different compression orientated variable capacitors are in the same layer.

FIGS. 33A-33E are schematic block diagrams of an example of a cell of the force detection system of FIGS. 32A-32C. FIG. 33A is a top view of a force sensing cell that includes a z-direction compressible capacitor, y-direction compressible capacitors, x-direction compressible capacitors, and a cell housing. The cell may further include a compression plate.

The z-direction compressible capacitor changes its capacitance in accordance with a force in the z direction, but negligibly changes its capacitances as result of an x-direction force or a y-direction force. The y-direction compressible capacitor changes its capacitance in accordance with a force in the y direction, but negligibly changes its capacitances as result of an x-direction force or a z-direction force. The x-direction compressible capacitor changes its capacitance in accordance with a force in the x direction, but negligibly changes its capacitances as result of an z-direction force or a y-direction force.

Thus, when an applied impact force that includes x, y, and z components is applied to the cell, the z-direction compressible capacitor changes its capacitance based on the z component of the applied impact force; the y-direction compressible capacitor changes its capacitance based on the y component of the applied impact force; and the x-direction compressible capacitor changes its capacitance based on the x component of the applied impact force. As such, the capacitance change of the z-direction compressible capacitor represents the z component of the impact force; the capacitance change of the y-direction compressible capacitor represents they component of the impact force; and the capacitance change of the x-direction compressible capacitor represents the x component of the impact force.

From the x, y, and z force components determined based on capacitance, the magnitude and direction of the impact force on the cell can be determined. In essence, it is a conversion from Cartesian coordinates to polar coordinates.

FIG. 33B is a side view of an embodiment of the cell of FIG. 33A. The cell includes the housing and the directional capacitors. In this side view, which is from the x-z plane, the z-direction compressible capacitor is between the two x-direction compressible capacitors. When an impact force is applied to the cell that includes an x and a z component, the z direction compressible capacitor changes its capacitance based on the z direction force component. With a positive x force component, the x-direction compressible capacitor in the positive x direction changes its capacitance based on the x direction force component. The x-direction compressible capacitor in the negative x direction does not change its capacitance assuming that when no force is applied, the capacitor is at its minimum (no compression) value.

In an embodiment, the x-direction compressible capacitors each have mid-point compression (e.g., 40% to 60% of full compression) when no impact force is applied to the cell. In this manner, when an x force is applied to the cell, one of the x-direction compressible capacitors compresses further and increases its capacitance while the other is compressed less and decreases its capacitance. The two changes are then used to determine the x force magnitude and direction.

The y-direction compressible capacitors function in a similar manner as the x-direction compressible capacitors, only in the y direction instead of x direction.

FIG. 33C is a side view of an embodiment of the cell of FIG. 33A. The cell includes the housing, the directional capacitors, and compression plate. In this side view, which is from the y-z plane, the z-direction compressible capacitor is below the compression plate, which is between the two y-direction compressible capacitors. When an impact force is applied to the cell that includes a y and a z component, the z direction compressible capacitor changes its capacitance based on the z direction force component. With a positive y force component, the y-direction compressible capacitor in the positive y direction changes its capacitance based on the y direction force component. The y-direction compressible capacitor in the negative y direction does not change its capacitance assuming that when no force is applied, the capacitor is at its minimum (no compression) value.

In an embodiment, the y-direction compressible capacitors each have mid-point compression (e.g., 40% to 60% of full compression) when no impact force is applied to the cell. In this manner, when a y force is applied to the cell, one of the y-direction compressible capacitors compresses further and increases its capacitance while the other is compressed less and decreases its capacitance. The two changes are then used to determine the y force magnitude and direction.

FIG. 33D is a top view of a force sensing cell that includes a z-direction compressible capacitor, x-direction compressible capacitors, and a cell housing. The cell may further include a compression plate. The compressible capacitors function as previously described. Such a force sensing cell is used in the force detection system where there is a z force component and an x force component and a negligible y force component. For example, the cell is used for medial to lateral force detection in a shoe where there will be negligible toe to heal force.

FIG. 33E is a top view of a force sensing cell that includes a z-direction compressible capacitor, y-direction compressible capacitors, and a cell housing. The cell may further include a compression plate. The compressible capacitors function as previously described. Such a force sensing cell is used in the force detection system where there is a z force component and a y force component and a negligible x force component. For example, the cell is used for in the toe area.

Figure 34:
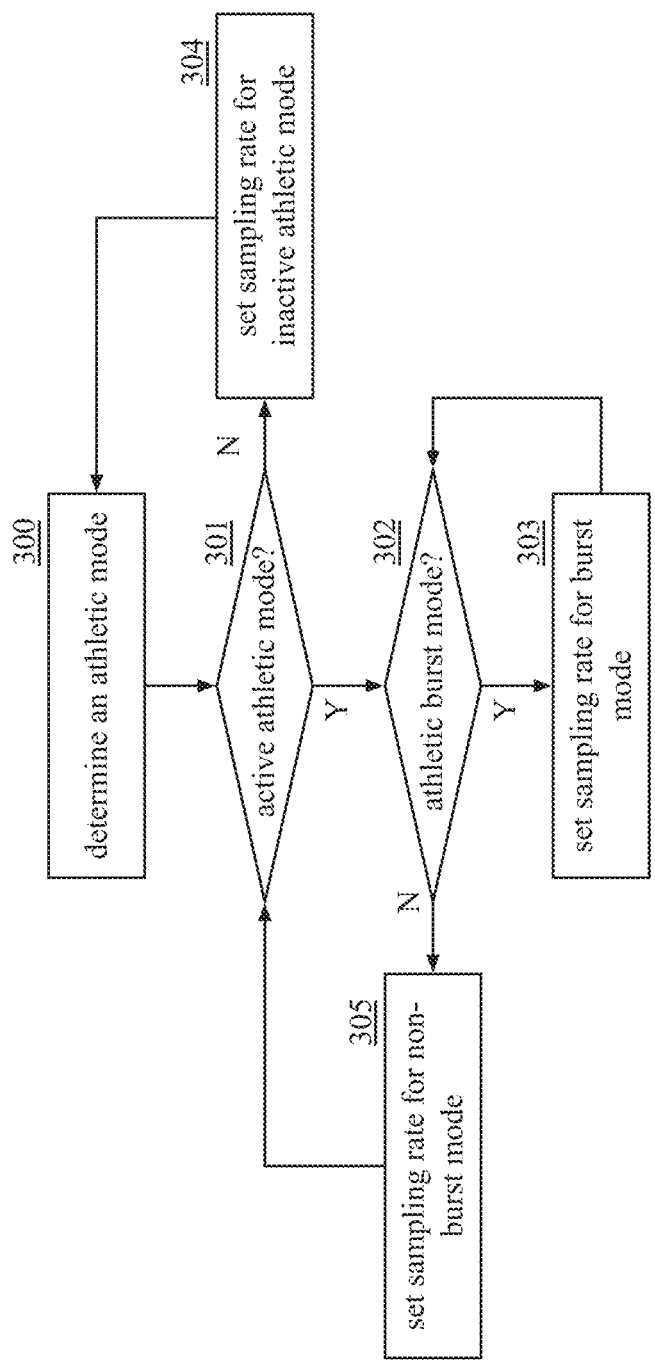
FIG. 34 is a logic diagram of an example of establishing a foot force sampling rate.

FIG. 34 is a logic diagram of an example of a method for establishing a foot force sampling rate. The method begins at step 300 where a processing module of a foot force detection system determines an athletic mode. For example, an athletic mode is of whether an athlete is actively engaged in an athletic event or is not actively engaged in an athletic event. For example, a golfer playing golf is actively engaged and, if the golfer is in the club house, the golfer is not actively engaged. As another example, a baseball player is actively engaged in playing baseball when the player is on his/her feet and is not actively engaged when seated (e.g., on the bench).

In an embodiment, the processing module detects an inactive to active foot force pattern of a shoe, and/or a pair of shoes, that includes the foot force detection system. For example, in golf, the processing module detects a foot pattern movement consistent with playing golf. As a specific example, a foot pattern of walking the course and/or of driving a golf cart. As another example, in baseball, the processing module detects a foot force pattern of being on the mound, in the batter's box, being on base, and/or being in the field.

The method branches at step 301 to step 302 when the athlete is actively engaged and to step 304 when the athlete is not actively engaged. At step 302, the processing module determines whether the athlete is in a burst mode. For example, a burst mode for a golfer is when the golfer is about ready to hit a golf ball through hitting the golf ball. As another example, a burst mode of a baseball player is when the player is ready to hit a baseball, to throw a baseball, and/or is in the field readying himself or herself to catch a baseball.

In an embodiment, the processing module determines the athletic burst mode by detecting an active to burst foot force pattern of a shoe, and/or pair of shoes, that includes the foot force detection system.

When in the burst mode, the method continues at step 303 where the processing module sets a second sampling rate for the foot force detection system based on the athletic burst mode for sampling foot force data. The second mode sampling rate is set between 100 samples per second to 10,000 or more samples per second depending on the athletic activity. For example, detecting foot force of a sprinter requires a high sampling rate (e.g., greater than 1 KHz) to capture multiple frames of foot force data for each foot strike. The method repeats at step 302.

When in the active athletic mode but not in the athletic burst mode, the method continues at step 305 where the processing module sets a first sampling rate for the foot force detection system. The first sampling rate is less than the second sampling rate (e.g., the athletic burst sampling rate). For example, the first sampling rate is in the range of 5% to 90% of the second sampling rate.

When not in the active mode, the method continues at step 304 where the processing module establishes an inactive sampling rate for the foot force detection system. The inactive sampling rate is set to a range of 0% to 90% of the first sampling rate (e.g., active but not in burst mode).

In an embodiment, the processing module determines the sampling rate for the foot force detection system further by determining a period of a foot to ground contact. The processing module then determines a duty cycle of the foot to ground contact for the period. The processing module then determines the sampling rate based on the duty cycle and the period. For example, the period of a foot to ground contact for a sprinter (e.g., the inverse of time between left foot strikes and/or the inverse of time between right foot strikes) is about 2 Hertz (0.5 seconds between left foot or right foot strikes, which assumes a 10 second time in a 100-meter dash and a stride length (left foot to right foot) of 2.5 meters).

Continuing with the sprinter example, the duty cycle is the contact time of the foot with ground. Assuming that the foot is in contact with the ground for 40 milli-Seconds (mS), then the duty is 0.04/0.5, which is 8%. If 100 foot-force samples are desired per foot strike, then a sample needs to be taken once every 40 mS/100, or once every 400 micro-Seconds ($\mu$S), which is a sampling rate of 2.5 KHz.

By varying the sampling rate during using of the foot force detection system reduces power consumption, which is an important commercial aspect of the foot force detection system. Note that in a three-hour baseball game or a football game, it is estimated that there is about 11 minutes of actual play. By adjusting the sampling rate to be low, other than during the actual play, significant power is saved than having a common sampling rate throughout a game.

Figure 35:
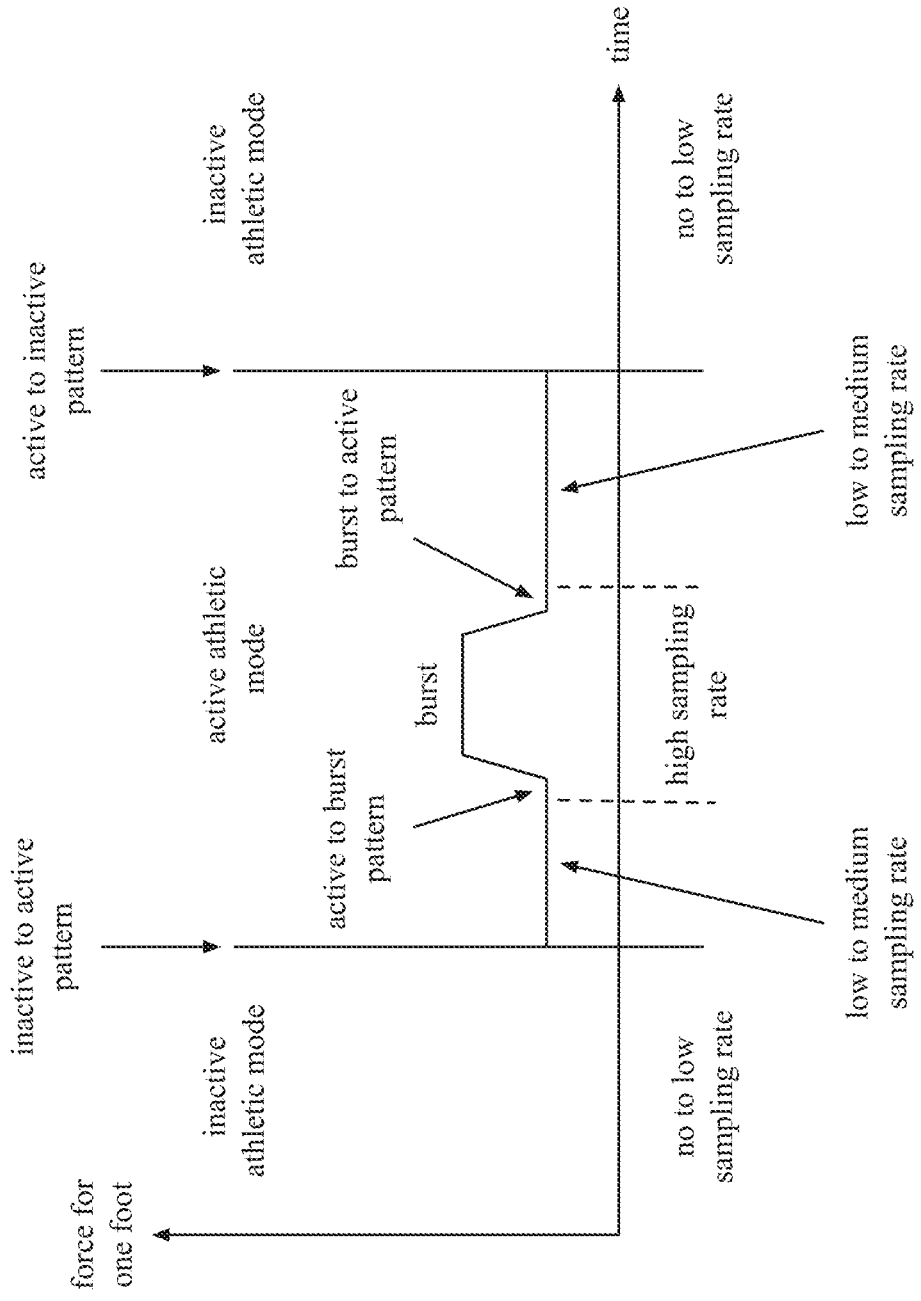
FIG. 35 is a schematic block diagram of an example of a foot force sampling rate.

FIG. 35 is a schematic block diagram of an example of a foot force sampling rate. As shown, force for a foot is the y-axis and time is on the x-axis. Time is broken down into a first inactive athletic mode interface, an active athletic mode interval, and a second inactive athletic mode interval. The active athletic mode interval includes an athletic burst period positioned in time between two active non-burst mode intervals.

During the inactive athletic modes, the sampling rate is set between 0 and some low rate (e.g., 1-20 Hz). When the foot force detection system detects an inactive to active foot pattern, the active athletic mode interval begins. In this mode, the sampling rate is set to a low to medium sampling rate (e.g., 20 Hz to a few hundred Hz).

When an active to burst foot pattern is detection, the burst athletic mode interval begins. In this mode, the sampling rate is set to a medium to high sampling rate (e.g., a few hundred Hz to 10 kHz or more). When the system detects a burst to active foot pattern, the sampling rate is adjusted to the low to medium rate. When the system detects an active to inactive foot pattern, the sampling rate is adjusted to the 0 to low rate.

Figure 36:
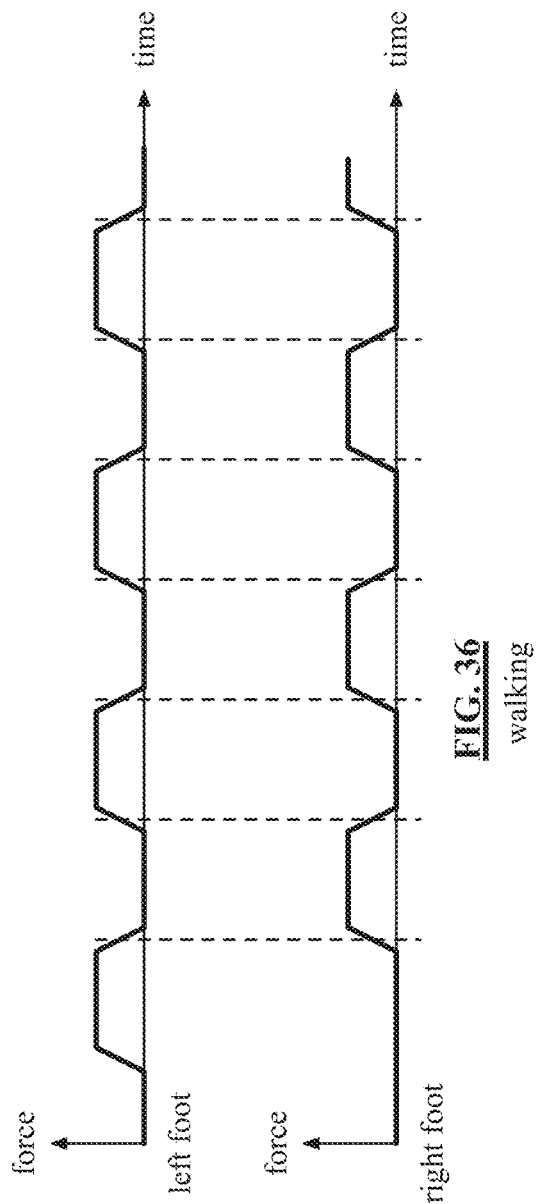
FIG. 36 is a schematic block diagram of an example of a foot force pattern.

FIG. 36 is a schematic block diagram of an example of a foot force pattern for walking. In this example, force is switched from the left foot to the right foot with some force overlap in time.

Figure 37:
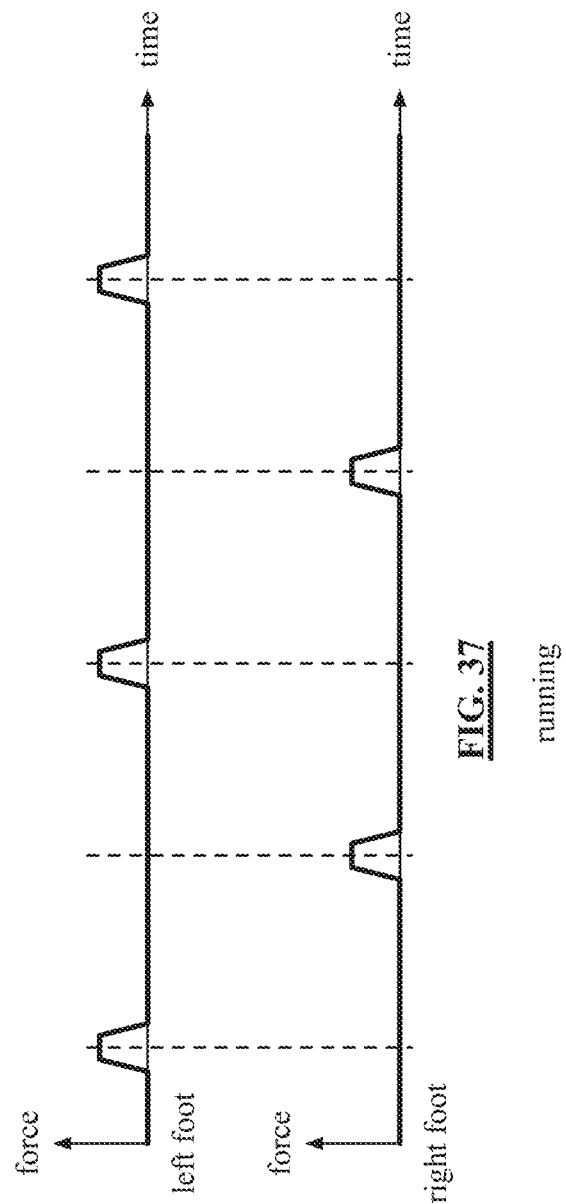
FIG. 37 is a schematic block diagram of another example of a foot force pattern.

FIG. 37 is a schematic block diagram of another example of a foot force pattern running. In this example, there are periods of time where neither foot is on the ground and short bursts of time when a foot is on the ground. In running, the foot force can be up to six times body weight.

Figure 38:
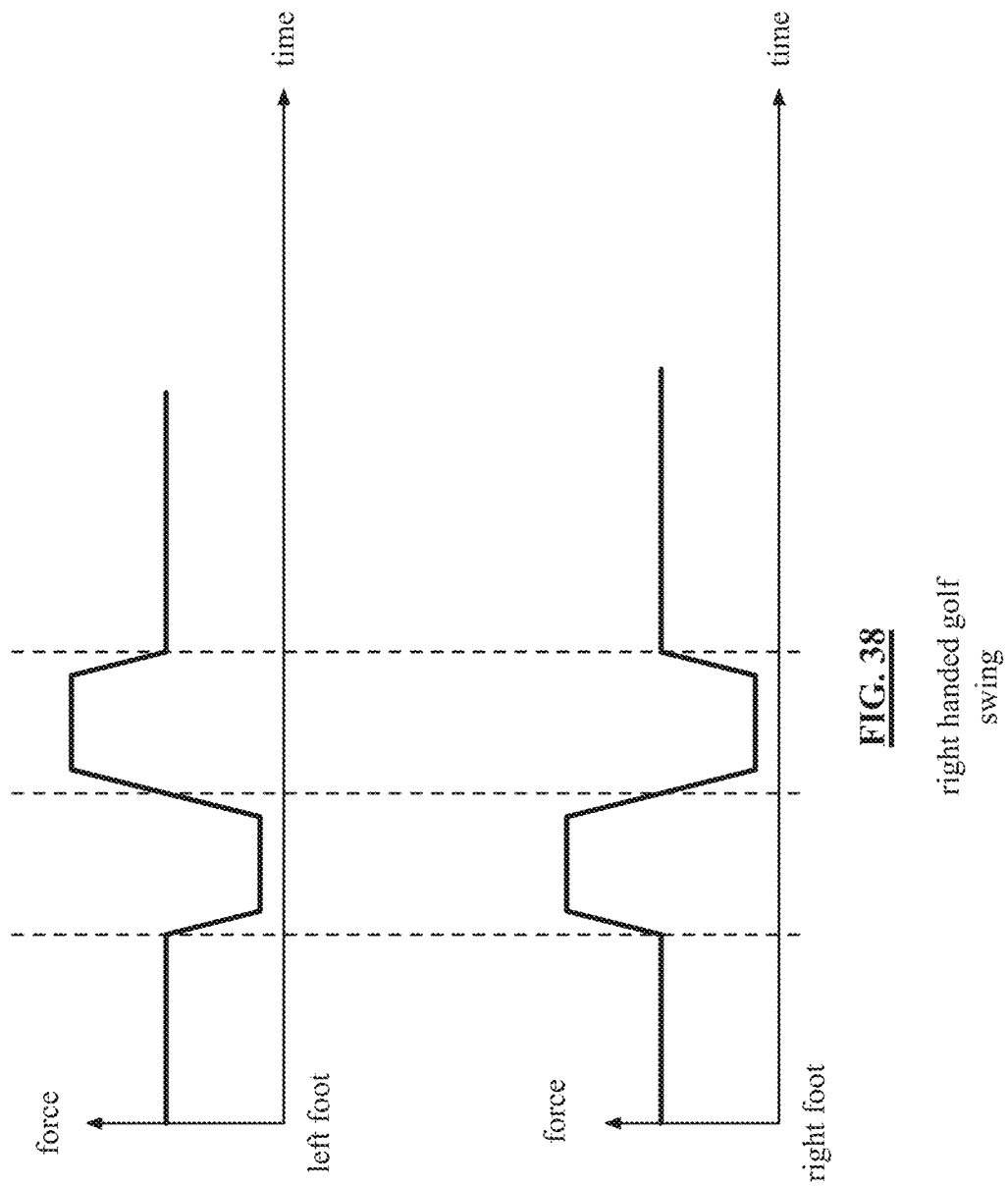
FIG. 38 is a schematic block diagram of another example of a foot force pattern.

FIG. 38 is a schematic block diagram of another example of a foot force pattern for hitting a golf ball or a baseball. Prior to hitting, weight is about equally distributed between the feet. During the backswing, more weight is transferred to the back leg and less is on the front foot. During the downswing, weight is being transferred from the back leg to the front leg. From the right foot to the left foot for a right-handed hitter.

At the point of contact, most of the weight is transferred to the front leg (e.g., the left foot for a righty). As the hitter follows through, the weight eventually balances back out to being equally distributed between both feet.

A combination of foot force patterns can be used to detect an inactive to active pattern, to detect an active to burst pattern, to detection a burst to active pattern, and an active to inactive pattern. For example, for a golfer, an inactive period would be detected when there is not pressure on either foot (e.g., sitting in a cart). The walking pattern of FIG. 36 is used to detect an inactive to active pattern (e.g., golfer is out of the cart and walking towards a golf ball).

When the golfer's feet settle to set up for a swing, the pattern of FIG. 38 is used to detect the active to burst pattern and the burst to active pattern. When the golfer stops walking and there is not force on either foot indicates the active to inactive pattern.

The patterns used to trigger the different sampling rates can be implemented in a variety of ways. For example, the pattern for a golfer is generic and includes a pattern as discussed above. As another example, the pattern for a golfer is unique to the golfer based on historical foot force data. As yet another example, the pattern for a sport is generic to the typical foot patterns of that sport. As a further example, the pattern for an athlete for a specific sport is unique to the athlete based on historical foot force data.

Figure 39:
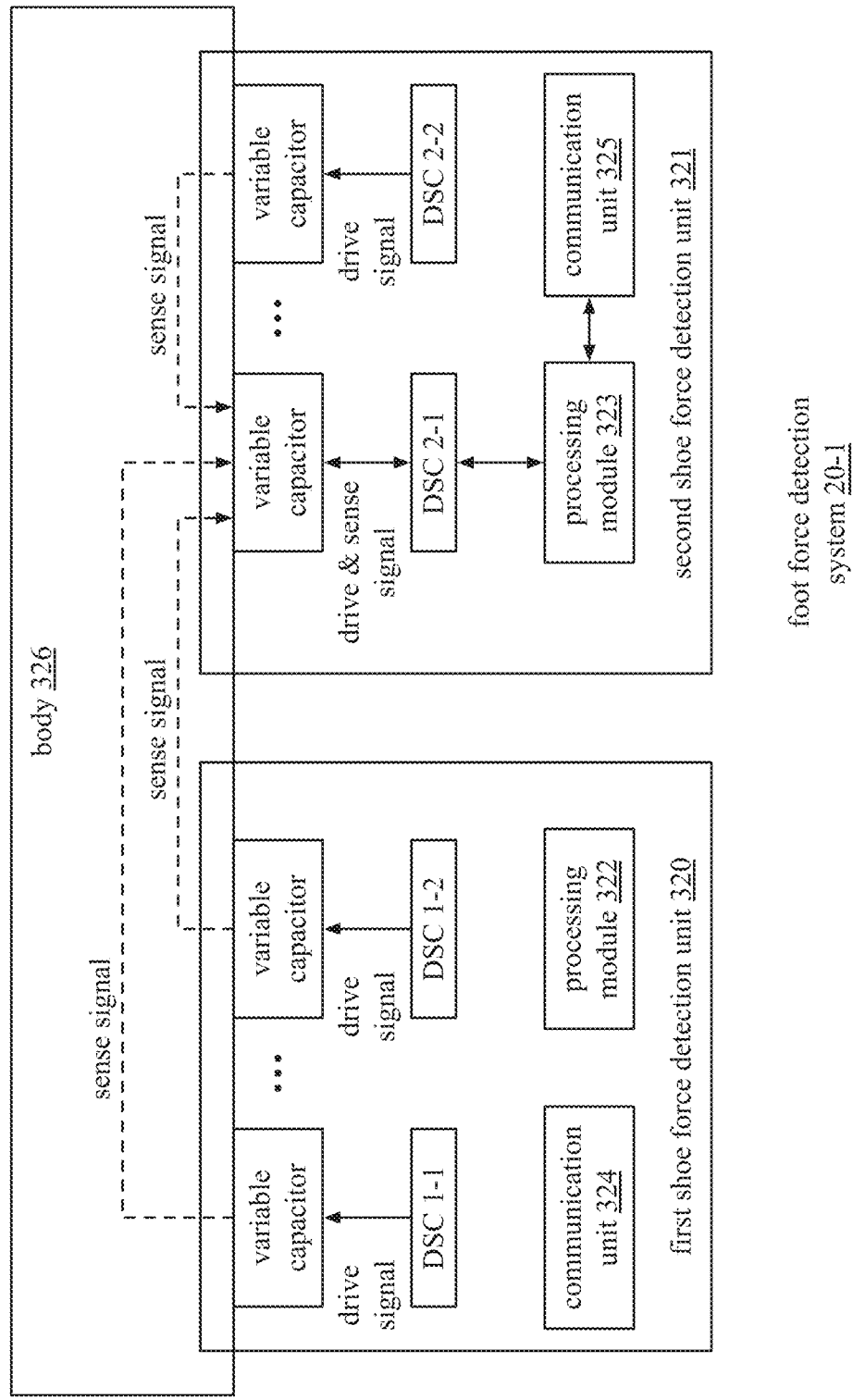
FIG. 39 is a schematic block diagram of an embodiment of a foot force detection system.

FIG. 39 is a schematic block diagram of an embodiment of a foot force detection system 20-1 that includes a first shoe force detection unit 320 and a second shoe force detection unit 321 that communication sensed signals via the body 326 of a user of the system 20-1. Each of the detection units 320 and 321 includes a plurality of variable capacitors, a plurality of drive sense circuits (DSC), a processing module 322, 323, and a communication unit 324, 325.

The variable capacitors vary their capacitance based on pressure. In addition, the variable capacitors have an electrically conductive plate to which the body, via the feet, is connected. One or more of the drive sense circuits (DSC) is operable to provide a drive signal to its corresponding variable capacitor and, on the same line, sense one or more sense signals of one or more variable capacitors. Other DSCs are operable to provide a drive signal to their corresponding variable capacitors.

In this example, DSC 2-1 of the second shoe force detection unit 321 is operable to provide a drive signal to its variable capacitor and to receive sense signals from its variable capacitor and from the variable capacitors associated with DSC 1-1,1-2, and 2-2. DSC 1-1 provides a first drive signal to its variable capacitor; DSC 1-2 provides a second drive signal to its variable capacitor; DSC 2-1 provides a third drive signal to its variable capacitor; and DSC 1-1 provides a fourth drive signal to its variable capacitor.

DSC 2-1 is further operable to receive a sense signal regarding its variable capacitor and sense signals regarding the other variable capacitors via the body of the wearer of the foot force detection system. A first sense signal corresponds to the first drive signal supplied to the variable capacitor associated with DSC 1-1; a second sense signal corresponds to the second drive signal supplied to the variable capacitor associated with DSC 1-2; a third sense signal corresponds to the third drive signal supplied to the variable capacitor associated with DSC 2-1; and a fourth sense signal corresponds to the fourth drive signal supplied to the variable capacitor associated with DSC 2-2.

DSC 2-1 supplies the third drive signal to its variable capacitor and generates the third sensed signal based on a characteristic of its variable capacitor. For example, DSC 2-1 generates the third sensed signal regarding an impedance of its variable capacitor. DSC 2-1 converts the third sense signal into a third digital signal. It does the same for the first, second, and fourth senses to produce first, second, and fourth digital signals.

In this example, processing module 323 and communication unit 325 are active, while processing module 322 and communication unit 324 are inactive. With one set of processing module and communication unit active at a time, overall power consumption of the foot force detection system 20-1 is reduced.

Processing module 323 generates a first digital impedance for the first variable capacitor based on the first digital signal; generates a second digital impedance for the second variable capacitor based on the second digital signal; generates a third digital impedance for the third variable capacitor based on the third digital signal; and generates a fourth digital impedance for the fourth variable capacitor based on the fourth digital signal. The digital impedances may be stored in memory and/or communicated to a computing entity via the communication unit 325.

Figure 40:
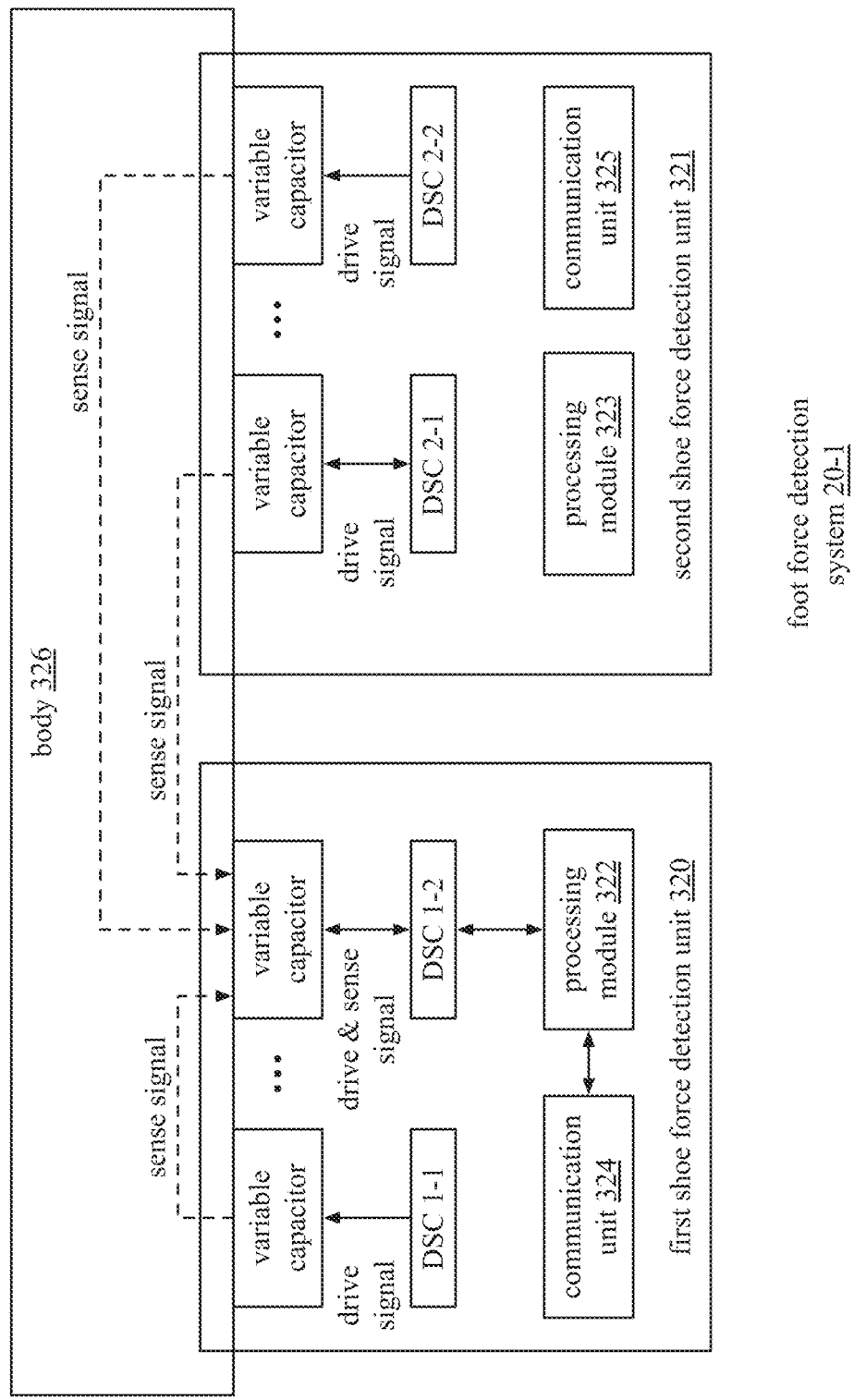
FIG. 40 is a schematic block diagram of another embodiment of a foot force detection system.

FIG. 40 is a schematic block diagram of another embodiment of a foot force detection system 20-1, which is similar to the system of FIG. 39. In this embodiment, DSC 1-2 is active to drive and sense signals and the other DSC are supplying drive signals. Further, processing module 322 and communication unit 324 are active and processing module 323 and communication unit 325 are inactive.

DSC 1-2 functions similarly to DSC 2-1 as described with reference to FIG. 39 to produce the first, second, third, and fourth digital signals. Processing module 322 processes the first-fourth digital signals to produce first-fourth digital impedances similarly to the processing performed by processing module 323 as discussed with reference to FIG. 39.

By switching back and forth between the first and second shoe force detection units being operable to process sensed signals and create digital impedance values therefrom, overall power consumption of the foot force detection system 20-1 is reduced. Further, the switching back and forth balances power consumption between the two shoe force detection units 320 and 321.

Figure 41:
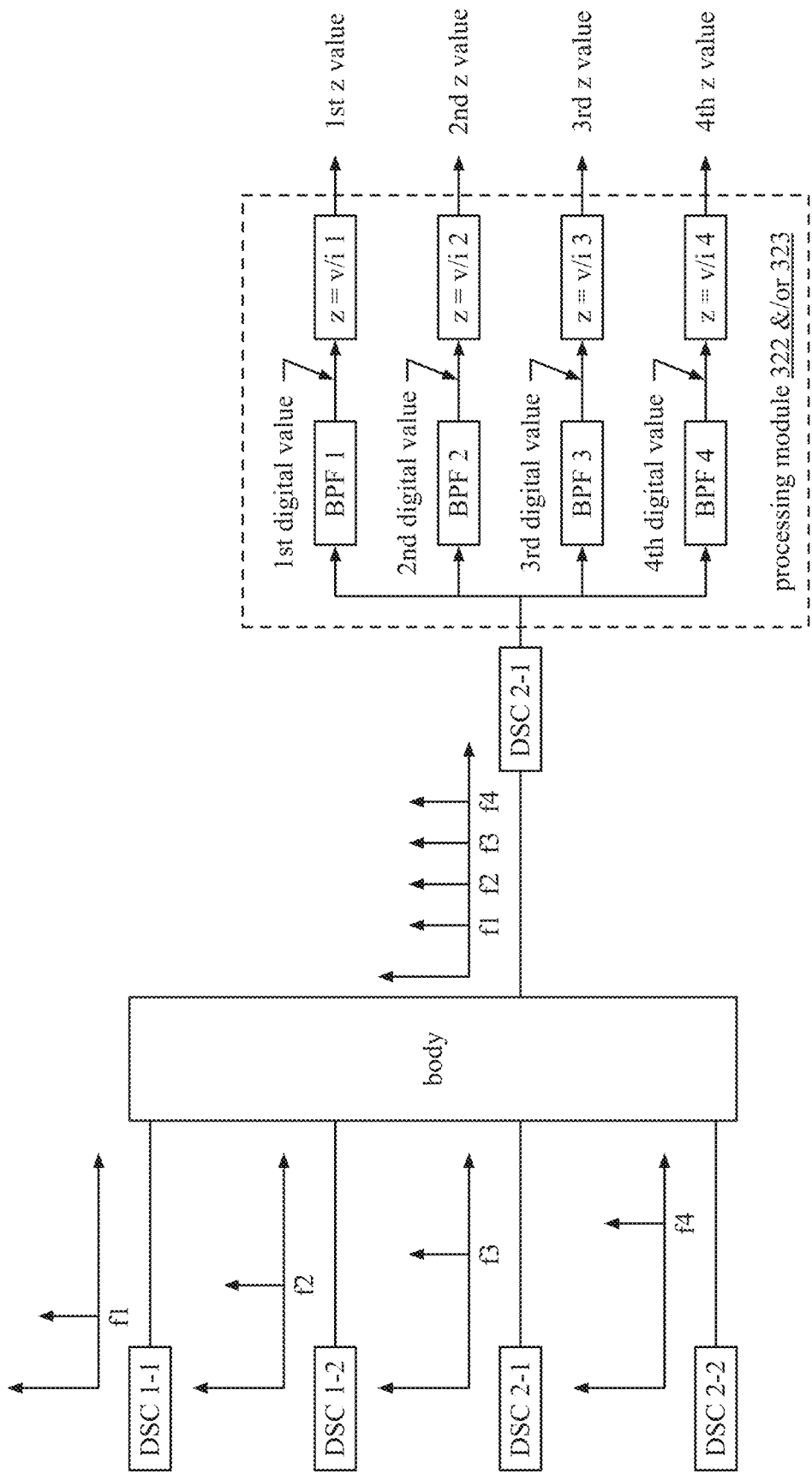
FIG. 41 is a schematic block diagram of an example of processing foot force detection.

FIG. 41 is a schematic block diagram of an example of processing foot force detection. In this example, the drive sense circuits (DSCs) of FIGS. 39 and 40 generate their respective drive signals using different frequencies. For example, DSC 1-1 generates a drive signal having an oscillating component at a first frequency (f1); DSC 1-2 generates a drive signal having an oscillating component at a second frequency (f2); DSC 2-1 generates a drive signal having an oscillating component at a third frequency (f3); and DSC 2-2 generates a drive signal having an oscillating component at a fourth frequency (f4).

In the example of FIG. 39, DSC 2-1 receives the sensed signals from itself and the other DSCs. In this example, the received signal has four frequency components f1-f4. The processing module is configured or includes, four bandpass filters (BPF 1-4), and four impedance calculation units (z=v/i 1-4). The BPFs separate the frequency components to produce the first, second, third, and fourth digital values.

For the first digital value, the first impedance calculation unit generates a first impedance therefrom. For example, the first digital value represents the current at the first frequency that is sourced to the first variable capacitor (i.e., the output of the op amp of the DSC corresponds to the current). The voltage supplied to the first variable capacitor is fixed based on the reference signal. Thus, for the first variable capacitor at the first frequency, voltage and current are known. As such, the first impedance value is equal to the voltage divided by the current. The other impedance values are calculated in a similar manner. Note that an impedance value is generated per interval of a sampling rate of the foot force detection system.

Figure 42:
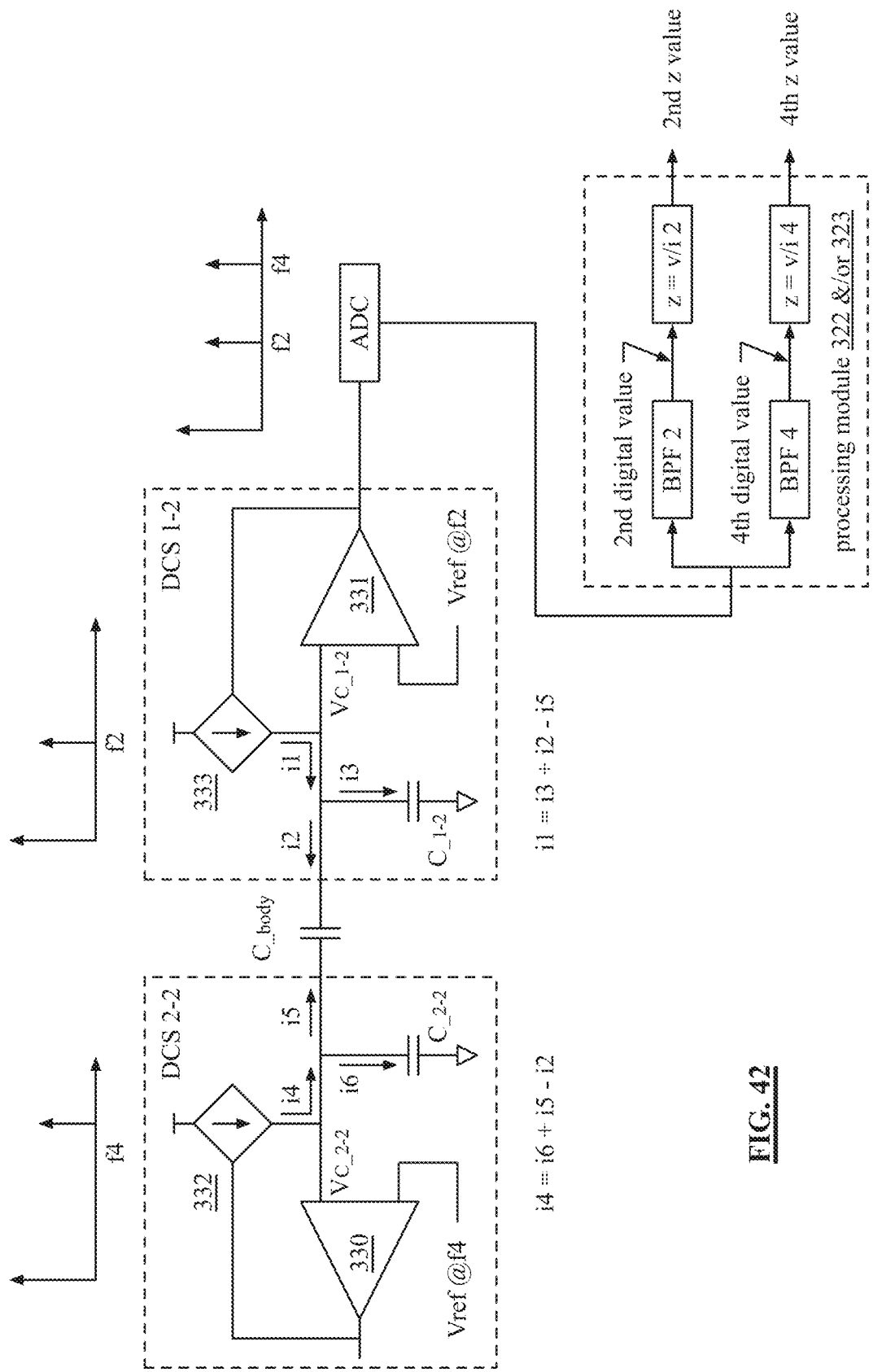
FIG. 42 is a schematic block diagram of another example of processing foot force detection.

FIG. 42 is a schematic block diagram of another example of processing foot force detection. In this example, DSC 2-2 and 1-2 are shown, which corresponds to variable capacitors 2 and 4 and frequencies f2 and f4 of the example of FIG. 40. The processing module 322, 323 is shown to include BPF 2 and 4 and impedance calculators 2 and 4.

Each of the DSCs are shown with just the op-amp 330, 331 and the dependent current source 332, 333. Capacitor $C_{-2-2}$ represents the variable capacitor associated with DSC 2-2 and capacitor $C_{-1-2}$ corresponds to the variable capacitor associated with DSC 1-2. Capacitor $C_{\_body}$ is the capacitance of the body, which is typically about 100 pF. In this example, capacitance of capacitors $C_{-1-2}$ and $C_{-2-2}$ range from 2.25 to 4.45 pF.

Each DSC functions to keep its input voltages of their respective op-amps equal. To do this, the output of the op amp is adjusted to adjust the current supplied by the respective dependent current source 332, 333. As the load increases in impedance of a DSC, the current it produces correspondingly increases, but the voltage at the inputs of the op amp remain constant. As such, DSC 2-2 keeps both inputs of its op amp equal to the reference voltage that has an oscillating component at frequency f4 by regulating current i4. Similarly, DSC 1-2 keeps both inputs of its op amp equal to the reference voltage that has an oscillating component at frequency f2 by regulating current i1.

Figure 43:
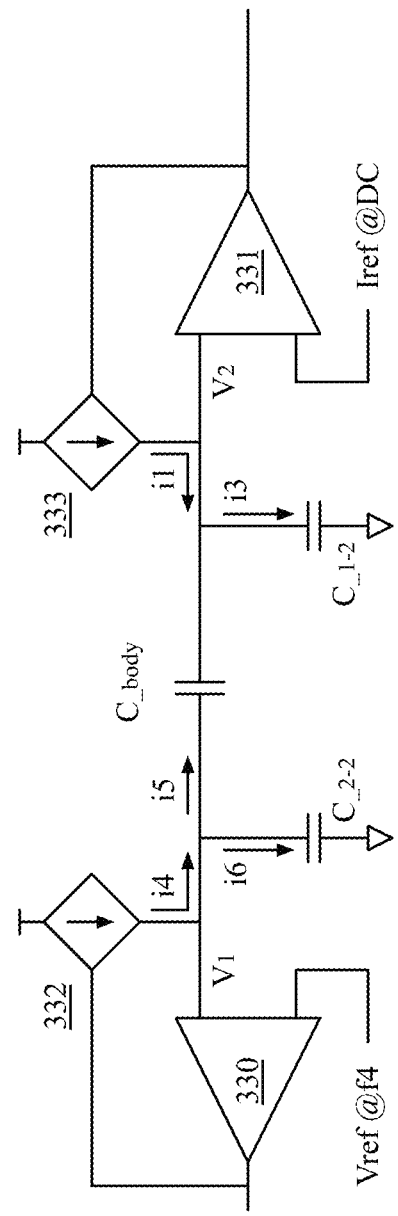
FIG. 43 is a schematic block diagram of another example of processing foot force detection.
Figure 44:
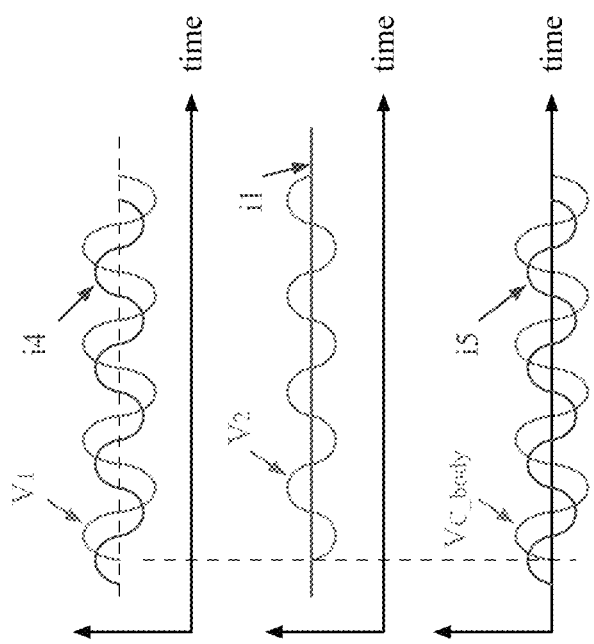
FIG. 44 is a graphic diagram of an example of signals of the example of FIG. 43.

As shown, i4=i6+i5−i2; i1=i3+i2−i5; $Z_{C\_2-2}=V_{C\_2-2}/i6$; and $Z_{C\_1-2}=V_{C\_1-2}/i3$. Thus, to determine the impedance of the variable capacitors ($Z_{C\_2-2}$ and $Z_{C\_1-2}$), i3 and i6 need to be independently determined. Due to the coupling of the body capacitance, determining i3 and i6 include a current component from both DSCs. FIGS. 43 and 44 illustrate an example of determining i3 and i6.

FIG. 43 is a schematic block diagram of another example of processing foot force detection. In this example, the reference signal received by op amp 330 of DSC 2-2 is a voltage reference signal that includes a DC component and an oscillating component that has a frequency at f4 (e.g., 10 KHz or more). The reference signal received by the op amp 331 of DSC 1-2 is a current reference signal that has a DC component. As such, i1 is equal to the reference current signal and V2 will vary based on load variance.

In the AC domain, i4=i6+i5; i1=i3−i5; i1=Iref=0. What is also known: V1=Vref @f4; $V_{C\_body}$=V1−V2; the body capacitance is known (e.g., 100 pF). The impedance of the body capacitor is calculated as $Z_{C\_body}=1/(2*\pi*f4*C_{\_body})$ and current i5 is calculated as $(V1-V2)/Z_{C\_body}$. Further, i3=Iref+i5, which in the AC domain, i3=i5. The impedance of $Z_{C\_1-2}$ is equal to V2/i3. From the preceding, the capacitance of $C_{-1-2}$ is calculated as $1/(2*\pi*f4*Z_{C\_1-2})$.

FIG. 44 is a graphic diagram of an example of signals of the example of FIG. 43. In this example, i4 lags V1 by 90 degrees since it is driving a primarily capacitor load (e.g., $C_{-2-2}$ in parallel with the series combination of $C_{\_body}$ and $C_{-1-2}$). With i1=Iref, then V2 is 180 degrees out of phase of V1 and its magnitude is scaled based on the capacitance ratio of $C_{\_body}$ to $C_{-1-2}$. $V_{C\_body}$ is equal to V1−V2 and $i5=V_{C\_body}/Z_{C\_body}$.

Figure 45:
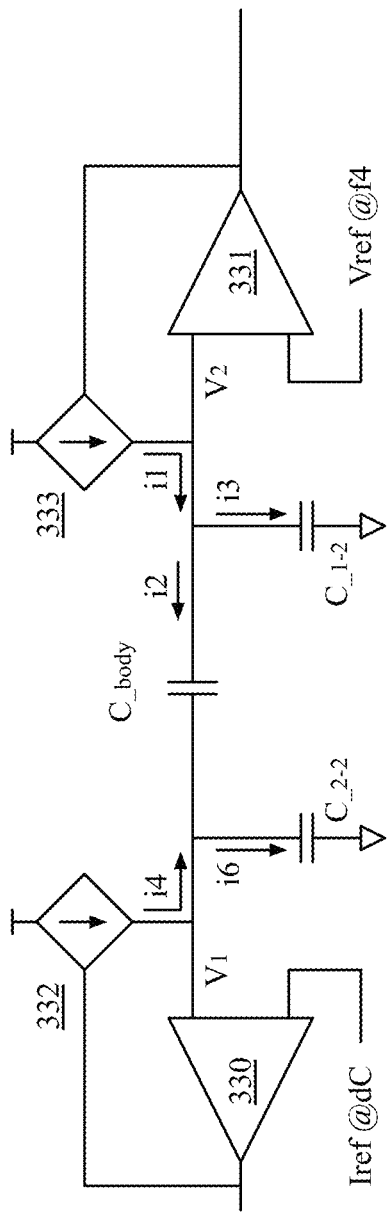
FIG. 45 is a schematic block diagram of another example of processing foot force detection.

FIG. 45 is a schematic block diagram of another example of processing foot force detection. In this example, the reference signal received by op amp 331 of DSC 1-2 is a voltage reference signal that includes a DC component and an oscillating component that has a frequency at f4 (e.g., 10 KHz or more). The reference signal received by the op amp 330 of DSC 2-2 is a current reference signal that has a DC component. As such, i4 is equal to the reference current signal and V1 will vary based on load variance.

In the AC domain, i1=i2+i3; i4=i6−i2; i4=Iref=0 (at AC). What is also known: V2=Vref @f4; $V_{C\_body}$=V2−V1; the body capacitance is known (e.g., 100 pF), the impedance of the body capacitor is known, and the impedance of $C_{-1-2}$ is known. Current i3 is calculated as $(V2)/Z_{C\_1-2}$. Further, i6=i2=i1−i3. Since i1 is known based on the output of op amp 331 and i3 was just calculated, i6 is known. Further, V1 is known for the output of op amp 330. As such, the impedance of $Z_{C\_2-2}$ is determined based on V1/i6. From the preceding, the capacitance of $C_{-2-2}$ is calculated as $1/(2*\pi*f4*Z_{C\_2-2})$.

Figure 46:
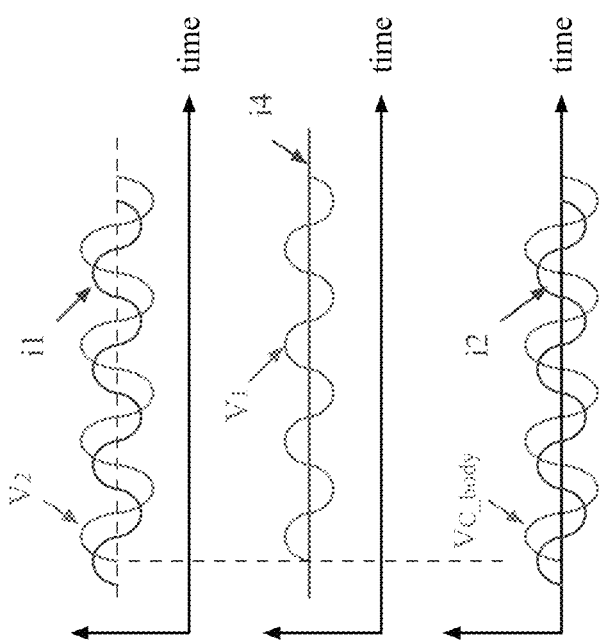
FIG. 46 is a graphic diagram of an example of signals of the example of FIG. 45.

FIG. 46 is a graphic diagram of an example of signals of the example of FIG. 45. In this example, i1 lags V2 by 90 degrees since it is driving a primarily capacitor load (e.g., $C_{-1-2}$ in parallel with the series combination of $C_{\_body}$ and $C_{-2-2}$). With i4=Iref, then V1 is 180 degrees out of phase of V2 and its magnitude is scaled based on the capacitance ratio of $C_{\_body}$ to $C_{-2-2}$. $V_{C\_body}$ is equal to V2−V1 and $i2=i6=V_{C\_body}/Z_{C\_body}$.

Figure 47:
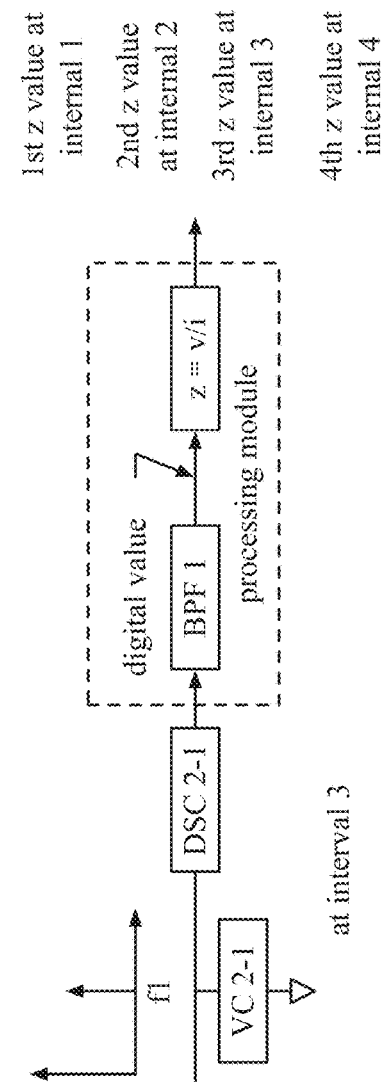
FIG. 47 is a schematic block diagram of an example of sampling period for foot force detection.

FIG. 47 is a schematic block diagram of an example of sampling period for foot force detection. In this example, two cycles of sampling are shown: sample cycle i and sample cycle i+1. Each sample cycle includes a plurality of time intervals. Four in this example.

For an interval of a sample cycle, a drive sense circuit (DSC) is enabled to provide a drive signal to its corresponding variable capacitor. In this manner, the same frequency can be used for the oscillating component of the reference signals for each of a plurality of DSCs.

Figure 48:
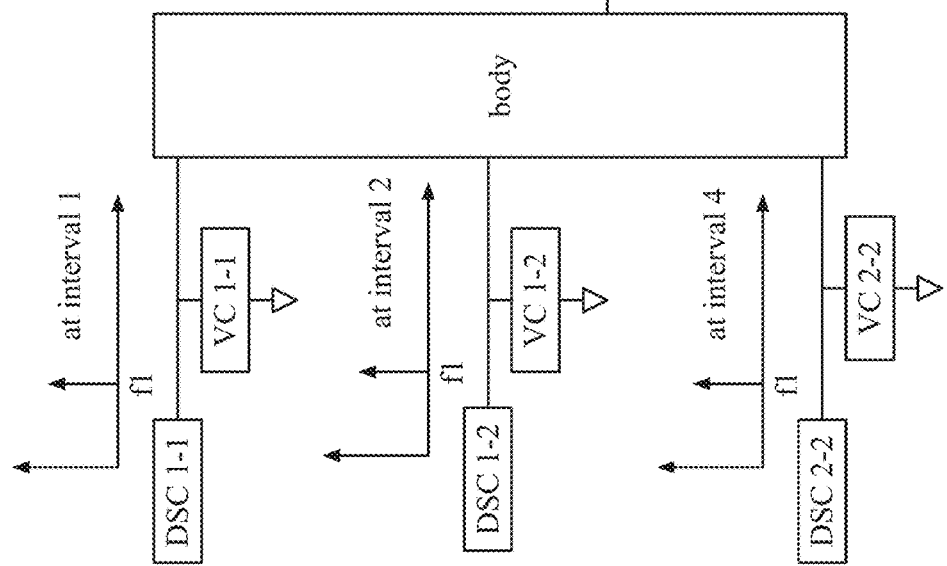
FIG. 48 is a schematic block diagram of another example of processing foot force detection.

FIG. 48 is a schematic block diagram of another example of processing foot force detection. In this example, DSC 1-1 is enabled in interval 1 of a four-interval sample cycle to provide a drive signal to its corresponding variable capacitor. The drive signal includes an oscillating component at frequency f1 (e.g., 10 KHz or higher). A first sensed signal is coupled through the body to DSC 2-1, which creates a digital signal therefrom. The BPF filters the digital signal to produce a digital value and the impedance calculator generates a digital impedance value for the first variable capacitor (VC 1-1).

The process is repeated for the second variable capacitor (VC 1-2) during the second time interval and for the fourth variable capacitor (VC 2-2) during the fourth interval. During the third interval, DSC 2-1 creates the sense signal directly from the third variable capacitor (VC 2-1). The sensed signal is converted into a digital signal and subsequently converted into a digital impedance value for the third variable capacitor. Such processing occurs during the sample cycles.

Figures 49, 50:
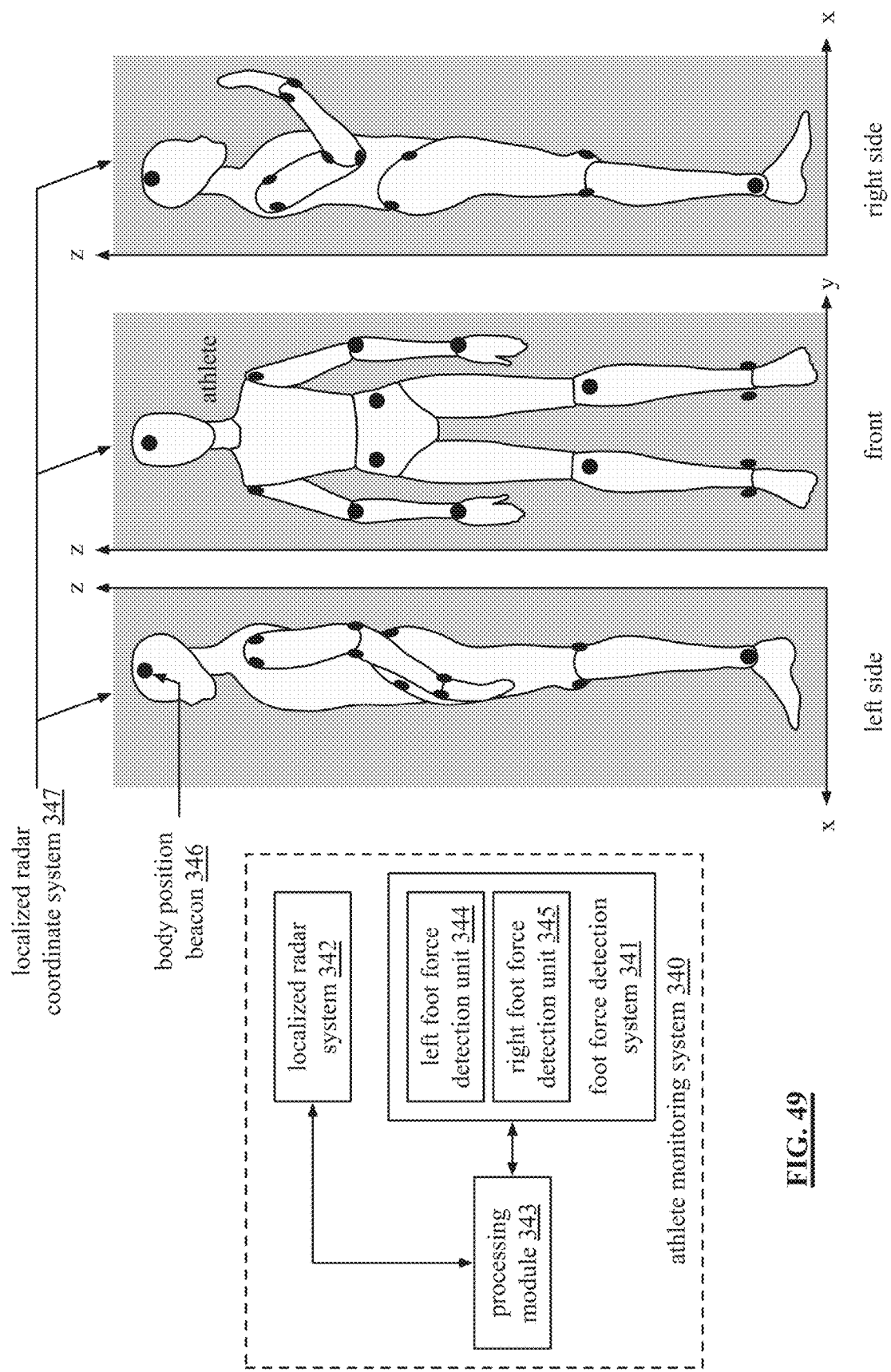
FIG. 49 is a schematic block diagram of an embodiment of an athlete monitoring system.
FIG. 50 is a schematic block diagram of an example of a local coordinate system of an athlete monitoring system.

FIG. 49 is a schematic block diagram of an embodiment of an athlete monitoring system 340. The system 340 includes a localized radar system 342, foot force detection system 341, and a processing module 343. The foot force detection system 341 includes a left foot force detection unit 344 and a right foot force detection unit 345. The foot force system 341, the first foot force detection unit 344, and/or the right foot force detection unit 345 may be implemented as previously discussed and/or subsequently discussed. Note that the system may be implemented and/or installed in a pair of shoes.

The system 340 also includes a plurality of body position beacons 346. When the system is in use, the body position beacons 346 are positioned on the body at various locations to track movement of the body. The localized radar system 342 creates a localized radar coordinate system 347, as shown in FIG. 50, in which the athlete is positioned. As shown in FIG. 50, the body position beacons are located on the body from head to toe and front to back. The number and location of beacons 346 depends on the athlete, the skill level of the athlete, the sport in which the athlete is participating, and/or a desired bio-mechanical functions of the athlete to be studied.

The localized radar system 342 samples positioning of the beacons with reference to the localized radar coordinate system 347 at a sampling rate to produce frames of body position data. The sampling rate depends on the anticipated speed of the body part movement and the desired granularity of movement data. For example, a pitcher's hand is moving at 100 miles per hour and, if a desired movement granularity is 5 millimeters, then the sampling rate needs to be 8,940 per second. As support, 100 mph=44,704 mm/sec; divide that by 5 mm yields 8,940 intervals/second.

Body parts that will not be moving as fast, for example, the core, can have a slower sampling rate. For example, if the maximum speed of the core is 10 mph and 5 mm movement resolution is desired, then the sampling rate would be 894 cycles per second.

The foot force detection system 341 generates, at its own sampling rate, a plurality of frames of left foot force data and a plurality of frames of right foot force data. The processing module 343 (which may be a separate processing module and/or a processing module of the localized radar system 342 and/or of the foot force detection system 341) correlates the frame of body position data with the frames left and right foot force data to produce an integrated ground-body interaction data and athletic movement data.

The system 340 is capable of providing in game and/or in practice athletic movement data and foot force data. It is the first athletic performance system to integrate both data types. It is also the first to provide in game and/or in practice accurate athlete movement data. Current movement data monitoring systems (e.g., bat speed, arm speed, digital pedometers, and the like), use estimates and can be as much as 30% off in their estimates. The present system 340 can provide up to 5 mm movement resolution at a sampling rate of 10 KHz, with millimeters of accuracy.

In an embodiment, the processing module correlates the data by time aligning a frame of the body position data, a frame of the left foot force data, and a frame of the right foot force data to produce frame correlated data. The processing module then determines, based on several frame correlated data, force vector motion data from the ground, through the shoes, and into the body. The processing module generates the integrated ground-body interaction data and athletic movement data based on the force vector motion data.

FIG. 5I is a schematic block diagram of an example of athlete monitoring by the localized radar system 342. The radar system 342 includes at least three receivers (3 shown, 352-354) located at different positions within the localized radar coordinate system and at least one transmitter (1 shown, 350) located at a different position within the localized radar coordinate system. During a cycle of the sampling rate, the transmitter 350 transmits a beacon signal 351 that is targeting a first RF device 346-1 (e.g., a first body position beacon such as an RFID tag or the like). The targeting may be done in a variety of ways. For example, the targeting is done using a frequency division multiplexing concept where each RF device is allocated, and tuned to, a unique frequency. As another example, the targeting is done using a time division multiplexing concept where, in a cycle of the sampling rate, the RF devices are allocated a time interval. In yet another example, a combination of time and frequency division multiplexing is used.

When the RF device 346-1 receives the beacon signal 351, it generates a ring-back signal 355 therefrom. In an embodiment, the RF device uses back scattering to create and transmit the ring-back signal 355. Each of the receivers 352-354 receive the ring-back signal.

The transmission of the beacon signal 351 and the reception of the ring-back signal 355 by each of the receivers are time-stamped. The processing module 343 processes the timing of signals to determine a relative position of the RF device to the receivers. For example, the receivers are located at known locations with respect to each other (e.g., are at known or determinable locations in the localized coordinate system).

The processing module calculates the distance between each receiver and the RF device based on the timestamps and a known processing time of the RF device to create the ring-back signal from the beacon signal. The processing module then triangulates the position of the RF device with respect to the receivers based on the distances to produce a relative position 356 of the RF device.

The processing module then maps the relative position 356 of the RF device to the localized coordinate system to produce a mapped location 357. Thus, on a sample-by-sample basis, the motion of the RF device is determined within the localized coordinate system.

Figure 52:
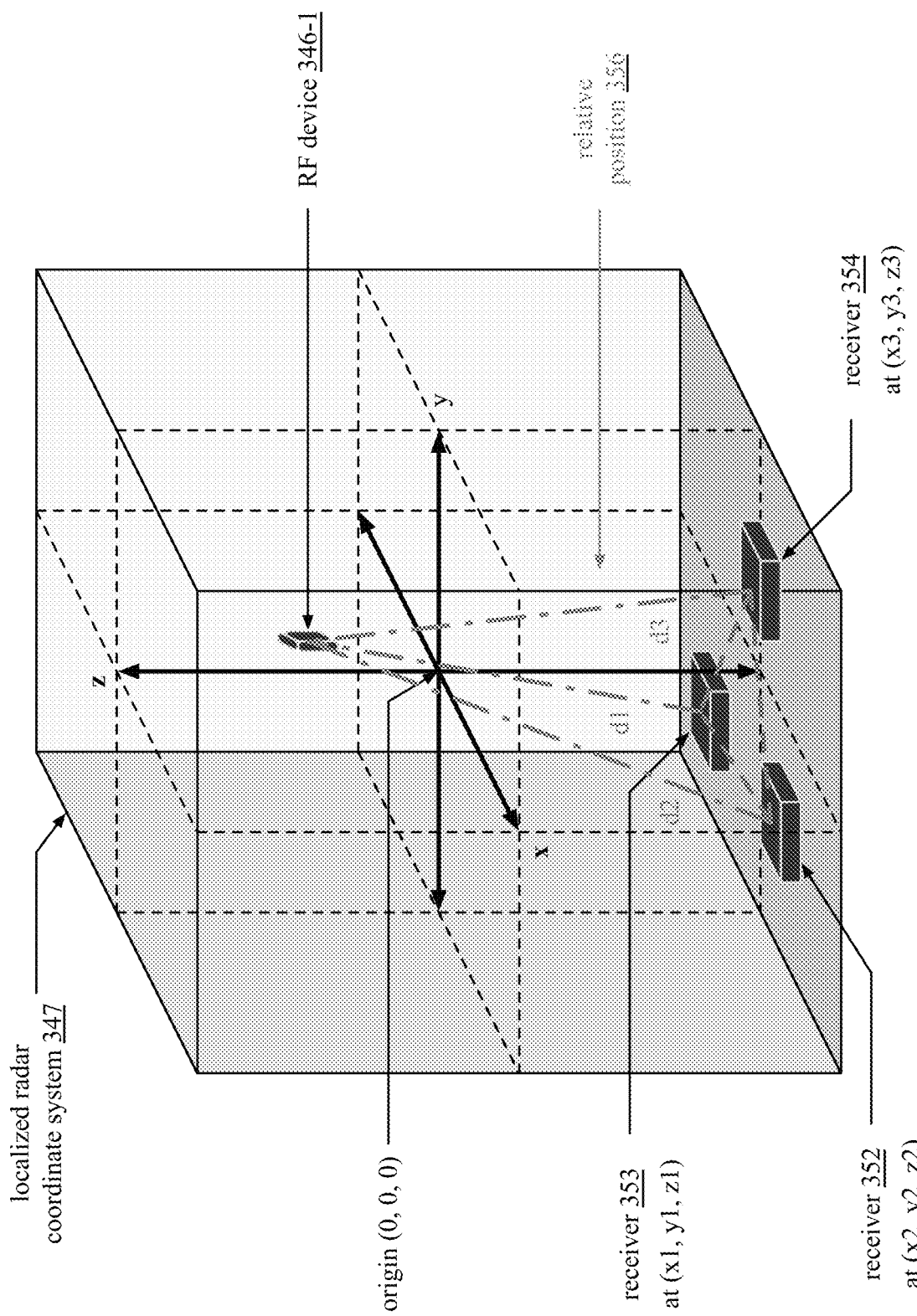
FIG. 52 is a schematic block diagram of an example of athlete relative positioning.

FIG. 52 is a schematic block diagram of an example of athlete relative positioning. In this example, the three receivers 353-354 are positioned within the localized radar coordinate system 347 at (x1, y1, z1), (x2, y2, z2), and (x3, y3, z3), respectively. The relative position 356 of the RF device 346-1 is based on the distances dl-d3 between the RF device and the receivers and the location of the receivers.

In an embodiment, the processing module determines the relative position 356 by, for a first receiver 353, a first time offset between the first beacon signal and the ring-back signal received by the first receiver to produce a first round-trip time. For example, the processing module subtracts the timestamp of the beacon signal from the timestamp of the received ring-back signal to produce a total time. The processing module then subtracts the processing time of the RF device to produce the ring-back signal from the total time to produce the first round-trip time. The processing module does similar processing for the second and third receivers.

The processing module then calculates a first distance between the first RF device and the first receiver based on the first round-trip time. For example, an RF signal travels at the speed of light (c), which is $3\times10^8$ m/second. Thus, the distance between the RF device and the first receiver is c*(first round-trip time)*0.5. The processing module calculates the distance between the RF device and the other two receivers in a similar manner. From the distances, the processing module calculates the relative position of the RF device 346-1.

Figure 53:
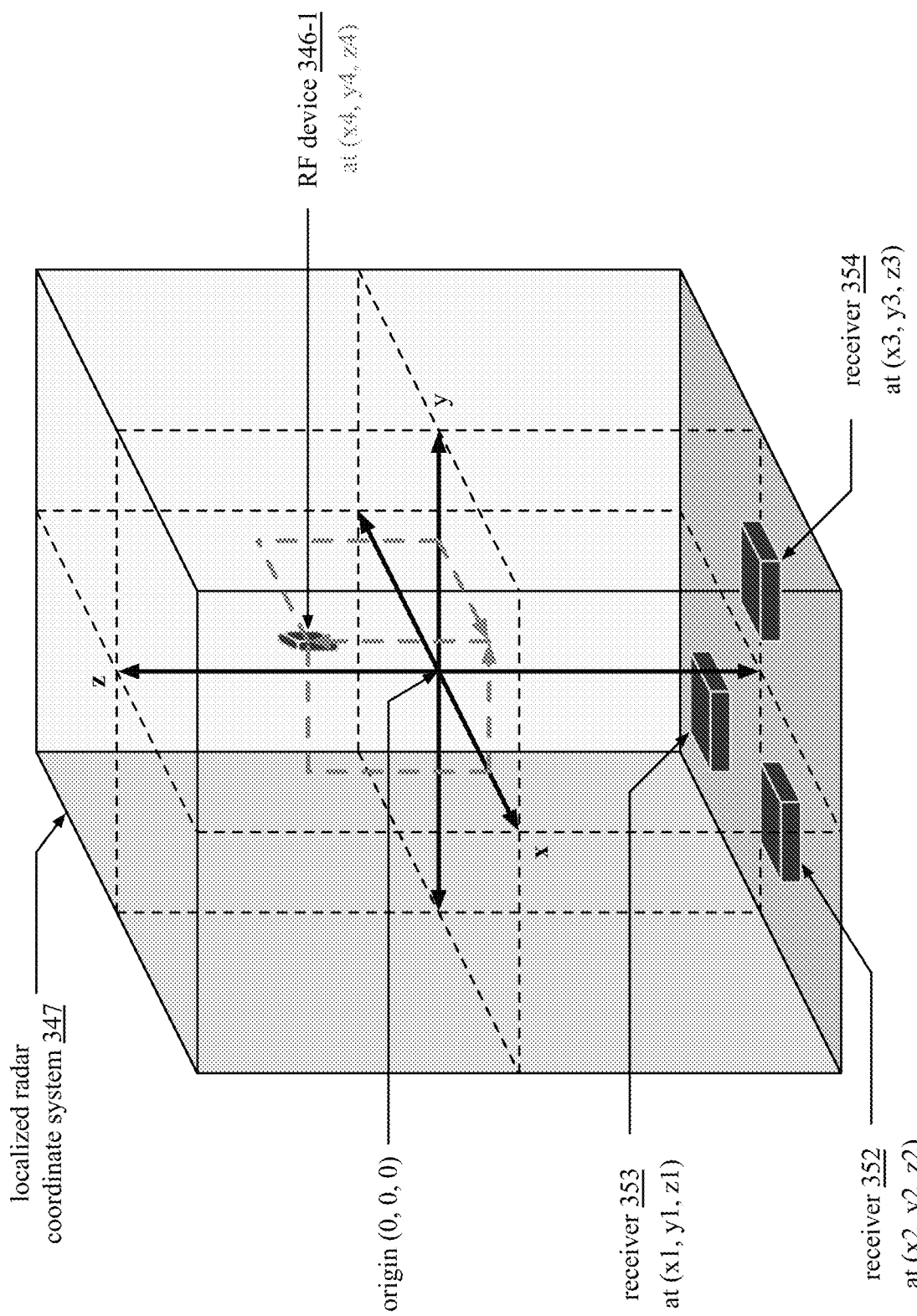
FIG. 53 is a schematic block diagram of an example of athlete coordinate system positioning.

FIG. 53 is a schematic block diagram of an example of athlete coordinate system positioning, which builds on the example of FIG. 52. The relative position of the RF device 346-1 is mapped to the coordinate system 347. For this sample of the position of the RF device, it is located at (x4, y4, z4).

FIG. 54 is a schematic block diagram of an example of determining athlete relative positioning. In an embodiment, the beacon signal includes a repetitive pattern (e.g., a square wave, a sinusoid, a triangle wave, etc.) at a given frequency. In this instance, the ring-back signal is a delayed representation of the repetitive pattern. The processing module determines the time offset between the beacon signal and the ring back signal over a plurality of cycles of the repetitive pattern. In an example, the processing module determines an offset for each cycle and processes the plurality of offsets (e.g., averages them, finds a mean, etc.) to produce the time offset. In another example, the processing module determines the time offset based on the start of the beacon signal and the end of the ring-back signal, subtracting out processing times, and factoring the number of cycles.

FIG. 55 is a schematic block diagram of another example of determining athlete relative positioning. In this example, the attenuation of an RF signal is plotted over distance. The greater the distance, the greater the attenuation. In air, the attenuation of an RF signal is calculatable as $Pr/Pt=(c/4*f*\pi*d)^2$. Thus, $d=(c/4*\pi*f)(Pt/Pr)^{1/2}$; where Pr is the power of the received RF signal, Pt is the power of the transmitted signal, c is the speed of light, f is the frequency of the RF signal, and d is the distance between the receiver and transmitter.

FIG. 56 is a schematic block diagram of another example of determining athlete relative positioning that uses the graph of FIG. 55. In this example, the local radar system includes at least three transmitter/receiver units (Tx/Rx). Each Tx/Rx unit transmits an RF signal at a known power level (e.g., Pt is known). The RF device 346-1 includes a power detection module that determines the received strength of the RF signal (e.g., Pr is determined). The RF device transmits the received signal strength back to the appropriate Tx/Rx unit.

The processing module calculates the distance between each of the Tx/Rx units and the RF device based on the curve of FIG. 55 and the corresponding equations. For example, if the frequency is 60 GHz, the transmit power is 100 μWatts and the received power is 15.85 μWatts, then the distance is about 1.00 meters. For a 4 mm resolution (e.g., d=1.004 meters), the received power changes to 15.72 μWatts.

As another example, at a frequency of 600 MHz, and a transmit power of 10 μWatts, the received power 1.00 meters away is 15.85 nWatts. For a 4 mm resolution (e.g., d=1.004 meters), the received power changes to 15.72 nWatts. Once the distances between the Tx/Rx units and the RF device are calculated, the relative position of the RF device is determined as previously discussed.

FIG. 57 is a logic diagram of an example of method for determining athlete positioning. The method begins at step 360 where the processing module determines, for a first receiver, a first power difference between a first component of the first beacon signal and the ring-back signal received by the first receiver. The method continues at step 361 where the processing module determines, for a second receiver, a second power difference between a second component of the first beacon signal and the ring-back signal received by the second receiver.

The method continues at step 362 where the processing module determines, for a third receiver, a third power difference between a third component of the first beacon signal and the ring-back signal received by the third receiver. In an embodiment, the first component is a first sinusoidal signal having a first frequency, the second component is a second sinusoidal signal having a second frequency, and the third component is a third sinusoidal signal having a third frequency.

The method continues at step 363 where the processing module calculates a first distance between the first RF device and the first receiver based on the first power difference and a path loss function (e.g., the curve of FIG. 55 and the corresponding equations). The method continues at step 364 where the processing module calculates a second distance between the first RF device and the second receiver based on the second power difference and the path loss function.

The method continues at step 365 where the processing module calculates a third distance between the first RF device and the third receiver based on the third power difference and the path loss function. The method continues at step 366 where the processing module calculates the relative position based on the first, second, and third distances.

FIG. 58 is a schematic block diagram of another example of athlete positioning. In this example, the origin of the localized radar coordinate system 347 is associated with a particular point on the athlete's body (e.g., belly button, heel of left foot, heel of right foot, top of head, etc.). In a specific example, the z-axis of the localized radar coordinate system is perpendicular to the ground, a positive direction is away from the ground, and passing through the origin; the x-axis of the localized radar coordinate system is parallel to the ground, has a positive direction to the front of the body, and passing through the origin; and the y-axis of the localized radar coordinate system is parallel to the ground, has a positive direction to the right of the body, and passing through the origin.

Figure 59:
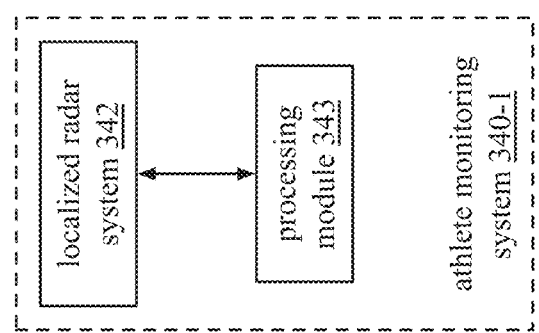
FIG. 59 is a schematic block diagram of an embodiment of an athlete monitoring system.

FIG. 59 is a schematic block diagram of an embodiment of an athlete monitoring system 340-1, which includes the localized radar system 342 and the processing module 343. The system further includes body position beacons placed on an athlete. The localized radar system creates a localized radar coordinate system in which the athlete is positioned. The localized radar system further functions to, at a sampling rate, produce a plurality of frames of body position data based on determining location of the body position beacons within the localized radar coordinate system. The processing module correlates the frames of body position data to athletic movement data.

Figure 60:
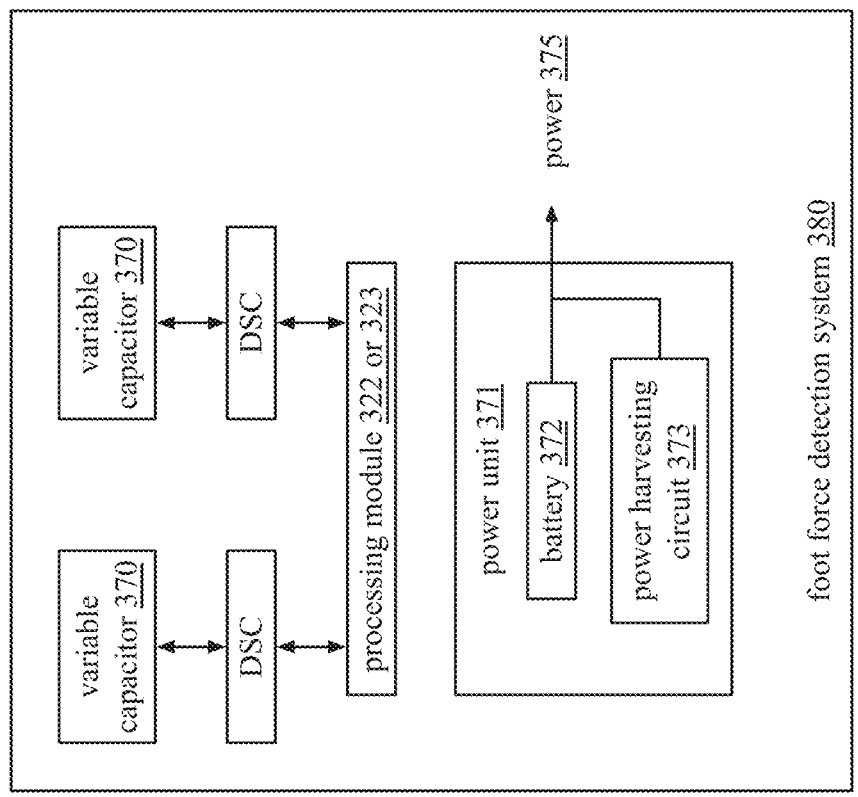
FIG. 60 is a schematic block diagram of another embodiment of foot force detection system.

FIG. 60 is a schematic block diagram of another embodiment of foot force detection system 380. The system 380 includes variable capacitors 370, drive sense circuits (DSC), one or more processing modules 322, 323, and a power unit 371. The power unit 371 includes a battery 372 and a power harvesting circuit 373, which individually, or collectively, produce power 375 that powers the system 380. The variable capacitors 370, the DSCs, and the processing module 322, 323 operate as previously discussed to produce digital impedance values for the capacitors 370, which varies based on pressure. The power harvesting circuit 373 may be implemented in a variety of ways as shown in the examples of FIGS. 62-65.

Figure 61:
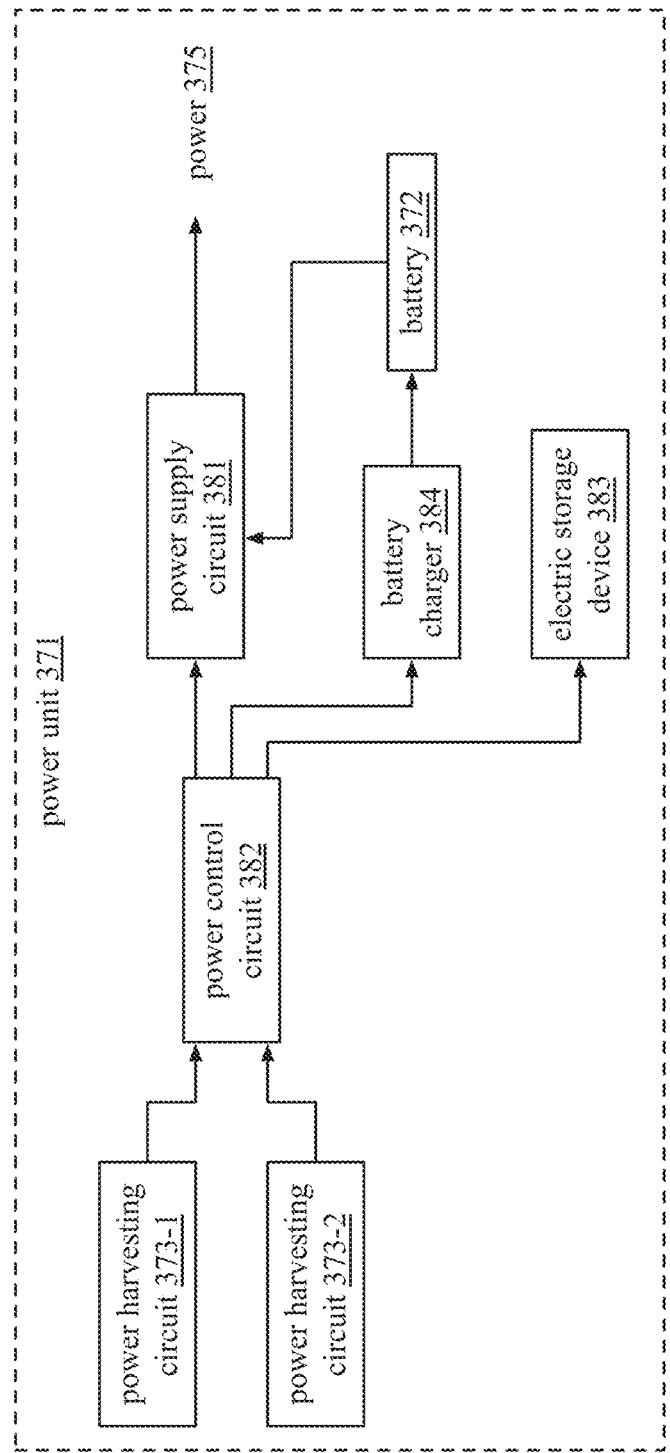
FIG. 61 is a schematic block diagram of an embodiment of a power unit of a foot force detection system.

FIG. 61 is a schematic block diagram of an embodiment of a power unit 371 of a foot force detection system 380. The power unit 371 includes two or more power harvesting circuits 373-1, -2, a power control circuit 382, a power supply circuit 381, a battery charger 384, an electric storage device 383 (optional), and the battery 372. The power supply circuit 381 may be implemented in a variety of ways to generate one or more DC voltages at current level to produce the power 375. For example, the power supply circuit is a linear regulator. As another example, the power supply is a buck, boost, or fly-back power supply. Each of the power harvesting circuits 373-1, -2 may be implemented in a variety of ways as shown in the examples of FIGS. 62-65.

The power control circuit 382 is a processing module, or portion of a processing module, that is programmed and/or configured to control the sources and/or distribution of power within the foot force detection system 380. In a first mode, the power control circuit provides electricity (e.g., voltage and current) of one or both of the power harvesting circuits to the power supply circuit 381. The power supply circuit 381 generates one or more DC voltages from the electricity. In this mode, the power harvesting circuit(s) is/are providing the power for the system 380.

In a second mode, the power control circuit 382 provides the electricity of one or more of the power harvesting circuits to the battery charger 384 for charging the battery 372. In a third mode, the power control circuit 382 provides the electricity of one or more of the power harvesting circuits to the electric storage device 383, which is a capacitor and/or an auxiliary battery coupled via the battery charger 384.

The processing module 322, 323 of the foot force detection system 380 determines which mode to use. Whenever a power harvesting circuit can produce electricity (e.g., a voltage and/or a current), the processing module determines how best to use the electricity and/or how best to extend a battery charge. When the system 380 is in use and a power harvesting circuit is producing electricity, the processing module enables the first mode such that the power harvesting circuit(s) is/are providing the power 375 for the system and the battery 372 is supplying little to no power. In an embodiment, the power harvesting circuits generate a voltage that is greater than the battery voltage such that, when a power harvesting circuit is active, is supplies a majority of the electricity (voltage and current) to the power supply circuit 381.

When a power harvesting circuit is producing electricity, the processing module determines the charge level of the battery. If battery charge is below a charge threshold (e.g., 75% charged), the processing module enables the second mode to provide electricity of a power harvesting circuit to the battery charger 384 to charge the battery. If battery charge at or above the charge threshold, the processing module enables the third mode to provide electricity of a power harvesting circuit to electric storage device 383 for storing the electricity (e.g., store charge by a capacitor or store voltage potential by a battery). When the system 380 is in use, the processing module can enable the second or third mode in conjunction with the first mode.

Figure 62:
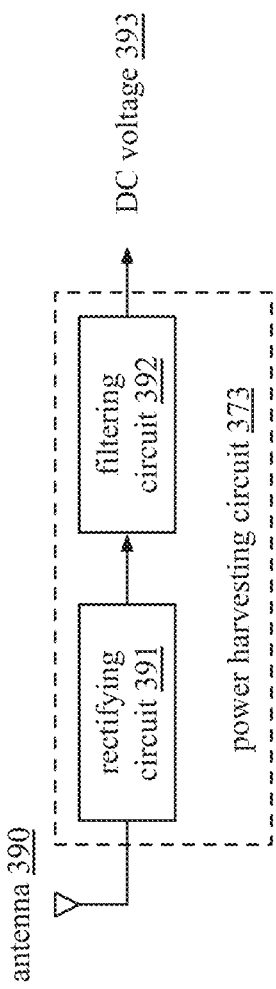
FIG. 62 is a schematic block diagram of an example of a power harvesting circuit of a power unit.

FIG. 62 is a schematic block diagram of an example of a power harvesting circuit 373 of a power unit 371. The power harvesting circuit 373 includes a radio frequency (RF) power harvesting unit (e.g., 514 of FIG. 100). The RF power harvesting circuit receives an RF signal via an antenna. The signal is a cell phone signal, an RFID signal, a WLAN, a Bluetooth signal, a ZigBee signal and/or a non-standard RF signal transmitted for the purpose of power harvesting. The RF power harvesting circuit rectifies the RF signal, using a rectifier circuit (e.g., full or half rectification), to produce a rectified signal. The RF power harvesting circuit filters the rectified signal, using a filter circuit (e.g., a capacitor and/or inductor) to produce a DC voltage 393.

Figure 63:
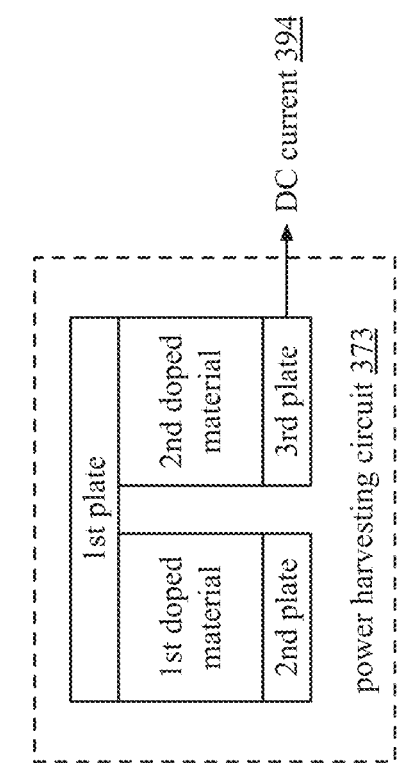
FIG. 63 is a schematic block diagram of another example of a power harvesting circuit of a power unit.

FIG. 63 is a schematic block diagram of another example of a power harvesting circuit 373 of a power unit 371. The power harvesting circuit 373 includes a thermoelectric generation unit, which converts heat into electrical power. The thermoelectric generation unit includes a first thermoelectric conductive plate, a second thermoelectric conductive plate, a third thermoelectric conductive plate, a first thermo doped material between the first and second thermoelectric conductive plates, and a second thermo doped material between the first and third thermoelectric conductive plates. The first and second doped materials (e.g., p-doped and n-doped semiconductors) are doped with different Seebeck coefficients.

In this configuration, when heat (e.g., of the body) is applied to the first plate, the doped materials cause current 394 to flow in the second and third plates, which are at a cooler temperature than the first plate. For instance, current (J) equals $-\sigma S \Delta T$, where $\sigma$ is the local conductivity, S is the Seebeck coefficient (thermopower), and $\Delta T$ is the temperature gradient.

Figure 64:
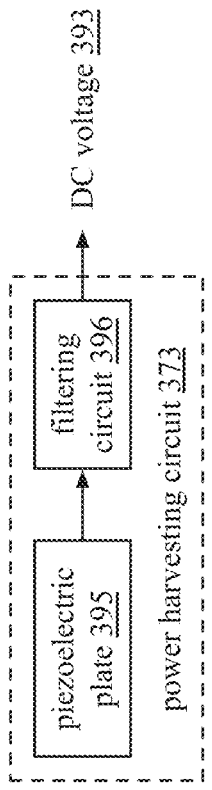
FIG. 64 is a schematic block diagram of another example of a power harvesting circuit of a power unit.

FIG. 64 is a schematic block diagram of another example of a power harvesting circuit 373 of a power unit 371. The power harvesting circuit 373 includes a piezoelectric plate 395 and a filtering circuit 396. The piezoelectric plate generates an AC signal when weight of a wearer of a shoe is applied to it. The filtering circuit 396 (e.g., a rectifier, a capacitor, and/or an inductor) converts the AC signal into a DC voltage 393.

Figure 65:
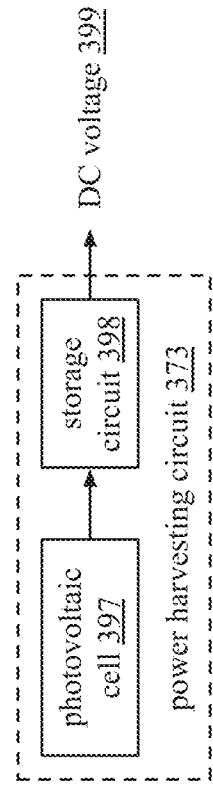
FIG. 65 is a schematic block diagram of another example of a power harvesting circuit of a power unit.

FIG. 65 is a schematic block diagram of another example of a power harvesting circuit 373 of a power unit 371. The power harvesting circuit 373 includes a photovoltaic cell 397 and a storage circuit 398. The photovoltaic cell 397 produces a current from light. The storage circuit 398 stores the current (e.g., a capacitor storage current as a charge and/or a battery that stores the current as a voltage potential) and produces therefrom a DC voltage 399.

FIGS. 66A and 66B are side view diagrams of an embodiment of a left shoe and a right shoe; each of which includes a shoe sensor system 416-L (left) and 416-R (right). The shoes may be sports specific athletic shoes (e.g., baseball, basketball, golf, tennis, track & field, running, etc.), walking shoes, dress shoes, work boots, hiking shoes or boots, etc.

In an embodiment, the shoe sensor system is located on or within the insole and/or midsole of the shoe and functions to capture a multitude of information. For example, the shoe sensor system 16 gathers data of a user's movements (e.g., running, jumping, walking, hitting a golf ball, hitting a baseball, pitching a baseball, playing basketball, etc.) for subsequent analysis (e.g., determine ground reaction forces, weight distribution, stride length, time duration of activity, imbalances in weight distribution, imbalances in stride length, elevation ascended, distance traveled, elevation descended, foot rotation, form, gait, etc.). The data includes ground reaction forces from a plurality of pressure sensing element and three-dimensional foot positioning data from one or more accelerometers and/or gyroscopes. In addition, the data is further analyzed to determine whether performance of a physical activity is being done optimally (e.g., with proper form, with consistency, without undue stress on the body, level of fatigue, etc.). When the physical activity is being performed less than optimally, the corrective measures are determined based on the cause, or causes, of the less than optimal performance.

With the shoe sensor system 416 within each shoe 412 and 414, the shoes can be used in game to collect in-game data. For example, the shoes are baseball spikes worn by a pitcher. Each shoe gathers foot force data from the plurality of pressure sensing elements and gathers three-dimensional (3D) foot data (e.g., x-y-z data from an accelerometer). The foot force data and the 3D foot data are sent via a wireless link (e.g., a Bluetooth link) to a computing device that is off the field of play. The computing device processes the data to determine ground reaction forces of various locations on each foot, weight distribution, balance, stride length, etc., which can be used to determine the pitcher's level of fatigue, efficiency, etc.

FIGS. 66C and 66D are side view diagrams of another embodiment of a left shoe and a right shoe; each of which includes a dongle 415, pressure sensing elements 420, and one or more accelerometers 422. The dongle 415 includes a control circuit that communicates with the pressure sensing elements 420 and the accelerometer(s) 422 and also wirelessly communications the collected data to a computing device. The dongle 415 is a relatively small device (e.g., less than 1 inch×1 inch×½ inch) that includes an exterior housing for containing a control circuit board. The dongle 415 may be clipped to the heel or lateral side of the shoe as shown in FIG. 66C or clipped or laced into the laces of the shoe as shown in FIG. 66D. Note that the dongle 415 may be attached to other locations on each shoe and in different locations from shoe to shoe. Further note that communication between the dongle 415 and the pressure sensors in the shoes may be done via the body.

Figure 67:
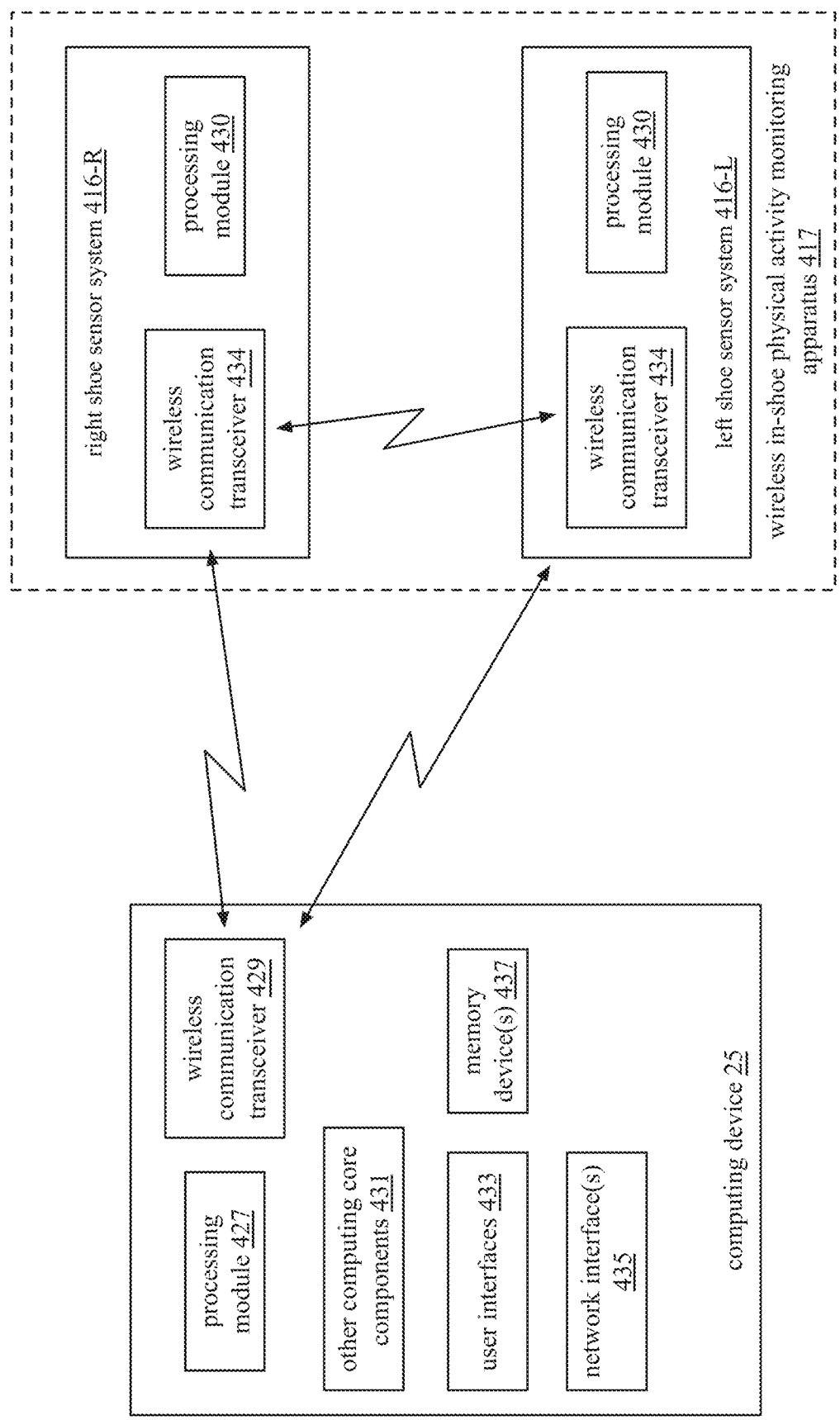
FIG. 67 is a schematic block diagram of an embodiment of a wireless in-shoe physical activity monitoring apparatus and a computing device.

FIG. 67 is a schematic block diagram of an embodiment of a wireless in-shoe physical activity monitoring apparatus 417 and a computing device 425. The wireless in-shoe physical activity monitoring apparatus 417 includes a right shoe sensor system 416-R and a left shoe sensor system 416-L. As will be described in greater detail with reference to FIG. 70 and other figures, each shoe sensor system 416 includes pressure sensor elements 420-1 through 420-x, an accelerometer 422, and control circuit 424. The control circuit 424 includes a power source circuit 424, a clock circuit 428, a processing module 430, memory 432, a wireless communication transceiver 434, and a sampling signal generator 435. The processing module 430 and the wireless communication transceiver 434 are shown in this Figure.

The computing device 425 is any electronic device that can communicate data, process data, and/or store data. As an example, the computing device 425 is a portable computing device and/or a fixed computing device. A portable computing device may be a social networking device, a gaming device, a cell phone, a smart phone, a personal digital assistant, a digital music player, a digital video player, a laptop computer, a handheld computer, a tablet, a video game controller, and/or any other portable device that includes a computing core. A fixed computing device may be a personal computer (PC), a computer server, a cable set-top box, a satellite receiver, a television set, a printer, a fax machine, home entertainment equipment, a video game console, and/or any type of home or office computing equipment that includes a computing core.

The computing device 425 includes a computing core, user interfaces 33, network interface(s) 435, a wireless communication transceiver 429, and memory device(s) 437. The user interfaces 433 includes one or more input devices (e.g., keypad, keyboard, touchscreen, voice to text, etc.), one or more audio output devices (e.g., speaker(s), headphone jack, etc.), and/or one or more visual output devices (e.g., video graphics display, touchscreen, etc.). The network interface(s) 435 includes one or more networking devices (e.g., a wireless local area network (WLAN) device, a wired LAN device, a wireless wide area network (WWAN) device (e.g., a cellular telephone transceiver, a wireless data network transceiver, etc.), and/or a wired WAN device). The memory device(s) 437 includes one or more flash memory devices, one or more hard drives, one or more solid state (SS) memory devices, and/or cloud memory.

The computing core includes a processing module 427 and other computing core components 431. The other computing core components include a video graphics processing unit 60, a memory controller, main memory (e.g., RAM), one or more input/output (I/O) device interface module, an input/output (I/O) interface, an input/output (I/O) controller, a peripheral interface, one or more USB interface modules, one or more network interface modules, one or more memory interface modules, and/or one or more peripheral device interface modules. Each of the interface modules includes a combination of hardware (e.g., connectors, wiring, etc.) and operational instructions stored on memory (e.g., driver software) that is executed by the processing module and/or a processing circuit within the interface module. Each of the interface modules couples to one or more components of the computing device 425. For example, one of the IO device interface modules couples to an audio output device. As another example, one of the memory interface modules couples to flash memory and another one of the memory interface modules couples to cloud memory (e.g., an on-line storage system and/or on-line backup system).

The wireless communication transceiver 429 of the computing device 425 and the wireless communication transceivers 434 of the shoe sensor systems 416 are of a like transceiver type (e.g., Bluetooth, WLAN, ZigBee, etc.). The transceivers 434 communicate directly with transceiver 429 to share gathered data by the respective shoe sensor systems 416 and/or to receiving instructions from the computing device 425. In addition to or in the alternative, the transceivers 434 communicate gathered data between them and one of the transceivers 434 communicates the collective data to the transceiver 429.

The computing device 425 processes the data to produce a variety of resultants. For example, the computing devices processes data from the shoe sensor systems 416 to determine a distance traveled during a time period, which may be an entire time duration of a physical activity, time intervals (e.g., 5-minute intervals, etc. As another example, the computing devices processes data from the shoe sensor systems 416 to determine stride length data (e.g., maximum stride length, minimum stride length, average stride length, stride length for a time interval, stride length of a distance segment, etc.).

As another example, the computing devices processes data from the shoe sensor systems 416 to determine a time duration of the physical activity (e.g., walking, running, playing a sport, executing an athletic movement, lifting weights, cross-fit training, etc.). As another example, the computing devices processes data from the shoe sensor systems 416 to determine a fatigue indication (e.g., shortening of stride, pace slowing, change in foot forces, etc.). As another example, the computing devices processes data from the shoe sensor systems 416 to determine injury prevention indicators (e.g., recognize change in data, where change is likely caused by fatigue, cramping, muscle strain, etc.).

As another example, the computing devices processes data from the shoe sensor systems 416 to determine elevation tracking for the time period (e.g., steps climbed, elevation changes in a run, a walk, or a hike, etc.). As another example, the computing devices processes data from the shoe sensor systems 416 to determine running optimization (e.g., proper foot positioning & weight distribution when running, balanced strides, stride length training, increase ground reaction force, reduce foot to ground contact time, etc.). As another example, the computing devices processes data from the shoe sensor systems 416 to determine rotational sport optimization (e.g., weight distribution, ground reaction forces, balance, linear movement, rotational movement, etc.).

The computing device 425 further includes operational instructions to generate a graphical user interface for the recording, gathering, and/or processing of the data of the shoe sensor systems 416. For example, the graphical user interface (GUI) displays information regarding the processing of the data. As a specific example, the GUI displays information about a run, such as time duration, stride length information, foot force information, gait information, etc. As another example, the GUI displays, in real time, foot forces and foot positioning during a physical activity to determine one or more of proper form, fatigue analysis, injury predictive analysis, weight distribution, and corrective measures of form.

In another embodiment, the foot force detection system includes first and second shoe force detection units (e.g., left shoe and right shoe systems 416 L & R). Each shoe force detection unit includes a plurality of pressure sensors, a processing module, and a communication unit. The pressure sensors, when active, produce force data. The processing module, when active, produces a digital representation of the force data. The communication unit of one of the shoe force detection units, when active, communicates foot force data with the communication unit of the other shoe force detection unit.

In an embodiment, the first communication unit includes a first shoe area network transceiver (e.g., a low power high frequency transceiver that is standard compliant or proprietary). The second communication unit includes a second shoe area network transceiver (e.g., a low power high frequency transceiver that is standard compliant or proprietary). In this embodiment, the foot force data is communicated via the first and second shoe area network transceivers. To communicate data to the computing entity, the first and/or second communication units include another transceiver that is compatible to a transceiver of the computing entity. In another embodiment, the first and second communication units communicate using light transceivers (e.g., IrDA compliant transceivers).

Figure 68:
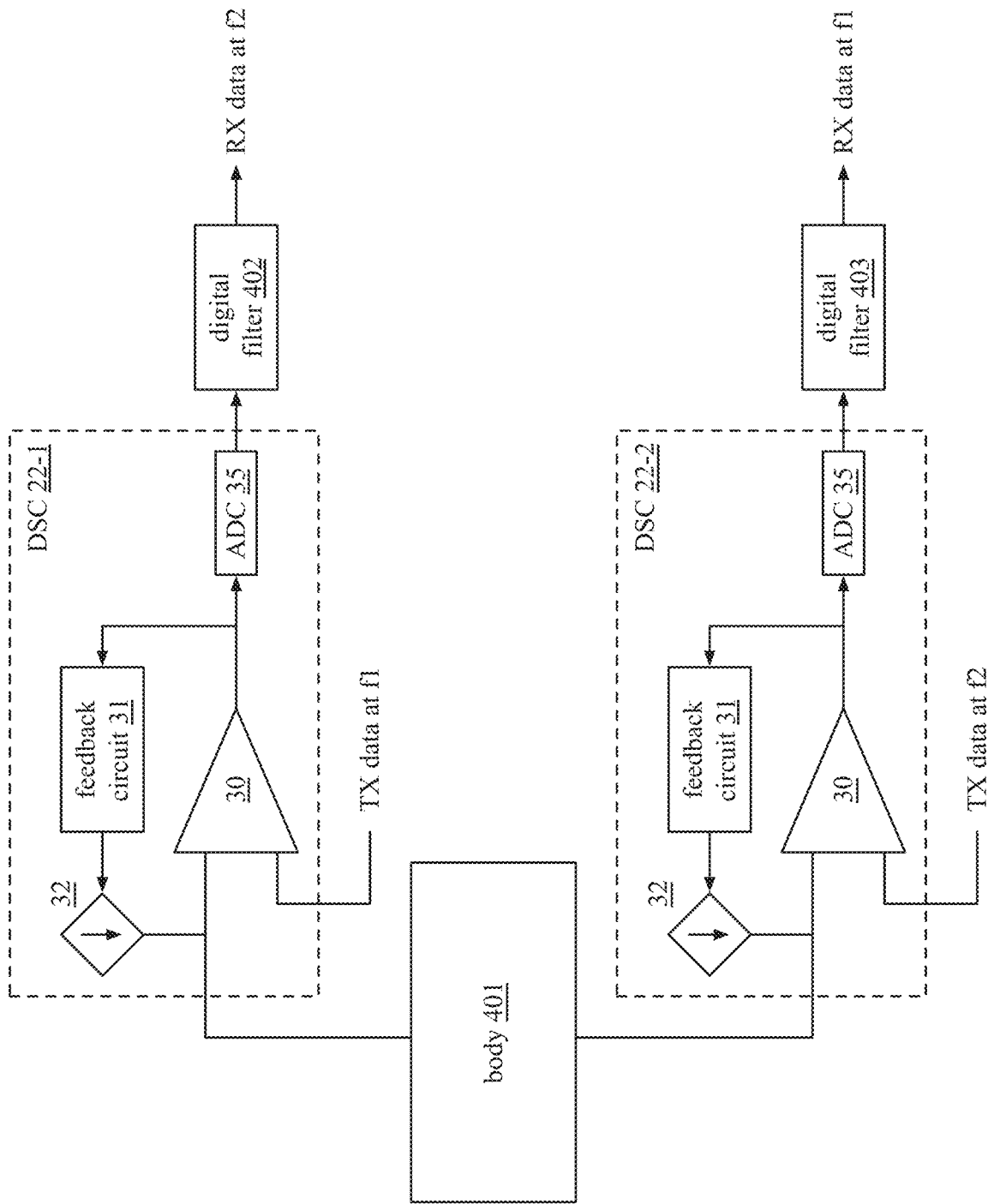
FIG. 68 is a schematic block diagram of an example of communication via the body.

FIG. 68 is a schematic block diagram of an example of communication via the body. In this example, each communication unit includes a drive sense circuit (DSC) 22 and a digital filter 402, 403. Each DSC 22 includes an op amp 30, an ADC 35, a feedback circuit 31, and a dependent current source 32.

For data to be communicated from DSC 22-1 to DCS 22-2 via the body, DSC 22-1 receives first transmit data that includes an oscillating component at a first frequency (f1). The data is modulated on the oscillating component using amplitude shift keying, phase shift keying, and/or amplitude modulation. Through the dependent current source, the first transmit signal at f1 is communicated through the body to DSC 22-2. Similarly, second transmit data (which has an oscillating component at f2) is transmitted from DSC 22-2 to DSC 22-1 via the body.

The op amp 30 of DSC 22-1 receives the second transmit signal at f2 via the body. Through the closed loop feedback, the second transmit signal at f2 is regulated out as an error signal. The error signal produced by the op amp, which includes a representation of the transmit signal at f2, is converted into a digital signal by the ADC 35. The digital filter 402 bandpass filters the digital signal to recover the second transmit signal at f2 as a received signal at f2.

Figure 69:
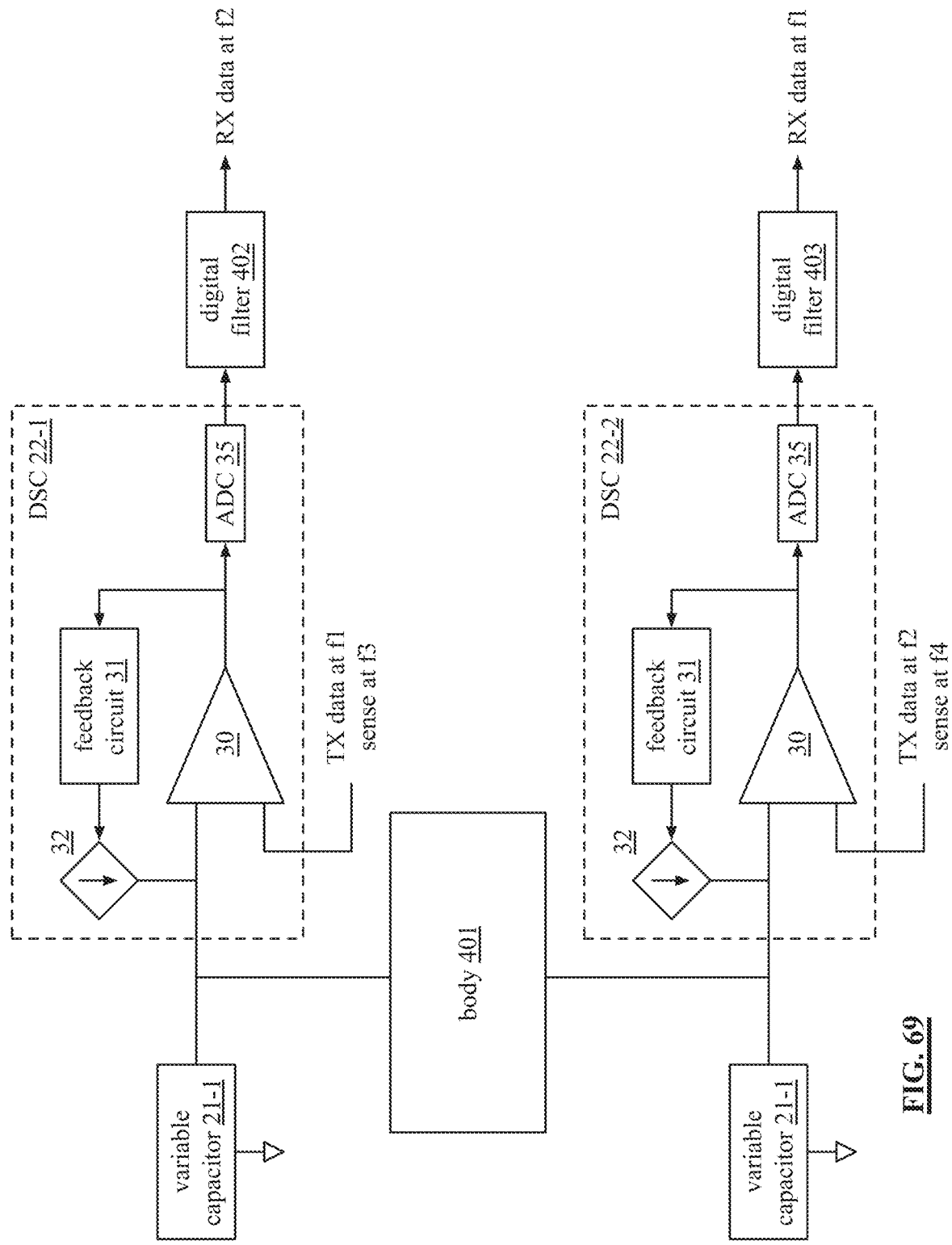
FIG. 69 is a schematic block diagram of an example of communication via the body.

FIG. 69 is a schematic block diagram of an example of communication via the body. This example is similar to the example of FIG. 68 with the addition of variable capacitors 21-1. In this example, DSC 22-1 and DSC 22-2 communicate with each other as described with reference to FIG. 68. In this example, DSC 22-1 senses its variable capacitor using a reference signal that has an oscillating component at f3 and DSC 22-2 senses its variable capacitor using a reference signal that has an oscillating component at f4 as previously discussed with at least reference to FIG. 4A.

Figure 70:
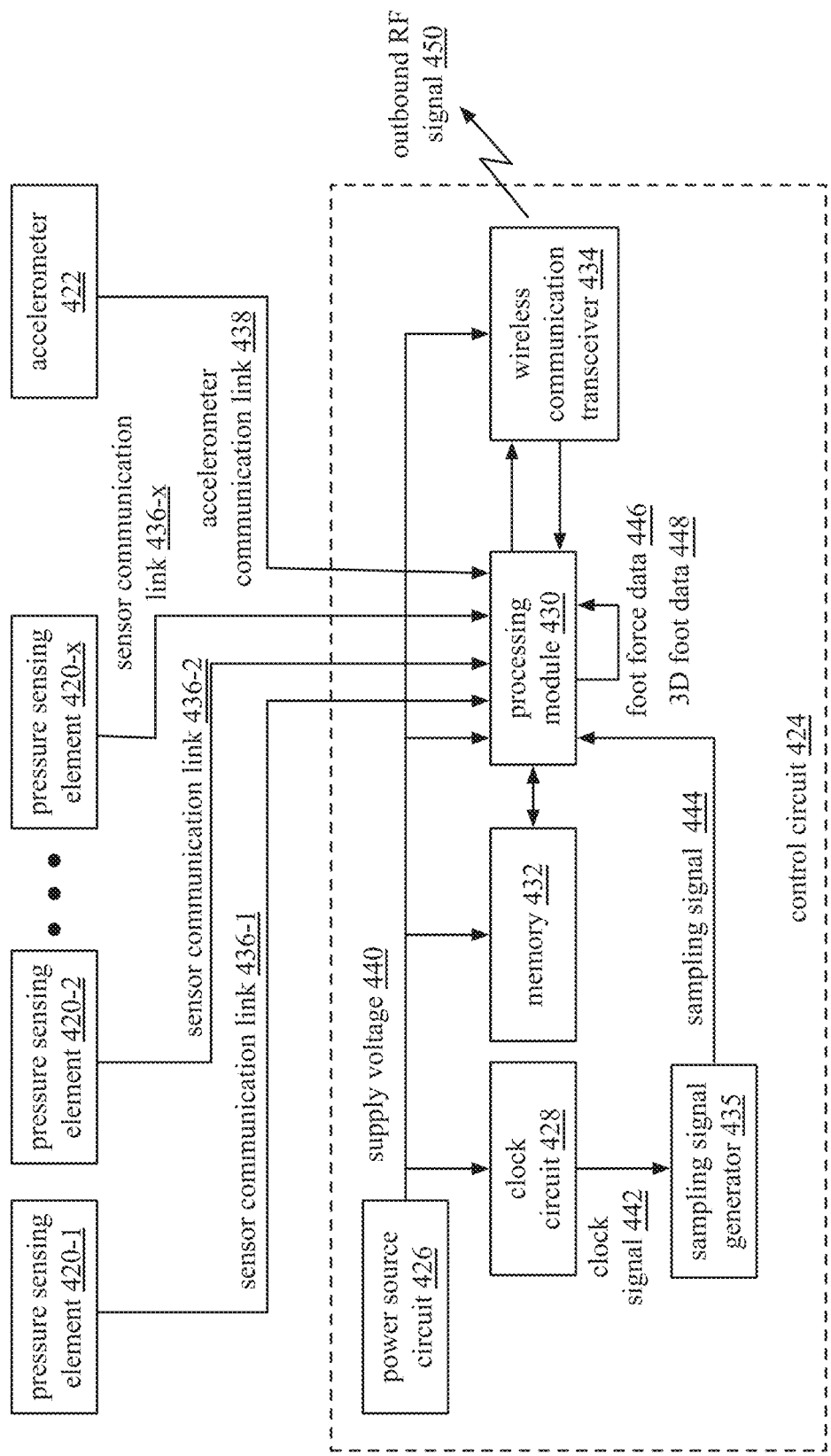
FIG. 70 is a schematic block diagram of an embodiment of a shoe sensor system.

FIG. 70 is a schematic block diagram of an embodiment of a shoe sensor system 416 that includes pressure sensor elements 420-1 through 420-x, an accelerometer 422, and control circuit 424. The control circuit 424 includes a power source circuit 426, a clock circuit 428, a processing module 430, memory 432, a wireless communication transceiver 434, and a sampling signal generator 435. The pressure sensing elements 420 includes one more of a resistive pressure sensor, a piezoelectric pressure sensor, a capacitive pressure sensor, and an inductive pressure sensor and are distributed in a pattern having a shape corresponding to an outline a human foot as will be discussed with reference to one or more subsequent figures.

The pressure sensing elements 420 are coupled to the processing module 430 via sensor communication links 436. As an example, a sensor communication link 436 includes a wired communication link such as a metal trace on a printed circuit board, a wire, a dedicated data bus, or a shared data bus. In another example, a sensor communication link 436 includes a wired communication path that is in accordance with a wired communication protocol. The wired communication protocol includes RS-422, Inter-Integrated Circuit bus (I2C), serial peripheral interface (SPI), microwire, 1-wire, etc.

As another example, a sensor communication link 436 includes an inductive communication path in accordance with a near field communication (NFC) communication protocol. As yet another example, a sensor communication link 436 includes a light communication base in accordance with a light-based communication protocol (e.g., Infrared, fiber optics, etc.). As a further example, a sensor communication link 436 includes a radio frequency (RF) communication path in accordance with a standardized wireless communication protocol (e.g., 60 GHz, Bluetooth, WLAN, ZigBee, etc.) or in accordance with a proprietary wireless communication protocol.

The accelerometer 422 is coupled to the processing module 430 via an accelerometer communication link 438. The accelerometer communication link 438 includes a wired communication link, a wired communication path in accordance with a wired communication protocol, an inductive communication path in accordance with a near field communication (NFC) communication protocol, a light communication base in accordance with a light-based communication protocol, and/or a radio frequency (RF) communication path in accordance with a wireless communication protocol.

In an example of operation, the power source circuit 426 generates one or more supply voltages 440 that powers the other devices of the control circuit 424. In an embodiment, the accelerometer 422 is on a common printed circuit board with the control circuit 424 and is powered by one of the supply voltages. In another embodiment, the accelerometer 422 is on a separate printed circuit board from the control circuit 424 and is powered by a power supply on the separate printed circuit board. In yet another embodiment, the accelerometer 422 is on a separate printed circuit board from the control circuit 424 but receives one of the supply voltages 440 via the accelerometer communication link 438.

In an embodiment, each of the pressure sensing elements are active device and receive one of the supply voltages 440 via their respective sensor communication link 436. In another embodiment, each of the pressure sensing elements are active device and receive one of the supply voltages 440 are passive devices and include a power harvesting circuit to generate a local supply voltage. In yet another embodiment, each of the pressure sensing elements are active device on a flexible circuit board, which includes a local power supply to generate the local supply voltage.

In an example embodiment, the power source circuit 426 includes a battery-powered power supply. The power supply is a DC-to-DC converter and/or a linear regulator. In another example, the power source circuit 426 includes the battery-powered power supply and a wired battery charger. In this example, the battery charger is connected via a wire to the battery of the battery-powered power supply for charging. In a specific example, the shoe includes a connector or plug that is accessible from the heel of the shoe. The battery charger is an external device that plugs into the connector. In yet another example, the power source circuit 426 includes the battery-powered power supply and a wireless battery charger. In a further example, the power source circuit 426 includes a radio frequency (RF) power harvesting circuit; an example of which will be described with reference to one or more subsequent drawings.

Continuing with the example of operation, the clock circuit 428 generates a clock signal 442. The clock signal 442 may be a sinusoidal signal, a pulse pattern, a square wave signal, or other type of signal having a clock rate (e.g., 10 KHz to 10 GHz). The sampling signal generator 435 generates one or more sampling signals 444 from the clock signal 442. For example, the sampling signal generator 435 is a buffer such that the sampling signal 444 is a buffered version of the clock signal 442. As another example, the sampling signal generator 435 is a phase locked loop (PLL) that multiples the rate of the clock signal 442 such that the sampling signal 444 has a rate that is "x" times the rate of the clock signal 442, where "x" is greater than 1.

As yet another example, the sampling signal generator 435 divides the rate of the clock signal 442 such that the sampling signal 444 has a rate that is "y" times the rate of the clock signal 42, where "y" is greater than 1. As a further example, the sampling signal generator 435 includes a digital delay line to create one or more sampling signals 444 from the clock signal. As a still further example, the sampling signal generator 435 includes a PLL and a digital delay line.

Continuing with the example of operation, the processing module 430 samples, in accordance with the sampling signal 444, data (e.g., a digital value or analog voltage representing a pressure being sensed) from the pressure sensing element to produce foot force data 446. The processing module 430 also samples, in accordance with the sampling signal 444, data (e.g., x-y-z coordinate data or polar coordinate data) from the first accelerometer to produce three-dimensional (3D) foot data 448. The processing module 430 may store the foot force data 446 and the 3D data in memory 432 and/or provide it to the wireless communication transceiver 434 for transmission to the computing device.

In an embodiment, the control circuit is on a printed circuit board (PCB) that is positioned within a hole of the midsole, is in the dongle, and/or is included in the insole. The PCB may be secured into the hole with an adhesive, with an encasing material, etc. The PCB is a single layer printed circuit board (PCB), a multiple layer PCB, a rigid PCB, a flexible PCB, a high frequency PCB, and/or an aluminum-backed PCB.

In another embodiment, the control circuit is on a printed circuit board (PCB) that is positioned within the dongle 415. The accelerometer 422 may be on the PCB with the control circuit and thus positioned within the hole of the midsole or within the dongle 415. In yet another embodiment, the accelerometer 422 is on a separate PCB from that of the control circuit 424. In one permeation of this embodiment, the accelerometer 422 is positioned within a second hole of the midsole regardless of whether the control circuit PCB is within the hole of the midsole or in the dongle.

FIG. 71 is a logic diagram of an example of a method executed by a processing module that may be implemented as operational instructions stored on a computer readable memory. The method begins at step 460 where the processing module (e.g., processing module 430 of the shoe sensor system 416 and/or processing module 427 of computing device 425) obtains foot force data. The foot force data created by sampling, in accordance with a sampling signal, data from the pressure sensing elements of a shoe sensor system.

On a per sample basis, the foot force data includes, from at least some of the pressure sensing elements, a pressure sensor indicator (e.g., an identifier of the particular pressure sensing element providing the data) and one or more of a pressure sensed value, a representation of the sensed pressure level, and a pressure measurement. As an example, a pressure sensing element generates a resistance from a resistive pressure sensor, a capacitance from a capacitance pressure sensor, an inductance from an inductor pressure sensor, or a frequency from a piezoelectric pressure sensor in response to an applied pressure. The resistance, the capacitance, the inductance, or the frequency is provided as the pressure sensed value (i.e., raw data of a pressure measurement).

The representation of the sensed pressure level is a digital value from a range of digital values or an analog voltage from a range of analog voltages that based on the resistance, the capacitance, the inductance, or the frequency generated by the pressure sensing element. For example, a five-bit digital value includes a range from 0-31 (decimal), where 0 corresponds to no pressure and 31 corresponds to maximum pressure of the pressure sensor. The representation of the sensed pressure level is not a pressure measurement, but a value in a range of values. The pressure measurement converts the representation of the sensed pressure level into an actual pressure measurement. As such, over a plurality of samples, the foot force data 446 includes, from each of at least some of the pressure sensing elements, the pressure sensor indicator and one or more of a plurality of pressure sensed values, a plurality of representations of sensed pressure levels, and a plurality of pressure measurements.

As an example of one sampling interval, assume that a resistive pressure sensor of the pressure sensing element has a maximum pressure of 200 pounds. For one sample, the resistive pressure sensor generates a resistance of 1,500 Ohms, where the resistance ranges from 100,000 Ohms with no pressure to 500 Ohms with 200 pounds of pressure. The 1,500 Ohms is converted to a digital value of 11000 (e.g., 24 in a digital scale of 0 to 31). The digital value is then converted in a pressure measurement of 150 pounds via a look up table or other type of calculation.

The method continues at step 462 where the processing module obtains three-dimensional (3D) foot data. The 3D foot data is created by sampling, in accordance with the sampling signal, data from a first accelerometer of the shoe sensor system. On a per sample basis, the 3D foot data includes an accelerometer identifier (e.g., an ID of the first accelerometer) and one of an x-y-z coordinate value, a representation of an x-y-z coordinate, and an x-y-z coordinate. The 3D foot data may further include an x-y-z origin coordinate. As such, over a plurality of samples, the 3D foot force data includes the accelerometer identifier and one of a plurality of x-y-z coordinate values, a plurality of representations of x-y-z coordinates, and a plurality of x-y-z coordinates.

As an example, the x-y-z origin coordinate is the origin of a reference Cartesian coordinate system corresponding to one of the shoes. Typically, when the shoe sensor is initialized to monitor a physical activity, an origin will be established based on a current location of the shoe for the reference Cartesian coordinate system. An x-y-z coordinate value is the raw data generated by the accelerometer for a given sample interval; the raw data includes a current x-axis acceleration, a current y-axis acceleration, and a current z-axis acceleration. A representation of the coordinate value is conversion of the raw accelerometer data into a x-y-z distance data based on the equation, for the x-axis) $x=v0t+\frac{1}{2}at2$, where x is the distance in the x-axis direction, t is the time interval, v0 is the initial velocity, and a is the acceleration in the x-axis. From the x distance, y distance, and z distance and the x-y-z coordinate of the previous sample (or the origin coordinate if this is the first sample interval) the current coordinate is determined, which corresponds to the x-y-z coordinate.

With respect to steps 460 and 462, in one embodiment, the processing module of the shoe sensor system obtains the foot force data by receiving it from the plurality of pressure sensing elements and obtains the three-dimensional foot data by receiving it from the first accelerometer. In another embodiment, the processing module of a computing device obtains the foot force data includes by receiving it from a transmitter of the wireless communication transceiver and obtains the three-dimensional foot data by receiving it from the transmitter.

The method continues at step 464 where the processing module correlates the foot force data and the three-dimensional foot data in accordance with the sampling signal to produce correlated foot data. In an example embodiment, the processing module of the shoe sensing system correlates the foot force data and the foot three-dimensional data to produce correlated foot data and the wireless communication transceiver transmits the correlated foot data within the outbound RF signals to the computing device.

The method continues at step 466 where the processing module processing the correlated foot data to determine physical activity data. The physical activity data includes, as will be subsequently discussed, distance traveled during a time period, stride length data, time, fatigue indication, injury prevention indicators, elevation tracking for the time period, running optimization, and rotational sport optimization.

In furtherance of the processing, the processing module adjusts the processing of the correlated foot data based on known nature of a physical activity. The known nature of the physical activity includes predicable motions of body parts (e.g., how the feet, legs, hands, arms, torso, and head move when running or walking; how the body is supposed to move when hitting a golf ball; how the body is supposed to move when throwing a ball or hitting a ball with a racket or a bat; etc.). The known nature of the physical activity may further be enhanced to account for age of the person engaging in the physical activity, the skill level of the person, and/or other personal characteristics that may affect performance of the physical activity (e.g., injuries, flexibility, height, weight, etc.).

As an example of adjusting of the processing, the processing module adjusts the rate of the sampling signal. For instance, when the physical activity is walking, less data points are needed than when the person is sprinting or jogging. As another example, the processing module using physical activity general movement data to enhance correlation of the foot force data and the foot three-dimensional data. As yet another example, the processing module using the physical activity general movement data to further determine the one or more of: the distance traveled during a time period, the stride length data, the time duration, the fatigue indication, the injury prevention indicators, the elevation tracking for the time period, the running optimization, and the rotational sport optimization.

As a still further example, the processing module using previous data of a wearer to determine the one or more of: the distance traveled during a time period, the stride length data, the time duration, the fatigue indication, the injury prevention indicators, the elevation tracking for the time period, the running optimization, and the rotational sport optimization. For example, if the person has a history of averaging 6 mph when jogging with an average stride length of 3 feet, then the shoe sensor system can be tuned to expect a pace of 6 mph and a stride length of about 3 feet, which will help improve accuracy of detecting foot strikes, etc.

FIG. 72 is an example of timing and data diagram of a shoe sensor system. The timing includes the sampling signal 444 that has a square wave 50% duty cycle clock and a sampling rate (e.g., 500 Hz to 50 KHz). The sampling clock 444 may have an alternative waveform (e.g., sinusoidal, a rectified sinusoidal signal, etc.) and may have an alternate duty cycle (e.g., 10% to 90%). With each sampling interval (e.g., sample 1, 2, 3, 4, etc.), each of the pressure sensing elements 420 and the accelerometer 422 provide data. The data may be 4-32 bits per element 420 and from the accelerometer 422 per sample interval.

The pressure sensing elements 420 provide the foot force data 446 and the accelerometer provides the 3D foot data 448. For each sample interval (e.g., sample 1, 2, 3, 4, etc.), the processing module 430 of the shoe sensor system correlates the foot force data 446 and the 3D foot data 448 to produce the correlated data 452. The correlation of the data 446 and 448 may be an aggregation of the data on a per sampling interval. For example, a data packet for sample 1 includes the foot force data 446 sampled from each of the pressure sensing elements taking during sampling interval 1, an ID for each of the pressure sensing element tied to their respective data, the 3D foot data from the accelerometer sampled during sampling interval 1, and an ID for the accelerometer tied to its data.

As another example of correlation, the processing module identifies a first foot force data point of the foot force data (i.e., the data from each of the pressure sensing elements sampled during the first sampling interval) and a first three-dimensional foot data point of the three-dimensional foot data (i.e., the data from the accelerometer sampled during the first sampling interval). The processing module then links the first foot force data point with the first three-dimensional foot data point for the first sampling interval. The linking includes aggregation, aggregation and encryption, aggregation and scrambling, forward error correction such as Reed Solomon, and/or common packet identifiers. For example, the data from each of the pressure sensing elements 420 and the accelerometer 422 is transmitted in its own data packet that includes the data, an ID of the device associated with the data, and a sampling interval indicator (e.g., a sampling interval number, a clock count, a timestamp, etc.). The processing module links the foot force data points and the 3D foot data for each of the other sampling intervals in a similar manner.

Figure 73:
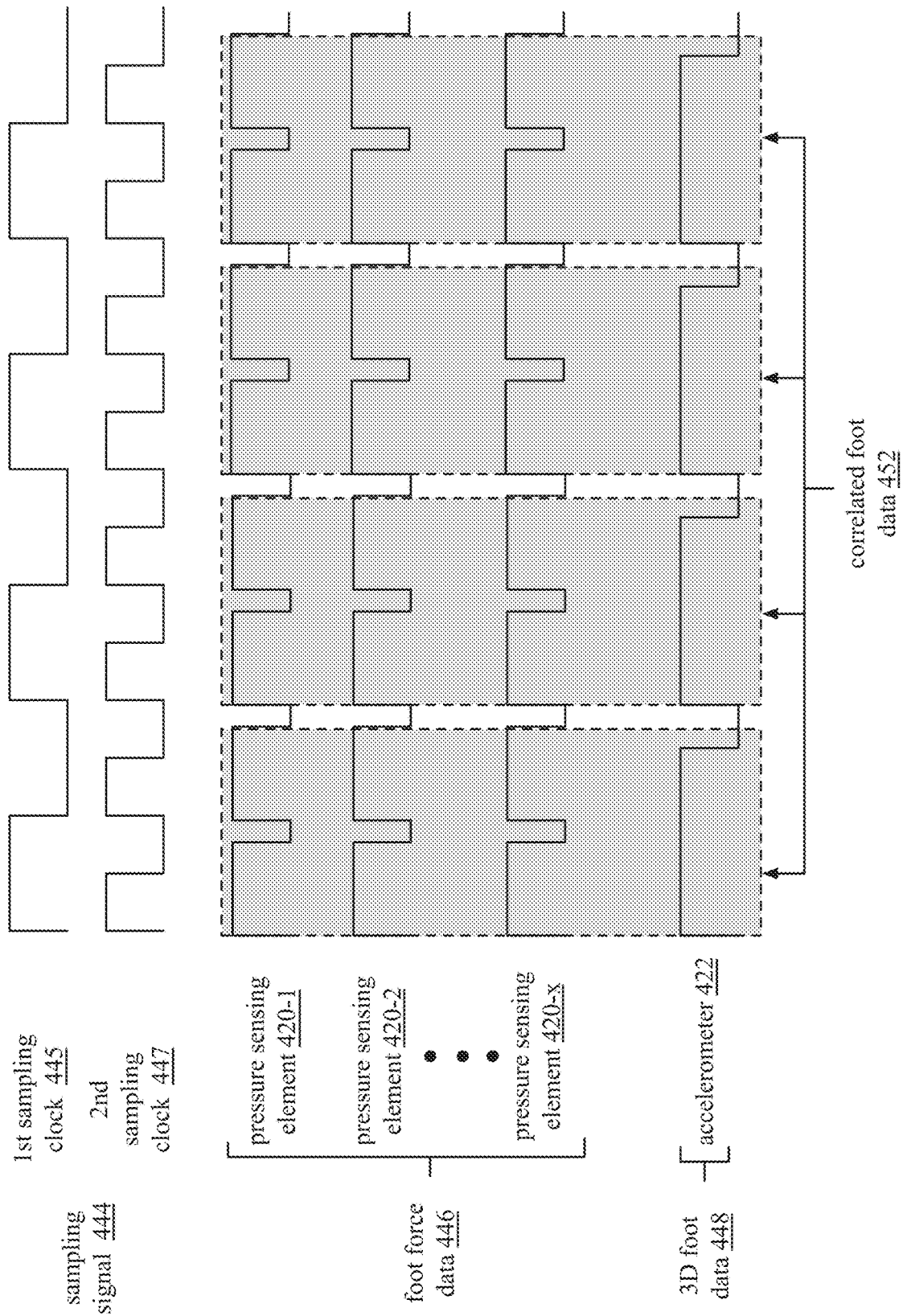

FIG. 73 is another example of timing and data diagram of a shoe sensor system. The timing includes a first sampling clock 445 and a second sampling clock 447. In this example, the second sampling clock 447 has a rate that is approximately twice that of the first sampling clock 445. The sampling clocks 445 and 447 are synced. The first sampling clock 445 is used to sample the data from the accelerometer 422 and the second clock 447 is used to sample the data from the pressure sensing modules 420.

As such, each of the pressure sensing elements produce two data samples per one data sample of the accelerometer. The data is correlated based on the slower clock signal such that, for each sampling interval of the first sampling clock 445, the correlated data includes two data samples from each of the pressure sensing elements and one data sample from the accelerometer.

Figure 74:
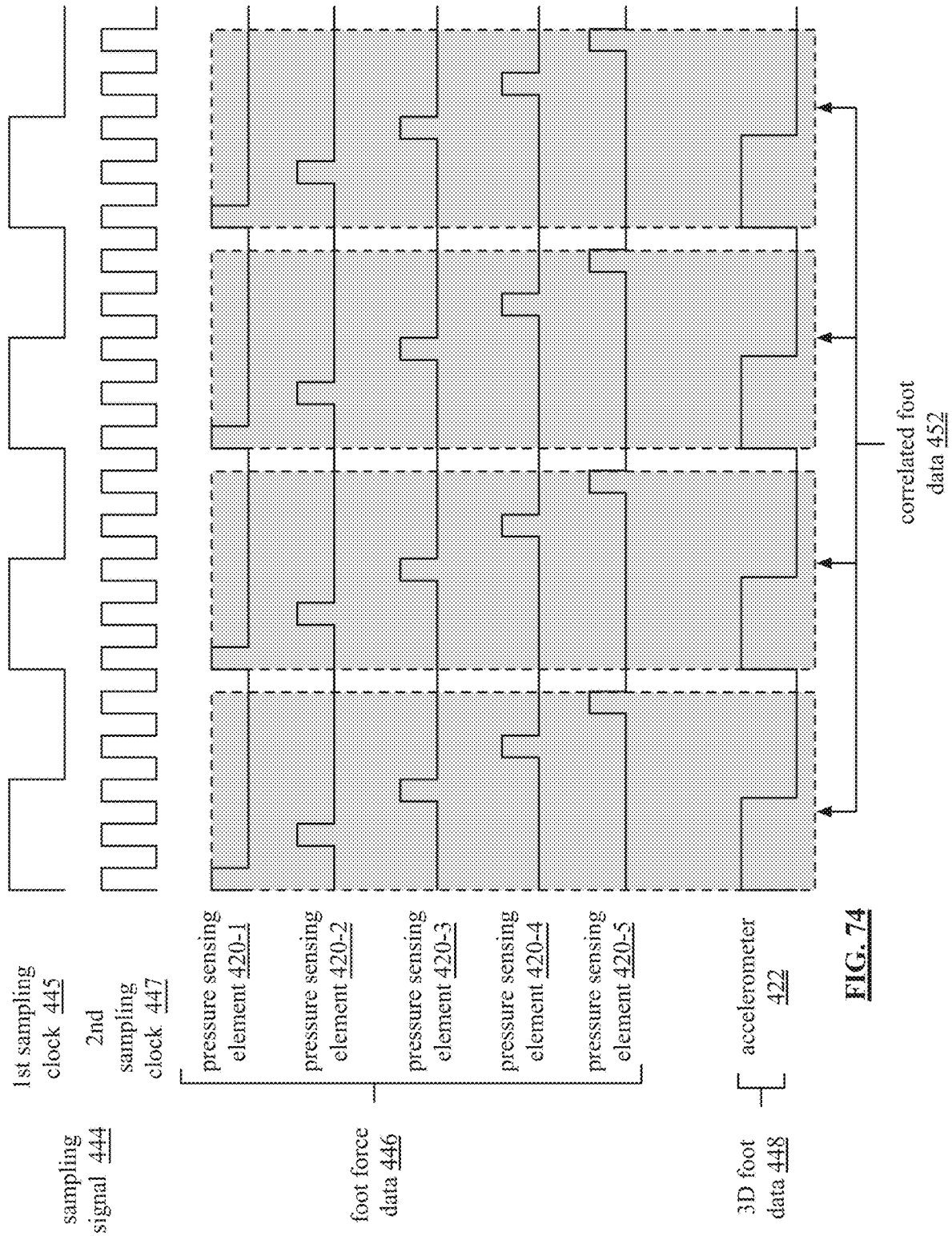

FIG. 74 is another example of timing and data diagram of a shoe sensor system. The timing includes a first sampling clock 445 and a second sampling clock 447. In this example, the second sampling clock 447 has a rate that is approximately five times that of the first sampling clock 445. The sampling clocks 445 and 447 are synced. The first sampling clock 445 is used to sample the data from the accelerometer 422 and the second clock 447 is used to sample the data from the pressure sensing modules 420.

During the first sample interval of the first clock 445, there are five cycles of the second sampling clock 447. A first cycle of the second sampling clock 447 is used to sample the first pressure sensing element; a second cycle is used to sample a second pressure sensing element; a third cycle is used to sample a third pressure sensing element; a fourth cycle is used to sample a fourth pressure sensing element; and a fifth cycle is used to sample a fifth pressure sensing element. As such, each of the pressure sensing elements produce one data sample per one data sample of the accelerometer. The data is correlated based on the slower clock signal such that, for each sampling interval of the first sampling clock 445, the correlated data includes one data sample from each of the pressure sensing elements and one data sample from the accelerometer.

Figure 75:
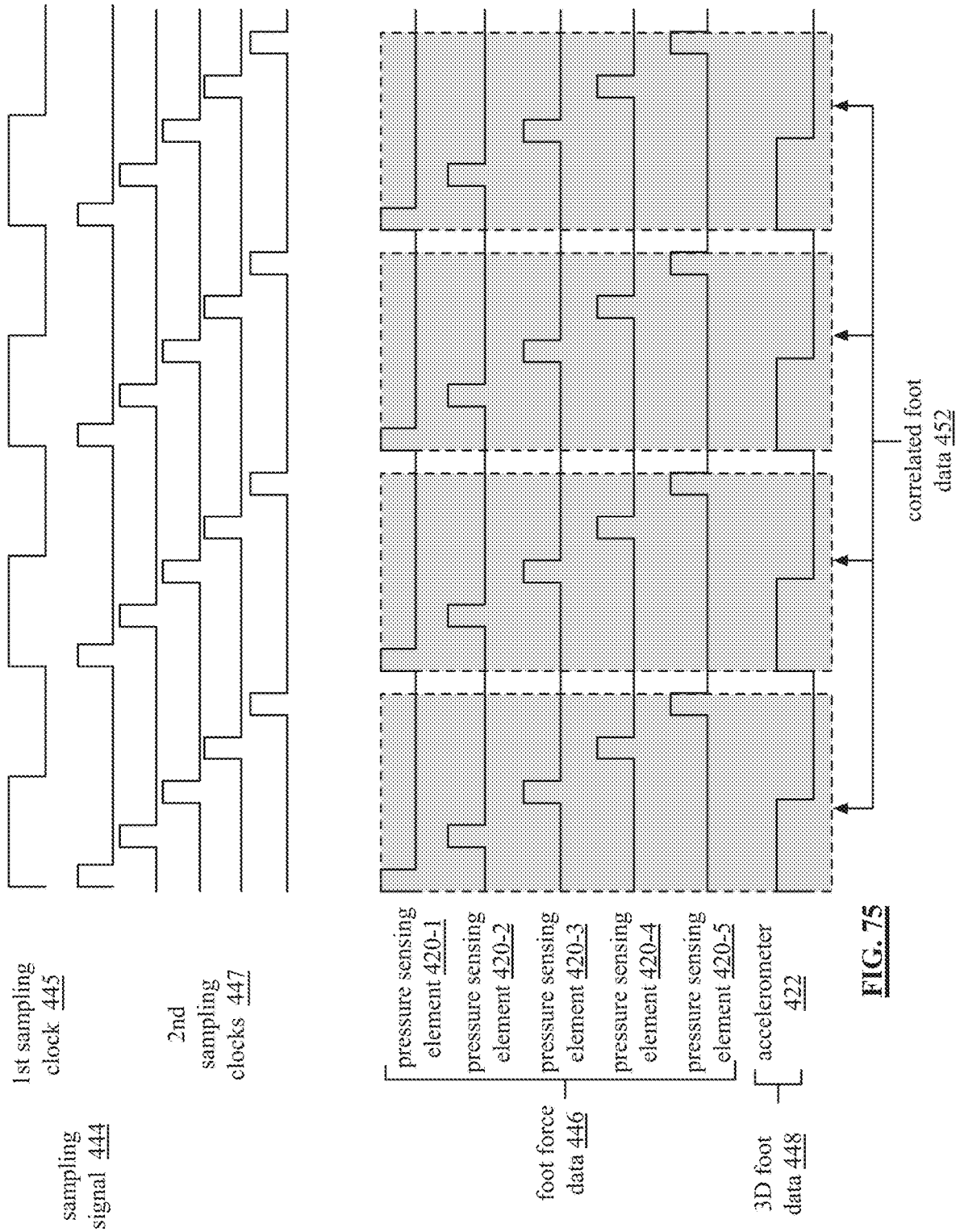

FIG. 75 is another example of timing and data diagram of a shoe sensor system. The timing includes a first sampling clock 445 and a plurality of second sampling clocks 447. In this example, each of the second sampling clock 447 has the same rate as the first sampling clock 445. The sampling clocks 445 and 447 are synced and the second sampling clocks are offset in time. The first sampling clock 445 is used to sample the data from the accelerometer 422 and the second clocks 447 are used to individually sample the data from the pressure sensing modules 420.

A first of the second sampling clocks 447 is used to sample the first pressure sensing element; a second of the second sampling clocks 447 is used to sample a second pressure sensing element; a third of the second sampling clocks 447 is used to sample a third pressure sensing element; a fourth of the second sampling clocks 447 is used to sample a fourth pressure sensing element; and a fifth of the second sampling clocks 447 is used to sample a fifth pressure sensing element. As such, each of the pressure sensing elements produce one data sample per one data sample of the accelerometer. The data is correlated based on the slower clock signal such that, for each sampling interval of the first sampling clock 445, the correlated data includes one data sample from each of the pressure sensing elements and one data sample from the accelerometer.

Figure 76:
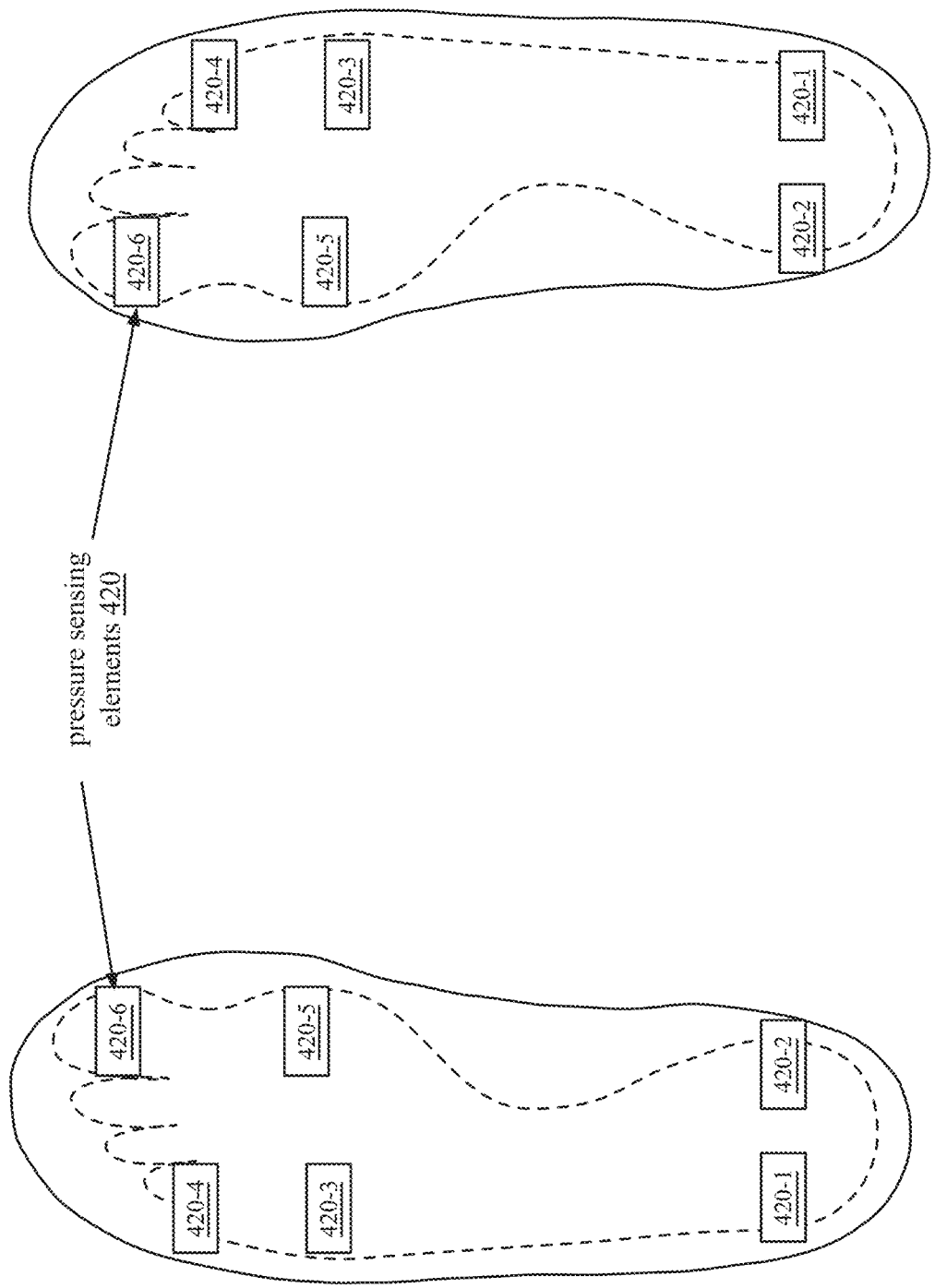
FIGS. 76A and 76B are top view diagrams of an example of positioning pressure sensing elements within a pair of shoes.

FIGS. 76A and 76B are top view diagrams of an example of positioning pressure sensing elements 420 within a pair of shoes. In this example, the pattern includes a first pressure sensing element 420-1 in a lateral heel position; a second pressure sensing element 420-2 in a medial heel position; a third pressure sensing element 420-3 in a lateral ball of foot position; a fourth pressure sensing element 420-4 in a lateral toe position; a fifth pressure sensing element 420-5 in a medial ball of foot position; and a sixth pressure sensing element 420-6 in a medial toe position.

In contrast to most foot force analysis systems, the present system includes pressure sensors in selected area, not across the entire surface area of the foot. Further, with the wireless features and modular design, it does not require any modules to be strapped on to the legs or the waist. Still further with a combination of pressures sensors and accelerometers, accurate physical activity data is obtained; not approximate data based on algorithms that predict physical activity from a few trigger points (e.g., arm movement for determine number of steps and to determine a distance traveled. Such approximations have a tolerance of about +/−10%. With the present system using measured physical activity data, the results will have a tolerance less than +/−1%.

Figure 77:
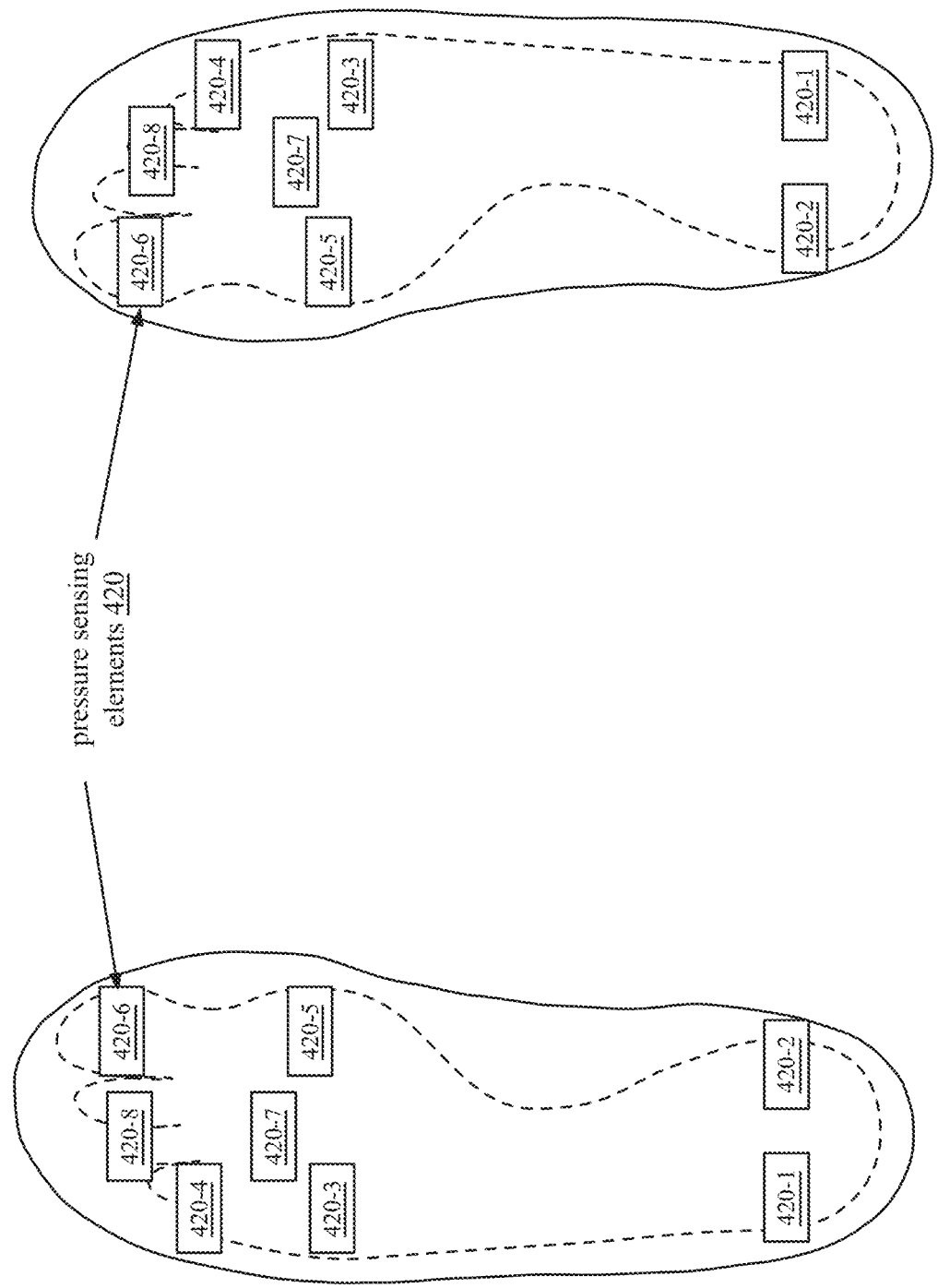
FIGS. 77A and 77B are top view diagrams of another example of positioning pressure sensing elements within a pair of shoes.

FIGS. 77A and 77B are top view diagrams of another example of positioning pressure sensing elements 420 within a pair of shoes. This example is similar to the one of FIGS. 76A and 76B with the addition of two more pressure sensing elements 420 per shoe. Each shoe includes a seventh pressure sensing element in a mid-ball of foot position 420-7 and an eighth pressure sensing element 420-8 in a mid-toe position.

Figure 78:
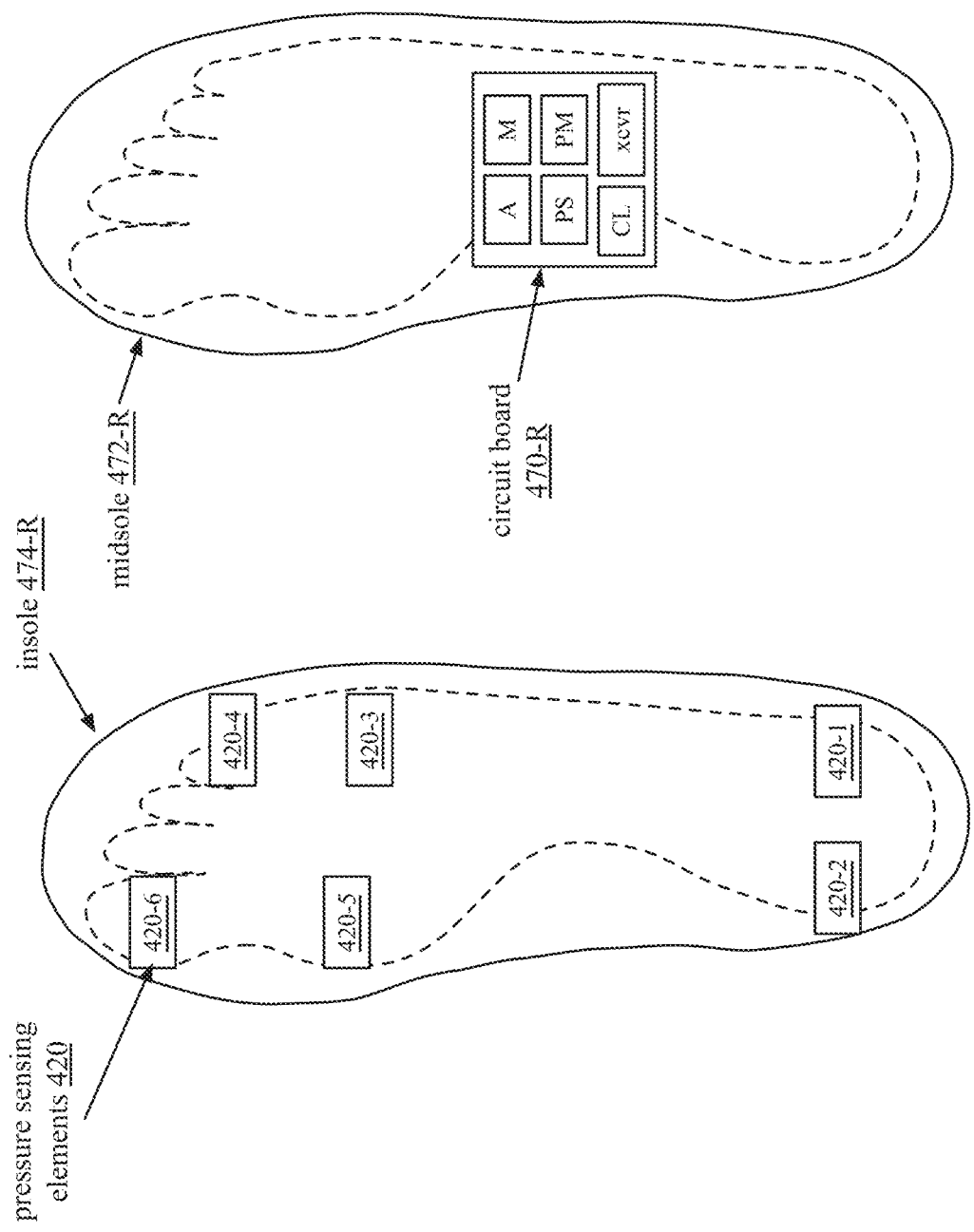
FIGS. 78A and 78B are top view diagrams of an example of the pressure sensing elements positioned with respect to an insole of a right shoe and the control circuit positioned with respect to a midsole of a right shoe.

FIGS. 78A and 78B are top view diagrams of an example of the pressure sensing elements 420 positioned with respect to an insole 474-R of a right shoe and the control circuit board 470-R positioned with respect to a midsole 472-R of a right shoe. FIG. 78A illustrates the insole 474-R with six pressure sensing elements 420-1 through 420-6 positioned as shown in FIG. 78B. In an embodiment, each of the pressure sensing elements 420 is attached to the surface of the insole 474-R via an adhesive or other bonding agent. In another embodiment, each of the pressure sensing elements 420 is fabricate into the insole 474-R as the insole is manufactured. In another embodiment, the pressure sensing elements 420 are fabricated on a flexible printed circuit board that overlays and/or is adhered to the top surface of the insole 474-R.

FIG. 78B illustrates the midsole 472-R in which the control circuit board 470-R is mounted. The control circuit board 470-R includes the power source (PS), memory (M), a processing module (PM), a wireless transceiver (XCVR), an accelerometer (A), and a clock circuit (CL). In an embodiment, the control circuit board 470-R is positioned within a hole in the midsole 472-R, where the hole does not extend all the through the midsole and is just deep enough to engulf the control circuit board. Once the control circuit board 470-R is positioned in the hole, it is held in place by an adhesive, a bonding agent, an encasing material, etc.

Electrical coupling between the pressure sensing elements 420 and the control circuit board is accomplished in a variety of ways. As an example, the control circuit board includes an electrical connector that mates to a corresponding electrical connector coupled to the pressure sensing elements. The connectors are positioned in the insole and midsole respectively as to provide minimal interference with the fit and comfort of the shoe.

As another example, the control circuit board 470-R is coupled to the pressure sensing elements via RF signals. One or more examples of RF coupling will be described with reference to one or more subsequent Figures. As yet another example, the control circuit board 470-R is coupled to the pressure sensing elements via NFC coils. One or more examples of NFC coupling will be described with reference to one or more subsequent Figures.

Figure 79:
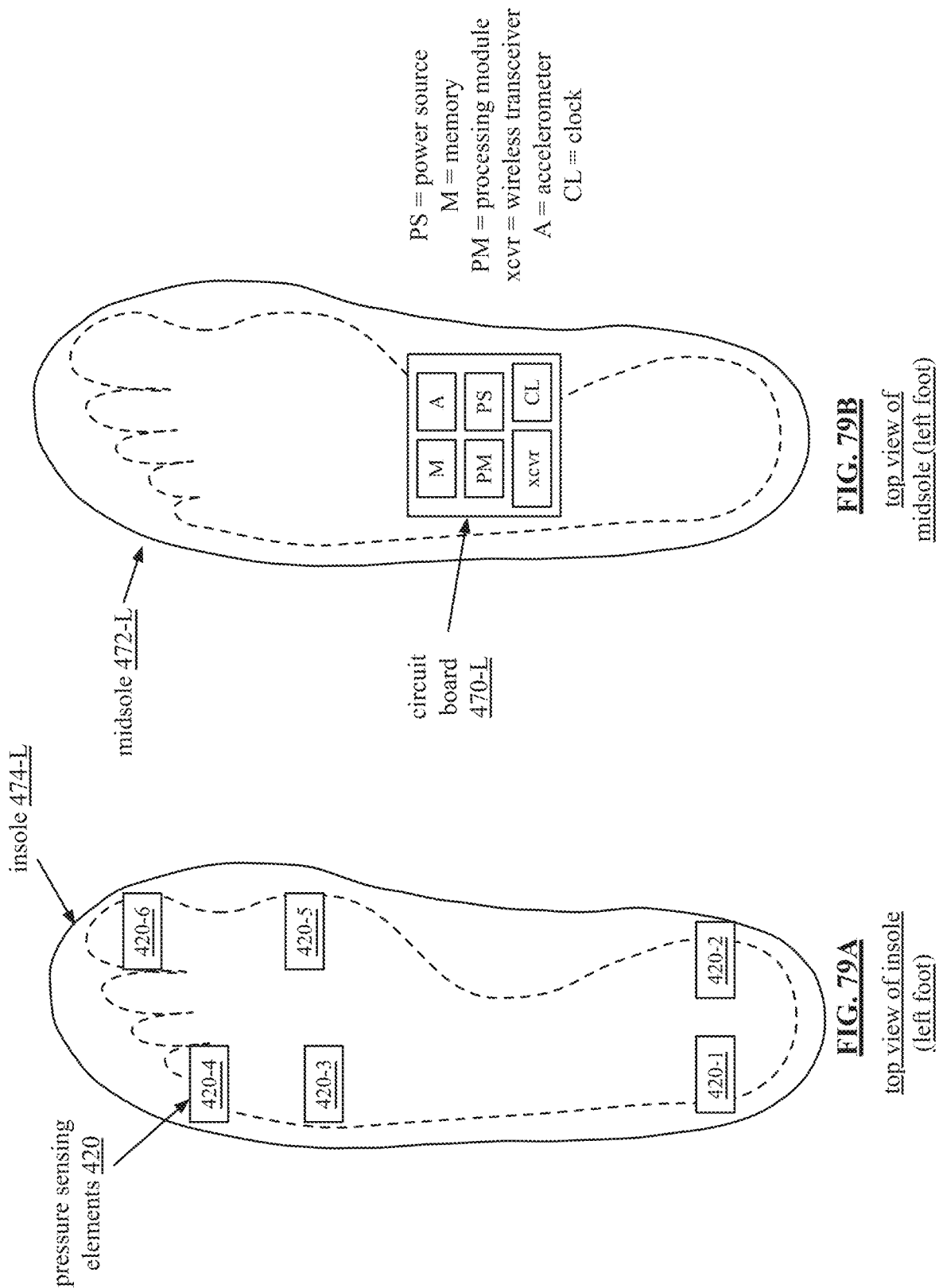
FIGS. 79A and 79B are top view diagrams of an example of the pressure sensing elements positioned with respect to an insole of a left shoe and the control circuit positioned with respect to a midsole of a left shoe.

FIGS. 79A and 79B are identical to FIGS. 78A and 78B, but FIGS. 79A and 79B are for the left shoe. As such, these Figures area top view diagrams of an example of the pressure sensing elements 420 positioned with respect to an insole 474-L of a left shoe and the control circuit board 470-L positioned with respect to a midsole 472-L of a left shoe.

Figure 80:
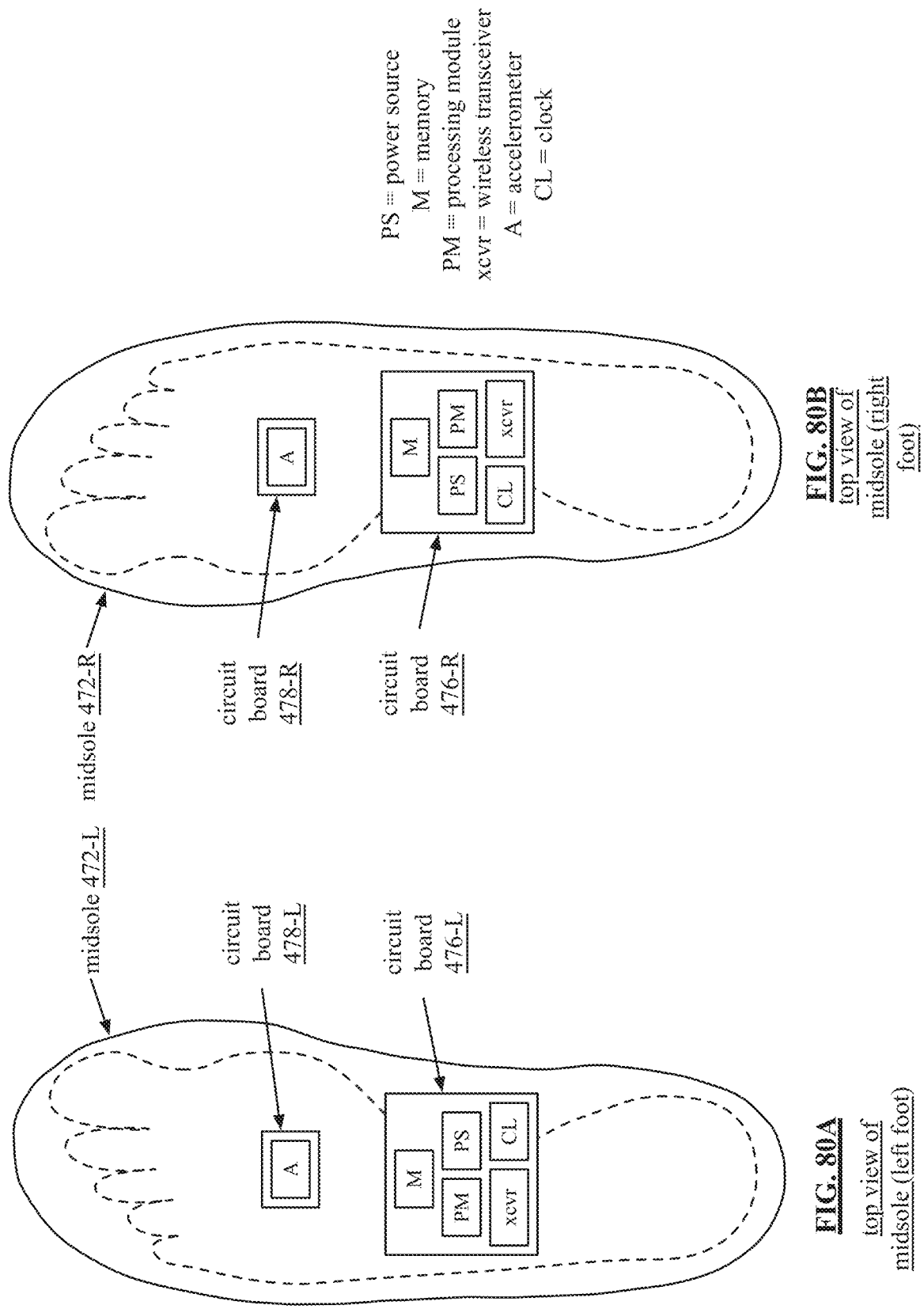
FIG. 80A is a top view diagram of another example of the control circuit and accelerometer positioned with respect to a midsole of a left shoe.
FIG. 80B is a top view diagram of another example of the control circuit and accelerometer positioned with respect to a midsole of a right shoe.

FIG. 80A is similar to FIG. 79B with the accelerometer (A) being on a separate circuit board 478-L from the control circuit board 476-L. In an example, the accelerometer circuit board 478-L is coupled to the control circuit board 476-L via a wired connection. In another example, the accelerometer circuit board 478-L is coupled to the control circuit board 476-L via a wireless connection.

FIG. 80B is identical to FIG. 80A but it is for the right midsole 472-R and includes an accelerometer circuit board 478-R and a control circuit board 476-R.

Figure 81:
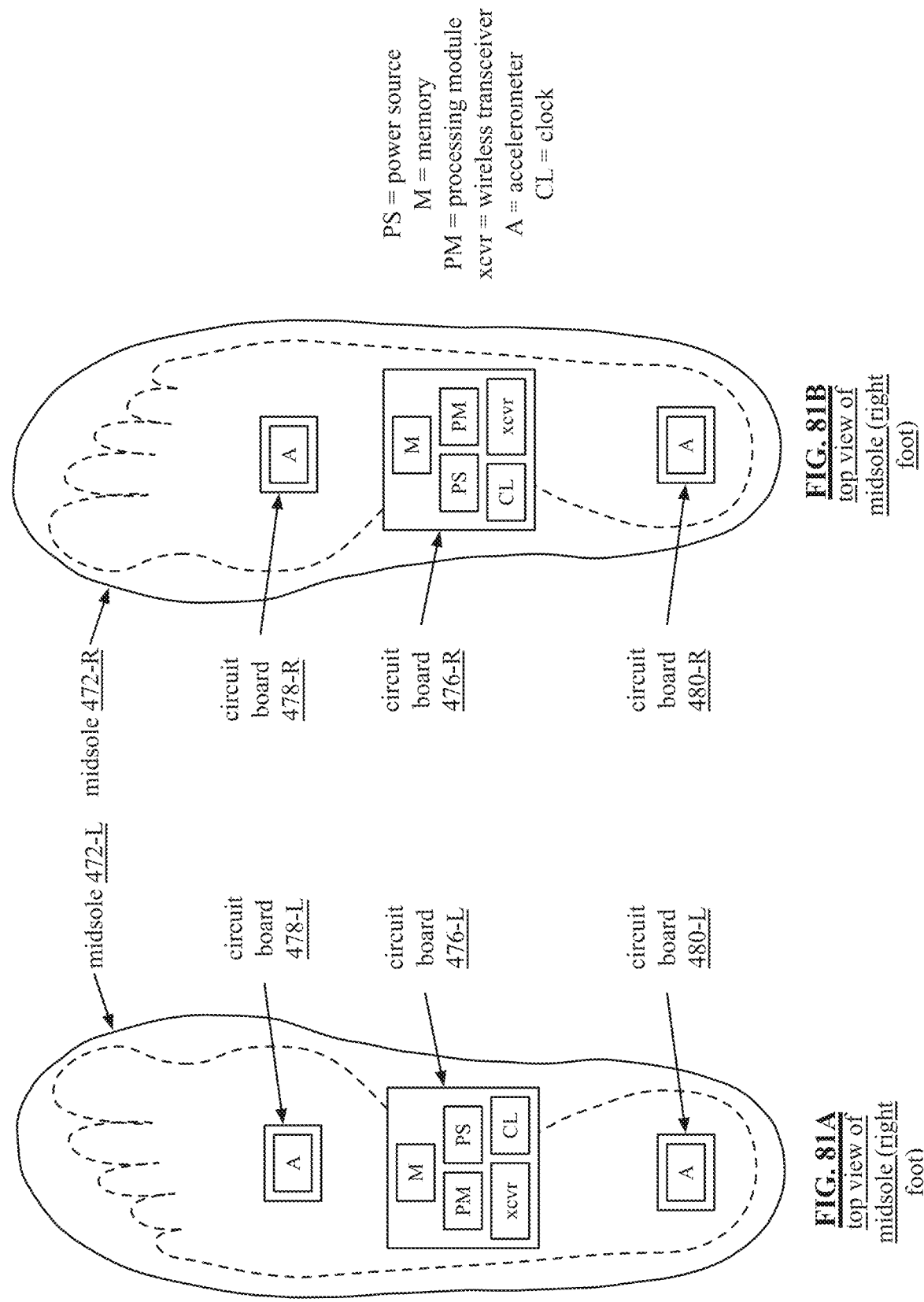
FIG. 81A is a top view diagram of another example of the control circuit and two accelerometers positioned with respect to a midsole of a left shoe.
FIG. 81B is a top view diagram of another example of the control circuit and two accelerometers positioned with respect to a midsole of a right shoe.

FIG. 81A is similar to FIG. 80A with the addition of a second accelerometer on another circuit board 480-L. In an example, the accelerometer circuit board 480-L is coupled to the control circuit board 476-L via a wired connection. In another example, the accelerometer circuit board 480-L is coupled to the control circuit board 476-L via a wireless connection. Note that the second accelerometer is positioned within the pattern of the foot and is at a distance from the first accelerometer.

In an example of operation, the second accelerometer provides second x-y-z coordinates (i.e., second 3D foot data) at a sample rate of the sampling signal to the processing module (PM). Recall that the first accelerometer provides first x-y-z coordinates at the sample rate to the processing module (PM). The processing module correlates the foot force data, the three-dimensional foot data, and the second three-dimensional foot data in accordance with the sampling signal to produce the correlated foot data.

The processing module (e.g., of the circuit board and/or of the computing devices) processes the first and second x-y-z coordinates to produce foot orientation data. For example, for a given sampling interval, the first x-y-z coordinates are processed to determine a first location of the first accelerometer and the second x-y-z coordinates are processed to determine a second location of the second accelerometer. With the distance between the first and second accelerometers known, the orientation of the foot is determined.

Each of the accelerometer boards 476-L and 478-L require power and a clock signal or sampling signal. In an embodiment, each board 476-L and 478-L includes its own power source circuit and clock circuit to generate the sampling signal. In another embodiment, each board 476-L and 478-L receives a power supply and a clock signal or sampling signal from the control circuit board 470-L. In yet another embodiment, each board 476-L and 478-L includes its own power source circuit and receives the clock or sampling signal from the control circuit board 470-L.

FIG. 81B is identical to FIG. 81A but it is for the right midsole 472-R and includes accelerometer circuit board 478-R, accelerometer circuit board 480-R, and a control circuit board 476-R.

Figure 82:
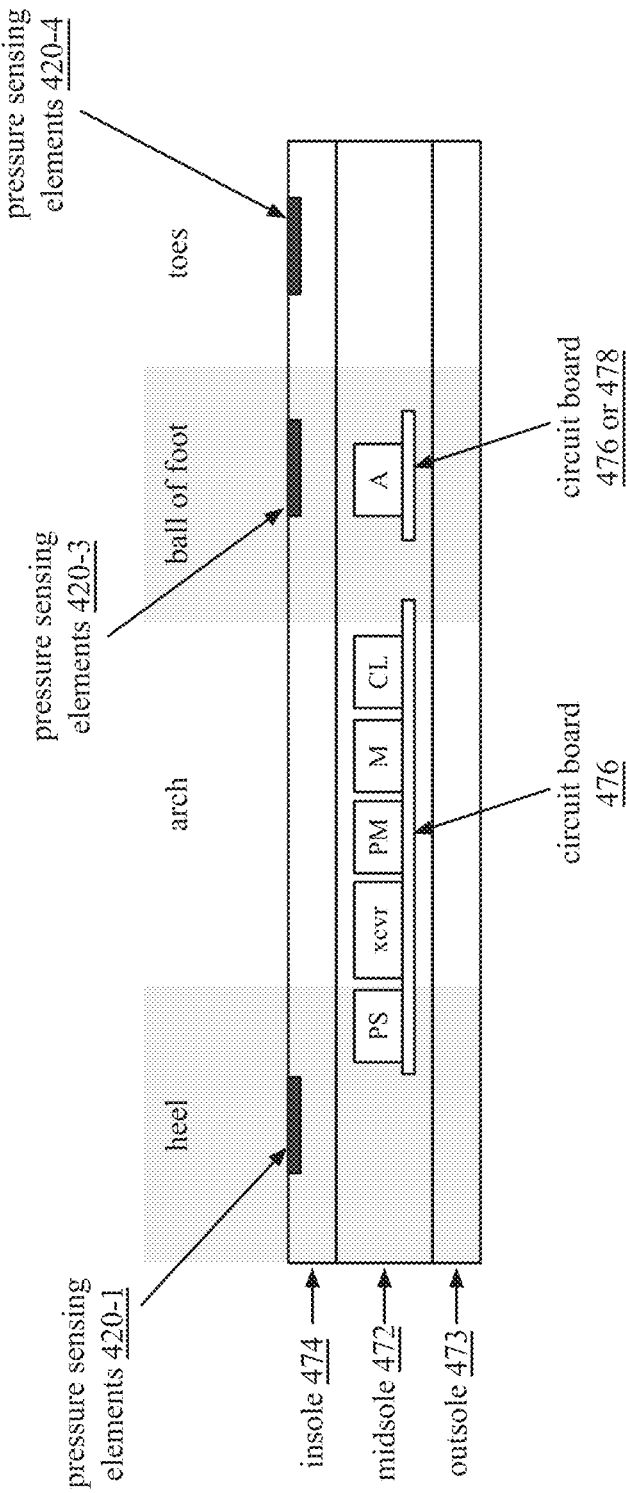
FIG. 82 is a side view diagram of another example of the pressure sensing elements positioned with respect to an insole of a shoe and the control circuit and accelerometer positioned with respect to a midsole of the shoe.

FIG. 82 is a side view diagram of another example of the pressure sensing elements 420 positioned with respect to an insole 474 of a shoe (e.g., left or right foot) and the control circuit board 76 and accelerometer (A) positioned with respect to a midsole 474 of the shoe. The shoe is further shown to include an outsole 473.

Each of the pressure sensing elements 420-1, 420-3, and 420-4 and the others not shown are positioned at or on the surface of the insole 474. Pressure sensing element 420-1 (and 420-2 not shown) are positioned in the heel section of the shoe; pressure sensing element 420-3 (and 420-5 not shown) are positioned in the ball of foot section of the shoe; pressure sensing element 420-4 (and 420-6 not shown) are positioned in the toe section of the shoe. The accelerometer (A) may be on the same PCB and the control circuit (i.e., board 476) or on its own PCB (i.e., board 478).

Figure 83:
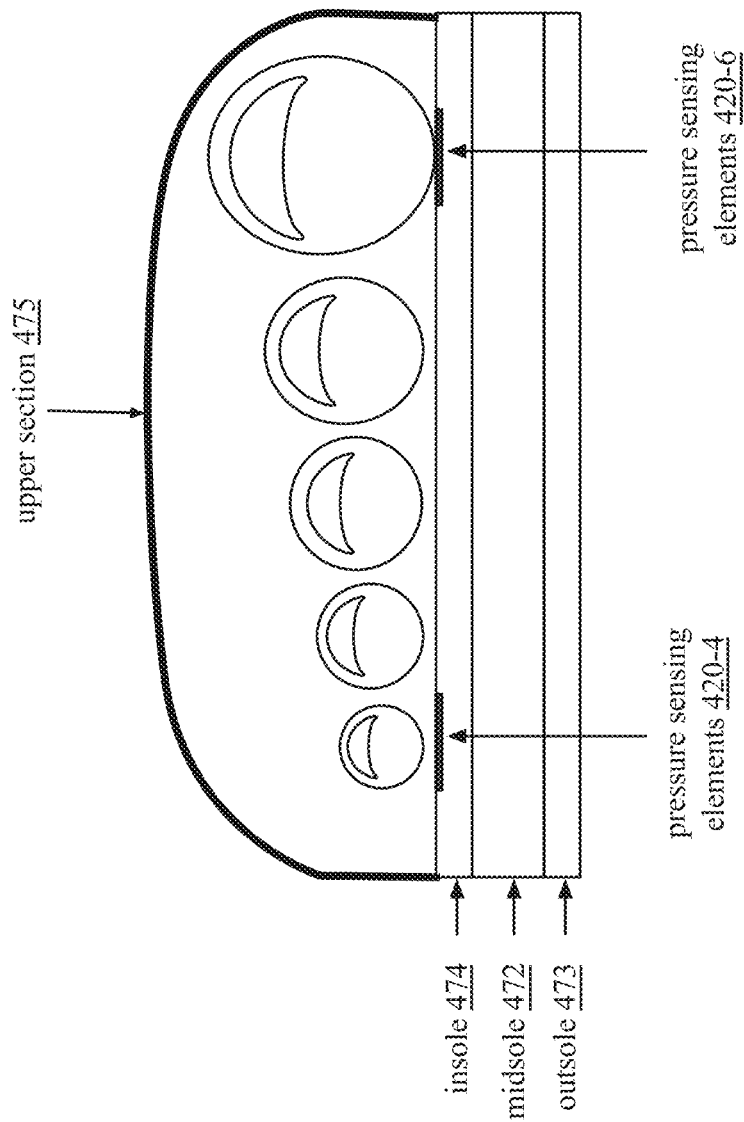
FIG. 83 is a front view diagram of another example of the pressure sensing elements positioned with respect to an insole of a shoe.

FIG. 83 is a front view diagram of another example of the pressure sensing elements 420-4 and 420-6 positioned with respect to an insole 474 of a shoe that also includes the midsole 472, the outsole 473, and an upper section 475. In this example, pressure sensing elements 420-4 is positioned on the lateral side of the shoe (e.g., approximately under the little toe or at the fifth metatarsal) and pressure sensing elements 420-6 is positioned on the medial side of the shoe (e.g., approximately under the big toe or at the first metatarsal).

Figure 84:
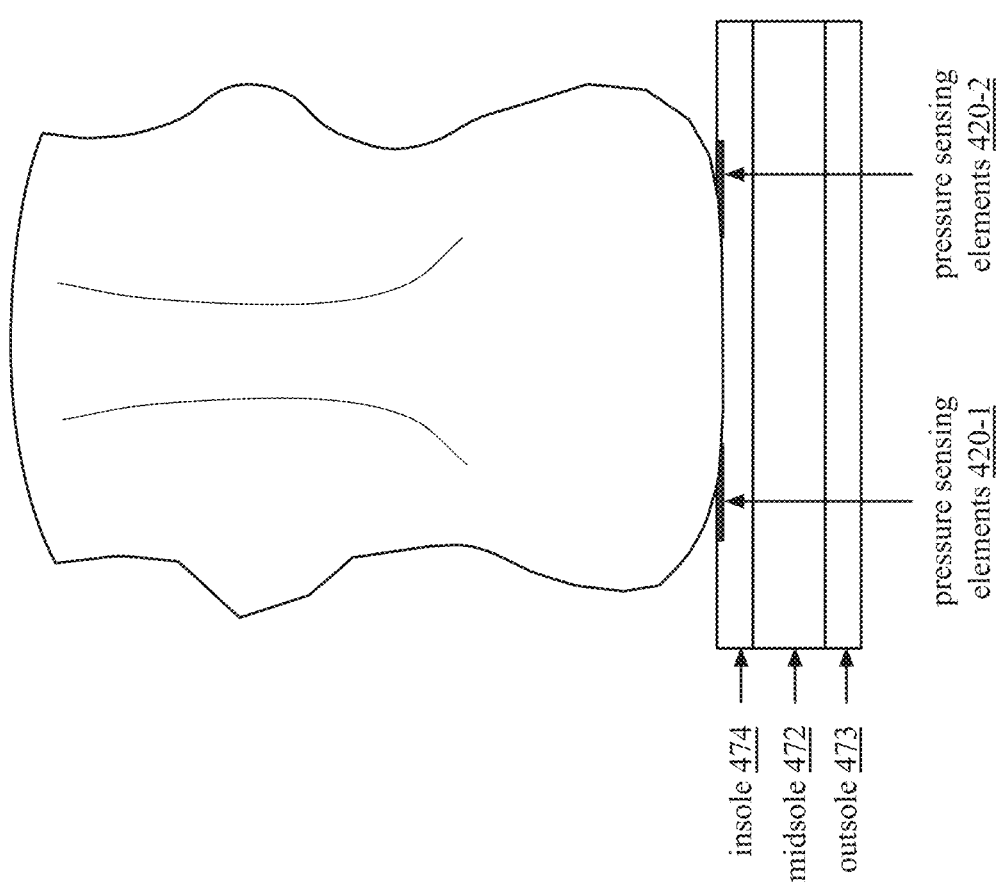
FIG. 84 is a rear-view diagram of another example of the pressure sensing elements positioned with respect to an insole of a shoe.

FIG. 84 is a rear-view diagram of another example of the pressure sensing elements 420-1 and 420-2 positioned with respect to an insole 474 of a shoe that also includes the midsole 472 and the outsole 473. In this example, pressure sensing elements 420-1 is positioned on the lateral side of the shoe (e.g., approximately under the outside of the heel) and pressure sensing elements 420-2 is positioned on the medial side of the shoe (e.g., approximately under the inside of the heel).

Figure 85:
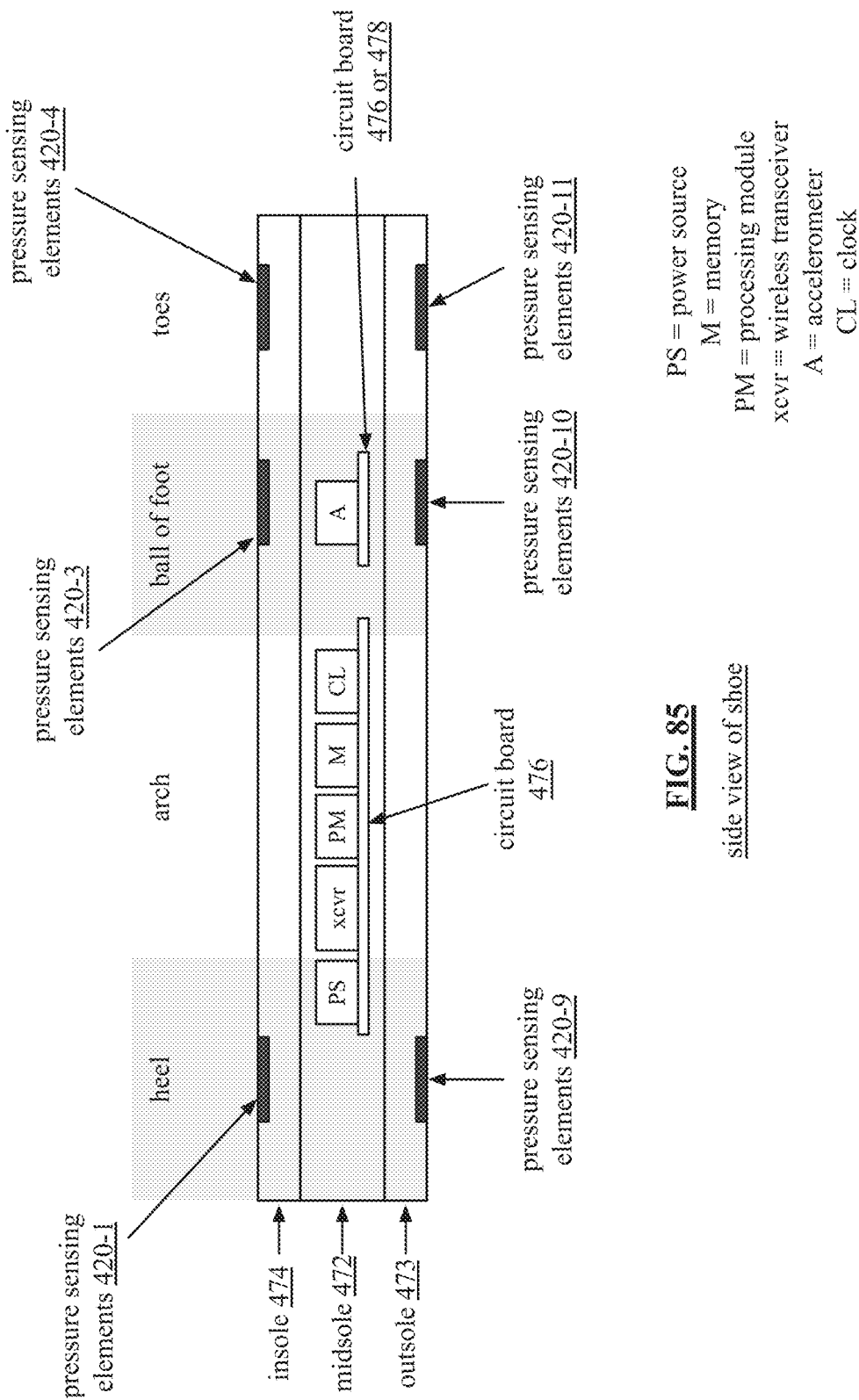
FIG. 85 is a side view diagram of another example of the pressure sensing elements positioned with respect to an insole of a shoe and the control circuit and accelerometer positioned with respect to a midsole of the shoe.

FIG. 85 is similar to FIG. 82 with the addition of pressure sensing elements positioned in the outsole 473. Assuming this a lateral side view of the shoe, pressure sensing element 420-9 is located underneath pressure sensing element 420-1 and is positioned at or near the surface of the outsole 473. Similarly, pressure sensing element 420-10 is located underneath pressure sensing element 420-3 and is positioned at or near the surface of the outsole 473 and pressure sensing element 420-11 is located underneath pressure sensing element 420-4 and is positioned at or near the surface of the outsole 473. The medial side may also include pressure sensing elements in the outsole 473 that mirror the top perspective positions of pressure sensing elements 420-2, 420-5, and 420-6.

With pressure sensing elements in both the insole 474 and outsole 473, pressure exerted by the foot into the can be measured as well as the pressure exerted by the shoe on to the ground or surface. With this data, the energy transfer effectiveness and energy transfer function of the shoe can be determined. For example, the energy transfer effectiveness measures the loss of energy as a result of the shoe. As another example, the energy transfer function corresponds to how the shoe transfers energy from the insole to the midsole.

FIG. 86 is a logic diagram of an example of generating foot force data. The method begins at step 700 where the processing module of a force detection system receives first data regarding a first set of pressure sensors, which are positioned in an insole of a shoe. In an example, the first set of pressure sensors includes a set of variable capacitors, and the system includes a first set of drive sense circuits coupled thereto.

The method continues at step 710 where the processing module generates a first digital representation of the first data. The method continues at step 702 where the processing module receives second data regarding a second set of pressure sensors, which are positioned in an outsole of a shoe. The method continues at step 703 where the processing module generates a second digital representation of the second data. The processing module then writes the digital representations of the first and second data to memory.

In an example, a first pressure sensor of the first set of pressure sensor is positioned in a ball of foot section of the insole and a first pressure sensor of the second set of pressure sensors positioned in a ball of foot section of the outsole. From a lateral side view, a front view, and a top view, the first pressure sensors of the first and second sets of pressure sensors are substantially aligned. In another example, a pressure sensor of the second set of pressure sensors includes a variable capacitor, a variable inductor, a variable resistor, and/or a piezoelectric transducer.

FIG. 87 is a logic diagram of another example of generating foot force data. An example method begins at step 704, where a processing module of a force detection system and/or by a processing module of a computing entity obtains, first x, y, and z force component data of a first pressure sensor when active in a shoe. The method continues at step 705 where the processing module obtains second x, y, and z force component data of a second pressure sensor of the force detection system when active in the shoe.

The method continues at step 706 where the processing module determines magnitude and direction of force traversing through at least a portion of a sole of the shoe based on the first and/or second x, y, and z force component data. For example, the processing module determines the magnitude and the direction of the force traversing through the at least the portion of the sole based on the second x, y, and z force component data. As another example, the processing module determines force loss of the at least the portion of the sole based on a difference between the first and second x, y, and z force component data.

FIG. 88 is a schematic block diagram of another example of generating foot force data. In this example, the first sensor in the insole has an angular force applied to it. The angular force includes an x component and a y component, from this perspective. The second sensor in the outsole has a second angular force applied to it. In this example, the y component of the angular force on the second sensor is less than the y component of angular force on the first sensor. This different is used to calculate the angle of the force traversing through the shoe, which can then be used to determine angle and/or magnitude of the force applied to the first sensor.

FIG. 89 is a schematic block diagram of another example of generating foot force data. This example is similar to that of FIG. 88 with a difference being that the second sensor is in a mat and not in the outsole. The sensed data can be used to determine the angle and/or magnitude of the force applied to the first sensor.

FIG. 90 is a schematic block diagram of another example of generating foot force data that detects horizontal movement and/or horizontal tilt of the foot within the shoe. In this example, the first sensor is on the medial side of the shoe and the second sensor is on the lateral side of the shoe. With more horizontal force component in the lateral side of the shoe than the medial side indicates that the foot is sliding and/or tilting towards the lateral side of the shoe, which is most often undesirable in athletics.

Figure 91:
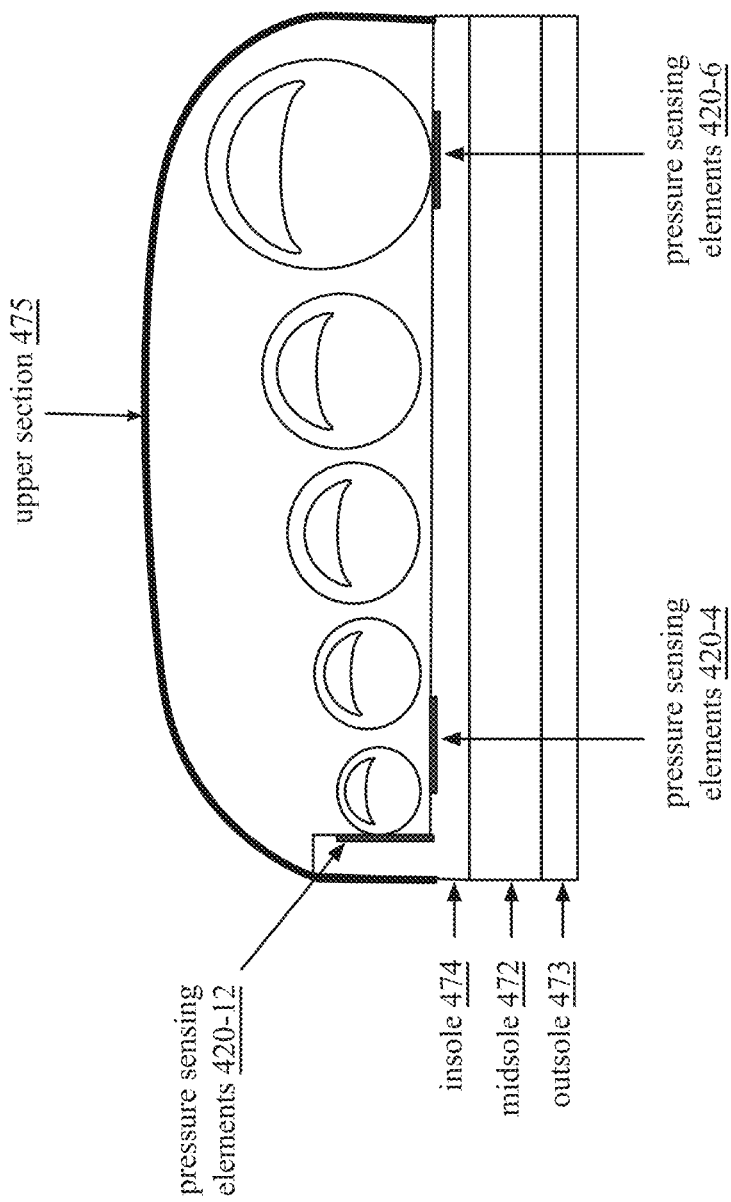
FIG. 91 is a front view diagram of another example of the pressure sensing elements positioned with respect to an insole of a shoe.

FIG. 91 is similar to FIG. 83 with the addition of a pressure sensing element 420-12 being positioned on the lateral wall of the shoe. The shoe may include more than one pressure sensing element along the lateral wall. With one or more pressure sensing elements along the lateral wall of the shoe, horizontal forces can be measured as the person is cutting, making a lateral movement, etc. while wearing the shoes.

Figure 92:
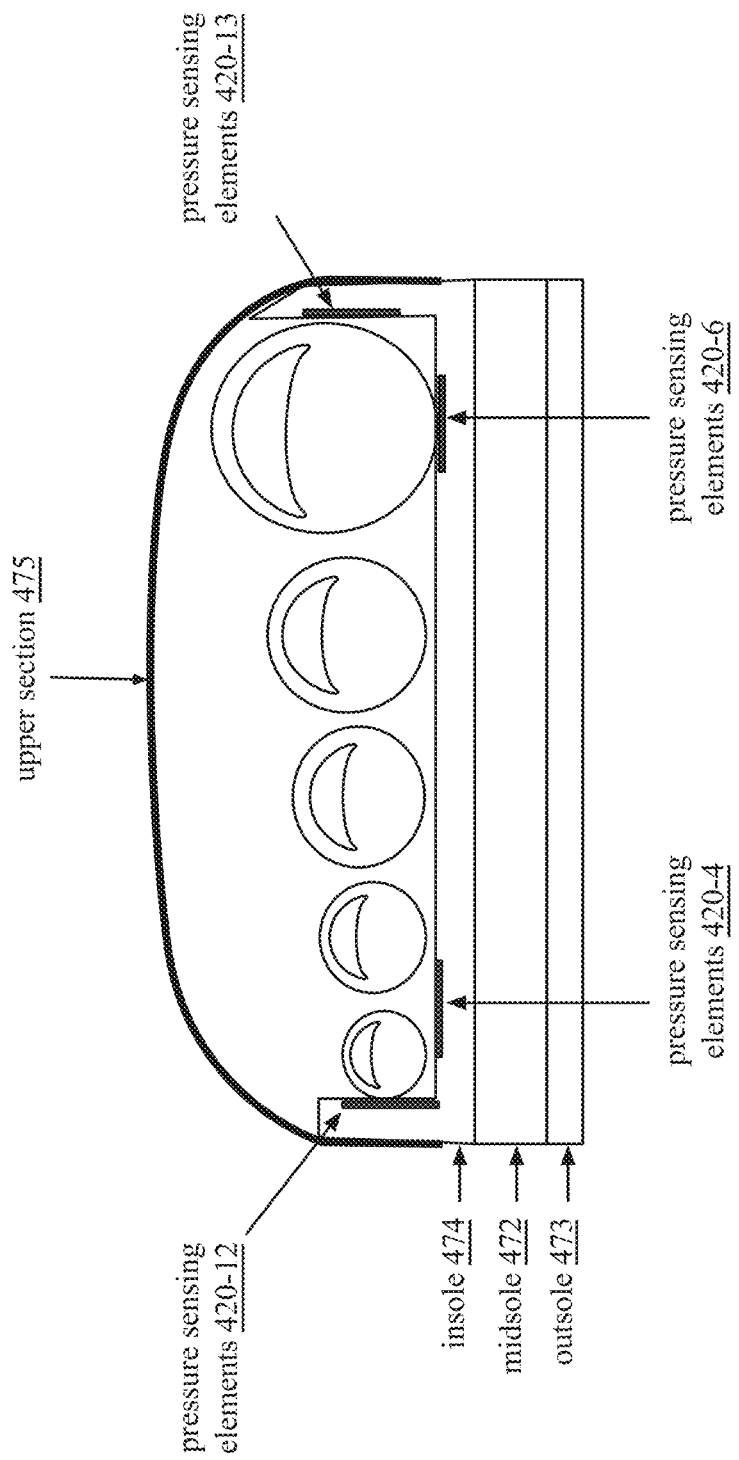
FIG. 92 is a front view diagram of another example of the pressure sensing elements positioned with respect to an insole of a shoe.

FIG. 92 is similar to FIG. 91 with the addition of a pressure sensing element 420-13 being positioned on the medial wall of the shoe. The shoe may include more than one pressure sensing element along the medial wall. With one or more pressure sensing elements along the medial wall of the shoe, horizontal forces in both directions can be measured as the person is cutting, making a lateral movement, etc. while wearing the shoes.

Figure 93:
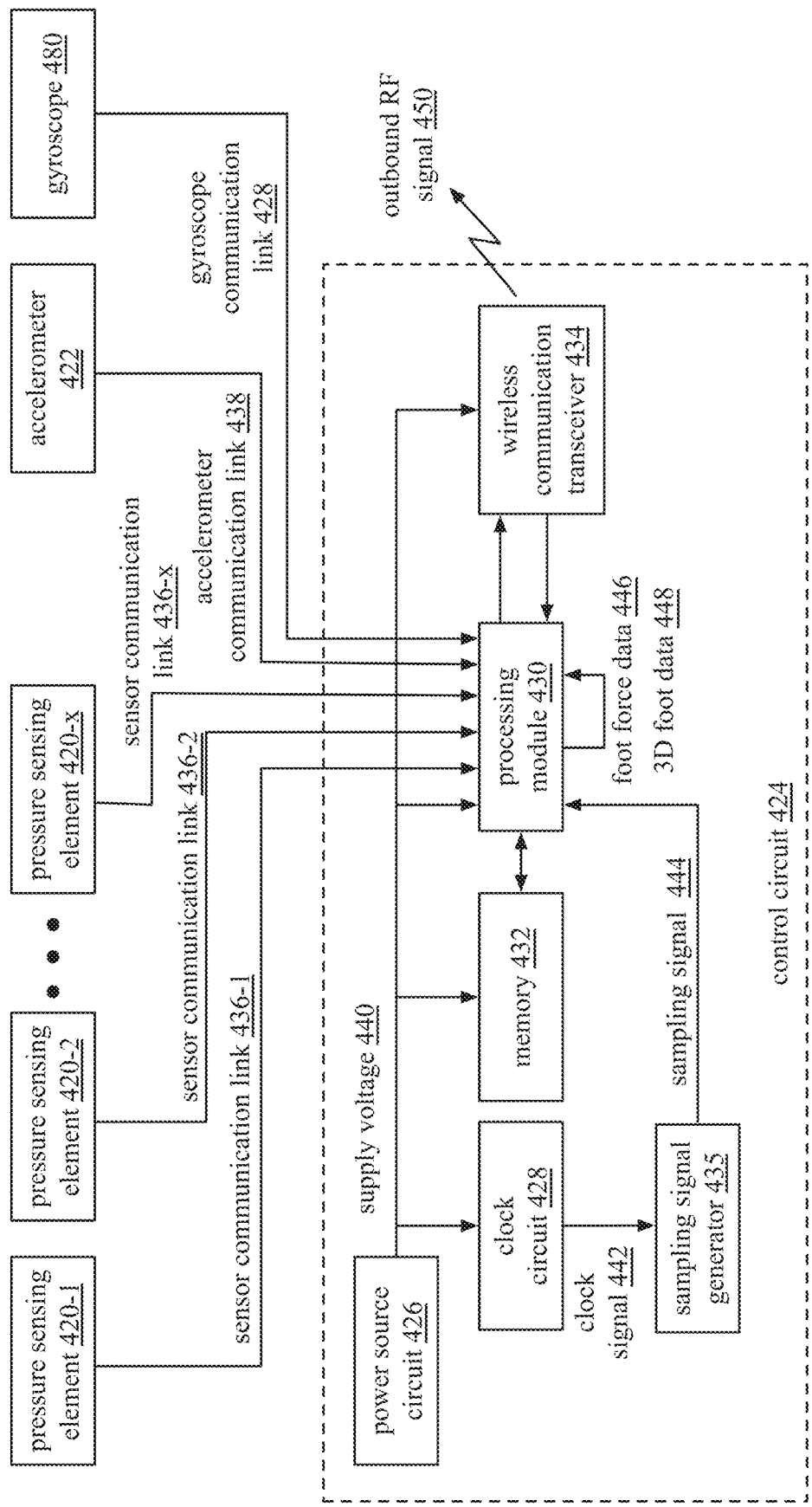
FIG. 93 is a schematic block diagram of another embodiment of a shoe sensor system.

FIG. 93 is a schematic block diagram of another embodiment of a shoe sensor system 416 R & L. In this embodiment, the system 416 further includes a gyroscope 480 that is coupled to the processing module of the control circuit 424 via a gyroscope communication link 482. The gyroscope communication link 482 is one or more of a wired communication link (e.g., a wire), a wired communication path in accordance with a wired communication protocol, an inductive communication path in accordance with a near field communication (NFC) communication protocol, a light communication base in accordance with a light-based communication protocol and a radio frequency (RF) communication path in accordance with a wireless communication protocol.

The gyroscope 480 may be on the same PCB as the control circuit 424, may be on a separate PCB with the accelerometer, or on its on PCB positioned within the shoe. Regardless of its inclusion of a PCB, the gyroscope generates pitch, yaw, and roll coordinates. The processing module 30 samples, in accordance with the sampling signal 444, the pitch, yaw, and roll coordinates to produce pitch, yaw, and roll data. The processing module 430 also correlates the pitch, yaw, and roll data with the foot force data 446 and the 3D foot data to produce the correlated data. The wireless communication transceiver 434 transmits the outbound RF signals 450, which includes the correlated data.

Figure 94:
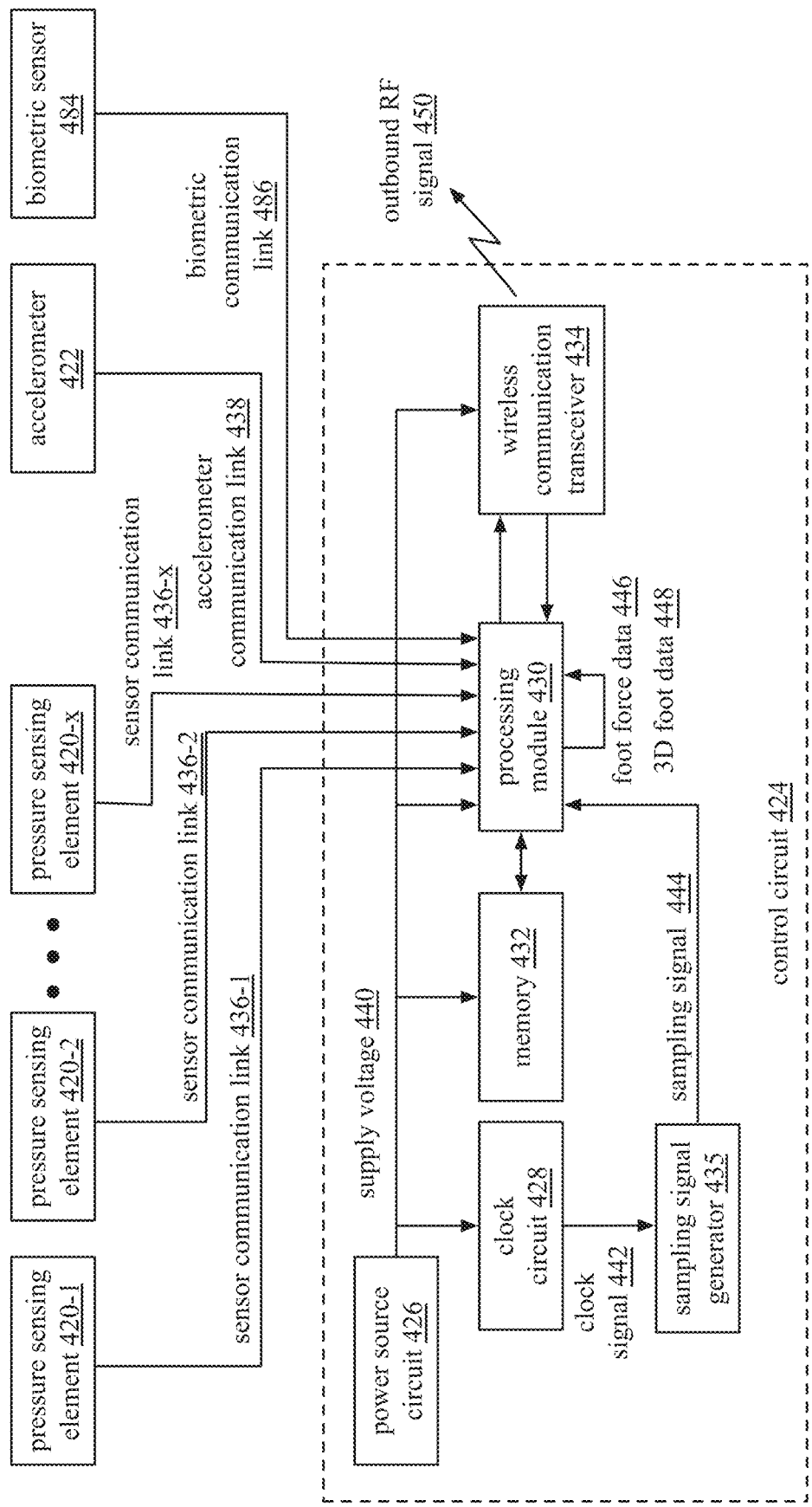
FIG. 94 is a schematic block diagram of another embodiment of a shoe sensor system.

FIG. 94 is a schematic block diagram of another embodiment of a shoe sensor system 416 R & L. In this embodiment, the system 416 further includes a biometric sensor 484 that is coupled to the processing module of the control circuit 424 via a biometric communication link 486. The biometric communication link 486 is one or more of a wired communication link (e.g., a wire), a wired communication path in accordance with a wired communication protocol, an inductive communication path in accordance with a near field communication (NFC) communication protocol, a light communication base in accordance with a light-based communication protocol and a radio frequency (RF) communication path in accordance with a wireless communication protocol.

The biometric sensor 484 is on, or in, the surface of the insole to measure a biometric condition of the person wearing the shoes via the person's feet. For instance, the biometric condition includes one or more of heart rate, perspiration, respiration, temperature, etc. As such, the biometric sensor 484 generates biometric indicators regarding one or more of heart rate, moisture level, respiration, and temperature.

The processing module 430 samples, in accordance with the sampling signal 444, the biometric indicators to produce biometric data. The processing module 430 also correlates the biometric data with the foot force data 446 and the 3D foot data to produce the correlated data. The wireless communication transceiver 434 transmits the outbound RF signals 450, which includes the correlated data.

To improve the connectivity of the biometric sensor 484 to the skin of the person wearing the shoes, the person may wear socks with metallic thread in the bottom of the sock. The metallic thread is woven into the sock at one or more locations that corresponds to the position of the biometric sensor. Note that each shoe may include a plurality of biometric sensors, each measuring a different biometric condition.

Figure 95:
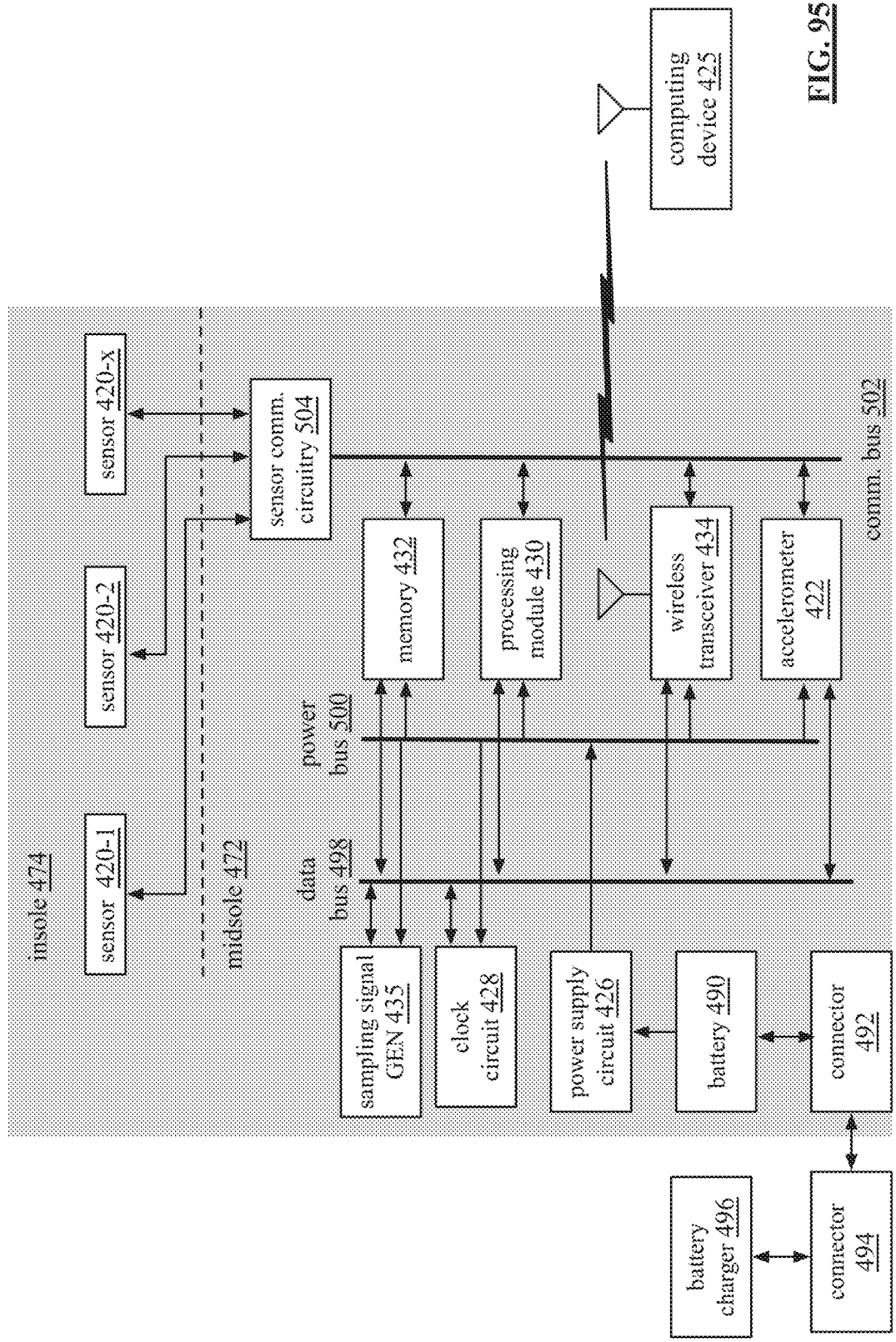
FIG. 95 is a schematic block diagram of another embodiment of a shoe sensor system.

FIG. 95 is a schematic block diagram of another embodiment of a shoe sensor system 416 R & L that wirelessly communicates with the computing device 425. The system 416 includes pressure sensor elements 420-1 through 420-x, an accelerometer 422, sensor communication circuit 504, a data bus 598, a power bus 510, a communication bus 502, a power source circuit 424, a clock circuit 428, a processing module 430, memory 432, a wireless communication transceiver 344, a sampling signal generator 435, a battery 496, a connector set 492 & 494, and a battery charger 496.

Each of the buses 498, 500, and 502 includes a single shared link, a plurality of shared links, a plurality of individual links, or a combination thereof. A link is a wired communication link (e.g., a wire), a wired communication path in accordance with a wired communication protocol, an inductive communication path in accordance with a near field communication (NFC) communication protocol, a light communication base in accordance with a light-based communication protocol and a radio frequency (RF) communication path in accordance with a wireless communication protocol.

The pressure sensor elements 420-1 through 420-x, the accelerometer 422, the power source circuit 424, the clock circuit 428, the processing module 430, the memory 432, the wireless communication transceiver 434, and the sampling signal generator 435 function as previously described with reference to one or more of the preceding figures and/or as will be described with reference to one or more of the subsequent figures.

The battery 490 is a rechargeable battery that powers the power supply circuit 426, which produces one or more supply voltages. The battery 490 is recharged by the battery charger 96, which may be an external device to the shoe or including within the shoe. In the example, shown, the battery charger 496 is an external device that is connected to the battery 490 via connectors 492 and 494. In an embodiment, the connectors 492 and 494 are wired connectors that provide electrical coupling via wires, pins, receptacles, etc. In another embodiment, the connectors 492 and 494 are wireless to provide NFC wireless charging. Note that the connector may be in the heel section of the shoe and positioned to not interfere with wearing of the shoes.

Figure 96:
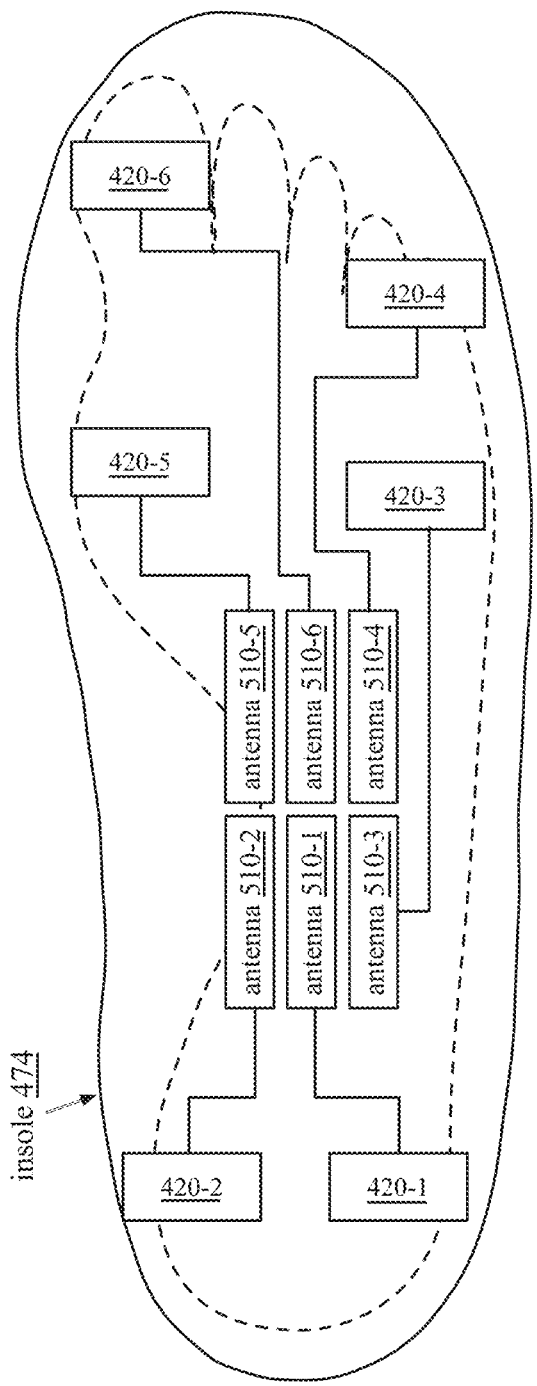
FIG. 96 is a top view diagram of an example of the pressure sensing elements and corresponding antennas positioned with respect to an insole of a shoe.
Figure 97:
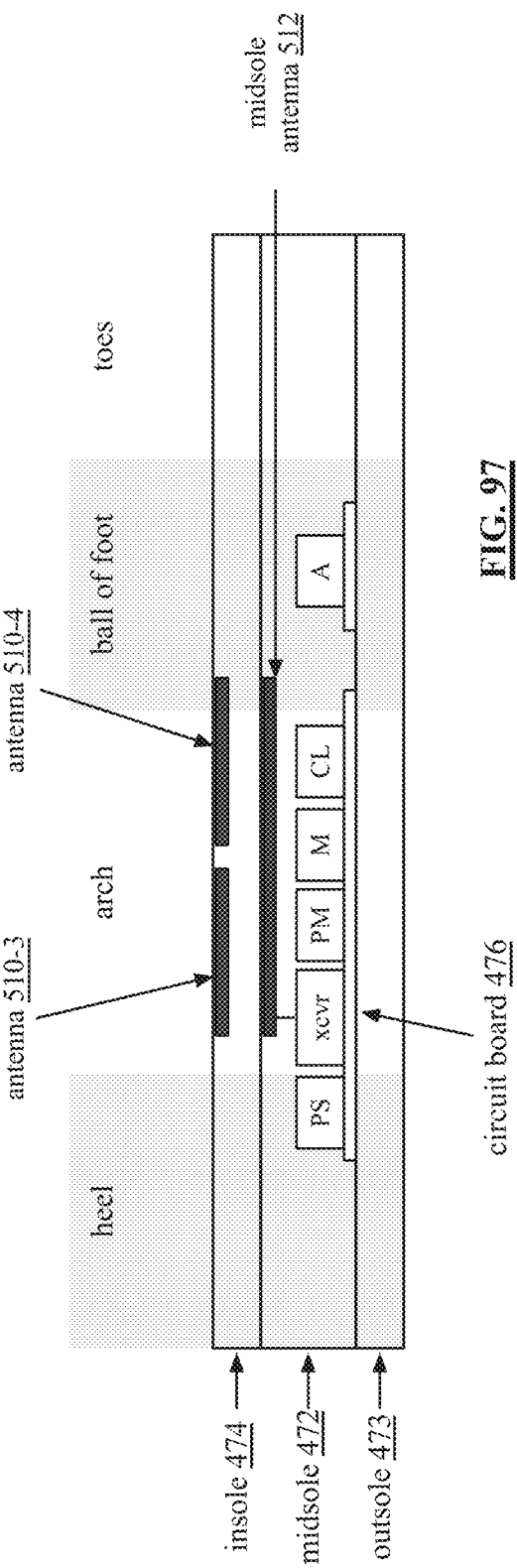
FIG. 97 is a side view diagram of an example of the antennas positioned with respect to an insole of a shoe and the control circuit, with an antenna, and accelerometer positioned with respect to a midsole of the shoe.

FIG. 96 is a top view diagram of an example of the pressure sensing elements 420 that are RF coupled to the control circuit 424. Each pressure sensing element 420 is one the insole 474 and associated with an antenna 510-1 through 510-6, where pressure sensing element 420-1 is associated with antenna 510-1 and so on. With reference to FIG. 97, which is a side view diagram of the shoe, the pressure sensing element antennas 510 are positioned over a midsole antenna 512. The midsole antenna 512 is coupled to the control circuit 424.

In an example of operation, the wireless transceiver (XCVR) is in a first mode to wirelessly communicate with the pressure sensing elements 420. In the first mode, the wireless transceiver generates a low power RF signal that includes a continuous wave portion to enable passive pressure sensing elements 420 to produce a supply voltage that powers the sensing element 420. The transceiver then generates RF control signals requesting the pressure sensing elements 420 to respond with their pressure sensing measurements.

After the control circuit 424 has gathered sufficient pressure sensing measurements from the sensing elements, the transceiver switches to a second mode to communicate the correlated data to the computing device 425. The transceiver switches between the first and second modes to gather data and to provide the data to the computing device. Note that the frequency used to communicate with the sensing elements may be the same or different than the frequency used to communicate with the computing device and the frequency ranges from a few hundred Mega Hertz to 60 GHz or more. As a specific example, the transceiver communicates with the computing device using a frequency of 2.4 GHz and communicates with the sensing elements using 60 GHz.

Figure 98:
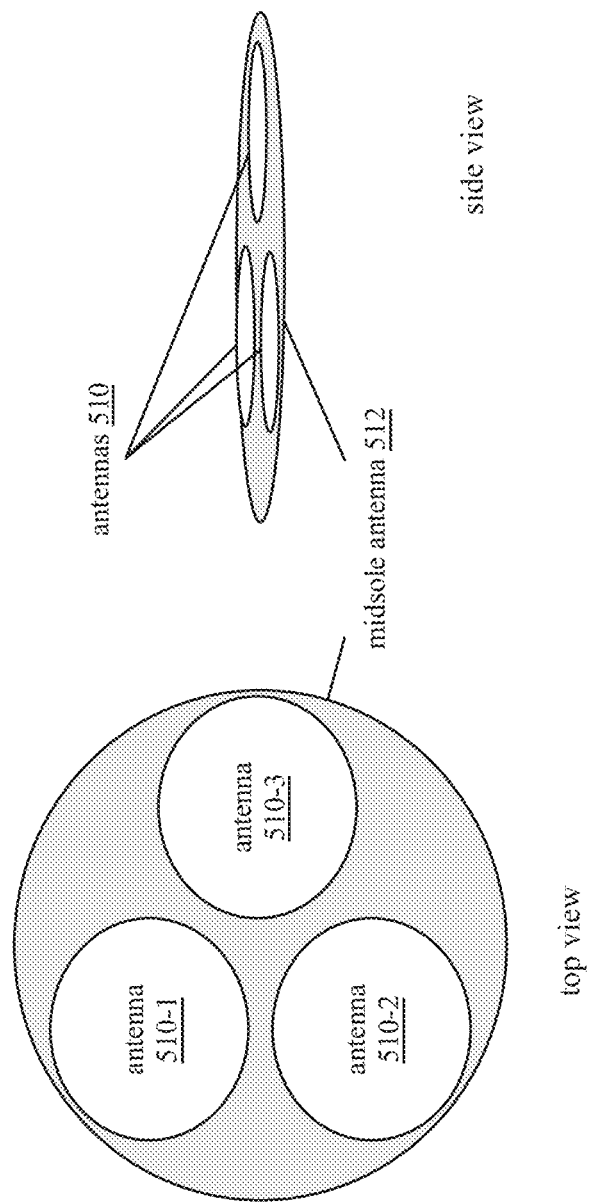
FIG. 98 is a top and a side view diagram of an example of the pressure sensing element antennas positioned with respect to the antenna of the control circuit.

FIG. 98 is a top and a side view diagram of an example of the pressure sensing element antennas 510 positioned with respect to the midsole antenna 512. In this example, the antenna 512 has a surface area that encompasses the surface area of the three (or more) pressure sensing element antennas 510. In an example, the midsole antenna 512 communicates with one pressure sensing element antenna 510 at a time. In another example, the midsole antenna 512 communicates with two or more pressure sensing element antennas 510 at the same time using a frequency division multiplexing scheme.

Figure 99:
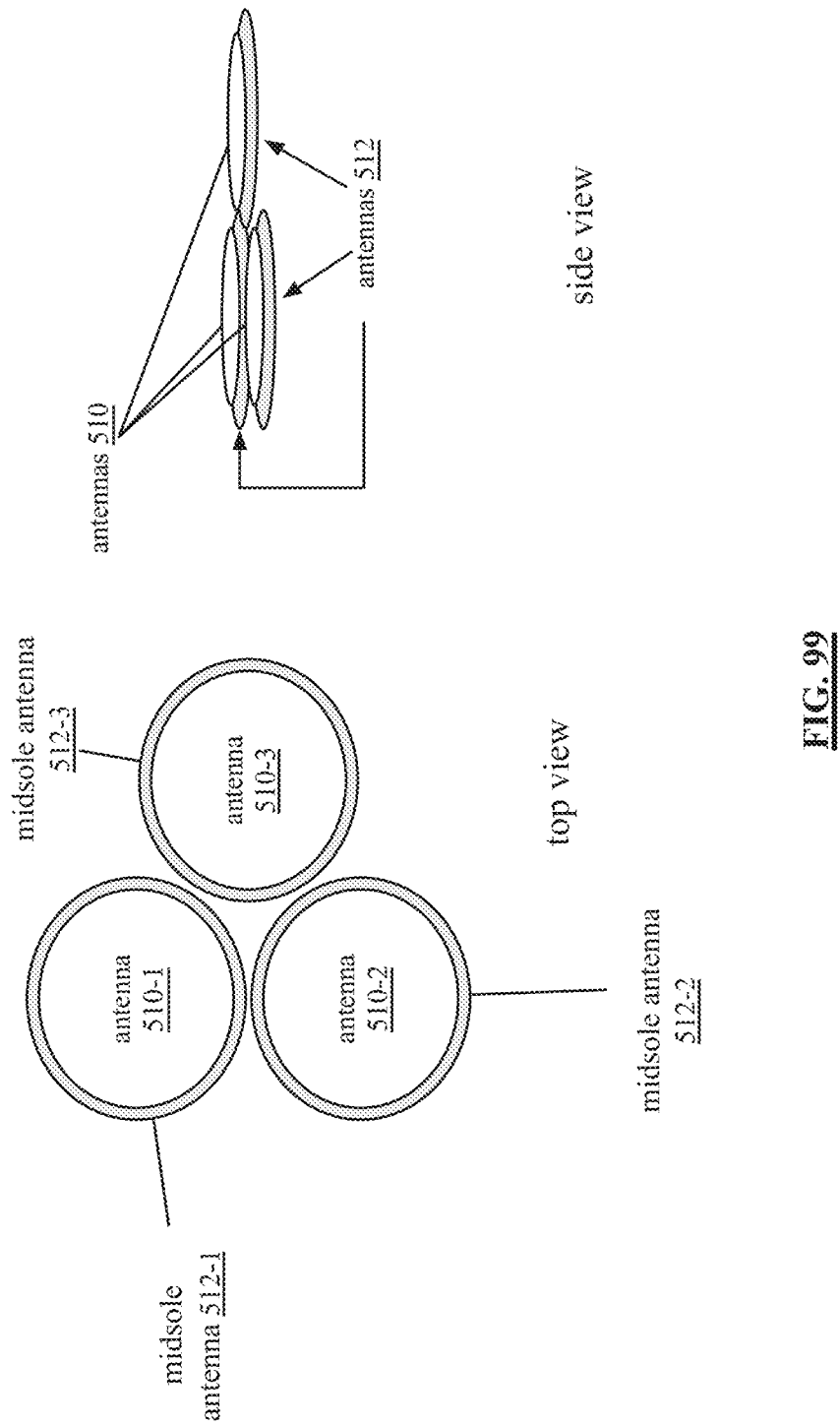
FIG. 99 is a top and a side view diagram of another example of the pressure sensing element antennas positioned with respect to the antenna of the control circuit.

FIG. 99 is a top and a side view diagram of another example of the pressure sensing element antennas 510 positioned with respect to multiple midsole antennas 512. In this example, each midsole antenna 512 has a surface area that is about the same size as the surface area of a pressure sensing element antenna 510. In an example, each midsole antenna 512 communicates with a corresponding pressure sensing element antenna 510 at a time using the same or different frequencies. In another example, each midsole antenna 512 communicates with its corresponding pressure sensing element antennas 510 in a time division multiplexing manner using the same or different frequencies.

Figure 100:
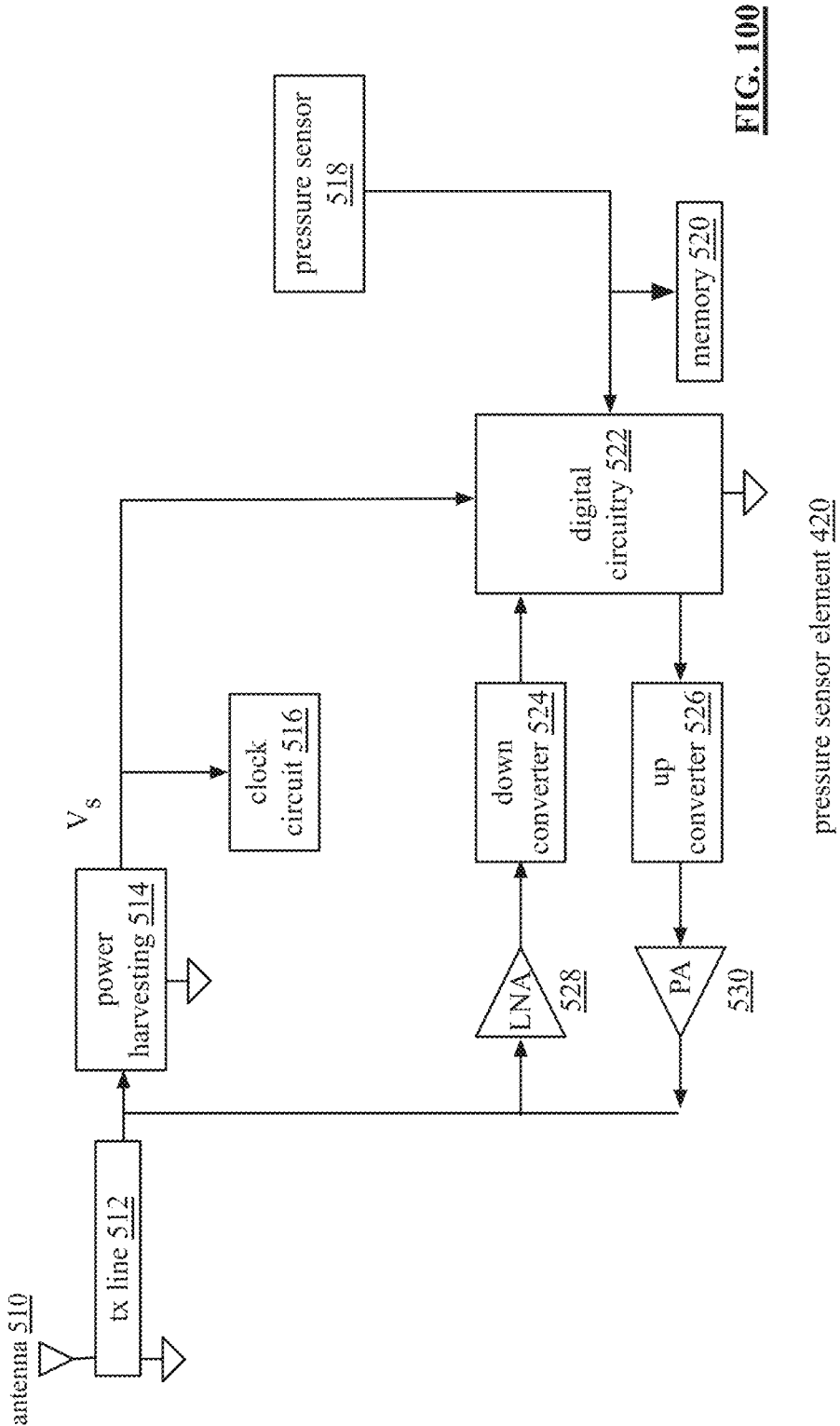
FIG. 100 is a schematic block diagram of an embodiment of a pressure sensing element.

FIG. 100 is a schematic block diagram of an embodiment of a pressure sensing element 420 that includes an antenna 510, a transmission line 512, a power harvesting circuit 514, a clock circuit 516, a pressure sensor 518, memory 520, digital circuitry 522, a down converter 524, an up converter 526, a low noise amplifier (LNA) 528 and a power amplifier (PA) 530. The transmission line 512 coupled the antenna 510 to the power harvesting circuit 514, the receiver 528, and the transmitter 530. Depending on the location of the antenna 510 and the pressure sensing element with the shoe, the transmission line 512 may be a few millimeters long to tens of centimeters long.

In an example of operation, the antenna 510 receives an RF signal from the control circuit (via the transceiver 434 and/or another transceiver). The power harvesting circuit 514 converts the RF signal into a supply voltage Vs, which powers the rest of the circuit. Once power is available, the pressure sensor 518 begins sensing pressure and provides pressure sensory signals to the digital circuitry 522. The digital circuitry 522, which may be implemented as a processing module, converts the pressure sensory signals into the pressure sensed data in accordance with a sampling clock generated by the clock circuit 516.

The up converter 526 converts the pressure sensed data into an RF signal that is amplified by the PA 530 and transmitted by the antenna 510. The digital circuitry 522, the up converter 526, and/or the PA 530 may use backscattering, Amplitude Shift Keying (ASK), Amplitude Modulation (AM), Frequency Shift Keying (FSK), and/or Phase Shift Keying (PSK) to convert the pressure sensed data into a transmitted RF signal. Note that the memory 520 may store the pressure sensed data until it is transmitted or may store the pressure sensed data indefinitely.

The pressure sensing element 420 may provide the pressure sensed data at predetermined intervals or in response to a request for data. For the latter, the antenna receives an inbound RF signal that is amplified by the LNA 528 and down converted into a baseband signal via the down converter 524. The digital circuitry 522 processes the baseband signal to identify the request for data.

Figure 101:
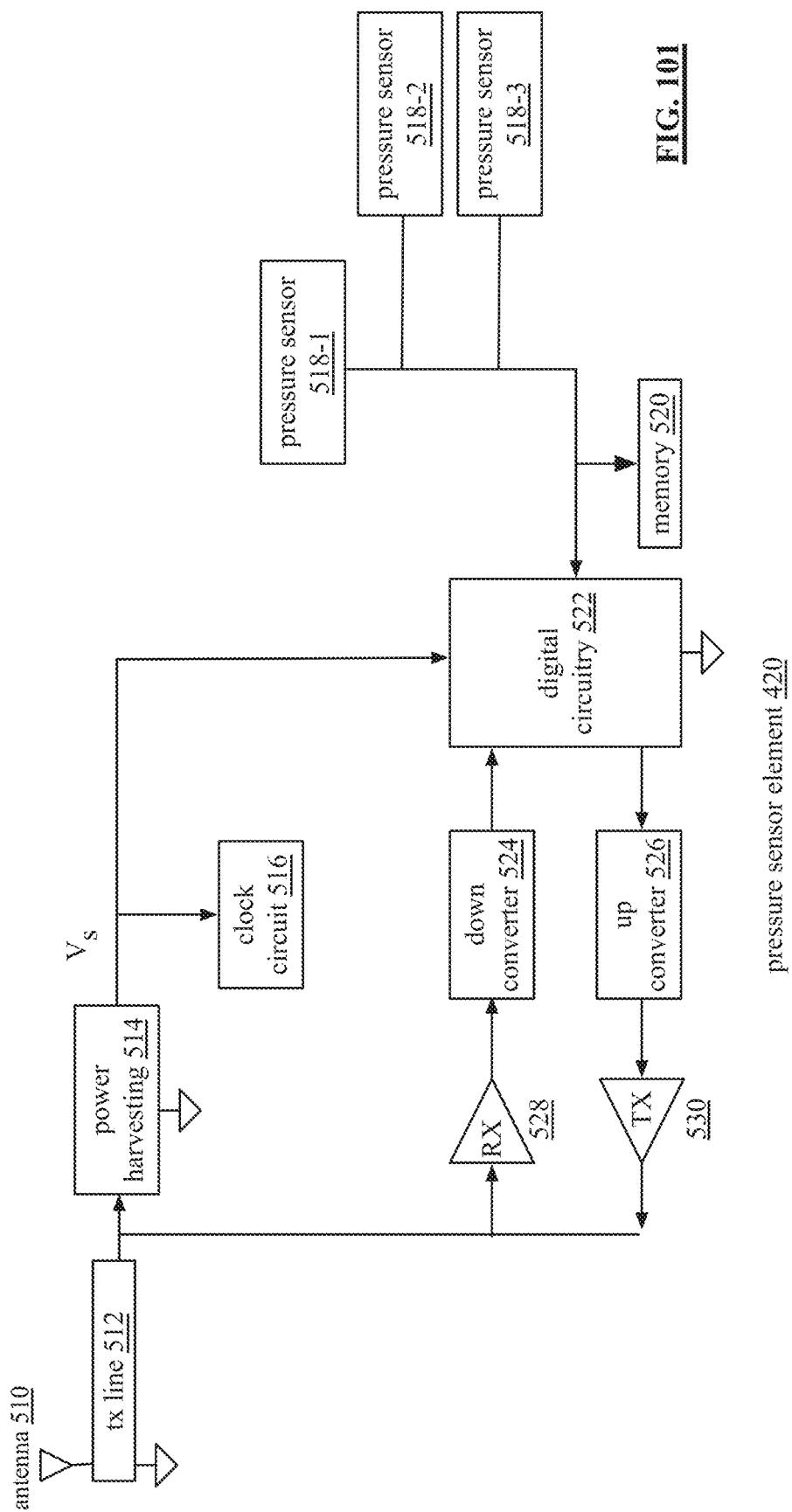
FIG. 101 is a schematic block diagram of another embodiment of a pressure sensing element.

FIG. 101 is a schematic block diagram of another embodiment of a pressure sensing element 420 that is similar to the one of FIG. 100 with the inclusion of a plurality of pressure sensors 518-1 through 518-3 (3 are shown but could include more or less than 3). The pressure sensors 518-1 through 518-3 may each be the same type of sensor (e.g., resistive, capacitive, inductive, piezoelectric, etc.) to sense pressure in a same area or in different areas. In an example, the pressure sensors are of the same type and have different pressure ratings (e.g., one from 10-100 force pounds, a second from 100-200 force pounds, and a third from 200-400 force pounds). In another example, the pressure sensors are of different types and of the same pressure ratings, which can be averaged and/or used for calibration.

Figure 102:
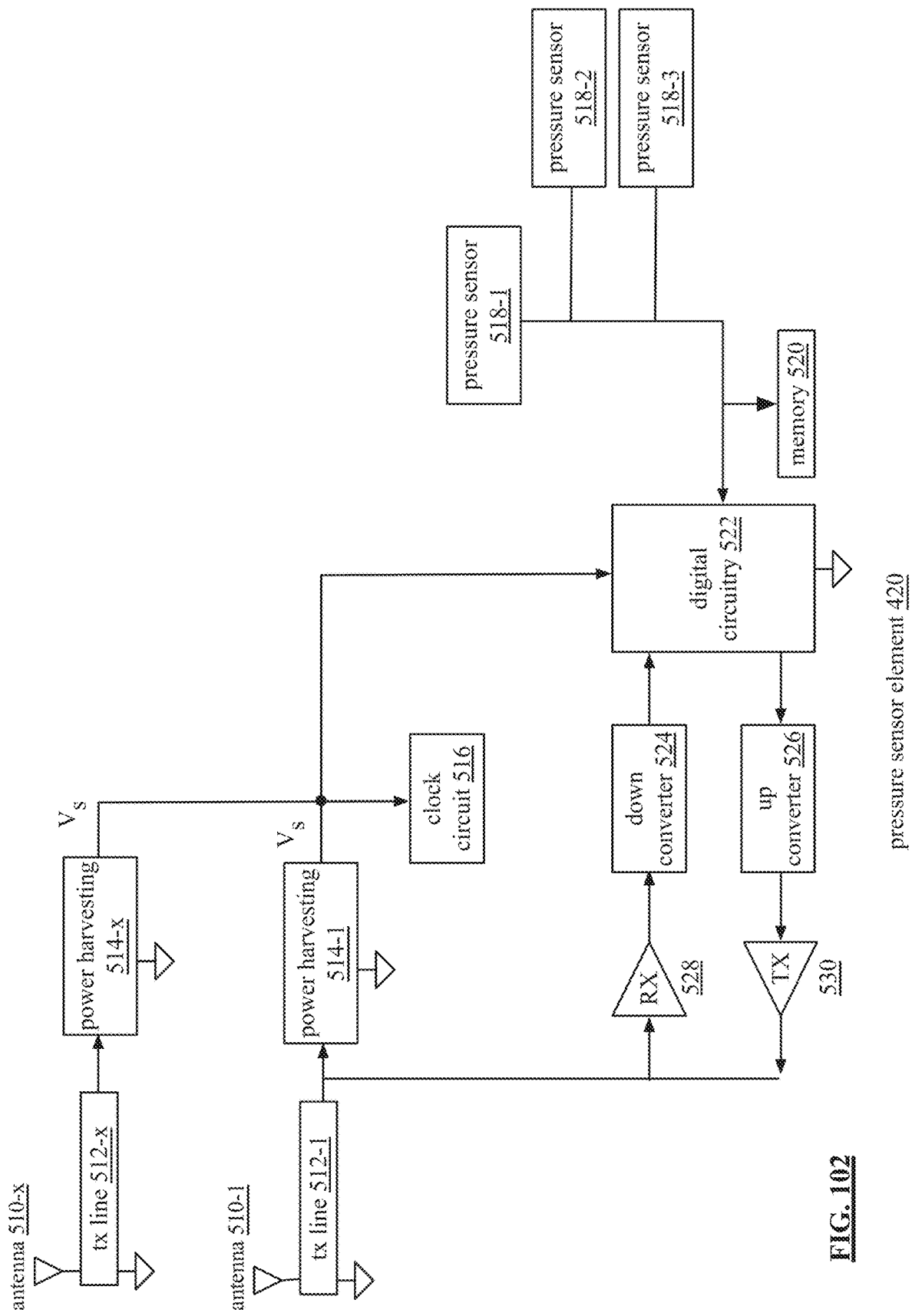
FIG. 102 is a schematic block diagram of another embodiment of a pressure sensing element.

FIG. 102 is a schematic block diagram of another embodiment of a pressure sensing element 420 that is similar to the one of FIG. 100 with the inclusion of multiple antennas 510-1 through 510-x, multiple transmission lines 512-1 through 512-x, and multiple power harvesting circuits 514-1 through 514-x. In this embodiment, the multiple antennas and power harvesting circuits increase the power available for the pressure sensing element 420.

Figure 103A:
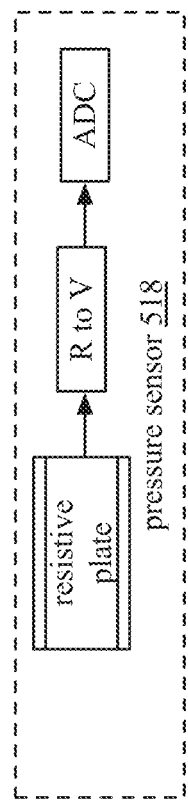
FIGS. 103A-103D are schematic block diagrams of example embodiments of a pressure sensor.

FIG. 103A is a schematic block diagram of a capacitive pressure sensor 518 that includes a capacitor (e.g., plates 1 and 2 and a dielectric), a capacitance to voltage converter (C to V), and an analog to digital converter (ADC). In an alternative embodiment, the ADC is in the digital circuitry of the pressure sensing element of FIGS. 100-102 or in the control circuit 424. When pressure is applied to the capacitor, the dielectric changes cause a capacitance change. The capacitance change is converted to an analog voltage by the capacitance to voltage converter. The ADC converts the analog voltage into a digital value that represented the pressure data.

Figure 103B:
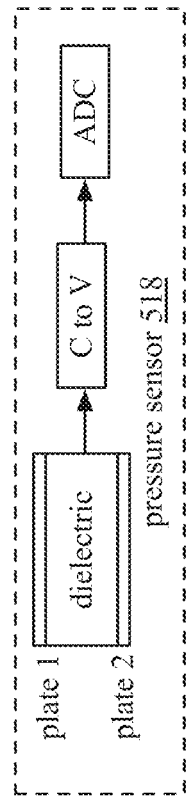

FIG. 103B is a schematic block diagram of a resistive pressure sensor 518 that includes a resistor (e.g., resistive plate), a resistance to voltage converter (R to V), and an analog to digital converter (ADC). In an alternative embodiment, the ADC is in the digital circuitry of the pressure sensing element of FIGS. 100-102 or in the control circuit 424. When pressure is applied to the resistive plate, its resistance changes. The resistive change is converted to an analog voltage by the resistance to voltage converter. The ADC converts the analog voltage into a digital value that represented the pressure data.

Figure 103C:
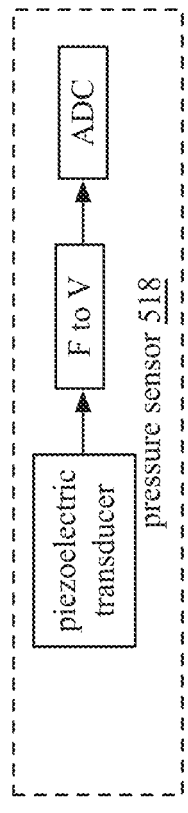

FIG. 103C is a schematic block diagram of an inductive pressure sensor 518 that includes an inductor (e.g., a coil proximal to a ground plane), an inductance to voltage converter (L to V), and an analog to digital converter (ADC). In an alternative embodiment, the ADC is in the digital circuitry of the pressure sensing element of FIGS. 100-102 or in the control circuit 424. When pressure is applied to the inductor, the coil is pressed closer to the ground plane causes an inductance change. The inductance change is converted to an analog voltage by the inductance to voltage converter. The ADC converts the analog voltage into a digital value that represented the pressure data.

Figure 103D:
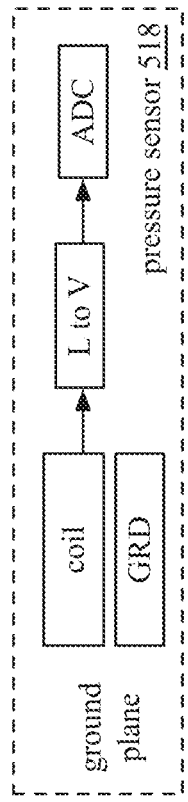

FIG. 103D is a schematic block diagram of a frequency pressure sensor 518 that includes a piezoelectric transducer, a frequency to voltage converter (F to V), and an analog to digital converter (ADC). In an alternative embodiment, the ADC is in the digital circuitry of the pressure sensing element of FIGS. 100-102 or in the control circuit 424. When pressure is applied to the piezoelectric transducer, its resonating frequency changes. The frequency change is converted to an analog voltage by the frequency to voltage converter. The ADC converts the analog voltage into a digital value that represented the pressure data.

Figure 104:
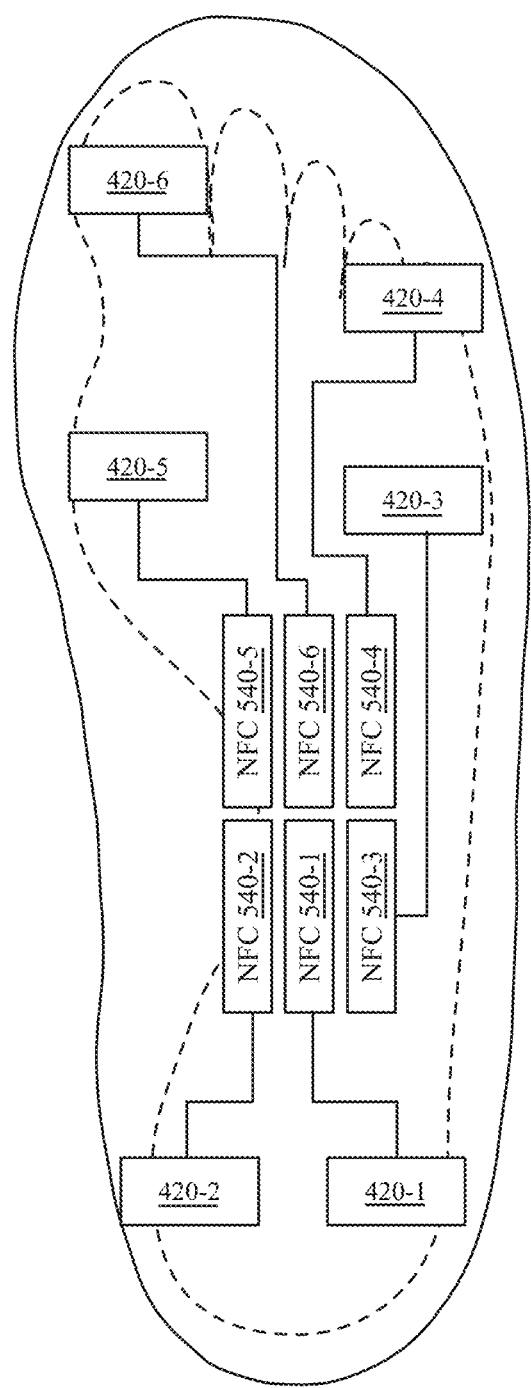
FIG. 104 is a top view diagram of an example of the pressure sensing elements and corresponding NFC coils positioned with respect to an insole of a shoe in accordance with the present invention.
Figure 105A:
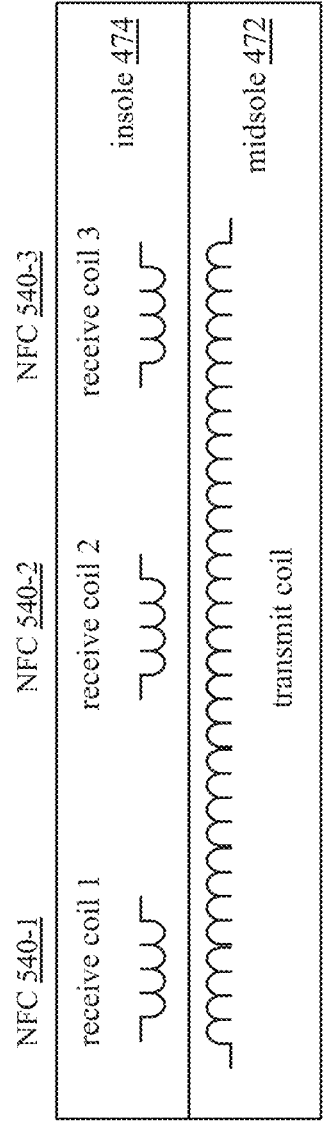
FIG. 105A is a side view diagram of an example of receiving NFC coils positioned with respect to an insole of a shoe and a transmitting NFC coil positioned with respect to a midsole of the shoe.
Figure 105B:
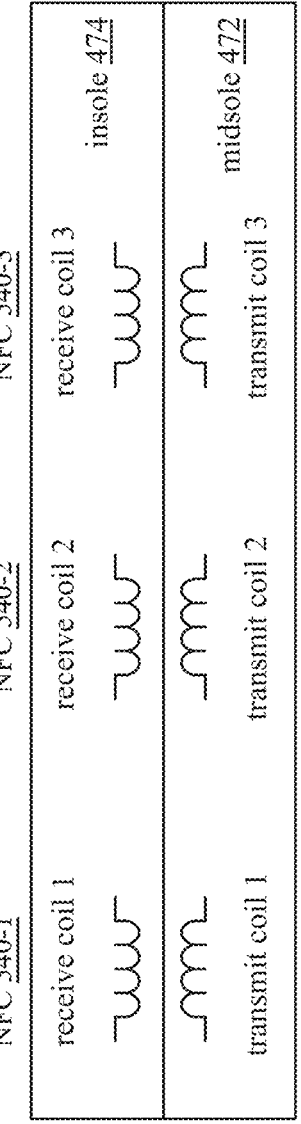
FIG. 105B is a side view diagram of an example of receiving NFC coils positioned with respect to an insole of a shoe and transmitting NFC coils positioned with respect to a midsole of the shoe.

FIG. 104 is a top view diagram of an example of the pressure sensing elements 420 that are inductively coupled to the control circuit 424. Each pressure sensing element 420 is one the insole 474 and associated with an NFC coil 540-1 through 540-6, where pressure sensing element 420-1 is associated with NFC coil 510-1 and so on. With reference to the side view diagram of FIG. 105, the pressure sensing element antennas 510 are positioned over a midsole NFC transmission coil, which is coupled to the control circuit 424. In the alternative and with reference to the side view diagram of FIG. 106, the pressure sensing element antennas 510 are positioned over corresponding midsole NFC transmission coils, which are coupled to the control circuit 424. The NFC coils may communicate using frequencies ranging from tens of MHz to tens of GHz, or more.

Figure 106:
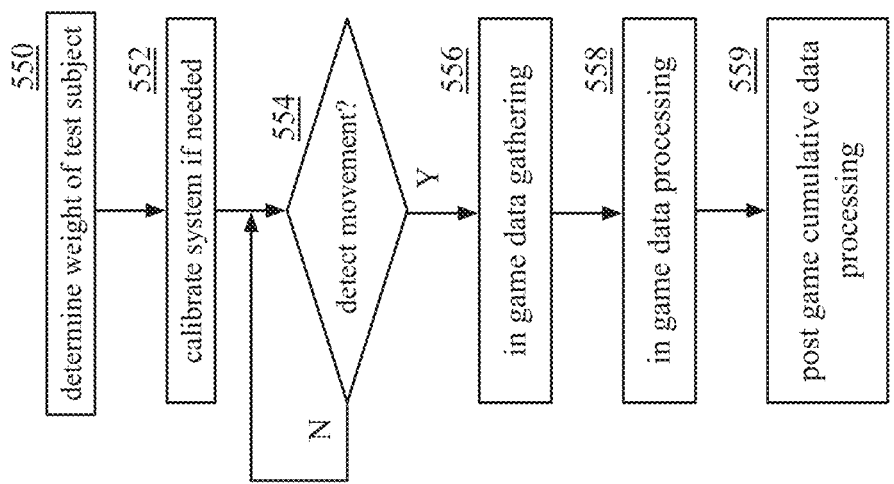
FIG. 106 is a logic diagram of another example of a method executed by a shoe sensor system.

FIG. 106 is a logic diagram of another example of a method executed by a shoe sensor system that begins at step 550 where the system determines the weight of the person wearing the shoes. For example, a person's weight can be determined by having them stand on one foot, take force measurements for this foot, stand on the other foot, and take force measurements for the other foot. From the force measurements, weight is calculated.

The method continues at step 552 where the system is calibrated if needed. For example, if the determination of a person's weight from the force measurements differs from a weight measurement from a scale, then the system can be calibrated (e.g., change coefficients for force measurements to weight conversion). Once the system is calibrated, the method continues at step 554.

At step 554, the system determines whether it detects movement. If not, the system waits until movement is detected and stays in a low power mode (e.g., reduced supply voltage, lower clock rate, no sampling, etc.). When movement is detected (e.g., accelerometer data is detected, the person enables the system to start tracking physical activity, detecting foot forces that corresponds to movement, etc.). The method then continues at step 556 where the system produces correlated data during a game, practice, or other event.

The method continues at step 558 where the system or the computing device processing the in-game correlation data to produce physical activity monitoring data. Various examples of processing the correlated data will be described with reference to one or more of FIGS. 107-116. The method continues at step 559 where the system or the computing device processes post game data. For example, the system or the computing device add the most recent game data to data from previous games to produce historical data.

FIG. 107 is a logic diagram of another example of a method executed by a shoe sensor system to determine the distance traveled during the time period (e.g., for the duration of the physical activity, a portion of the physical activity, etc.). The method begins at step 560 where the processing module (e.g., processing module 430 of the system and/or processing module 427 of the computing device 425) determines a first x-y coordinate from a first three-dimensional foot data point (e.g., from an x-y-z coordinate from the accelerometer) that corresponds to the beginning of the time period. For example, the first x-y coordinate corresponds to the first data sampled from the accelerometer when the system was activated to record physical activity data. As another example, the first x-y coordinate corresponds to the first data sampled from the accelerometer at the start of a new time interval of the physical activity monitoring.

The x-y coordinate of the x-y-z coordinate correspond to a position on the surface of the ground and the z-coordinate of the x-y-x coordinate corresponds to an up position with respect to the ground. The first x-y-x coordinate corresponds to an original of a reference Cartesian or Polar coordinate system for tracking the distance the shoes travel.

The method continues at step 562 where the processing module determines a next x-y coordinate from a next three-dimensional foot data point. The next 3D foot data point corresponds to the accelerometer data taking at the next sampling interval, or point, of the sampling clock with respect to the previous sampling interval using absolute values to get an accumulation of movement. For example, the first x-y-z coordinate was taking at sampling interval 0, the second x-y-z coordinate was taking at sampling interval 1, the third x-y-z coordinate was taking at sampling interval 2, and so on until the last sampling interval of the time period.

The method continues at step 564 where the processing module determines a next delta distance based on a difference between the first x-y coordinate and the next x-y coordinate. For example, if the first x-y coordinate is 0,0 and the second x-y coordinate is 0.5, 0.75, then the delta distance includes a delta x of 0.5 and a delta y of 0.75. For the next sampling interval, the third x-y coordinate is 0.65, 1.125. As such, the delta x from the second to third coordinate is 0.15 and the delta y is 0.375. For each sampling interval, the delta distance may be stored for further and/or subsequent processing.

The method continues at step 566 where the processing module adds the next delta distance to an accumulation of previous delta distances to produce an updated accumulation of delta distances. For example, after sampling interval 1, the processing module adds the new delta data of 0.5 for delta x and 0.75 for delta y to the accumulated delta data (which is 0, 0 since the tracking process is just beginning). The result of the adding yields an updated accumulated delta distance of 0.5, 0.75. Continuing with the example for sample interval 2, the new delta data includes 0.15 for delta x and 0.375 for delta y. Adding the new delta data to the accumulated data yields an updated accumulated data of 0.65, 1.125.

The method continues at step 668 where the processing module determines whether the end of the time period has been reached. For example, the user ends the tracking of physical activity. As another example, detecting a stoppage of the physical activity. As yet another example, detection of expiration of the time period. If the time period has not ended, the method repeats at step 562 for the next data from the next sampling interval. If the time period has ended, the method continues at step 570 where the accumulated data is outputted as the distance traveled during the time period.

FIG. 108 is a logic diagram of another example of a method executed by a shoe sensor system to determine stride length data. Stride length data includes one or more of maximum length, minimum stride length, average stride length for the duration of the physical active, average stride length for an interval of the overall duration, imbalances between left-to-right stride and/or right-to-left stride, etc.

The method begins at step 580 where the processing module (e.g., processing module 430 of the system and/or processing module 427 of the computing device 425) determines a first left x-y coordinate from a first left three-dimensional foot data point that corresponds to a left foot being in contact with a surface (e.g., track, ground, court, sidewalk, road, etc.).

The method continues at step 582 where the processing module determines a first right x-y coordinate from a first right three-dimensional foot data point that corresponds to a right foot being in contact with the surface after the left foot has been in contact with the surface. The method continues at step 584 where the processing module determines a left foot to right foot stride length based on the first left x-y coordinate and the first right x-y coordinate. This can be repeated for each step taking by the person wearing the shoes.

FIG. 109 is a logic diagram of another example of a method executed by a shoe sensor system to determine stride length data; in particular, right to left stride data. The method begins at step 586 where the processing module (e.g., processing module 430 of the system and/or processing module 427 of the computing device 425) determines a first right x-y coordinate from a first right three-dimensional foot data point that corresponds to a right foot being in contact with a surface (e.g., track, ground, court, sidewalk, road, etc.).

The method continues at step 588 where the processing module determines a first left x-y coordinate from a first left three-dimensional foot data point that corresponds to a left foot being in contact with the surface after the right foot has been in contact with the surface. The method continues at step 590 where the processing module determines a right foot to left foot stride length based on the first right x-y coordinate and the first left x-y coordinate. This can also be repeated for each step taking by the person wearing the shoes.

FIG. 110 is a logic diagram of another example of a method executed by a shoe sensor system to determine the time duration. The method begins at step 600 where the processing module (e.g., processing module 430 of the system and/or processing module 427 of the computing device 425) counts clock cycle of the clock signal from a beginning of the time duration until an end of the time duration to produce a clock cycle count. The method continues at step 602 where the processing module interprets the clock cycle count in light of a clock rate of the clock signal to determine the time duration. For example, if the clock rate is 100 Hz, the number of cycles is 10,000, then the time duration is 10,000/100 or 100 seconds.

FIG. 111 is a logic diagram of another example of a method executed by a shoe sensor system to determine a fatigue indication. The fatigue indicator includes, but is not limited to, shortening of stride, pace slowing, change in foot forces, imbalance between left to right stride and right to left stride, etc. The method begins at step 604 where the processing module (e.g., processing module 430 of the system and/or processing module 427 of the computing device 425) detects, based on changes in the correlated foot data over time within the time period, one or more of a shortening of stride length, a slowing of pace, and a change in foot force (e.g., more, less, more in heel, more on outside edge, etc.). The method continues at step 606 where the processing module interprets the one or more of a shortening of stride length, a slowing of pace, and a change in foot force to determine a fatigue level.

Figure 112:
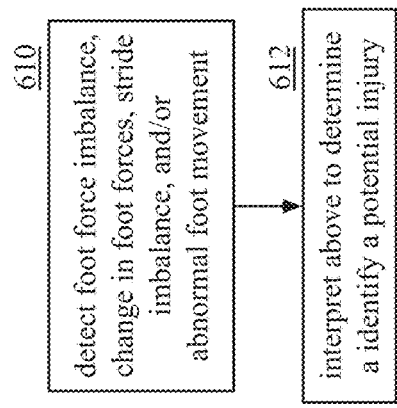
FIG. 112 is a logic diagram of another example of a method executed by a shoe sensor system.

FIG. 112 is a logic diagram of another example of a method executed by a shoe sensor system to determine one or more injury prevention indicators. An injury prevention indicator includes, but is not limited to, recognize change in data that is likely caused by fatigue, cramping, muscle strain, imbalance in strides, imbalance in foot forces, etc.

The method begins at step 610 where the processing module (e.g., processing module 430 and/or processing module 427 of the computing device 425) detects an abnormality based on changes in the correlated foot data over some period of time within the time period (e.g., from interval to interval, at various time check points, etc.). The abnormality includes, but is not limited to, an imbalance in foot force between the feet, a change in foot forces of one or both feet, an imbalance in stride lengths, an imbalance in stride height (e.g., differing z components from stride to stride) between the feet, and foot movement outside of a movement deviation range (e.g., rolled ankle, dragging a foot, etc.).

The method continues at step 612 where the processing module interprets the abnormality to identify a potential injury (e.g., a potential hamstring issue, a potential calf injury, etc.). The method continues at step 614 where the processing module determines a preventive measure based on the potential injury and/or the abnormality. For example, the preventive measure is to restrict training to a maximum amount of time per day. As another example, the preventive measure is to rest for a certain number of days. As yet another example, the preventive measure is to get treatment on the body part.

Figure 113:
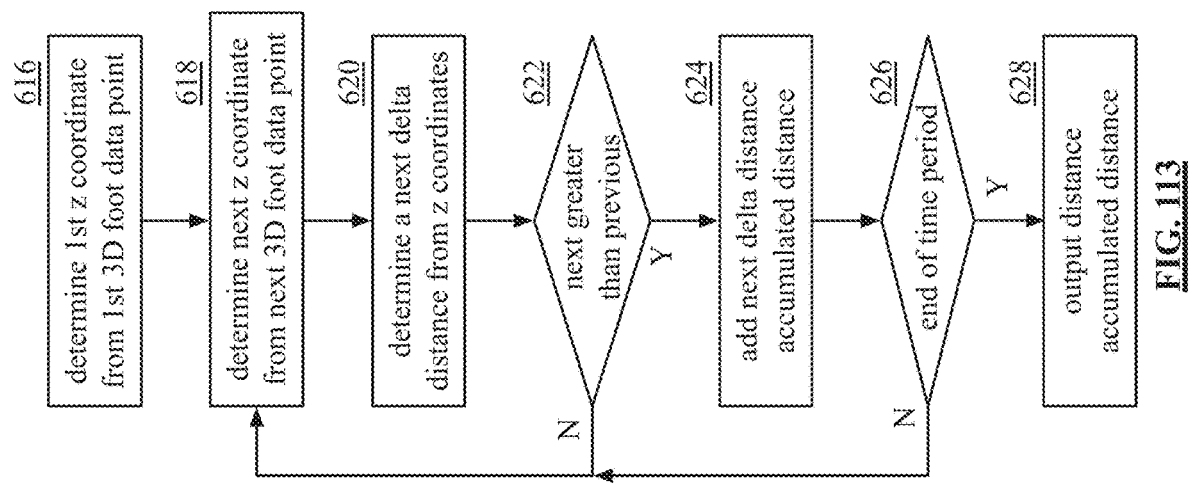
FIG. 113 is a logic diagram of another example of a method executed by a shoe sensor system.

FIG. 113 is a logic diagram of another example of a method executed by a shoe sensor system to determine elevation tracking for the time period while performing the physical activity (e.g., steps climbed, elevation changes while running, walking, and/or hiking). The method begins at step 616 where the processing module (e.g., processing module 430 and/or processing module 427 of the computing device 425) determines a first z coordinate from a first three-dimensional foot data point (e.g., first x-y-z coordinate as previously described) that corresponds to the beginning of the time period.

The method continues at step 618 where the processing module determines a next z coordinate from a next three-dimensional foot data point (e.g., a next x-y-z coordinate as previously discussed) that corresponds to a next sampling point of the sampling clock within the time period. The method continues at step 620 where the processing module determines a next delta distance based on a difference between the first z coordinate and the next z coordinate. The method continues at step 622 where the processing module determines whether the next delta distance is greater than or equal to zero. When it is not, the method continues at step 618.

When the next delta distance is greater than or equal to zero, the method continues at step 624 where the processing module adds the next delta distance to an accumulation of previous delta distances to produce an updated accumulation of delta distances. The method continues to step 2626 where the processing module determines whether the time period has ended. When the time period has not ended, the method repeats as step 618.

When the next sampling point corresponds to the end of the time period, the method continues at step 628 where the processing module provides the updated accumulation of delta distances as the elevation change that occurred during the time period. For example, the accumulated z distance is 100 feet, which can be equated to ascending 10 flights of stairs.

Figure 114:
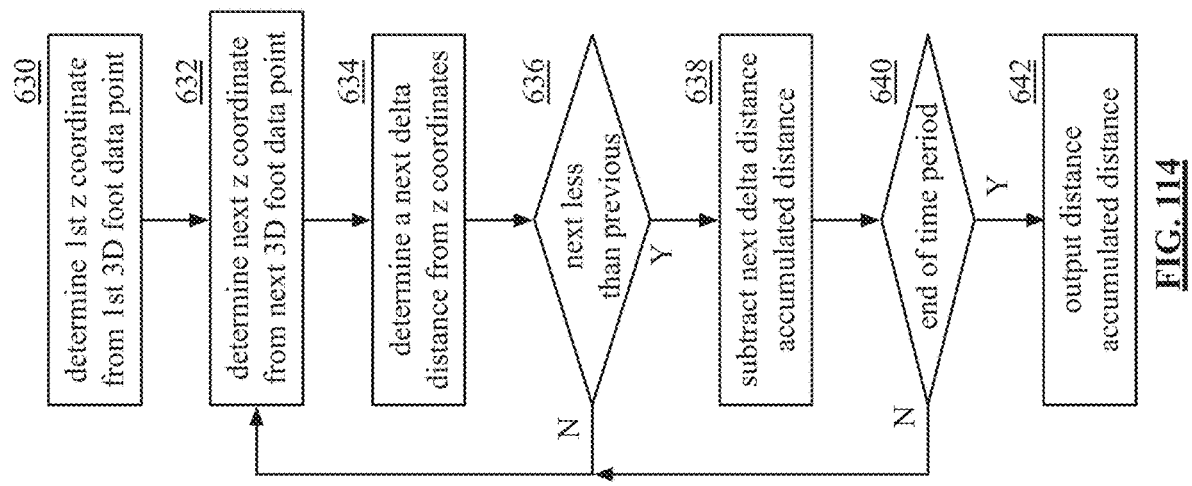
FIG. 114 is a logic diagram of another example of a method executed by a shoe sensor system.

FIG. 114 is a logic diagram of another example of a method executed by a shoe sensor system to determine negative elevation tracking (e.g., descending) for the time period while performing the physical activity. The method begins at step 630 where the processing module (e.g., processing module 430 and/or processing module 427) determines a first z coordinate from a first three-dimensional foot data point (e.g., first x-y-z coordinate as previously described) that corresponds to the beginning of the time period.

The method continues at step 632 where the processing module determines a next z coordinate from a next three-dimensional foot data point (e.g., a next x-y-z coordinate as previously discussed) that corresponds to a next sampling point of the sampling clock within the time period. The method continues at step 634 where the processing module determines a next delta distance based on a difference between the first z coordinate and the next z coordinate. The method continues at step 636 where the processing module determines whether the next delta distance is less than or equal to zero. When it is not, the method continues at step 632.

When the next delta distance is less than or equal to zero, the method continues at step 638 where the processing module adds the next delta distance to an accumulation of previous delta distances to produce an updated accumulation of delta distances. The method continues to step 640 where the processing module determines whether the time period has ended. When the time period has not ended, the method repeats as step 632.

When the next sampling point corresponds to the end of the time period, the method continues at step 642 where the processing module provides the updated accumulation of delta distances as the elevation change that occurred during the time period. For example, the accumulated z distance is −100 feet, which can be equated to descending 10 flights of stairs.

Figure 115:
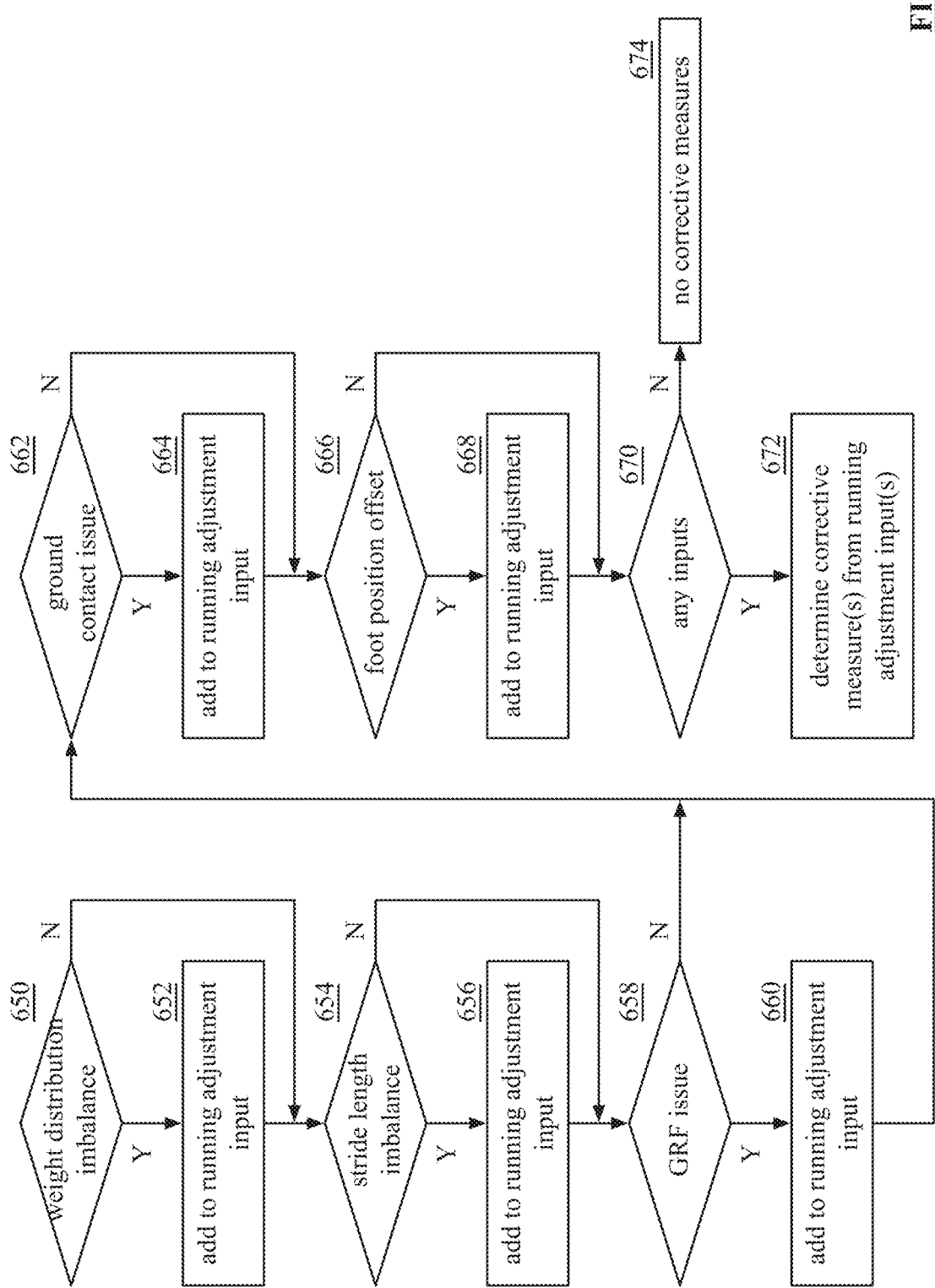
FIG. 115 is a logic diagram of another example of a method executed by a shoe sensor system in accordance with the present invention.

FIG. 115 is a logic diagram of another example of a method executed by a shoe sensor system to determine running optimization, which includes one or more of proper foot positioning, proper weight distribution, balanced strides, stride length training, increase ground reaction force, reduce foot to ground contact time, etc. The method begins at step 650 where the processing module (e.g., processing module 430 and/or processing module 427) determines whether there is a weight imbalance between strides, over a number of strides, and/or over a period of time. For example, a weight imbalance is detected when more force is exerted when one foot strikes the ground versus the other shoe. If yes, the method continues at step 652 where the processing module adds weight distribution issue to a list of running adjustment inputs.

When the weight distribution issue has been added to the running adjustments inputs or there is not a weight distribution issue, the method continues at step 654 where the processing module determines whether a stride length imbalance exists. If yes, the method continues at step 656 where the processing module adds stride length imbalance issue to a list of running adjustment inputs.

When the stride length imbalance issue has been added to the running adjustments inputs or there is not a stride length imbalance issue, the method continues at step 658 where the processing module determines whether a ground reaction force (GRF) issue exists. For example, GRF is the force between the foot and the ground when running. If the GRF is too low, the person is not driving his or her legs hard enough. If the GRF is too high, then the person may be landing wrong, driving too hard, etc. If the GRF issues exists, the method continues at step 660 where the processing module adds the GRF issue to a list of running adjustment inputs.

When the GRF issue has been added to the running adjustments inputs or there is not a GRF issue, the method continues at step 662 where the processing module determines whether a ground contact issue exists. For example, for speed, a runner desired a minimum amount of contact time with the ground per stride. When the contact time with the ground is too high, the runner is losing time. If the ground contact issue exists, the method continues at step 664 where the processing module adds the ground contact issue to a list of running adjustment inputs.

When the ground contact issue has been added to the running adjustments inputs or there is not a ground contact issue, the method continues at step 666 where the processing module determines whether a foot position offset exists. For example, the processing interprets the correlated foot data to determine that foot positioning is offset by at least a foot positioning threshold from an optimal foot positioning. For example, the left foot rolls out several inches when striding from the left foot to left foot contact with the ground. This wastes energy and may lead to an injury. If there is a foot position offset, the method continues at step 668 where the processing module adds the foot position offset to a list of running adjustment inputs.

The method continues at step 670 where the processing module determines whether any inputs are in the running adjustment inputs. If not, the method continues at step 674 where no corrective measures are provided. If, however, there is at least one input in the running adjustment inputs, the method continues at step 672 where the processing module generates one or more corrective measures based on the running adjustment inputs. The corrective measures include training for improving stride length, reducing contact time, improving GRF, etc.

Figure 116:
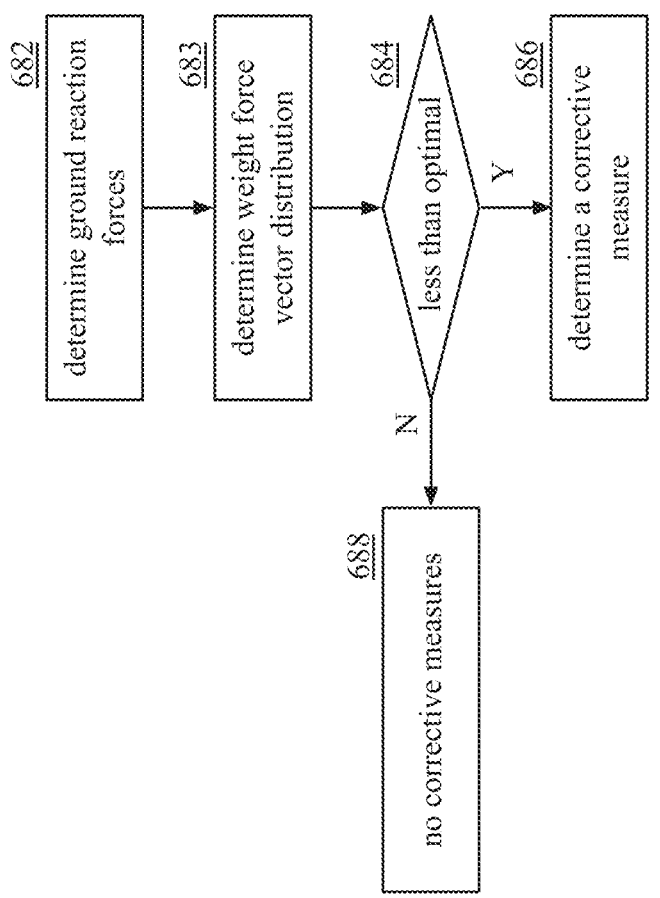

FIG. 116 is a logic diagram of another example of a method executed by a shoe sensor system to determine the rotational sport optimization (e.g., improve weight distribution, improve GRF, improve balance, improve linear movement, improve rotational movement, improve linear and/or rotation power, etc.). The method begins at step 682 where the processing module determines ground reaction force during performance of an athletic movement of a rotational sport (e.g., baseball, golf, tennis, lacrosse, football, basketball, etc.).

The method continues at step 683 where the processing module determines weight force vector distribution between medial and lateral side of the foot and between forefoot and heel based on the ground reaction forces. The method continues at step 684 where the processing module determines whether the weight force vector distribution is less than optimal. When it is not, the method continues at step 688 where no corrective measures are provided. When the weight force vector distribution is less than optimal, the method continues at step 686 where the processing module determines a corrective measure to optimize the weight force vector distribution during performance of the athletic movement.

In the preceding discussion, various figures were used to illustrate various aspects of inventive subject matter. If it is determined that an inconsistency existed between two figures, then the inconsistency shall be resolved in favor of the lower numbered figure.

It is noted that terminologies as may be used herein such as bit stream, stream, signal sequence, etc. (or their equivalents) have been used interchangeably to describe digital information whose content corresponds to any of a number of desired types (e.g., data, video, speech, text, graphics, audio, etc. any of which may generally be referred to as 'data').

As may be used herein, the terms "substantially" and "approximately" provide an industry-accepted tolerance for its corresponding term and/or relativity between items. For some industries, an industry-accepted tolerance is less than one percent and, for other industries, the industry-accepted tolerance is 10 percent or more. Other examples of industry-accepted tolerance range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than +/−1%). Some relativity between items may range from a difference of less than a percentage level to a few percent. Other relativity between items may range from a difference of a few percent to magnitude of differences.

As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to".

As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may be used herein, one or more claims may include, in a specific form of this generic form, the phrase "at least one of a, b, and c" or of this generic form "at least one of a, b, or c", with more or less elements than "a", "b", and "c". In either phrasing, the phrases are to be interpreted identically. In particular, "at least one of a, b, and c" is equivalent to "at least one of a, b, or c" and shall mean a, b, and/or c. As an example, it means: "a" only, "b" only, "c" only, "a" and "b", "a" and "c", "b" and "c", and/or "a", "b", and "c".

As may also be used herein, the terms "processing module", "processing circuit", "processor", "processing circuitry", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, processing circuitry, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, processing circuitry and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with one or more other routines. In addition, a flow diagram may include an "end" and/or "continue" indication. The "end" and/or "continue" indications reflect that the steps presented can end as described and shown or optionally be incorporated in or otherwise used in conjunction with one or more other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While transistors may be shown in one or more of the above-described figure(s) as field effect transistors (FETs), as one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid-state memory, a hard drive memory, cloud memory, thumb drive, server memory, computing device memory, and/or other physical medium for storing digital information.

As applicable, one or more functions associated with the methods and/or processes described herein can be implemented via a processing module that operates via the non-human "artificial" intelligence (AI) of a machine. Examples of such AI include machines that operate via anomaly detection techniques, decision trees, association rules, expert systems and other knowledge-based systems, computer vision models, artificial neural networks, convolutional neural networks, support vector machines (SVMs), Bayesian networks, genetic algorithms, feature learning, sparse dictionary learning, preference learning, deep learning and other machine learning techniques that are trained using training data via unsupervised, semi-supervised, supervised and/or reinforcement learning, and/or other AI. The human mind is not equipped to perform such AI techniques, not only due to the complexity of these techniques, but also due to the fact that artificial intelligence, by its very definition—requires "artificial" intelligence—i.e., machine/non-human intelligence.

As applicable, one or more functions associated with the methods and/or processes described herein can be implemented as a large-scale system that is operable to receive, transmit and/or process data on a large-scale. As used herein, a large-scale refers to a large number of data, such as one or more kilobytes, megabytes, gigabytes, terabytes or more of data that are received, transmitted and/or processed. Such receiving, transmitting and/or processing of data cannot practically be performed by the human mind on a large-scale within a reasonable period of time, such as within a second, a millisecond, microsecond, a real-time basis or other high speed required by the machines that generate the data, receive the data, convey the data, store the data and/or use the data.

As applicable, one or more functions associated with the methods and/or processes described herein can require data to be manipulated in different ways within overlapping time spans. The human mind is not equipped to perform such different data manipulations independently, contemporaneously, in parallel, and/or on a coordinated basis within a reasonable period of time, such as within a second, a millisecond, microsecond, a real-time basis or other high speed required by the machines that generate the data, receive the data, convey the data, store the data and/or use the data.

As applicable, one or more functions associated with the methods and/or processes described herein can be implemented in a system that is operable to electronically receive digital data via a wired or wireless communication network and/or to electronically transmit digital data via a wired or wireless communication network. Such receiving and transmitting cannot practically be performed by the human mind because the human mind is not equipped to electronically transmit or receive digital data, let alone to transmit and receive digital data via a wired or wireless communication network.

As applicable, one or more functions associated with the methods and/or processes described herein can be implemented in a system that is operable to electronically store digital data in a memory device. Such storage cannot practically be performed by the human mind because the human mind is not equipped to electronically store digital data.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A force sensing structure comprises:
a plurality of variable capacitors arranged in a layer; and
a plurality of drive sense circuits operably coupled to the plurality of variable capacitors, wherein:
a first drive sense circuit of the plurality of drive sense circuits senses capacitance of a first variable capacitor of the plurality of variable capacitors;
a second drive sense circuit of the plurality of drive sense circuits senses capacitance of a second variable capacitor of the plurality of variable capacitors, wherein the capacitance of the first and second variable capacitors provide an indication of a force vector applied to the plurality of variable capacitors; and
a perimeter support structure to house the plurality of variable capacitors, wherein the perimeter support structure includes a capacitor holding structure to substantially hold the plurality of variable capacitors in desired locations within the perimeter support structure.

2. The force sensing structure of claim 1, wherein the first variable capacitor comprises:
"n" number of conductive layers, where "n" is two or more;
"n-1" insulating layers, wherein an insulating layer of the "n-1" insulating layers is between two conductive layers of the "n" number of conductive layers; and
two connections, wherein the "n" number of conductive layers, the "n-1" insulating layers, and the two connections are arranged in a stack.

3. The force sensing structure of claim 1 further comprises:
a force coupling layer positioned proximal to the plurality of variable capacitors, wherein the force coupling layer receives the force vector and distributes the force vector to the plurality of variable capacitors.

4. The force sensing structure of claim 3, wherein the force coupling layer comprises:
a compression plate having dimensions to overlap the layer of the plurality of variables capacitors.

5. The force sensing structure of claim 3, wherein the force coupling layer comprises:
a variable capacitor having dimensions to overlap the layer of the plurality of variables capacitors.

6. The force sensing structure of claim 1, wherein the perimeter support structure further comprises:
a plate holding structure to substantially hold a compression plate in a desired position within the perimeter support structure that is proximal to a desired position of the plurality of variable capacitors within the perimeter support structure.

7. A force sensing system comprises:
a force sensing structure that includes:
a plurality of variable capacitors arranged in a layer;
a plurality of drive sense circuits operably coupled to the plurality of variable capacitors, wherein:
a first drive sense circuit of the plurality of drive sense circuits senses capacitance of a first variable capacitor of the plurality of variable capacitors;
a second drive sense circuit of the plurality of drive sense circuits senses capacitance of a second variable capacitor of the plurality of variable capacitors; a third drive sense circuit of the plurality of drive sense circuits senses capacitance of a third variable capacitor of the plurality of variable capacitors;
a perimeter support structure to house the plurality of variable capacitors, wherein the perimeter support structure includes a capacitor holding structure to substantially hold the plurality of variable capacitors in desired locations within the perimeter support structure; and
a processing module operable to:
receive the capacitances of the first, second, and third variable capacitors;
determine a reference plane based on the capacitances of the first, second, and third variable capacitors; and
determine a force vector based on the reference plane.

8. The force sensing system of claim 7, wherein the first variable capacitor comprises:
"n" number of conductive layers, where "n" is two or more;
"n-1" insulating layers, wherein an insulating layer of the "n-1" insulating layers is between two conductive layers of the "n" number of conductive layers; and
two connections, wherein the "n" number of conductive layers, the "n-1" insulating layers, and the two connections are arranged in a stack.

9. The force sensing system of claim 7, wherein the force sensing structure further comprises:
a force coupling layer positioned proximal to the plurality of variable capacitors, wherein the force coupling layer receives the force vector and distributes the force vector to the plurality of variable capacitors.

10. The force sensing system of claim 9, wherein the force coupling layer comprises:
a compression plate having dimensions to overlap the layer of the plurality of variables capacitors.

11. The force sensing system of claim 9, wherein the force coupling layer comprises:
a variable capacitor having dimensions to overlap the layer of the plurality of variables capacitors.

12. The force sensing system of claim 7, wherein the perimeter support structure further comprises:
a plate holding structure to substantially hold a compression plate in a desired position within the perimeter support structure that is proximal to a desired position of the plurality of variable capacitors within the perimeter support structure.

13. The force sensing system of claim 7, wherein the processing module is further operable to:
generate xyz data to represent the force vector.

14. The force sensing system of claim 7 further comprises:
the force sensing structure is positioned within a shoe and is operable to receive a foot force from a wearer of the shoe, wherein the determined force vector is representative of the foot force.

15. The force sensing system of claim 7 further comprises:
a second force sensing structure that includes:
a second plurality of variable capacitors arranged in a layer;
a second plurality of drive sense circuits operably coupled to the plurality of variable capacitors, wherein:
a fourth drive sense circuit of the second plurality of drive sense circuits senses capacitance of a fourth variable capacitor of the second plurality of variable capacitors;
a fifth drive sense circuit of the second plurality of drive sense circuits senses capacitance of a fifth variable capacitor of the second plurality of variable capacitors;
a sixth drive sense circuit of the second plurality of drive sense circuits senses capacitance of a sixth variable capacitor of the second plurality of variable capacitors; and
a processing module operable to:
receive the capacitances of the fourth, fifth, and sixth variable capacitors;
determine a second reference plane based on the capacitances of the fourth, fifth, and sixth variable capacitors; and
determine a second force vector based on the second reference plane.

16. The force sensing system of claim 15, wherein the processing module is further operable to:
generate an overall force vector based on the force vector and the second force vector.

\* \* \* \* \*